US011931336B2

(12) United States Patent
Rinsch et al.

(10) Patent No.: US 11,931,336 B2
(45) Date of Patent: *Mar. 19, 2024

(54) ENHANCING AUTOPHAGY OR INCREASING LONGEVITY BY ADMINISTRATION OF UROLITHINS

(71) Applicant: Amazentis SA, Lausanne (CH)

(72) Inventors: Christopher L. Rinsch, Lausanne (CH); William Blanco-Bose, La Croix (CH); Bernard Schneider, Pully (CH); Laurent Mouchiroud, Morges (CH); Dongryeol Ryu, Renens (CH); Penelope Andreux, Eclepens (CH); Johan Auwerx, Buchillon (CH)

(73) Assignee: Amazentis SA, Lausanne (CH)

( * ) Notice: Subject to any disclaimer, the term of this patent is extended or adjusted under 35 U.S.C. 154(b) by 337 days.

This patent is subject to a terminal disclaimer.

(21) Appl. No.: 17/324,490

(22) Filed: May 19, 2021

(65) Prior Publication Data
US 2021/0353591 A1 Nov. 18, 2021

Related U.S. Application Data

(63) Continuation of application No. 13/929,455, filed on Jun. 27, 2013, now Pat. No. 11,020,373.

(60) Provisional application No. 61/791,137, filed on Mar. 15, 2013, provisional application No. 61/712,886, filed on Oct. 12, 2012, provisional application No. 61/665,137, filed on Jun. 27, 2012.

(51) Int. Cl.
| A61K 31/37 | (2006.01) |
| A61K 31/00 | (2006.01) |
| A61K 31/366 | (2006.01) |
| A61K 31/7048 | (2006.01) |
| A61K 45/06 | (2006.01) |
| C07D 311/80 | (2006.01) |

(52) U.S. Cl.
CPC .............. *A61K 31/37* (2013.01); *A61K 31/00* (2013.01); *A61K 31/366* (2013.01); *A61K 31/7048* (2013.01); *A61K 45/06* (2013.01); *C07D 311/80* (2013.01)

(58) Field of Classification Search
CPC ...... A61K 31/37; A61K 31/00; A61K 31/366; A61K 31/7048; A61K 45/06; C07D 311/80
USPC ........................................................ 514/455
See application file for complete search history.

(56) References Cited

U.S. PATENT DOCUMENTS

| 5,073,545 A | 12/1991 | Arima et al. |
| 8,183,282 B2 | 5/2012 | Seeram et al. |
| 8,894,993 B2 | 11/2014 | Ghosal |
| 9,962,366 B2 | 5/2018 | Rinsch et al. |
| 11,020,373 B2 * | 6/2021 | Rinsch ................ A61P 19/02 |
| 11,166,972 B2 * | 11/2021 | Andreux ............ A61K 31/706 |
| 2005/0234031 A1 | 10/2005 | Schrimpf et al. |
| 2007/0197567 A1 | 8/2007 | Sherris |
| 2008/0031862 A1 | 2/2008 | Ghosal |
| 2009/0326057 A1 * | 12/2009 | Seeram ................ A61P 35/00 |
| | | 514/460 |
| 2011/0263521 A1 | 10/2011 | Moutet et al. |
| 2020/0397748 A1 | 12/2020 | Rinsch et al. |
| 2021/0353591 A1 | 11/2021 | Rinsch et al. |
| 2023/0233523 A1 | 7/2023 | Rinsch et al. |

FOREIGN PATENT DOCUMENTS

| CN | 103442594 A | 12/2013 |
| JP | 2010280627 A | 12/2010 |
| WO | WO-2000/06134 A2 | 2/2000 |
| WO | WO-2002/094984 A2 | 11/2002 |
| WO | WO-2005/077899 A2 | 8/2005 |
| WO | WO-2006/007310 A2 | 1/2006 |
| WO | WO-2007/101247 A2 | 9/2007 |
| WO | WO-2007/127263 A2 | 11/2007 |
| WO | WO-2008/016554 A1 | 2/2008 |
| WO | WO-2007/133249 A3 | 2/2009 |
| WO | WO-2009/120799 A2 | 10/2009 |
| WO | WO-2011/011721 A2 | 1/2011 |
| WO | WO-2012/088519 A2 | 6/2012 |
| WO | WO-2012/113835 A1 | 8/2012 |

OTHER PUBLICATIONS

Rubinsztein et al Cell, 2011, 146, 682-695 (Year: 2011).*
Andreaux et al., "Appendix A: The mitophagy activator urolithin A is safe and induces a molecular signature of improved mitochondrial and cellular health in humans," Nature Metabolish, 1:595-603 (2019).
Gimenez-Bastida J. A. et al., Ellagitannin metabolites, urolithin A glucuronide and its aglycone urolithin A, ameliorate TNF-induced inflammation and associated molecular markers in human aortic endothelial cells, 56(5): 784-796 (2012).
Ishimoto H. et al., "In vivo anti-inflammatory and antioxidant properties of ellagitannin metabolite urolithin A." Bioorg Med Chem Lett, 21(19): 5901-5904 (2011).
Johanningsmeier et al., "Pomegranate as a Functional Food and Nutraceutical Source" Annu. Rev. Food Sci. Technol, 2:181-201 (2010).
Liu et al., "Appendix C: Impact of Urolithin A vs Placebo Supplementation on Muscle Endurance and Mitochondrial Health in the Elderly: A Randomized Clinical Trial," Manuscript Draft.

(Continued)

*Primary Examiner* — Yevgeny Valenrod
(74) *Attorney, Agent, or Firm* — Foley Hoag LLP; Dana M. Gordon; Lawrence P. Tardibono

(57) ABSTRACT

Disclosed are methods, compounds, and compositions useful for increasing autophagy and promoting longevity. The methods, compounds, and compositions relate to urolithins and urolithin precursors and use thereof. Certain urolithins are represented by Formula I, while certain urolithin precursors are represented by Formula IV. The urolithin may be urolithin A, urolithin B, urolithin C, or urolithin D. The urolithin precursor may be ellagic acid or an ellagitannin. The methods include in vivo, ex vivo, and in vitro uses of the compounds and compositions.

20 Claims, 40 Drawing Sheets

(56) References Cited

OTHER PUBLICATIONS

Singh et al., "Appendix B: Urolithin A improves leg muscle strength, exercise performance and mitochondrial health in a proof-of-concept clinical trial in overweight adults," Manuscript Draft.
Stout et al., "Mitochondria's Role in Skin Ageing," Biology, 8(29): 12 pages (2019).
Verzelloni E. et al., "Antiglycative and neuroprotective activity of colonderived polyphenol catabolites." Mol. Nutr. Food Res, 55(1):35-43 (2011).
Adams et al., "Pomegranate Ellagitannin-Derived Compounds Exhibit Antiproliferative and Antiaromatase Activity in Breast Cancer Cells In Vitro," Cancer Prev Res, 3: 108-113 (2010).
Andreaux et al., "The mitophagy activator urolithin A is safe and induces a molecular signature of improved mitochondrial and cellular health in humans," Nature Metabolish, 1:595-603 (2019).
Berry Health Benefits Symposium (2009 Berry Health Benefis Symposium).
Bhattacharyya et al., "Beneficial Effect of Processed Shilajit on Swimming Exercise Induced Impaired Energy Status of Mice," Pharmacologyonline, 1: 817-825 (2009).
Bhattacharyya et al., "Shilajit Dibezno-a-Pyrones: Mitochondria Targeted Antioxidants," Pharmacologyonline, 2: 690-698 (2009).
Bialonska, et al., "Urolithins, Intenstinal Microbial Metabolites of Pomegranate Ellagitannins, Exhibit Potent Antioxidant Activity in a Cell-Based Assay," J Agric Food Chem, 57(21); 10181-10186, 2009.
Cerda et al., "Repeated oral administration of high doses of the pomegranate ellagitannin punialagin to rats for 37 days is not toxic," J. Agric. Food Chem., 51(11):3493-3501 (2003).
Chen et al., "Coordination of Autophagy and the Proteasome in Resolving Endoplasmic Reticulum Stress," Veterinary Pathology 48(1):245-253 (2011).
Chen, T. et al., "Rapamycin and other longevity-promoting compounds enhance the generation of mouse induced pluripotent stem cells", *Aging Cell*, 10(5):908-911 (Anatomical Society of Great Britain and Ireland, UK, Jun. 14, 2011).
Dr. Mark Percival, "Antioxidants," Clinical Nurtition Insights, 1998.
Du et al., "Starving Neurons Show Sex Difference in Autophagy," The Journal of Biological Chemistry, 284(4): 2383-2396 (2009).
Ghosal et al., "Effects of shilajit and its active constituents on learning and memory in rats," Phytotherapy Res, 7(1): 29-34 (1993).
Ghosal et al., "Shilajit. Part 4. Chemistry of Two Bioactive Benzopyrone Metabolites," J Chem Research (S), 11: 350-351 (1989).
Gulcin et al., "Antioxidant and Antiradical Activities of L-carnitine," Life Sciences, 78: 803-811 (2006).
International Search Report and Written Opinion from corresponding PCT application PCT/US2013/048310 dated Jan. 22, 2014.

Kasimsetty, S. G. et al., "Colon Cancer Chemopreventive Activities of Pomegranate Ellagitannins and Urolithins", *Journal of Agricultural and Food Chemistry*, 58(4):2180-2187 (American Chemical Society, USA, Feb. 24, 2010).
Kiss, A. K. et al., "Epigenetic modulation of mechanisms involved in inflammation: Influence of selected polyphenolic substances on histone acetylation state", *Food Chemistry*, 131(3): 1015-1020 (Elsevier Ltd., Netherlands, Sep. 26, 2011).
Landete, J. M., "Ellagitannins, ellagic acid and their derived metabolites: A review about source, metabolism, functions and health", *Food Research International*, 44(5):1150-1160 (Elsevier Applied Science, Barking, GB, Apr. 17, 2011).
Larossa, M. et al., "Anti-inflammatory properties of a pomegranate extract and its metabolite urolithin-A in a colitis rat model and the effect of colon inflammation on phenolic metabolism", *Journal of Nutritional Biochemistry*, 21:717-725 (Elsevier Inc., 2010).
Lin et al., "Pharmacological Promotion of Autophagy Alleviates Steatosis and Injury in Alcoholic and Non-alcoholic Fatty Liver Conditions in Mice," J Hepatol. May 2013; 58(5):993-999.
Manach et al., "Bioavailability and bioefficacy of polyphenols in humans. I. Review of 97 bioavailability studies [1-3]," Am. J. Clin. Nutr. 81(suppl):230S-242S (2005).
Markaki et al., "Modeling human diseases in Caenorhabditis elegans," Biotechnol J, 5:1261-1276 (2010).
Mingorance et al., "Critical update for the clinical use of L-carnitine analogs in cardiometabolic disorders," Vascular Health and Risk Management, 7:169-176 (2011).
Reuter et al., "Carnitine and Acylcarnitines Pharmacokinetic, Pharmacological and Clinical Aspects," Clin Pharmacokinet, 51 (9): 553-572 (2012).
Saul, N. et al., "Diversity of Polyphenol Action in *Caenohabditis elegans*: Between Toxicity and Longevity", *Journal of Natural Products*, 74(8): 1713-1720 (American Chemical Society and American Society of Pharmacognosy, USA, Aug. 26, 2011).
Seeram, N. P. et al., "Pomegranate Ellagitannin-Derived Metabolites Inhibit Prostate Cancer Growth and Localize to the Mouse Prostate Gland", *J. Agric. Food Chem.*, 55:7732-7737 (American Chemcal Society, USA, 2007).
Silverman et al., "Modeling molecular and cellular aspects of human disease using the nematode caenorhabditis elegans," Pediatric Research, 65(1):10-18 (2009).
Uchida, "Pathologic Changes and Autophagy: New Insights for the Pathogenesis of Animal Diseases," Veterinary Pathology 54(6):881-884 (2017).
Zenjun et al., "Distribution of Ellagic Acids in Plantae and Thier Bioactivies," Natural Product Research and Development, 22:519-524 and 540 (2010).
De Meyer et al., "Autophagy in the cardiovascular system," Biochimica et Biophysica Acta 1793: pp. 1485-1495 (2009).
Hipkiss, "Aging, proteotoxicity, mitochondria, glycation, NAD+ and carnosine: possible inter-relationships and resolution of the oxygen paradox", Frontiers in aging neuroscience: 10 (2010).

\* cited by examiner

Figure 9A
Figure 9B
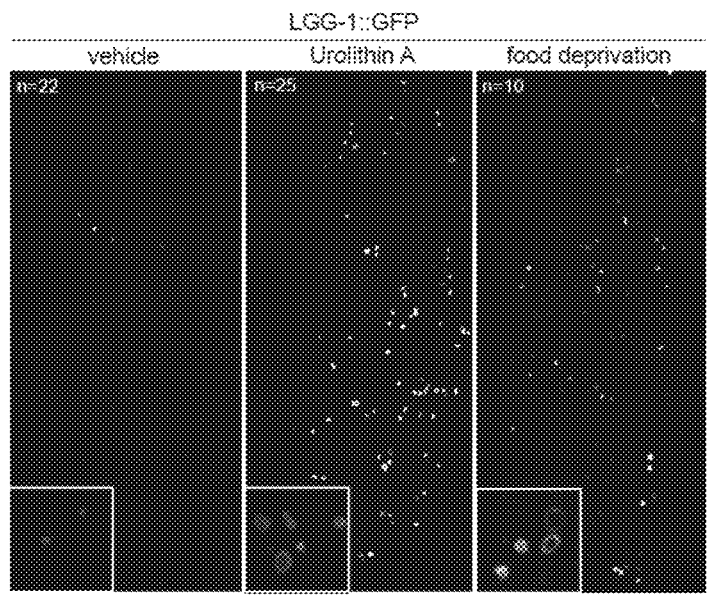
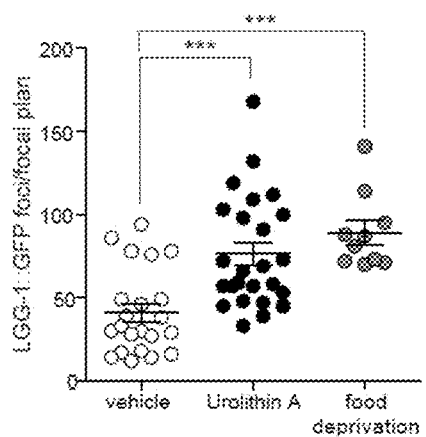
Figure 10A
Figure 10B
Figure 10C
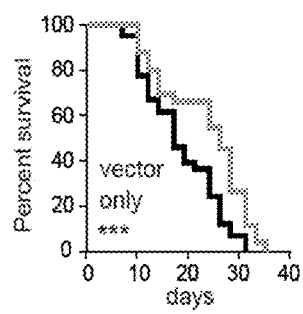
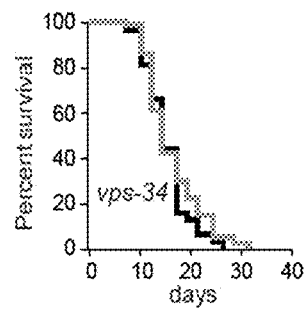
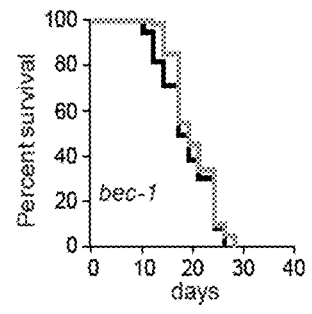

Mode K Cells

Primary Hepatocytes

C2C12 Mouse Myoblasts

Human Primary Myoblasts

** p<0.01, t-test

Human Primary Aortic Endothelial Cells

* p=0.05, t-test

Mouse liver following urolithin A treatment

Mouse Gastrocnemius Muscle

** $p<0.01$, t-test

Compound 1

Compound 2

Compound 3

Compound 4

Compound 5

Compound 6

Compound 7

Compound 8

Compound 9

Compound 10

Compound 11

Compound 12

References: Reactions A, B, C and *Tetrahedron Lett.* 2005, 46, 3197-3200

Compound 13

References: Reactions C, D and WO2005/061440 A1, p. 27

Compound 14

References: Reactions A, B and C

Compound 15

References: Reactions C and D

Compound 16

References: Reactions A, B and C

Compounds 17 & 18

Compounds 17 & 18 (cont.)

References: Reaction B, C, Org. Lett. 2007, 9, 2831-2833 and Tetrahedron 2007, 63, 10464-10465, Tetrahedron 2011, 67, 3804-3814 and Synthesis 2010, 3736-3740

Compound 19

References: Reactions C, D, J. Org. Chem. 2001, 66, 954-961 and Org. Lett. 2007, 9, 2831-2833

Compound 20

Compound 21

Compound 22

Compound 23

Compound 24

Compound 25

ENHANCING AUTOPHAGY OR INCREASING LONGEVITY BY ADMINISTRATION OF UROLITHINS

RELATED APPLICATIONS

This application is a continuation of U.S. patent application Ser. No. 13/929,455, filed Jun. 27, 2013; which claims benefit of priority to U.S. Provisional Patent Application No. 61/791,137, filed Mar. 15, 2013; U.S. Provisional Patent Application No. 61/712,886, filed Oct. 12, 2012; and U.S. Provisional Patent Application No. 61/665,137, filed Jun. 27, 2012.

BACKGROUND

Autophagy is a lysosomal degradation pathway in both animals and plants that is essential for development, differentiation, homeostasis, and survival. In animals, autophagy serves principally as an adaptive mechanism to protect organisms against diverse pathologies, including infection, cancer, neurodegeneration, heart disease, and aging. The repertoire of routine housekeeping functions performed by autophagy includes elimination of defective proteins and organelles, prevention of the accumulation of abnormal protein aggregates, and elimination of intracellular pathogens. The autophagy pathway is uniquely capable of degrading entire organelles, such as mitochondria, peroxisomes, and endoplasmic reticulum.

Multiple reports indicate that proteins required for autophagy induction, such as sirtuin 1, have reduced expression in aged tissues; levels of autophagy have been shown to diminish with age. Reduced levels of autophagy have also been associated with obesity, diabetes, cancer, neurodegenerative diseases, cardiovascular disease, osteoarthritis, and age-related macular degeneration.

A number of compounds that stimulate autophagy have been identified, including rapamycin, resveratrol, metformin, spermidine, and glucosamine.

Urolithins are ellagitannin- and ellagic acid-derived metabolites produced, e.g., by mammalian colonic microflora, including human colonic microflora. Urolithins are known to exhibit anti-oxidant activity.

SUMMARY OF THE INVENTION

An aspect of the invention is a method of increasing autophagy in an animal, comprising the step of administering to an animal in need thereof an effective amount of a urolithin or a precursor thereof, thereby increasing autophagy in the animal.

An aspect of the invention is a method of increasing longevity in an animal, comprising the step of administering to an animal in need thereof an effective amount of a urolithin or a precursor thereof, thereby increasing longevity of the animal.

An aspect of the invention is a method of increasing autophagy in a cell, comprising the step of contacting a cell with an effective amount of a urolithin or a precursor thereof, thereby increasing autophagy in the cell.

An aspect of the invention is a method of increasing longevity of a cell, comprising the step of contacting a cell with an effective amount of a urolithin or a precursor thereof, thereby increasing longevity of the cell.

An aspect of the invention is a method of increasing autophagy of eukaryotic cells in vitro, comprising the step of contacting eukaryotic cells in vitro with an effective amount of a urolithin or a precursor thereof, thereby increasing autophagy in the eukaryotic cells in vitro.

An aspect of the invention is a method of increasing longevity of eukaryotic cells in vitro, comprising the step of contacting eukaryotic cells in vitro with an effective amount of a urolithin or a precursor thereof, thereby increasing longevity of the eukaryotic cells in vitro.

An aspect of the invention is a composition comprising a urolithin or a precursor thereof; and a compound selected from the group consisting of rapamycin, resveratrol, metformin, and spermidine.

An aspect of the invention is a compound of Formula II

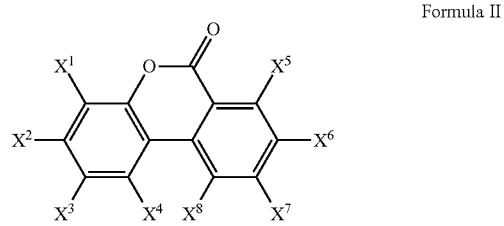

Formula II wherein
$X^1$, $X^2$, $X^3$, $X^4$, $X^5$, $X^6$, $X^7$, and $X^8$ are independently selected from the group consisting of H and OH; and with the proviso that the compound is not a compound of Formula II wherein
$X^1$, $X^2$, $X^3$, $X^4$, $X^5$, $X^6$, $X^7$, and $X^8$ are H;
$X^1$ is OH, and $X^2$, $X^3$, $X^4$, $X^5$, $X^6$, $X^7$, and $X^8$ are H;
$X^2$ is OH, and $X^1$, $X^3$, $X^4$, $X^5$, $X^6$, $X^7$, and $X^8$ are H (urolithin B);
$X^3$ is OH, and $X^1$, $X^2$, $X^4$, $X^5$, $X^6$, $X^7$, and $X^8$ are H;
$X^4$ is OH, and $X^1$, $X^2$, $X^3$, $X^5$, $X^6$, $X^7$, and $X^8$ are H;
$X^5$ is OH, and $X^1$, $X^2$, $X^3$, $X^4$, $X^6$, $X^7$, and $X^8$ are H;
$X^6$ is OH, and $X^1$, $X^2$, $X^3$, $X^4$, $X^5$, $X^7$, and $X^8$ are H;
$X^7$ is OH, and $X^1$, $X^2$, $X^3$, $X^4$, $X^5$, $X^6$, and $X^8$ are H;
$X^8$ is OH, and $X^1$, $X^2$, $X^3$, $X^4$, $X^5$, $X^6$, and $X^7$ are H;
$X^1$ and $X^2$ are OH, and $X^3$, $X^4$, $X^5$, $X^6$, $X^7$, and $X^8$ are H;
$X^1$ and $X^5$ are OH, and $X^2$, $X^3$, $X^4$, $X^6$, $X^7$, and $X^8$ are H;
$X^1$ and $X^7$ are OH, and $X^2$, $X^3$, $X^4$, $X^5$, $X^6$, and $X^8$ are H;
$X^1$ and $X^8$ are OH, and $X^2$, $X^3$, $X^4$, $X^5$, $X^6$, and $X^7$ are H;
$X^2$ and $X^3$ are OH, and $X^1$, $X^4$, $X^5$, $X^6$, $X^7$, and $X^8$ are H;
$X^2$ and $X^4$ are OH, and $X^1$, $X^3$, $X^5$, $X^6$, $X^7$, and $X^8$ are H;
$X^2$ and $X^5$ are OH, and $X^1$, $X^3$, $X^4$, $X^6$, $X^7$, and $X^8$ are H;
$X^2$ and $X^6$ are OH, and $X^1$, $X^3$, $X^4$, $X^5$, $X^7$, and $X^8$ are H (urolithin A);
$X^2$ and $X^7$ are OH, and $X^1$, $X^3$, $X^4$, $X^5$, $X^6$, and $X^8$ are H;
$X^3$ and $X^4$ are OH, and $X^1$, $X^2$, $X^5$, $X^6$, $X^7$, and $X^8$ are H;
$X^3$ and $X^5$ are OH, and $X^1$, $X^2$, $X^4$, $X^6$, $X^7$, and $X^8$ are H;
$X^3$ and $X^6$ are OH, and $X^1$, $X^2$, $X^4$, $X^5$, $X^7$, and $X^8$ are H;
$X^5$ and $X^6$ are OH, and $X^1$, $X^2$, $X^3$, $X^4$, $X^7$, and $X^8$ are H;
$X^5$ and $X^8$ are OH, and $X^1$, $X^2$, $X^3$, $X^4$, $X^6$, and $X^7$ are H;
$X^6$ and $X^7$ are OH, and $X^1$, $X^2$, $X^3$, $X^4$, $X^5$, and $X^8$ are H;
$X^1$, $X^2$, and $X^5$ are OH, and $X^3$, $X^4$, $X^6$, $X^7$, and $X^8$ are H;
$X^1$, $X^2$, and $X^6$ are OH, and $X^3$, $X^4$, $X^5$, $X^7$, and $X^8$ are H;
$X^1$, $X^5$, and $X^8$ are OH, and $X^2$, $X^3$, $X^4$, $X^6$, and $X^7$ are H;
$X^2$, $X^4$, and $X^6$ are OH, and $X^1$, $X^3$, $X^5$, $X^7$, and $X^8$ are H;
$X^2$, $X^4$, and $X^7$ are OH, and $X^1$, $X^3$, $X^5$, $X^6$, and $X^8$ are H;
$X^2$, $X^6$, and $X^7$ are OH, and $X^1$, $X^3$, $X^4$, $X^5$, and $X^8$ are H (urolithin C);

X², X⁶, and X⁸ are OH, and X¹, X³, X⁴, X⁵, and X⁷ are H;
X², X⁷, and X⁸ are OH, and X¹, X³, X⁴, X⁵, and X⁶ are H;
X¹, X², X⁵, and X⁶ are OH, and X³, X⁴, X⁷, and X⁸ are H;
X¹, X², X⁵, and X⁷ are OH, and X³, X⁴, X⁶, and X⁸ are H;
X¹, X², X⁶, and X⁷ are OH, and X³, X⁴, X⁵, and X⁸ are H (urolithin D);
X¹, X⁶, X⁷, and X⁸ are OH, and X², X³, X⁴, and X⁵ are H;
X², X³, X⁶, and X⁷ are OH, and X¹, X⁴, X⁵, and X⁸ are H;
X², X⁴, X⁵, and X⁸ are OH, and X¹, X³, X⁶, and X⁷ are H;
X², X⁴, X⁶, and X⁷ are OH, and X¹, X³, X⁵, and X⁸ are H;
X¹, X², X⁴, X⁵, and X⁷ are OH, and X³, X⁶, and X⁸ are H;
X¹, X², X⁶, X⁷, and X⁸ are OH, and X³, X⁴, and X⁵ are H; and
X¹, X², X³, X⁶, X⁷, and X⁸ are OH, and X⁴ and X⁵ are H.

An aspect of the invention is a compound of Formula III

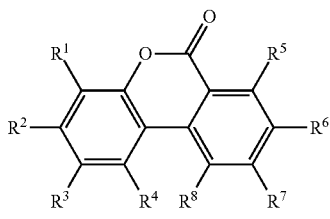

Formula III wherein
R¹, R², R³, R⁴, R⁵, R⁶, R⁷, and R⁸ are independently selected from the group consisting of H and OR;
R is H, substituted or unsubstituted alkyl, substituted or unsubstituted aryl, a substituted or unsubstituted monosaccharide, or a substituted or unsubstituted oligosaccharide; and
with the proviso that the compound is not a compound of Formula III wherein
R¹, R², R³, R⁴, R⁵, R⁶, R⁷, and R⁸ are H;
R¹ is OR, and R², R³, R⁴, R⁵, R⁶, R⁷, and R⁸ are H;
R² is OR, and R¹, R³, R⁴, R⁵, R⁶, R⁷, and R⁸ are H;
R³ is OR, and R¹, R², R⁴, R⁵, R⁶, R⁷, and R⁸ are H;
R⁴ is OR, and R¹, R², R³, R⁵, R⁶, R⁷, and R⁸ are H;
R⁵ is OR, and R¹, R², R³, R⁴, R⁶, R⁷, and R⁸ are H;
R⁶ is OR, and R¹, R², R³, R⁴, R⁵, R⁷, and R⁸ are H;
R⁷ is OR, and R¹, R², R³, R⁴, R⁵, R⁶, and R⁸ are H;
R⁸ is OR, and R¹, R², R³, R⁴, R⁵, R⁶, and R⁷ are H;
R¹ and R² are OR, and R³, R⁴, R⁵, R⁶, R⁷, and R⁸ are H;
R¹ and R⁵ are OR, and R², R³, R⁴, R⁶, R⁷, and R⁸ are H;
R¹ and R⁷ are OR, and R², R³, R⁴, R⁵, R⁶, and R⁸ are H;
R¹ and R⁸ are OR, and R², R³, R⁴, R⁵, R⁶, and R⁷ are H;
R² and R³ are OR, and R¹, R⁴, R⁵, R⁶, R⁷, and R⁸ are H;
R² and R⁴ are OR, and R¹, R³, R⁵, R⁶, R⁷, and R⁸ are H;
R² and R⁵ are OR, and R¹, R³, R⁴, R⁶, R⁷, and R⁸ are H;
R² and R⁶ are OR, and R¹, R³, R⁴, R⁵, R⁷, and R⁸ are H;
R² and R⁷ are OR, and R¹, R³, R⁴, R⁵, R⁶, and R⁸ are H;
R² and R⁸ are OR, and R¹, R³, R⁴, R⁵, R⁶, and R⁷ are H;
R³ and R⁴ are OR, and R¹, R², R⁵, R⁶, R⁷, and R⁸ are H;
R³ and R⁵ are OR, and R¹, R², R⁴, R⁶, R⁷, and R⁸ are H;
R³ and R⁶ are OR, and R¹, R², R⁴, R⁵, R⁷, and R⁸ are H;
R³ and R⁷ are OR, and R¹, R², R⁴, R⁵, R⁶, and R⁸ are H;
R³ and R⁸ are OR, and R¹, R², R⁴, R⁵, R⁶, and R⁷ are H;
R⁴ and R⁸ are OR, and R¹, R², R³, R⁵, R⁶, and R⁷ are H;
R⁵ and R⁶ are OR, and R¹, R², R³, R⁴, R⁷, and R⁸ are H;
R⁵ and R⁷ are OR, and R¹, R², R³, R⁴, R⁶, and R⁸ are H;
R⁵ and R⁸ are OR, and R¹, R², R³, R⁴, R⁶, and R⁷ are H;
R⁶ and R⁷ are OR, and R¹, R², R³, R⁴, R⁵, and R⁸ are H;
R⁶ and R⁸ are OR, and R¹, R², R³, R⁴, R⁵, and R⁷ are H;
R¹, R², and R³ are OR, and R⁴, R⁵, R⁶, R⁷, and R⁸ are H;
R¹, R², and R⁵ are OR, and R³, R⁴, R⁶, R⁷, and R⁸ are H;
R¹, R², and R⁶ are OR, and R³, R⁴, R⁵, R⁷, and R⁸ are H;
R¹, R², and R⁸ are OR, and R³, R⁴, R⁵, R⁶, and R⁷ are H;
R¹, R⁵, and R⁸ are OR, and R², R³, R⁴, R⁶, and R⁷ are H;
R¹, R⁷, and R⁸ are OR, and R², R³, R⁴, R⁵, and R⁶ are H;
R², R³, and R⁴ are OR, and R¹, R⁵, R⁶, R⁷, and R⁸ are H;
R², R⁴, and R⁶ are OR, and R¹, R³, R⁵, R⁷, and R⁸ are H;
R², R⁴, and R⁷ are OR, and R¹, R³, R⁵, R⁶, and R⁸ are H;
R², R⁵, and R⁸ are OR, and R¹, R³, R⁴, R⁶, and R⁷ are H;
R², R⁶, and R⁷ are OR, and R¹, R³, R⁴, R⁵, and R⁸ are H;
R², R⁶, and R⁸ are OR, and R¹, R³, R⁴, R⁵, and R⁷ are H;
R², R⁷, and R⁸ are OR, and R¹, R³, R⁴, R⁵, and R⁶ are H;
R³, R⁵, and R⁸ are OR, and R¹, R², R⁴, R⁶, and R⁷ are H;
R³, R⁷, and R⁸ are OR, and R¹, R², R⁴, R⁵, and R⁶ are H;
R⁶, R⁷, and R⁸ are OR, and R¹, R², R³, R⁴, and R⁵ are H;
R¹, R², R⁵, and R⁶ are OR, and R³, R⁴, R⁷, and R⁸ are H;
R¹, R², R⁵, and R⁷ are OR, and R³, R⁴, R⁶, and R⁸ are H;
R¹, R², R⁶, and R⁷ are OR, and R³, R⁴, R⁵, and R⁸ are H;
R¹, R⁶, R⁷, and R⁸ are OR, and R², R³, R⁴, and R⁵ are H;
R², R³, R⁴, and R⁶ are OR, and R¹, R⁵, R⁷, and R⁸ are H;
R², R³, R⁵, and R⁷ are OR, and R¹, R⁴, R⁶, and R⁸ are H;
R², R³, R⁶, and R⁷ are OR, and R¹, R⁴, R⁵, and R⁸ are H;
R², R⁴, R⁵, and R⁸ are OR, and R¹, R³, R⁶, and R⁷ are H;
R², R⁴, R⁶, and R⁷ are OR, and R¹, R³, R⁵, and R⁸ are H;
R², R⁵, R⁶, and R⁷ are OR, and R¹, R³, R⁴, and R⁸ are H;
R², R⁶, R⁷, and R⁸ are OR, and R¹, R³, R⁴, and R⁵ are H;
R¹, R², R⁴, R⁵, and R⁷ are OR, and R³, R⁶, and R⁸ are H;
R¹, R², R⁶, R⁷, and R⁸ are OR, and R³, R⁴, and R⁵ are H;
R², R³, R⁴, R⁵, and R⁷ are OR, and R¹, R⁶, and R⁸ are H;
R², R³, R⁶, R⁷, and R⁸ are OR, and R¹, R⁴, and R⁵ are H;
R², R⁴, R⁶, R⁷, and R⁸ are OR, and R¹, R³, and R⁵ are H;
R², R⁵, R⁶, R⁷, and R⁸ are OR, and R¹, R³, and R⁴ are H;
R¹, R², R³, R⁶, R⁷, and R⁸ are OR, and R⁴ and R⁵ are H;
R², R³, R⁴, R⁶, R⁷, and R⁸ are OR, and R¹ and R⁵ are H; and
R², R⁴, R⁵, R⁶, R⁷, and R⁸ are OR, and R¹ and R³ are H.

An aspect of the invention is a compound of Formula V

Formula V wherein
X⁹, X¹⁰, X¹¹, X¹², X¹³, and X¹⁴ are independently selected from the group consisting of H and OH; and
with the proviso that the compound is not a compound of Formula V wherein
X⁹, X¹⁰, X¹¹, X¹², X¹³, and X¹⁴ are H;
X¹⁰ is OH, and X⁹, X¹¹, X¹², X¹³, and X¹⁴ are H;

$X^9$ and $X^{12}$ are OH, and $X^{10}$, $X^{11}$, $X^{13}$, and $X^{14}$ are H;
$X^9$ and $X^{13}$ are OH, and $X^{10}$, $X^{11}$, $X^{12}$, and $X^{14}$ are H;
$X^9$ and $X^{14}$ are OH, and $X^{10}$, $X^{11}$, $X^{12}$, and $X^{13}$ are H;
$X^{10}$ and $X^{13}$ are OH, and $X^9$, $X^{11}$, $X^{12}$, and $X^{14}$ are H;
$X^{10}$, $X^{11}$, and $X^{13}$ are OH, and $X^9$, $X^{12}$, and $X^{14}$ are H;
$X^9$, $X^{10}$, $X^{12}$, and $X^{14}$ are OH, and $X^{11}$ and $X^{13}$ are H;
$X^9$, $X^{10}$, $X^{13}$, and $X^{14}$ are OH, and $X^{11}$ and $X^{12}$ are H (ellagic acid);
$X^9$, $X^{10}$, $X^{11}$, $X^{13}$, and $X^{14}$ are OH, and $X^{12}$ is H; and
$X^9$, $X^{10}$, $X^{11}$, $X^{12}$, $X^{13}$, and $X^{14}$ are OH.

An aspect of the invention is a compound of Formula VI

Formula VI

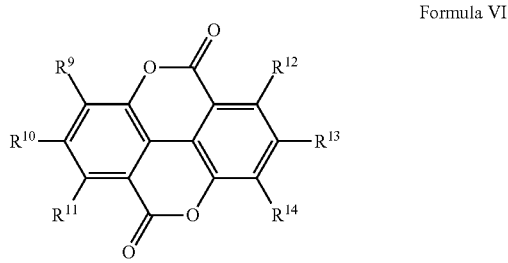

wherein
$R^9$, $R^{10}$, $R^{11}$, $R^{12}$, $R^{13}$, and $R^{14}$ are independently selected from the group consisting of H and OR;
R is H, substituted or unsubstituted alkyl, substituted or unsubstituted aryl, a substituted or unsubstituted monosaccharide, or a substituted or unsubstituted oligosaccharide; and
with the proviso that the compound is not a compound of Formula VI wherein
$R^9$, $R^{10}$, $R^{11}$, $R^{12}$, $R^{13}$, and $R^{14}$ are H;
$R^{10}$ is OR, and $R^9$, $R^{11}$, $R^{12}$, $R^{13}$, and $R^{14}$ are H;
$R^9$ and $R^{12}$ are OR, and $R^{10}$, $R^{11}$, $R^{13}$, and $R^{14}$ are H;
$R^9$ and $R^{13}$ are OR, and $R^{10}$, $R^{11}$, $R^{12}$, and $R^{14}$ are H;
$R^9$ and $R^{14}$ are OR, and $R^{10}$, $R^{11}$, $R^{12}$, and $R^{13}$ are H;
$R^{10}$ and $R^{13}$ are OR, and $R^9$, $R^{11}$, $R^{12}$, and $R^{14}$ are H;
$R^9$, $R^{10}$, and $R^{13}$ are OR, and $R^{11}$, $R^{12}$, and $R^{14}$ are H;
$R^9$, $R^{10}$, and $R^{14}$ are OR, and $R^{11}$, $R^{12}$, and $R^{13}$ are H;
$R^{10}$, $R^{11}$, and $R^{13}$ are OR, and $R^9$, $R^{12}$, and $R^{14}$ are H;
$R^9$, $R^{10}$, $R^{12}$, and $R^{13}$ are OR, and $R^{11}$ and $R^{14}$ are H;
$R^9$, $R^{10}$, $R^{12}$, and $R^{14}$ are OR, and $R^{11}$ and $R^{13}$ are H;
$R^9$, $R^{10}$, $R^{13}$, and $R^{14}$ are OR, and $R^{11}$ and $R^{12}$ are H;
$R^{10}$, $R^{11}$, $R^{12}$, and $R^{13}$ are OR, and $R^9$ and $R^{14}$ are H;
$R^9$, $R^{10}$, $R^{11}$, $R^{12}$, and $R^{13}$ are OR, and $R^{14}$ is H;
$R^9$, $R^{10}$, $R^{11}$, $R^{13}$, and $R^{14}$ are OR, and $R^{12}$ is H; and
$R^9$, $R^{10}$, $R^{11}$, $R^{12}$, $R^{13}$, and $R^{14}$ are OR.

An aspect of the invention is a composition comprising a first compound; and a second compound selected from the group consisting of rapamycin, resveratrol, metformin, and spermidine, wherein the first compound is a compound of any one of Formulas II, III, V, or VI.

An aspect of the invention is a method of increasing autophagy in a cell, comprising contacting the cell with an effective amount of a compound of any one of Formulas II, III, V, or VI, thereby increasing autophagy in the cell.

An aspect of the invention is a method of increasing longevity in an animal, comprising administering to an animal in need thereof an effective amount of a compound of any one of Formulas II, III, V, or VI, thereby increasing longevity of the animal.

An aspect of the invention is a method of increasing longevity of eukaryotic cells in vitro, comprising contacting eukaryotic cells in vitro with an effective amount of a compound of any one of Formulas II, III, V, or VI, thereby increasing longevity of the eukaryotic cells in vitro.

BRIEF DESCRIPTION OF THE DRAWINGS

FIG. 8A illustrates basal and uncoupled respiration (FCCP) in 10-day-old control worms treated with 0.1% DMSO and ten-day-old-worms treated with 30 µM urolithin A in 0.1% DMSO. FIG. 8B illustrates representative area under the curve (AUC) of uncoupled (FCCP) respiration in ten-day-old control worms treated with vehicle (0.1% DMSO) or 30 µM urolithin A in 0.1% DMSO. Results are expressed as mean±SEM. *, p<0.05 (Student's t-test). OCR, oxygen consumption rate. FIG. 8C illustrates comparison of basal respiration between one-day-old and ten-day-old worms treated with vehicle (0.1% DMSO). FIG. 8D illustrates comparison of basal respiration between one-day-old and ten-day-old worms treated with UA (30 µM).

FIG. 9A is a group of three confocal images depicting the effect of urolithin A on autophagy induction in C. elegans. FIG. 9B is a corresponding dot graph depicting the effect of urolithin A on autophagy induction. ***, p<0.001 (student's t-test).

FIGS. 10A-10C are three graphs depicting survival curves, showing the effect of inactivation by RNAi of vps-34 and bec-1 on the longevity phenotype induced by urolithin A treatment in C. elegans. Both vps-34 (FIG. 10B) and bec-1 (FIG. 10C) inhibitions totally suppress the lifespan phenotype observed in worms treated with urolithin A (50 µM) and fed with empty vector (FIG. 10A). Survival analyses were performed using the Kaplan Meier method and the significance of differences between survival curves calculated using the log rank test. ***, p<0.001 (log rank test).

DETAILED DESCRIPTION OF THE INVENTION

Overview

Autophagy is a process by which cells degrade their own components, recycling amino acids and other building blocks that can be reused. Such degradation is performed by lysosomal acidic hydrolases. It is a tightly regulated process that plays an important role in normal cell growth, development, and homeostasis, helping to maintain a balance between the synthesis, degradation, and subsequent recycling of cellular products. It is a major mechanism by which starving cells can reallocate nutrients from less-essential processes to more essential processes.

During nutrient starvation, increased levels of autophagy lead to the breakdown of non-vital components and the release of nutrients, ensuring that vital processes can continue. Mutant yeast cells that have a reduced autophagic capability rapidly perish in nutrient-deficient conditions. A gene known as Atg7 has been implicated in nutrient-mediated autophagy, and studies in mice have shown that starvation-induced autophagy was impaired in Atg7-deficient mice. Komatsu M et al. (2005) *J Cell Biol.* 169:425-434.

Autophagy degrades damaged organelles, cell membranes, and proteins. The failure of autophagy is thought to be an important factor in the accumulation of cell damage and, therefore, aging.

Three types of autophagy can be distinguished, depending on the pathway along which cellular components are delivered to lysosomes: macroautophagy, microautophagy, and chaperone-mediated autophagy (CMA).

Macroautophagy

Figure 1:
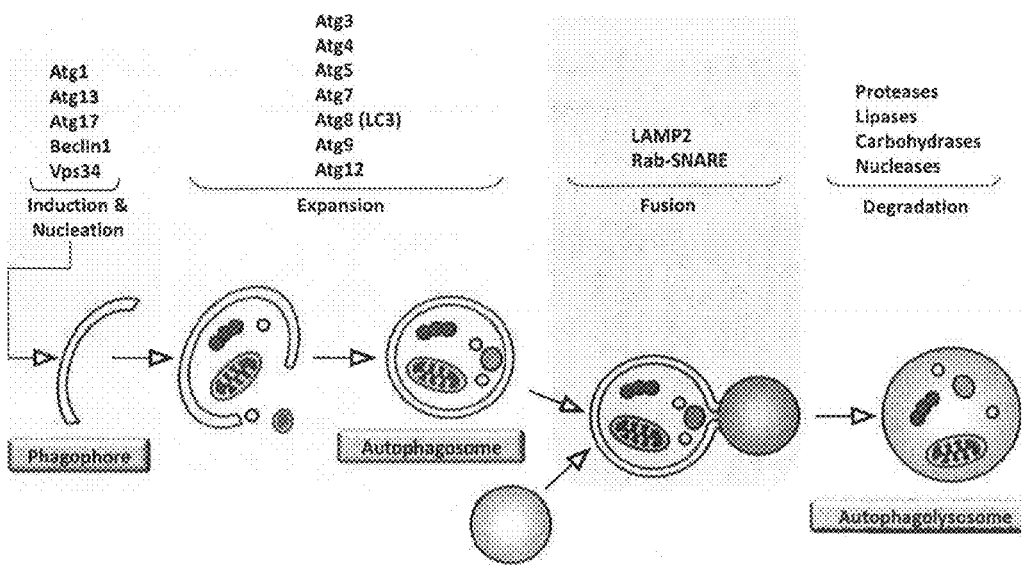
FIG. 1 is a schematic diagram depicting four steps of macroautophagy: induction and nucleation, expansion, fusion, and degradation. Proteins involved in each step are indicated above each step. The role of p62 and LC3 is explained schematically, whereby p62 helps to transport cellular material into the autophagosome by binding to LC3.
Figure 1:
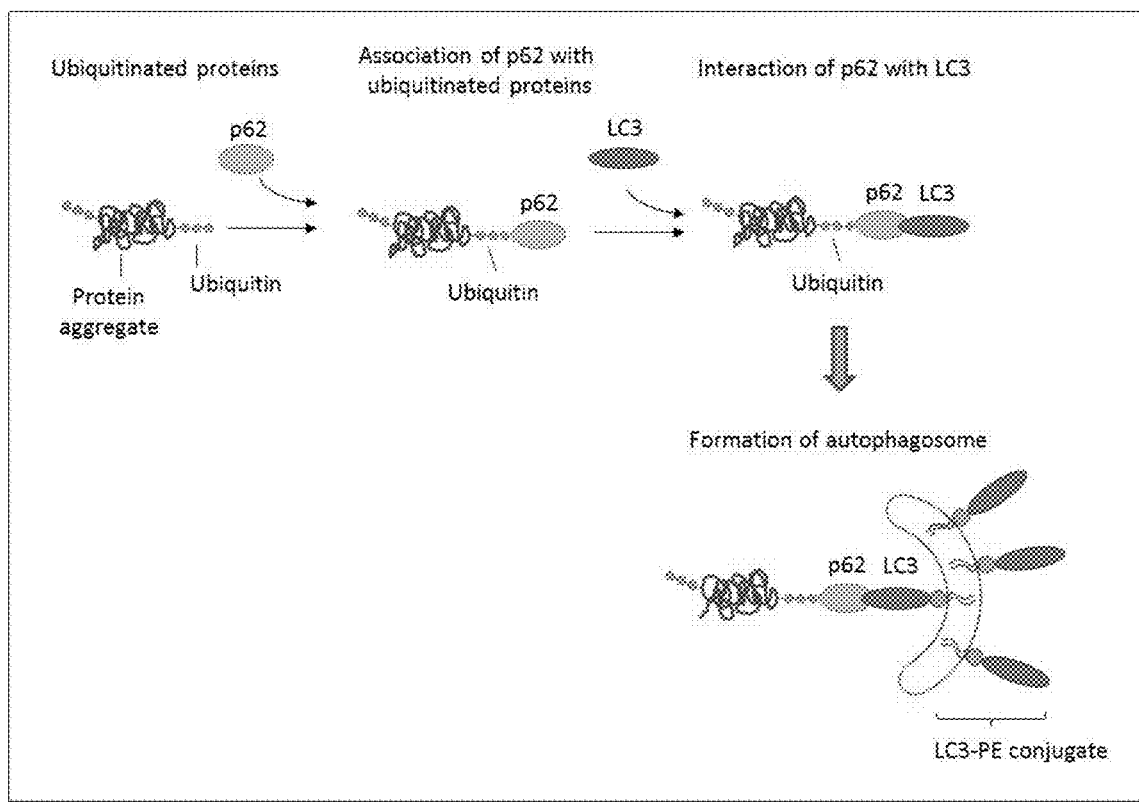

Macroautophagy involves the degradation of long-lived proteins and whole cellular organelles through a multistep process (FIG. 1). Macroautophagy begins with the formation of a double-layered isolation membrane (phagophore) around the molecules and/or organelles to be degraded. The phagophore engulfs cytosolic components and seals around the content, forming an autophagosome. Eventually, the autophagosome fuses with a lysosome, evolving into an autophagolysosome (or autolysosome), wherein lysosomal hydrolases digest the cargo. Microautophagy involves the direct sequestration of cytosolic components through invaginations or armlike projections of the lysosomal membrane. Microautophagy may serve for the turnover of long-lived proteins; however, the significance and regulation of this type of autophagy remain poorly understood. Finally, chaperone-mediated autophagy is a highly selective process devoted to the degradation of soluble cytosolic proteins.

The microtubule-associated protein 1A/1B-light chain 3 (LC3), a mammalian homolog of the yeast Atg8, is a soluble protein with a molecular mass of approximately 17 kDa which is distributed ubiquitously in mammalian tissues and cultured cells. It is processed immediately after its synthesis by Atg4B, a cysteine protease, that exposes the C-terminal glycine residue (LC3-I). During autophagy, autophagosomes engulf cytoplasmic components, including cytosolic proteins and organelles. Concomitantly, a cytosolic form of LC3 (LC3-I) is conjugated to phosphatidylethanolamine (PE) to form and LC3-PE conjugate (LC3-II), which is recruited to autophagosomal membranes (FIG. 1).

p62, also known as sequestosome-1, was identified as a novel partner of the atypical protein kinase Cs (aPKCs) and is a ubiquitously expressed cellular protein. p62 is known to have domains that interact with and bind to ubiquitinated proteins, and it has been identified as a component of inclusion bodies observed in human diseases, especially neurodegenerative diseases (e.g., Alzheimer's disease, Parkinson's disease, amyotrophic lateral sclerosis) as well as in liver diseases. p62 also has been identified as an LC3 interacting protein and it has been demonstrated that an 11 amino acid sequence in the mouse p62 serves to recognize the LC3 protein. As seen in FIG. 1, LC3 binds to p62 and transports it (and any ubiquitinated proteins or cell components bound to it) into the autophagosome, where it is degraded. Consequently, one of the hallmarks of autophagy is an increase in the ratio of LC3-II/LC3-I with a concomitant decrease in the level of cellular p62.

Of the three types of autophagy described, macroautophagy is the best characterized in mammalian cells. Starvation is the strongest stimulus of macroautophagy. During nutrient deprivation, macroautophagy breaks down cellular components, generating amino acids, fatty acids, and carbohydrates, which can be harnessed for energy production and for the synthesis of essential cellular molecules. Macroautophagy is also involved in specific cytosolic rearrangements during embryogenesis and postnatal development. Furthermore, macroautophagy is induced during viral or bacterial infections, in hypoxia, and under various stress conditions, including radiation exposure and increased reactive oxygen species (ROS) generation. In these circumstances, macroautophagy is essential for the maintenance of cell homeostasis by its promotion of the removal of damaged components. Indeed, impairments in macroautophagy induce premature aging and shorten the lifespan in several organisms, including *C. elegans*, yeast, and *Drosophila*. Hars E S et al. (2007) *Autophagy* 3:93-95; Matecic M et al. (2010) *PLoS Genet.* 6:e1000921; Lee J H et al. (2010) *Science* 327:1223-1228. Conversely, upregulation of macroautophagy is proposed to be a major mechanism underlying the lifespan-extending properties of calorie restriction. Toth M L et al. (2008) *Autophagy* 4:330-338; Morselli E et al. (2010) *Cell Death Dis.* 1:e10.

More than 35 Atg (AuTophaGy-related) proteins have been identified in yeasts and mammals; however, the precise role each Atg protein plays during autophagy is not yet fully established. As illustrated in FIG. 1, the process of macroautophagy can be divided into discrete steps, namely, induction and nucleation, expansion, fusion, and degradation. The induction phase is mediated by the ULK1-Atg13-FIP200 kinase complex. The regulation of the nucleation stage, which consists of the recruitment of Atg proteins to the phagophore assembly site, is not yet completely understood. However, the vacuolar protein sorting-34 (Vps34), a class III phosphatidylinositol-3-kinase (PI3K), is required for this step. Vps34 associates with Beclin1, the mammalian homologue of yeast Atg6, and subsequently recruits Atg14 and Vps15 (p150) to the preautophagosomal structure. The elongation and expansion of the phagophore membrane require two ubiquitin-like conjugation systems involving Atg12 (conjugated to Atg5) and Atg8/microtubule-associated protein 1 light chain-3 (LC3, conjugated to phosphatidyl ethanolamine), along with other Atg proteins such as Atg9 and Atg16. The fusion of the autophagosome with a lysosome relies on canonical cellular fusion machinery that consists of the Rab-SNARE (Soluble N-ethylmaleimide-sensitive factor Attachment protein REceptor) system and requires the presence of lysosomal membrane-associated protein-2 (LAMP-2) and the UV radiation resistance-associated gene (UVRAG). Finally, the digestion of the cargo is accomplished by lysosomal hydrolases, followed by the transportation of degraded components into the cytoplasm by lysosomal efflux transporters such as Atg22.

With regard to the regulation of macroautophagy, mTOR, the mammalian target of rapamycin, is considered to be a major checkpoint, linking the cellular nutritional state with the level of ongoing autophagy. Under nutrient-rich conditions, mTOR is active and inhibits the ULK1-Atg13-FIP200 complex required for the induction of macroautophagy. Energy deprivation leads to mTOR inactivation and stimulation of AMP-activated protein kinase (AMPK), which both induce macroautophagy. AMPK functions as an energy-sensing kinase and is activated by increases in the cellular AMP to ATP ratio. Under such circumstances, AMPK promotes autophagy by directly activating ULK1 and by relieving the mTOR-mediated inhibition of macroautophagy.

Macroautophagy can be selectively directed toward the removal of particular targets, e.g., peroxisomes (pexophagy), endoplasmic reticulum (reticulophagy), intracellular lipids (lipophagy), ribosomes (ribophagy), and intracellular pathogens (xenopathy). Likewise, mitochondria can be selectively targeted for degradation via macroautophagy (mitophagy).

Mitophagy: A Specialized Form of Macroautophagy

Mitophagy is a highly selective process that can promote the elimination of dysfunctional or unnecessary mitochondria. Wang K et al. (2011) *Autophagy* 7:297-300. The loss of mitochondrial membrane potential ($\Delta\psi_m$) represents a major trigger of mitophagy. Indeed, laser-induced photo damage of selected mitochondria inside living hepatocytes results in the rapid dissipation of $\Delta\psi_m$, followed by the quick removal of depolarized mitochondria through mitophagy. In addition, oxidative damage can lead to the formation of asymmetrical daughter mitochondria characterized by different $\Delta\psi_m$, with autophagy specifically targeting mitochondria with lower $\Delta\psi_m$. Apart from the degradation of damaged mitochondria under stress conditions, mitophagy is essential for mitochondrial turnover in the basal state and during cell differentiation, such as the maturation of reticulocytes into mature red blood cells.

Investigations into the molecular regulation of mitophagy have unveiled several mitophagy-specific proteins. Parkin and Pink1 are believed to play important roles in the selective degradation of damaged mitochondria, at least under certain circumstances. Parkin is a cytosolic E3-ubiquitin ligase that is selectively recruited to dysfunctional mitochondria and assists in their removal by mitophagy. Narenda D (2008) *J Cell Biol.* 183:795-803. Pink1 is imported into healthy mitochondria through a $\Delta\psi_m$-dependent process and is degraded by the presenilin-associated rhomboidlike (PARL) protease. Matsuda N et al. (2010) *J Cell Biol.* 189:211-221. The dissipation of $\Delta\psi_m$ results in the accumulation of Pink1 on the mitochondrial surface, leading to the recruitment of Parkin, which ubiquitinates outer membrane proteins, including the voltage-dependent anion channel (VDAC). It is proposed that ubiquitin-tagged mitochondria are targeted directly to autophagic vacuoles through the interaction of ubiquitinated proteins with the autophagosomal marker LC3 (Atg8). In addition, Parkin can ubiquitinate the inner mitochondrial membrane and apoptosis regulator protein B-cell lymphoma-2 (Bcl-2), thereby de-repressing Beclin1.

Recent evidence also suggests that the opening of the mitochondrial permeability transition pore (mPTP) may be required for the selective removal of damaged mitochondria. Opening of the mPTP causes a sudden increase of the inner membrane permeability to solutes with molecular weight up to 1500 Da. This results in mitochondrial depolarization, activation of the mitochondrial ATPase (i.e., ATP synthase operating in reverse), and swelling and rupture of the outer membrane. The loss of $\Delta\psi_m$ subsequent to permeability transition targets individual mitochondria for degradation. The loss of $\Delta\psi_m$ and the activation of macroautophagy are prevented by cyclosporin A, an inhibitor of the mPTP component cyclophilin D. Furthermore, starvation fails to induce macroautophagy in cyclophilin D-deficient murine cardiomyocytes, whereas autophagy is enhanced even under fed conditions in cardiac cells from mice overexpressing cyclophilin D. The nicotinamide adenine dinucleotide (NAD)-dependent deacetylase sirtuin-3 (SIRT3) appears to be critically involved in the control of mPTP by modulation of cyclophilin D.

Similar to the mPTP, the apoptotic proteins Bnip3 (Bcl-2 and adenovirus E1B 19-kDa-interacting protein-3) and Nix (Nip3-like protein X) are thought to trigger selective mitophagy through mitochondrial depolarization. Moreover, Bnip3 may induce mitophagy by competitively disrupting the inhibitory interaction between Bcl-2 and Beclin1. Finally, Nix associates with mitochondrial membranes and directly interacts with LC3 (Atg8).

Although the molecular regulation of mitophagy has not yet been completely elucidated, the mTOR/AMPK pathway is proposed to be a major checkpoint. AMPK, in addition to stimulating mitochondrial removal through autophagy, enhances the activity of sirtuin-1 (SIRT1) and its downstream target PGC-1α, resulting in stimulation of mitochondrial biogenesis. Hence, through the activity of AMPK, mitophagy and mitochondrial biogenesis are coordinately regulated, maintaining a healthy and functional pool of mitochondria in the cell.

Lipophagy is a recently recognized alternative pathway of lipid metabolism in which intracellular lipid droplet triglycerides and cholesterol are taken up by autophagosomes and delivered to lysosomes for degradation by acidic hydrolases, thereby releasing free fatty acids. Lipophagy, therefore, functions to regulate intracellular lipid stores, cellular levels of free lipids, such as fatty acids, and energy homeostasis.

Xenophagy is a recently recognized mechanism of defense against various types of intracellular pathogens, including *Mycobacterium tuberculosis, Salmonella typhimurium, Legionella pneumophila, Brucella species, Chlamydia species, Coxiella burnetti, Listeria monocytogenes, Shigella flexneri, Rickettsia* species, *Mycobacterium marinum, Burkholderia species*, and *Francisella tularensis*.

Microautophagy involves lysosomes directly engulfing cytoplasm by invagination, protrusion, or septation of the lysosomal limiting membrane.

Chaperone-Mediated Autophagy

Chaperone-mediated autophagy (CMA) concerns only those proteins that have a consensus peptide sequence that can be recognized by the binding of a hsc70-containing chaperone/co-chaperone complex. The CMA substrate/chaperone complex then moves to the lysosomes, where the CMA receptor lysosome-associated membrane protein type-2a (LAMP-2A) recognizes it. The protein is unfolded and translocated across the lysosome membrane assisted by the lysosomal hsc70 on the other side. Thus, CMA substrates are translocated across the lysosomal membrane on a one-by-one basis, whereas in macroautophagy and microautophagy the substrates are engulfed or sequestered in bulk. Moreover, CMA degrades only certain proteins and not organelles.

Exemplary Therapeutic Indications for Increased Autophagy

Compounds, compositions, and methods of the invention can be used to treat and prevent any of the following therapeutic indications for increased autophagy.

Autophagy Protects Organisms from Metabolic Stress

Nutrient deprivation, growth factor depletion, and hypoxia can induce metabolic stress leading to the induction of autophagy and to the generation of free amino acids and fatty acids. These can be recycled in a cell-autonomous fashion and be used for 1) de novo synthesis of proteins important in the stress response, and 2) fueling the TCA cycle to maintain ATP function. The importance of this process is demonstrated in the inability of mice and *C. elegans* with deficiencies in the ATG proteins important for autophagy to resist starvation. Thus, a critical role for autophagy is the mobilization of intracellular energy resources to meet cellular and organismal demand for metabolic substrates.

Induction of Autophagy for Treatment of the Heart Cardiomyocyte function and survival rely critically on the presence of basal levels of cardiomyocyte autophagy. Autophagic recycling of damaged cellular components in nutrient-rich conditions constitutes a major means of protein and organelle quality control, ridding the cell of defective (e.g., misfolded or oxidized) proteins and dysfunctional organelles. This fact is highlighted by the observation that abrogation of autophagic pathways in adult heart by conditional inactivation of either the Atg5 or Atg7 genes triggers rapid-onset cardiac hypertrophy, left ventricular dilation, and diminished cardiac output.

Danon disease, a condition marked by severe and progressive myopathy, stems from defective fusion of autophagosomes with lysosomes. In early cardiac development, Atg5 disruption provokes in utero defects and embryonic lethality. At the other end of the age spectrum, age-related declines in the efficiency of autophagic clearance likely contribute to progressive accumulation of defective proteins and organelles which ultimately lead to functional deterioration over time. Normal aging is associated with loss of cardiac function mainly due to impaired relaxation during diastole. Varying formulations of caloric restriction (CR) can prolong lifespan and improve LV diastolic function; the underlying mechanisms are believed to be the induction of autophagy. Together, these facts highlight the vital housekeeping role for cardiomyocyte autophagy as a mechanism of protein and organelle surveillance and quality control.

Autophagy Can Improve Skeletal Muscle Function in Setting of Muscular Atrophy Skeletal muscle adapts its capacity to levels of load and utilization. A central aspect of this adaption is the regulation of fiber remodeling through degeneration or regeneration of muscle fibers.

In the absence of muscle activity, muscular atrophy occurs, resulting in decreased muscular capacity. This atrophy has been shown to occur due to increased levels of oxidative stress in disused muscle. Attenuation of this oxidative stress could lead to decreased atrophy.

The autophagy process, and in particular mitophagy are important in clearing damaged mitochondria and reducing the effects of increased oxidative stress on muscle functional capacity. Failure of the autophagy process has been shown to be an important contributing factor to muscle disuse atrophy, by failing to remove damaged mitochondria. This decrease in mitochondria turnover leads to an accumulation of dysfunctional organs and ensuing muscle damage.

Preserving Autophagy Function During Aging can Improve Sarcopenia

Skeletal muscle atrophy and impaired muscle strength represent an important health issue and may occur as a consequence of immobilization, disuse, injury, starvation, and aging. In particular, advanced age is ineluctably accompanied by the loss of muscle mass and strength. This condition, known as sarcopenia of aging, has significant effects on individual health and impacts the severity of frailty. Moreover, poor muscular strength is highly predictive of disability and mortality, and general weakness often results in the loss of independent living, thereby affecting individual quality of life and imposing a high burden on healthcare expenditure. Aside from aging, skeletal muscle can undergo significant atrophy following disuse.

Sarcopenia is characterized by a gradual loss of muscle proteins. The size of stable post-mitotic tissues, such as skeletal and cardiac muscles, is regulated by protein turnover, and skeletal muscle is influenced by a balance between protein synthesis and degradation and the turnover of contractile proteins. A key factor influencing the development of sarcopenia is the imbalance between the rates of protein synthesis and degradation. Protein degradation in skeletal muscle cells is essentially mediated by the activity of two highly conserved pathways: the autophagic lysosomal pathway and the ubiquitin-proteasome pathway.

Recent studies have shown that the impaired autophagy seen in ATG7 null muscles is characterized by muscle atrophy, weakness, and features of myofiber degeneration. Consequently, autophagy has been found to be essential for myofiber maintenance and for the clearance of damaged proteins and altered organelles.

Autophagy, which is activated when skeletal muscle is under nutritional stress (such as metabolic stress), plays a role in the catabolic condition and in the degradation of macromolecules and organelles. Catabolic pathways are accelerated during exercise to supply energy and substrates to the muscle for continuation of contractions. It has been well established that the rates of amino acid (relatively small) and glucose oxidation are increased during endurance exercise, and increased energy consumption is likely required to induce autophagy. It has been shown that autophagy is required for myofiber maintenance and for the clearance of damaged proteins and altered organelles.

Mild exercise has been shown to improve muscle function and decrease the decline in muscle function observed in sarcopenia. These positive benefits are at least in part due to an exercise induced improvement in the autophagy process. In aging mice, the autophagy proteins LC3-II, Beclin-1, ATG7, and MuRF-1 significantly decrease with age in muscle. However, mice undergoing a training regimen during the aging process show a significantly attenuated decrease in these autophagy proteins. In overweight older women, mild exercise has been shown to increase the transcript levels of the autophagy regulators LCB3, Atg7, and LAMP-2 and thus improve the autophagy process. Thus, preservation of autophagy may play an important role in skeletal myocyte homeostasis and optimal mitochondrial turnover in aged muscle.

An age-related attenuation of autophagy has been shown and results in a diminished efficiency of protein degradation and the clearance of damaged organelles. A decrease in proteolytic activity has been considered responsible, at least in part, for the accumulation of damaged cellular components in almost all tissues of aging organisms.

Improving Autophagy as a Therapeutic Target for Muscle Degenerative Diseases

Muscular dystrophies are a group of genetic, hereditary muscle diseases characterized by defects in muscle proteins. These defects result in progressive skeletal muscle damage accompanied by myofiber necrosis and chronic local inflammation, leading to substitution of myofibers by connective and adipose tissue. In Duchenne muscular dystrophy (DMD), the most severe form of these diseases, the continuous and progressive skeletal muscle damage leads to complete paralysis and death of patients, usually by respiratory and/or cardiac failure.

The therapeutic protocols currently in use, based on corticosteroid administration, provide some delay in the progression of the disease, but they are associated with severe side effects. Therapies that substitute corticosteroids or at least may act as corticosteroid-sparing drugs are thus being actively pursued, and biological mechanisms relevant to skeletal muscle homoeostasis are explored, in order to identify new targets.

Autophagy is emerging as an important process that limits muscle damage. Inhibition/alteration of autophagy contributes to myofiber degeneration leading to accumulation of abnormal organelles. Mutations that inactivate Jumpy, a phosphatase that counteracts the activation of VPS34 for autophagosome formation and reduces autophagy, are associated with a centronuclear myopathy. This observation suggests that unbalanced autophagy is pathogenic in muscle degeneration. Likewise, hyperactivation of Akt as a consequence of muscle-specific deletion of the mammalian target of rapamycin (mTOR) leads to inhibition of autophagy and to a muscle phenotype resembling the one observed in muscular dystrophy. The validity of autophagy modulation as a therapeutic strategy has been shown in a mouse model of Ulrich myopathy characterized by defective autophagy and accumulation of dysfunctional organelles. Forced reactivation of autophagy in these animals yielded a beneficial therapeutic response.

In vivo and ex vivo analyses have shown that autophagy is defective in both the human (DMD) and mouse (mdx) muscular dystrophy and that such defect contributes to the pathogenesis of the disease. Muscle biopsies from DMD patients have been shown to have significantly lower levels of LC3 II and significant accumulation of p62, a protein known to be incorporated into autophagosomes and efficiently degraded, with respect to tissues from control, non-affected individuals.

A low protein diet has been shown in mice to lead to a prolonged induction of autophagy. In mice with DMD fed a low protein diet, an induction of autophagy leads to an improvement and management in the disease progression. Significant improvements in muscle function have been observed with an improvement of whole body tension, reduced muscle fibrosis, decreased collagen disposition, reduced accumulation of damaged organelles and reduced apoptosis of muscle fibers.

This demonstrates that induction of autophagy is an important homoeostatic mechanism that is disrupted in dystrophic muscles and indicates that novel therapeutic approaches aimed at reactivating autophagy can serve as a valuable strategy to reduce muscle damage in DMD.

Autophagy Protects the Liver from Oxidative Stress and Disease

During liver diseases such as cancer and cirrhosis, the liver can undergo tissue hypoxia. This process has been shown to induce an autophagy process, which if inhibited resulted in increased apoptosis of liver cells.

In α1-antitrypsin deficiency, the most common genetic cause of human liver disease, there is significant chronic inflammation and eventual carcinogenesis. In this disease, a point mutation occurs in α1-antitrypsin Z (ATZ) leading to improperly folding and accumulation of aggregates. Deletion of ATG5 in hepatic cell lines lead to an accumulation of the mutant ATZ protein, demonstrating the important role for autophagy in reducing the impact of liver disease.

Autophagy is Important in Limiting Ischemic Reperfusion Injury

With advancing age, patients are more likely to acquire primary and secondary hepatic malignancies that are amenable to surgical resection and transplantation. Though the elderly patients may be treated surgically, the aged liver has significantly decreased reparative capacity following ischemia and reperfusion injury associated with these operations.

Ischemic preconditioning is the only promising strategy for improving the outcome of liver surgery, but its beneficial effects are limited to young patients. To date, no therapeutic strategy can suppress the age-dependent ischemia and reperfusion injury.

A reduction in autophagy has been observed in the old cells subjected to a severe stress such as ischemia followed by reperfusion. Studies have shown that by overexpression of autophagy genes in aged livers of mice, autophagy was increased and hepatocyte cell survival was increased after ischemia and reperfusion. Consequently, defective autophagy has been shown to be a causal mechanism for the age-dependent hepatic reperfusion injury and that enhancement of autophagy has been demonstrated to offer therapeutic benefit and reducing age-mediated liver ischemia reperfusion injury.

Autophagy in Intestinal Epithelial Cells as a Therapeutic Target.

The intestinal epithelium interfaces directly with a diverse community of bacteria that includes benign commensals, opportunistic pathogens, and overt pathogens, and consequently is the first line of defense against bacterial invasion of host tissues. One means that the epithelial cells employ to defend themselves includes secreting antimicrobial proteins. Unfortunately, there are some intestinal pathogens, including *Salmonella* tyhpimurium or opportunistically invasive commensal bacteria, such as *Enterococcus faecalis*, which can avoid this first line of defense and enter the epithelial cells.

Autophagy has been shown to be essential for the recognition and degradation of intracellular pathogens, acting as an innate barrier to infection. In cell culture, autophagy has been shown to limit the replication of certain bacterial species.

It has been shown via genetic studies of inflammatory bowel disease (IBD) that autophagy plays an important role in the intestinal immune homeostasis. IBD is a chronic inflammatory disease of the intestine that arises from dysregulated interactions with resident microbiota.

Recently, it has been shown that polymorphisms in genes in the autophagic pathway are linked to Crohn's disease (CD). Crohn's disease is a chronic form of IBD that can affect any part of the gastrointestinal system, but is usually found in the colon or terminal ileum. The average onset is at 27 years of age in humans, and is usually present throughout the normal lifespan of the individual. It is characterized by severe colitis, strictures, and perianal fistulas, typically requiring surgery.

The chronic inflammatory process characteristic of CD requires the intensive interaction between intestinal epithelial cells and immune competent cells. In CD, there is an exaggerated immune response to the intestinal microbiota, characterized by an abnormal increase in Th17 cells, which play a major role in autoimmunity, and a down-regulation of Treg cells important for controlling the immune response.

It has recently been shown that intestinal epithelial cell autophagy is essential for mammalian intestinal defense against invasive bacteria. Autophagy in the epithelial cells protects against the dissemination of invasive bacteria. Following oral infection with the invasive pathogen *Salmonella typhimurium* as well as *Enterococcus faecalis*, mouse epithelial cells activate autophagy as a consequence of exposure to these pathogens. Autophagy was also shown to be critical to limit the extra-intestinal spread of *S. typhimurium*. This indicates that autophagy is a key epithelial cell-autonomous mechanism of antibacterial defense that protects against dissemination of intestinal bacteria.

The present invention provides the know-how to use compounds that include urolithins and their precursors as enhancers of autophagy for the administration to and the treatment of individuals with inflammatory bowel disease (IBD) or Crohn's disease (CD) and in need of increasing the levels of autophagy in their in the epithelial cells of the intestine in order to treat either IBD or CD.

Autophagy is Important in Aging Cardiac Muscle

The effects of autophagy induction on improved outcome for ischemic injury and muscle maintenance makes it especially relevant for cardiac muscle maintenance and protection from injury. Cardiac muscle undergoes progressive decline in mitochondrial function, similar to that observed in skeletal muscle, resulting in an increase in reactive oxygen species, as well as an increase in the accumulation of defective organelles. The clearance of these damaged organelles by autophagy is important for the maintenance of cardiac muscle function. As autophagy decreases with age, promoting autophagy can serve to protect cardiac muscle function.

Cardiac muscle is also strongly exposed to ischemic episodes during cardiac infarcts. The level of cardiac muscle damage that these ischemic episodes produce is strongly dependent on the ability of the cells to mount an effective autophagy response to clear damaged organelles. In aged animals, a defective autophagy response leads to an increase in cardiac muscle damage after ischemic events. Thus, promotion of autophagy during these acute events could serve to protect cardiac muscle from damage.

Autophagy is Important in the Inflammatory Process

Due to the role of autophagy in clearing defective organelles, a defect in this process leads to a buildup of cellular debris and the induction of apoptosis. Autophagy also plays an important role in defending the organism against microbial pathogens by inducing their degradation. Additionally, autophagy plays an important role in the trafficking events that activate innate and adaptive immunity.

The autophagic removal of apoptotic corpses is critical for preventing danger signals that could lead to an inflammation response. In an impaired autophagy response, where apoptotic clearance is not efficient the resulting induction of inflammation, could overcome tolerance to self-antigens leading to autoimmune diseases such as systemic lupus erythematosus. Thus, induction of autophagy could serve to decrease inflammatory responses and the development of autoimmune diseases.

Applications of Autophagy for Treatment of Disorders of the Liver

A number of features of hepatocytes and the liver as a whole make this organ particularly dependent on autophagy. The liver is rather unique in its regenerative properties as while hepatocytes are normally in a quiescent state, they retain the ability to quickly enter the cell cycle when there is a loss of liver tissue due to injury or surgical removal. The lack of cell turnover makes hepatocytes particularly vulnerable to the effects of impaired autophagy, as cells having long lives accumulate high levels of damaged organelles, protein aggregates, etc. that are normally cleared by autophagy. This leads to cellular injury and potentially to transformation.

Hepatocellular Lipid Metabolism

The liver serves as the second largest repository of stored lipids in the body after adipose tissue. Hepatocytes are a major cellular storehouse for neutral lipids in the form of triglycerides (TGs) and cholesterol esters contained in specialized organelles termed lipid droplets (LD). Autophagy mediates the breakdown of intracellular LD stores through the process of lipophagy. This enables the hepatocytes to rapidly mobilize their lipid stores in times of metabolic need. The loss of hepatocyte autophagy leads to a marked increase in hepatic TG and cholesterol content, indicating that lipophagy limits lipid accumulation by the liver in vivo. Also, lipophagy controls cellular energy homeostasis by providing free fatty acids (FFA) from the breakdown of TGs, which subsequently drives mitochondrial 0-oxidation and cellular ATP generation. It has been shown that the autophagosomal protein LC3, critical for autophagosome membrane formation, associates with LDs.

Autophagy Protects Against Hepatic Diseases

SERPINA1/α1-anti-trypsin deficiency (ATD) is the most common genetic cause of human liver disease in children. This disease is caused by homozygosity for the SERPINA1/α1-antitrypsin Z allele SERPINA1-Z, a point mutation, which renders the hepatic secretory glycoprotein SERPINA1 prone to misfolding, polymerization, and aggregation. The mutant SERPINA1-Z protein accumulates in hepatocytes and the levels of SERPINA1 found in the blood and body fluids are reduced to 10-15% of those normally observed. Accumulation of mutant SERPINA1-Z in the endoplasmic reticulum (ER) of hepatocytes leads to liver damage by a gain-of-function. It has been shown that intracellular degradation of SERPINA1-Z aggregates and polymers involves the autophagic pathway.

The drug carbamazepine, known to induce autophagy, was recently shown to be effective in cell based and mouse model of ATD. Carbamazepine increases autophagic degradation of SERPINA1-Z in cultured cells and when provided orally to the PiZ mouse model of ATD, it reduced the hepatic load of SERPINA1-Z. Additionally, inducing autophagy reduced hepatic fibrosis. Consequently, drugs enhancing autophagy are attractive candidates for improving the liver disease that develops in some patients with ATD.

The present invention provides the know-how to use compounds that include urolithins and their precursors as enhancers of autophagy for the treatment of individuals with ATD and in need of increasing the levels of autophagy in their liver and hepatocytes in order to reduce liver toxicity.

Autophagy Protects Against Nonalcoholic Fatty Liver Disease

Nonalcoholic fatty liver disease (NAFLD) is an important component of the metabolic syndrome together with obesity and diabetes. NAFLD encompasses a spectrum of hepatic abnormalities that range from simple fatty liver or steatosis, to fatty liver with hepatocellular injury and inflammation, which is known as nonalcoholic steatohepatitis (NASH). NAFLD is now the most prevalent liver disease in the USA and accounts for about 75% of all chronic liver diseases.

The most important role of autophagy in fatty liver disease could be to regulate the process of excessive lipid accumulation. In fact, mice with a hepatocyte-specific knockout of Atg7, a protein required for autophagy, consuming a high-fat diet led to a marked increase in liver TGs and cholesterol content, showing that autophagy defects can induce hepatic steatosis. When considering NASH, while its exact causes are unknown, free fatty acid (FFA)-induced lipotoxicity has been implicated in the mechanisms of hepatocellular injury of this disease. Evidence points to the fact that hepatocyte autophagy renders the cells more resistant to injury from FFA.

Autophagy is an attractive therapeutic target for the treatment and prevention of both NAFLD and NASH. Therapeutic intervention to increase autophagy may reverse not only the hepatic manifestations of NAFLD, including hepatocellular steatosis and injury, but also some of the underlying metabolic abnormalities of the disease via its effects on insulin resistance. Additionally, treatment by increasing autophagy may prevent common end-stage complications of NAFLD, such as hepatocellular carcinoma.

The present invention provides the know-how to use compounds that include urolithins and their precursors as enhancers of autophagy for the treatment of individuals with NAFLD and in need of increasing the levels of autophagy in their liver and hepatocytes in order to treat these conditions.

Autophagy Protects Against Alcoholic Liver Disease

Alcoholic liver disease (ALD) is a major cause of chronic liver disease, and like NAFLD, has a wide spectrum of pathogenic features, that range from steatosis to sever acute alcoholic hepatitis, fibrosis, cirrhosis, and hepatocellular carcinoma.

Autophagy has been shown to play a role in treating ALD. For example, induction of autophagy by administration of rapamycin significantly suppresses acute alcohol-induced steatosis. Also, a common feature of chronic alcohol abuse is the formation of hepatic protein aggregates known as Mallory-Denk bodies, which are cytosolic inclusion bodies enriched with Krt8/keratin 8 and Krt18 and proteins that include ubiquitin. Rapamycin treatment significantly reduces the number of Mallory-Denk bodies in proteasome inhibitor-treated KRT8 transgenic mice.

Consequently, enhancing hepatic autophagy is an attractive target for improving alcohol-induced liver disease. The present invention provides the know-how to use compounds that include urolithins and their precursors as enhancers of autophagy for the treatment of individuals with ALD and in need of increasing the levels of autophagy in their liver and hepatocytes in order to treat this condition.

Autophagy Protects Against Drug-Induced Liver Injury

Most drugs are metabolized and detoxified in the liver, making the liver the principal target for drug damage. Liver injury due to drugs is a common cause for the withdrawal of approved drugs on the market, and it is thought that drug-induced hepatotoxicity is responsible for more than half of acute cases of liver failure. Acetaminophen, also known as paracetamol and N-acetyl-p-aminophenol (APAP), is a widely used antipyretic and analgesic drug and is also the most common source of severe drug-induced hepatotoxicity. At therapeutic levels APAP is safe, but overdosing leads to toxicity mainly due to its reactive metabolite, N-acetyl-p-benzoquinone imine (NAPQI). NAPQI can deplete hepatic stores of glutathione (GSH), an intracellular antioxidant. Following the depletion of GSH, NAPQI is known to react with cellular proteins as well as mitochondrial proteins to form protein adducts. These APAP-induced mitochondrial protein adducts can then lead to mitochondrial damage and subsequent necrosis.

When autophagy is enhanced with rapamycin, APAP-induced necrosis is significantly inhibited, both in cultured primary hepatocytes and in the livers of mice. Treatment with rapamycin two hours after APAP administration has been seen to significantly improve APAP-induced liver injury, even though APAP metabolism and hepatic GSH depletion have already occurred. This is particularly important as patients at risk for hepatotoxicity from an acute APAP overdose do not receive medical care until they are past the metabolic phase. Consequently, pharmacologic intervention targeting an enhancement of autophagy holds a potential therapeutic benefit for individuals with a risk of APAP hepatotoxicity following an overdose.

The present invention provides the know how-to use compounds that include urolithins and their precursors as enhancers of autophagy for the treatment of individuals at risk of hepatotoxicity due to drug side effects and in need of increasing the levels of autophagy in their liver and hepatocytes in order to treat or prevent the potential drug toxicity.

Autophagy is Important in Limiting Ischemia/Reperfusion Injury

Ischemia/reperfusion (I/R) injury is a causal factor contributing to morbidity and mortality. The vulnerability of the liver to I/R injury is a major obstacle to liver resection and transplantation surgery where reperfusion after sustained ischemia is unavoidable during hepatectomy and vascular reconstruction. Mitochondrial dysfunction is known to be one of the critical downstream events that lead to I/R-mediated cell death.

Autophagy clears abnormal or dysfunctional mitochondria to ensure an optimal cellular function and survival. With impaired or insufficient mitophagy, cells accumulate damaged mitochondria, which subsequently leads to uncontrolled ROS formation, mitochondrial DNA mutation, energetic failure, and ultimately cell death. Consequently, the failure of mitophagy to remove a small number of damaged mitochondria during I/R can have a significant impact on hepatocellular function and viability. Mitophagy is essential for hepatic function and survival following I/R injury.

While minimizing I/R injury plays an important role in the outcome of transplanted young livers, aged livers are even more susceptible to negative impact of I/R injury. In the case of aged livers, hepatocytes fail to respond to the I/R stress and upregulate their endogenous protective autophagy response. Similar to young livers following prolonged ischemia, aged livers after short-term ischemia accumulate dysfunctional mitochondria, undergo mitochondrial permeability transition, and lose their viability soon after reperfusion.

Methods of enhancing autophagy, including pre-ischemia nutrient depletion and over expression of pro-autophagy genes ATG7 or BECN1, lead to the suppression of the mitochondrial permeability transition and increases hepatocyte survival following reperfusion.

This indicates that treatments with agents that induce autophagy in the liver will offer protection during a situation of I/R and help to minimize cellular injury. Such treatments are applicable in situations of the transplantation of both young and aged livers. Treatments may involve: (i) pre-treatments of the liver tissue ex vivo by perfusion of the liver with a solution that contains an inducer of autophagy; (ii) treatment of the liver donor with an autophagy inducer; or (iii) treatment of the liver recipient prior to, during the operation and/or immediately after the surgical intervention. Of course, these treatment modalities may be applied individually or in any combination (for example: 1 and 2; 2 and 3; 1 and 3; 1, 2, and 3).

The present invention provides the know-how to use compounds that include urolithins and their precursors as enhancers of autophagy for the treatment of individuals and their livers, that may be at risk of I/R injury. These compounds may be provided orally or parenterally to the donor or recipient, or provided in a preconditioning solution that may be applied to the resected liver tissue.

Autophagy and Osteoarthritis

Osteoarthritis (OA) is the most common aging-related joint pathology and is characterized by degradation of cartilage extracellular matrix (ECM) and reduced cartilage cellularity. Changes in the articular cartilage appear to be critical in OA initiation and progression. Chondrocytes are the only cell population of adult articular cartilage. The capacity of the adult articular chondrocytes to regenerate the normal cartilage matrix architecture is limited and declines with aging, due to cell death and abnormal responsiveness to anabolic stimuli. Articular cartilage is characterized by a very low rate of cell turnover and it has been shown that autophagy play an important role in chondrocyte cellular function and survival. In fact, autophagy is a constitutively active and protective process for the maintenance of cartilage homeostasis. Studies have shown both in joint aging and OA in humans and in mice that there is a reduction in the expression of autophagy regulators, which was accompanied by an increase in chondrocyte apoptosis. Compromised autophagy is thought to contribute to the development of OA. It has been shown that treatment with the compound rapamycin, a known inducer of autophagy, has been able to increase activation of LC3 in cartilage in an animal model of OA and consequently reduce the severity of articular cartilage degradation. In the present invention, urolithins and their precursors have been shown to increase the levels of autophagy in tissues following oral consumption, making them ideal candidates for the treatment and reduction of the severity of osteoarthritis in young and aging humans and mammals.

Metabolic Syndrome, Diabetes, and Obesity

Compounds and methods of the invention are useful in the treatment and prevention of metabolic syndrome, type 2 diabetes mellitus, and obesity. As used herein, the term "metabolic syndrome" refers to a combination of medical disorders that, when occurring together, increase the risk of developing cardiovascular disease and diabetes. It affects one in five people in the United States and prevalence increases with age. Some studies have shown the prevalence in the United States to be an estimated 25% of the population. In accordance with the International Diabetes Foundation consensus worldwide definition (2006), metabolic syndrome is central obesity plus any two of the following:

Raised triglycerides: >150 mg/dL (1.7 mmol/L), or specific treatment for this lipid abnormality;

Reduced HDL cholesterol: <40 mg/dL (1.03 mmol/L) in males, <50 mg/dL (1.29 mmol/L) in females, or specific treatment for this lipid abnormality;

Raised blood pressure: systolic BP>130 or diastolic BP>85 mm Hg, or treatment of previously diagnosed hypertension; and Raised fasting plasma glucose: (FPG)>100 mg/dL (5.6 mmol/L), or previously diagnosed type 2 diabetes.

Autophagy and Neurodegenerative Diseases

In neurodegenerative diseases, brain tissue accumulates autophagosomes, demonstrating an increase in autophagy, which in model organisms has been shown to have a protective effect. It plays an important role in clearing the misfolded proteins that accumulate as a result of several neurodegenerative diseases. These include proteins that have polyQ repeats as seen as in Huntington's diseases and spinocerebellar ataxia, mutant α-synucleins involved in Parkinson's as well as tau aggregates.

Knockdown of ATG genes important in autophagy in *C. elegans* resulted in increased aggregate formation and toxicity of PolyQ proteins. In Alzheimer's disease the autophagy process is impaired as a result of a defect in autophagosomal maturation that could be an important reason for aggregate accumulation. By contrast, autophagy induction by rapamycin in both *Drosophila* and mouse models of polyQ disease protected these animals from neurotoxicity. These results demonstrate that autophagy induction can have a protective role in neuronal cells against neurodegeneration.

The development of neurodegenerative diseases in patients implies that autophagy can reach a saturation point in which the ability to degrade mutant protein aggregates is exceeded. Thus, promotion of autophagy could help in delaying the onset of neurodegeneration disease.

Cognitive Disorder

Compounds and methods of the invention are useful for treating a cognitive disorder. As used herein, a cognitive disorder refers to any condition that impairs cognitive function. In one embodiment, "cognitive disorder" refers to any one or more of delirium, dementia, learning disorder, attention deficit disorder (ADD), and attention deficit hyperactivity disorder (ADHD). In one embodiment, the cognitive disorder is a learning disorder. In one embodiment, the cognitive disorder is attention deficit disorder (ADD). In one embodiment, the cognitive disorder is attention deficit hyperactivity disorder (ADHD).

Compounds and methods of the invention are useful for improving cognitive function, even in the absence of a cognitive disorder. As used herein, "cognitive function" refers to any mental process that involves symbolic operations, e.g., perception, memory, attention, speech comprehension, speech generation, reading comprehension, creation of imagery, learning, and reasoning. In one embodiment, "cognitive function" refers to any one or more of perception, memory, attention, and reasoning. In one embodiment, "cognitive function" refers to memory.

Methods for measuring cognitive function are well known and can include, for example, individual or battery tests for any aspect of cognitive function. One such test is the Prudhoe Cognitive Function Test. Margallo-Lana et al. (2003) *J Intellect Disability Res.* 47:488-492. Another such test is the Mini Mental State Exam (MMSE), which is designed to assess orientation to time and place, registration, attention and calculation, recall, language use and comprehension, repetition, and complex commands. Folstein et al. (1975) *J Psych Res.* 12:189-198. Other tests useful for measuring cognitive function include the Alzheimer Disease Assessment Scale-Cognitive (ADAS-Cog) (Rosen et al. (1984) *Am J Psychiatry.* 141(11):1356-64) and the Cambridge Neuropsychological Test Automated Battery (CANTAB) (Robbins et al. (1994) *Dementia.* 5(5):266-81). Such tests can be used to assess cognitive function in an objective manner, so that changes in cognitive function, for example in response to treatment in accordance with methods of the invention, can be measured and compared.

Protein Misfolding and Aggregation

These diseases and disorders, which are collectively referred to herein as "amyloid-related diseases", fall into two main categories: (a) those which affect the brain and other parts of the central nervous system; and (b) those which affect other organs or tissues around the body.

Examples of amyloid-related diseases which fall under these two categories are listed in the following two sections; however, many other examples of rare, hereditary amyloid-related diseases are known which are not included here, and additional forms of amyloid-related disease are likely to be discovered in future.

Neurodegenerative Diseases Associated with Amyloidosis

Many different neurodegenerative diseases are associated with the misfolding and aggregation of a specific protein or peptide in a particular part of the brain, or elsewhere in the central nervous system, depending on the specific disease. Examples of such diseases follow.

Various forms of Alzheimer's disease (AD) as well as Down's syndrome, hereditary cerebral hemorrhage with amyloidosis (HCHWA, Dutch type), cerebral amyloid angiopathy, and possibly also mild cognitive impairment and other forms of dementia are associated with the aggregation of a 40/42-residue peptide called β-amyloid, Aβ(1-40) or Aβ(1-42), which forms insoluble amyloid fibers and plaques in the cerebral cortex, hippocampus or elsewhere in the brain, depending on the specific disease. Alzheimer's disease is also associated with the formation of neurofibrillary tangles by aggregation of a hyperphosphorylated protein called tau, which also occurs in frontotemporal dementia (Pick's disease).

Parkinson's disease (PD), dementia with Lewy bodies (DLB), and multiple system atrophy (MSA) are associated with the aggregation of a protein called α-synuclein, which results in the formation of insoluble inclusions called Lewy bodies. Huntington's disease (HD), spinal and bulbar muscular atrophy (SBMA, also known as Kennedy's disease), dentatorubral pallidoluysian atrophy (DRPLA), different forms of spinocerebellar ataxia (SCA, types 1, 2, 3, 6 and 7), and possibly several other inheritable neurodegenerative diseases are associated with the aggregation of various proteins and peptides that contain abnormally expanded glutamine repeats (extended tracts of polyglutamine). Creutzfeldt-Jakob disease (CJD), bovine spongiform encephalopathy (BSE) in cows, scrapie in sheep, kuru, Gerstmann-Straussler-Scheinker disease (GSS), fatal familial insomnia, and possibly all other forms of transmissible encephalopathy are associated with the self-propagating misfolding and aggregation of prion proteins.

Amyotrophic lateral sclerosis (ALS), and possibly also some other forms of motor neuron disease (MND) are associated with the aggregation of a protein called superoxide dismutase.

Familial British dementia (FBD) and familial Danish dementia (FDD), respectively, are associated with aggregation of the ABri and ADan peptide sequences derived from the BRI protein.

Hereditary cerebral hemorrhage with amyloidosis (HCHWA, Icelandic type) is associated with the aggregation of a protein called cystatin C.

Systemic Diseases Associated with Amyloidosis

In addition to the neurodegenerative diseases listed above, a wide variety of systemic ageing-related or degenerative diseases are associated with the misfolding and aggregation of a particular protein or peptide in various other tissues around the body (i.e., outside of the brain). Examples of such diseases follow.

Type II diabetes mellitus (also known as adult-onset diabetes, or non-insulin dependent diabetes mellitus) is associated with the aggregation of a 37-residue peptide called the islet amyloid polypeptide (IAPP, or "amylin"), which forms insoluble deposits that are associated with the progressive destruction of insulin-producing β cells in the islets of Langerhans within the pancreas.

Dialysis-related amyloidosis (DRA) and prostatic amyloid are associated with the aggregation of a protein called $\beta_2$-microglobulin, either in bones, joints and tendons in DRA, which develops during prolonged periods of hemodialysis, or within the prostate in the case of prostatic amyloid.

Primary systemic amyloidosis, systemic AL amyloidosis and myeloma-associated amyloidosis are associated with the aggregation of immunoglobulin light chain (or in some cases immunoglobulin heavy chain) into insoluble amyloid deposits, which gradually accumulate in various major organs such as the liver, kidneys, heart and gastrointestinal (GI) tract.

Reactive systemic AA amyloidosis, secondary systemic amyloidosis, familial Mediterranean fever, and chronic inflammatory disease are associated with the aggregation of serum amyloid A protein, which forms insoluble amyloid deposits that accumulate in major organs such as the liver, kidneys and splee. Senile systemic amyloidosis (SSA), familial amyloid polyneuropathy (FAP) and familial amyloid cardiomyopathy (FAC) are associated with the misfolding and aggregation of different mutants of transthyretin protein (TTR), which form insoluble inclusions in various organs and tissues such as the heart (especially in FAC), peripheral nerves (especially in FAP) and gastrointestinal (GI) tract. Another form of familial amyloid polyneuropathy (FAP, type II) is associated with the aggregation of apolipoprotein AI in the peripheral nerves. Familial visceral amyloidosis and hereditary non-neuropathic systemic amyloidosis are associated with misfolding and aggregation of various mutants of lysozyme, which form insoluble deposits in major organs such as the liver, kidneys and spleen.

Finnish hereditary systemic amyloidosis is associated with aggregation of a protein called gelsolin in the eyes (particularly in the cornea).

Fibrinogen α-chain amyloidosis is associated with aggregation of the fibrinogen A β-chain, which forms insoluble amyloid deposits in various organs, such as the liver and kidneys.

Insulin-related amyloidosis occurs by the aggregation of insulin at the site of injection in diabetics.

Medullary carcinoma of the thyroid is associated with the aggregation of calcitonin in surrounding tissues.

Isolated atrial amyloidosis is associated with the aggregation of atrial natriuretic peptide (ANP) in the heart.

Various forms of cataract are associated with the aggregation of γ-crystallin proteins in the lens of the eyes.

Autophagy and Endothelial Cell Function and Associated Diseases

Endothelial Cell Dysfunction

Global endothelial cell dysfunction occurs in several diverse diseases such as diabetes, hypertension, chronic kidney disease, and atherosclerosis. In these diseases endothelial cell dysfunction is thought to occur as a result of stress-induced premature senescence (SIPS). SIPS is characterized by subverted autophagy and lysosomal dysfunction, with the accumulation of autolysosomal vacuoles.

Endothelial cell dysfunction also occurs as a result of aging with an increased incidence of cardiovascular diseases. This increase in cell dysfunction correlates with a decrease in autophagy. In older humans, expression of autophagy markers in arterial endothelial cells was impaired by 50% ($P<0.05$) and was associated with a 30% ($P<0.05$) reduction in arterial endothelium-dependent dilatation (EDD). Similarly, in C57BL/6 control mice aging was associated with a 40% decrease ($P<0.05$) in arterial markers of autophagy and a 25% reduction ($P<0.05$) in EDD, demonstrating that impaired autophagy is a cause of age-related arterial dysfunction.

In old mice, treatment with the autophagy-enhancing agent trehalose restored expression of autophagy markers, rescued NO-mediated EDD by reducing oxidative stress, and normalized inflammatory cytokine expression. The present invention provides the know-how to use compounds that include urolithins and their precursors as enhancers of autophagy for the treatment of individuals having health conditions linked to endothelial cell dysfunction and in need thereof.

Endothelial Cell Injury

Endothelial cell injury can occur as a result of disease processes such as sickle cell anemia or thalassemia in which pathologically high levels of heme and iron release can occur. Severe skeletal muscle damage, as well as cardiac ischemia injury results in the release of the heme protein, myoglobin, which also results in endothelial cell injury. This damage to the vascular endothelial cells can lead to vascular dysfunction and an increase in cardiovascular complications. Endothelial cell injury caused by heme toxicity is associated with a progressive decrease in endothelial cell mitochondrial membrane potential, leading to apoptosis.

Micro- and macro-vascular complications are commonly seen in diabetic patients, and endothelial dysfunction contributes to the development and progression of the complications. Abnormal functions in endothelial cells lead to the increase in vascular tension and atherosclerosis, followed by systemic hypertension as well as increased incidence of ischemia and stroke in diabetic patients. Mitochondrial dysfunction appears to be central to the vascular endothelial dysfunction. Enhanced mitochondrial fission and/or attenuated fusion leads to mitochondrial fragmentation and disruption of the endothelial physiological function. Abnormal mitochondrial biogenesis and disturbance of mitochondrial autophagy increase the accumulation of damaged mitochondria, such as irreversibly depolarized or leaky mitochondria, and facilitate cell death. Augmented mitochondrial ROS production and $Ca^{2+}$ overload in mitochondria not only cause the maladaptive effect on the endothelial function, but also are potentially detrimental to cell survival.

Endothelial cell injury can also result from cardiac procedures such as angioplasty, bypass surgery, and valve replacement. Upregulation of autophagy should lead to a reduction in the injury to the associated endothelial cells.

Strategies that increase autophagy would have clear therapeutic potential. The present invention provides the know-how to use compounds that include urolithins and their precursors as enhancers of autophagy for the treatment of individuals having health conditions linked to endothelial cell injury resulting from disease processes such as diabetes, sickle cell anemia, or thalassemia, as well as protecting endothelial cells from the more acute effects of severe muscle injury.

Autophagy and Cancer

Autophagy and cancer have similar regulatory pathways, with several tumor suppression genes such as PTEN, TSC1 and TSC2 leading to the upstream inhibition of TOR signaling, leading to the stimulation of autophagy. Additionally, the autophagy protein, Beclin1 has been identified as a tumor suppressor deleted in many human cancers. These results demonstrate that autophagy plays an important role in tumor suppression.

Aging

By far the greatest risk factor for neurodegenerative diseases, such as Alzheimer's disease (AD), Parkinson's disease (PD), and amyotrophic lateral sclerosis (ALS), is aging. Mitochondria have been thought to contribute to aging through the accumulation of mitochondrial DNA (mtDNA) mutations and net production of reactive oxygen species (ROS). Although most mitochondrial proteins are encoded by the nuclear genome, mitochondria contain many copies of their own DNA. Human mtDNA is a circular molecule of 16,569 base pairs that encodes 13 polypeptide components of the respiratory chain, as well as the rRNAs and tRNAs necessary to support intramitochondrial protein synthesis using its own genetic code. Inherited mutations in mtDNA are known to cause a variety of diseases, most of which affect the brain and muscles—tissues with high energy requirements. It has been hypothesized that somatic mtDNA mutations acquired during aging contribute to the physiological decline that occurs with aging and aging-related neurodegeneration. It is well established that mtDNA accumulates mutations with aging, especially large-scale deletions and point mutations. In the mtDNA control region, point mutations at specific sites can accumulate to high levels in certain tissues: T414G in cultured fibroblasts, A189G and T408A in muscle, and C150T in white blood cells. However, these control-region "hot spots" have not been observed in the brain. Point mutations at individual nucleotides seem to occur at low levels in the brain, although the overall level may be high. Using a polymerase chain reaction (PCR)-cloning-sequencing strategy, it was found that the average level of point mutations in two protein-coding regions of brain mtDNA from elderly subjects was ~2 mutations per 10 kb. Noncoding regions, which may be under less selection pressure, potentially accumulate between twice and four times as many. The accumulation of these deletions and point mutations with aging correlates with decline in mitochondrial function. For example, a negative correlation has been found between brain cytochrome oxidase activity and increased point-mutation levels in a cytochrome oxidase gene (CO1).

Net production of ROS is another important mechanism by which mitochondria are thought to contribute to aging. Mitochondria contain multiple electron carriers capable of producing ROS, as well as an extensive network of antioxidant defenses. Mitochondrial insults, including oxidative damage itself, can cause an imbalance between ROS production and removal, resulting in net ROS production. The importance to aging of net mitochondrial ROS production is supported by observations that enhancing mitochondrial antioxidant defenses can increase longevity. In *Drosophila*, overexpression of the mitochondrial antioxidant enzymes manganese superoxide dismutase (MnSOD) and methionine sulfoxide reductase prolongs lifespan. This strategy is most successful in short-lived strains of *Drosophila*, and has no effect in already long-lived strains. However, it has recently been shown that overexpression of catalase experimentally targeted to mitochondria increased lifespan in an already long-lived mouse strain.

Improving Activity During Aging

Activity in animals is driven largely by circadian rhythm and is synchronized to the environment. Disruption of the circadian rhythm or a desynchronization with the environment can lead to increase in nighttime wakefulness or daytime naps.

Normal aging is accompanied by declining locomotor activity, altered circadian rhythms, as well as altered sleep and food intake patterns. These effects lead to a decrease in alertness and vigilance decreases in the elderly, leading to an increase in nighttime wakefulness, as well as an increase in daytime naps. Activity patterns can also be disrupted in a similar way by disease, such as Alzheimer's Disease.

Age-dependent changes in activity rhythms are also observed in other animals, for example, rats, hamsters, mice and dogs, with an increase in fragmentation and a decrease in synchronization with the environment. These age-dependent circadian disruptions have been linked to the degeneration of the suprachiasmatic nucleus of the hypothalamus. Sleep disruption in both humans and rodents have been shown to contribute to age-dependent cognitive dysfunction.

The increasing disruption of circadian rhythms is accompanied by a gradual decline in motor activity with age in several species, including humans, mice, monkeys, and dogs. Of particular note, the daytime activity of senior dogs (>10 years of age) declines as compared to young and middle-aged dogs. These changes in activity can be monitored by devices intended to measure activity, for example, by means of an accelerometer or by employing motion sensing cameras.

Many of the disruptions seen in aging as a result of decreased activity are also observed in younger populations where cultural trends have resulted in decreased activity, accompanied with increased caloric intake, leading to an obesity epidemic. The resulting caloric imbalance has led to an increase in several disease conditions such as type 2 diabetes, colon cancer, and metabolic syndrome, as well as mental health issues. Several prospective cohort studies and meta-analysis in humans have shown that physical inactivity is associated with an elevated risk for the development of metabolic syndrome, type 2 diabetes, hypertension, coronary artery disease, stroke, and cardiovascular disease.

Both humans and animals, particularly dogs, would benefit from the present invention and its ability to improve activity both during the youth and aging periods of life.

In one embodiment, the urolithin or precursor would increase activity of the recipient, human or animal. In yet another embodiment, the increase in activity is an increase by 1% to 100%. For example, the activity may be increased by 1%, 2%, 3%, 4%, 5%, 6%, 7%, 8%, 9%, or 10%. In certain embodiments, the increase in activity is an increase of 5-10%, 10-15%, 15-20%, 20-25%, 25-30%, 30-35%, 35-40%, 40-45%, 45-50%, 50-55%, 55-60%, 60-65%, 65-70%, 70-75%, 75-80%, 80-85%, 85-90%, 90-95%, and 95-100%.

In one embodiment, treatment by urolithin or a precursor thereof would increase activity and lead to a reduction in risk of metabolic syndrome. In one embodiment, treatment by urolithin or a precursor thereof would increase activity and lead to a reduction in risk of type 2 diabetes. In one embodiment, treatment by urolithin or a precursor thereof would increase activity and lead to a reduction in risk of hypertension, coronary artery disease, stroke, and cardiovascular disease. In one embodiment, treatment by urolithin or a precursor thereof would increase activity and improve cognitive function.

Mood Disorders

Compounds and methods of the invention are useful for treating a mood disorder (also known as an affective disorder). As used herein, a "mood disorder" refers to a disturbance in emotional state, such as is set forth in the Diagnostic and Statistical Manual of Mental Disorders, published by the American Psychiatric Association. Mood disorders include but are not limited to major depression, postpartum depression, dysthymia, and bipolar disorder. In one embodiment, the mood disorder is major depression.

Compounds and methods of the invention are useful for treating or preventing a stress-induced or stress-related mood disorder. As used herein, a "stress-induced or stress-related mood disorder" refers to a disturbance in emotional state that is induced or related to stress. Such mood disorders are sometimes referred to as reactive mood disorders and are to be distinguished from other mood disorders, e.g., so-called organic mood disorders.

Compounds and methods of the invention are useful for treating an anxiety disorder. As used herein, an "anxiety disorder" refers to a dysfunctional state of fear and anxiety, e.g., fear and anxiety that is out of proportion to a stressful situation or the anticipation of a stressful situation. In one embodiment, an anxiety disorder is any one or combination of generalized anxiety disorder, panic disorder, panic disorder with agoraphobia, agoraphobia, social anxiety disorder, obsessive-compulsive disorder, and post-traumatic stress disorder. In one embodiment, an anxiety disorder is any one or combination of generalized anxiety disorder, obsessive-compulsive disorder, panic disorder, post-traumatic stress disorder, and social anxiety disorder. In one embodiment, an anxiety disorder is generalized stress disorder. In one embodiment, an anxiety disorder is post-traumatic stress disorder. In one embodiment, an anxiety disorder is a stress-induced anxiety disorder.

Compounds and methods of the invention are useful for treating or preventing a stress-induced or stress-related anxiety disorder. As used herein, a "stress-induced or stress-related anxiety disorder" refers to a dysfunctional state of fear and anxiety that is induced or related to stress. Such anxiety disorders are sometimes referred to as reactive anxiety disorders and are to be distinguished from other anxiety disorders, e.g., so-called organic anxiety disorders.

For purposes of this invention, each of the foregoing diseases or conditions is associated with, or characterized by, reduced or decreased autophagy, or would benefit from increased autophagy, and therefore would benefit from the administration of urolithins and their precursors.

Table 1 summarizes some of the types of cells affected by autophagy and the beneficial effects of autophagy in those cells.

TABLE 1

Health Benefits of Increased Autophagy

| Cell Type | Condition Improved by Autophagy |
|---|---|
| All cells | Maintenance of the amino acid pool during starvation |
| | Anti-aging |
| | Tumor suppression |
| | Clearance of intracellular microbes |
| | Clearance of protein aggregates |
| Neurons | Prevention of neurodegeneration |
| | Alleviation of symptoms related to neurodegeneration |
| | Clearance of protein aggregates |
| Acinar cells of the pancreas | Improved outcome in acute pancreatitis |
| Smooth muscle cells | Improved outcome in various heart conditions such as heart disease, cardiac hypertrophy, left ventricular dilation, Danon disease |
| | Amelioration of cardiomyopathy resulting from diabetes |
| | Preventing cardiac deterioration with age |
| | Improvement outcome from ischemia/reperfusion injury |
| | Protection of cells from ischemia and hypoxic conditions resulting from myocardial function |
| | Improved cardiac output |
| | Improved left ventricular diastolic function |
| | Improvement in blood pressure |
| | Protection of cells during cardiac procedures such as angioplasty, bypass, valve replacement |
| Intestinal epithelial cells | Improvement of immune response to intracellular bacteria; Crohn's disease; inflammatory bowel disease (IBD) |
| Podocytes in kidney | Podocyte resistance to injury, which can be caused by the following diseases: minimal change disease, focal segmental glomerulosclerosis, diabetic nephropathy, membrane glomerulopathy, lupus nephritis, and experimental glomerular disease |
| Skeletal muscle cells | Protection against glucose intolerance, leptin resistance, high cholesterol and triglycerides in high fat diets |
| | Improved muscle function |
| | Reduction in sarcopenia |
| | Improved balance and coordination |
| | Improvement in muscle strength |
| | Increase in muscle mass |
| | Reduction in muscle atrophy |
| | Improvement in muscle endurance |
| | Improved outcome for muscular dystrophy |
| | Improvement in muscle recovery following exercise |
| | Protection against muscle damage |
| Liver tissue | Clearance of mutant alpha-antitrypsin |
| | Improved outcome in nonalcoholic fatty liver disease (NAFLD), non-alcoholic steatohepatitis (NASH), and alcoholic liver disease (ALD) |
| Liver hepatocyte | Protection against glucose intolerance, leptin resistance, high cholesterol and triglycerides in high fat diets |
| | Treatment of obesity and type II diabetes |
| | Improvement outcome from ischemia/reperfusion injury |
| | Protection against drug induced liver injury |
| | Protection of liver tissue |
| Pancreatic beta cells | Protection against glucose intolerance, leptin resistance, high cholesterol and triglycerides in high fat diets |
| Adipocytes | Protection against glucose intolerance, leptin resistance, high cholesterol and triglycerides in high fat diets |
| | Treatment of obesity and type II diabetes |

TABLE 1-continued

Health Benefits of Increased Autophagy

| Cell Type | Condition Improved by Autophagy |
|---|---|
| Endothelial cells | Improves endothelial cell dysfunction which can occur as a result of diabetes, hypertension, chronic kidney disease, atherosclerosis and aging |
| | Protects against endothelial cell injury resulting from disease processes such as, diabetes, sickle cell anemia or thalassemia, as well as from severe muscle injury. |
| | Protection of cells from ischemia and hypoxic conditions resulting from myocardial function |
| | Improved angiogenesis |
| | Protection of cells during cardiac procedures such as angioplasty, bypass, valve replacement |
| Chondrocytes/cartilage | Reduction in osteoarthritis in joints |
| Osteoblasts | Improvement of tissue mineral density |
| | Increased bone strength |
| Lens epithelial cells | Reduction in age-related cataracts |
| Retinal cells | Reduction in age related macular degeneration |
| Ganglion cell layer | Protection from diabetic retinopathy |
| Inner nuclear layer | |
| Outer nuclear layer | |
| Retinal pigment epithelial cells | |
| Retinal photoreceptors | Improved outcome from intraocular inflammation or uveitis |
| | Reduction in photoreceptor injury from uveitis |
| Glaucomatous tissue | Reduction in glaucomatous neurodegeneration |
| Keratinocytes | Treatment of intracellular skin infections, warts, psoriasis |
| | Protection of skin from environmental insults i.e. UV light, anti-aging |
| | Reduction of skin injury from excessive lipid oxidation commonly observed in aged and diseased skin |
| Lung cells | Clearance of protein aggregates in pulmonary cells |
| | Improved outcome from pulmonary emphysema cause by al-antrypsin |
| | Chronic obstructive pulmonary disorder |
| Alveolar macrophages | Improved outcome for chronic obstructive pulmonary disease |
| Airway epithelial cells | Reduction in protein aggregates in cystic fibrosis |
| | Improved clearance of aggresomes that accumulate mutant cystic fibrosis transmembrane conductance regulator (CFTR) protein |
| | Improved outcome for human idiopathic pulmonary fibrosis |
| Immune cells | Reduction of auto-immune disorders |
| | Improved immune response to infection from pathogens |

Exemplary Compounds of the Invention

Compounds of the invention include certain urolithins and precursors thereof. These compounds can be used to practice any of the methods herein, including but not limited to increasing autophagy or longevity, and for the treatment or prevention of the various diseases and conditions described herein.

In certain embodiments, the invention relates to urolithins. As used herein, a "urolithin" refers to a compound of Formula I:

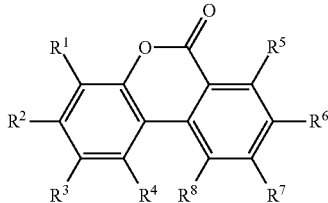

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

As used herein, the term "alkyl" refers to a straight chain or branched, noncyclic or cyclic, unsaturated or saturated aliphatic hydrocarbon radical containing carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

As used herein, the term "aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

As used herein, the term "monosaccharide" refers to a simple sugar of the formula $(CH_2O)_n$. The monosaccharides can be straight-chain or ring systems, and can include a saccharose unit of the formula —CH(OH)—C(=O)—. Examples of monosaccharides include erythrose, threose, ribose, arabinose, xylose, lyxose, allose, altrose, glucose, mannose, gulose, idose, galactose, talose, erythrulose, ribulose, xyulose, psicose, fructose, sorbose, tagatose, erythropentulose, threopentulose, glycerotetrulose, glucopyranose, fructofuranose. In certain embodiments, monosaccharide refers to glucopyranose.

As used herein, the term "oligosaccharide" refers to saccharide consisting of at least two, up to 10 glycosidically linked monosaccharide units, preferably of 2 to 8 monosaccharide units, more preferably of 2 to 7 monosaccharide units, and even more preferably of 2 to 6 monosaccharide units or of 2 to 5 monosaccharide units.

The term "substituted" as used herein (for example, in the context of a substituted heterocyclyl or substituted aryl) means that at least one hydrogen atom is replaced with a substituent. "Substituents" within the context of this invention include halogen, hydroxy, oxo, cyano, nitro, imino, thioxo, amino, alkylamino, dialkylamino, alkyl, alkoxy, alkylthio, haloalkyl, aryl, aralkyl, heteroaryl, heteroarylalkyl, heterocycle and heterocyclealkyl, as well as —$NR_aR_b$, —$NR_aC(=O)R_b$, —$NR_aC(=O)NR_aNR_b$, —$NR_aC(=O)OR_b$—$NR_aSO_2R_b$, —$C(=O)R_a$, —$C(=O)OR_a$, —$C(=O)NR_aR_b$, —$OC(=O)NR_aR_b$, —$OR_a$, —$SR_a$, —$SOR_a$, —$S(=O)_2R_a$, —$OS(=O)_2R_a$, —$S(=O)_2OR_a$, =$NSO_2R_a$ and —$SO_2NR_aR_b$. In the foregoing, $R_a$ and $R_b$ in this context may be the same or different and independently hydrogen, alkyl, haloalkyl, cycloalkyl, aryl, aralkyl, heterocyclyl. In addition, the foregoing substituents may be further substituted with one or more of the above substituents.

Figure 2:
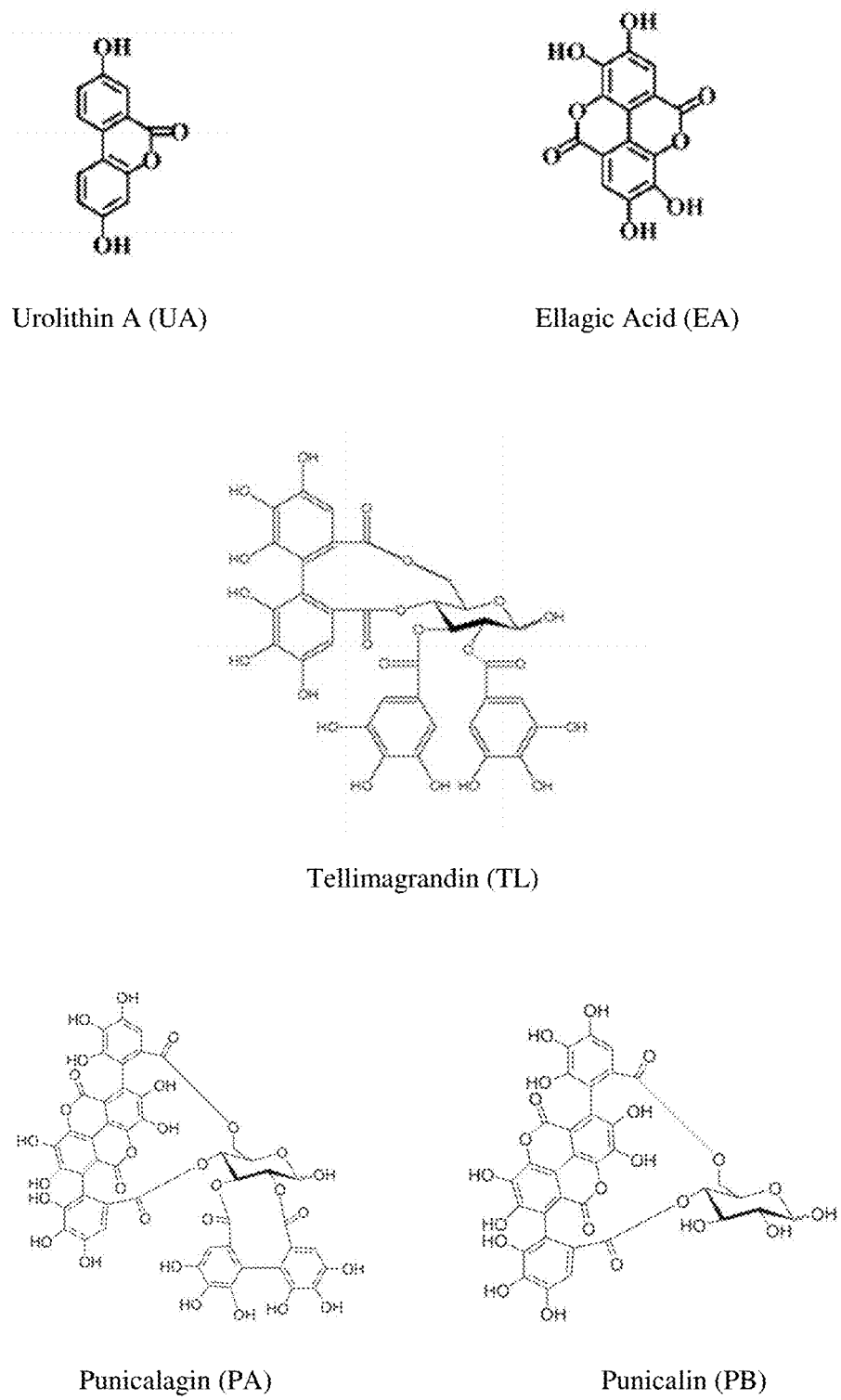
FIG. 2 depicts structural formulas for urolithin A (UA), ellagic acid (EA), tellimagrandin (TL), punicalagin (PA), and punicalin (PB).

In one embodiment, the urolithin is urolithin A.
In one embodiment, the urolithin is urolithin B.
In one embodiment, the urolithin is urolithin C.
In one embodiment, the urolithin is urolithin D.
In one embodiment, a "urolithin" refers to any one or combination of urolithin A, urolithin B, urolithin C, and urolithin D (see, for example, FIG. 2 and FIG. 3). In one embodiment, a urolithin is urolithin A, urolithin B, urolithin C, urolithin D, or any combination of urolithin A, urolithin B, urolithin C, and urolithin D. In one embodiment, a urolithin is urolithin A, urolithin B, urolithin C, or any combination of urolithin A, urolithin B, and urolithin C. In one embodiment, a urolithin is urolithin A, urolithin B, or a combination of urolithin A and urolithin B. In one embodiment, a urolithin is urolithin A.

In one embodiment, a urolithin is provided as an isolated urolithin, e.g., isolated from a natural source or prepared by total synthesis. Isolated urolithins may be synthesized de novo. See Examples 1-4.

In one embodiment, a urolithin is provided as a purified urolithin.

In one embodiment, a "urolithin" as used herein is or can include a glucuronated, methylated, or sulfated urolithin.

In certain embodiments, the invention relates to a compound of Formula II

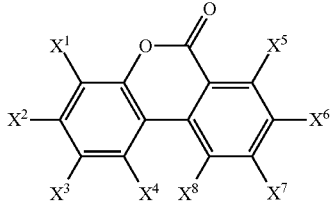

Formula II wherein
$X^1$, $X^2$, $X^3$, $X^4$, $X^5$, $X^6$, $X^7$, and $X^8$ are independently selected from the group consisting of H and OH;
with the proviso that the compound is not a compound of Formula II wherein
$X^1$, $X^2$, $X^3$, $X^4$, $X^5$, $X^6$, $X^7$, and $X^8$ are H;
$X^1$ is OH, and $X^2$, $X^3$, $X^4$, $X^5$, $X^6$, $X^7$, and $X^8$ are H;
$X^2$ is OH, and $X^1$, $X^3$, $X^4$, $X^5$, $X^6$, $X^7$, and $X^8$ are H (urolithin B);
$X^3$ is OH, and $X^1$, $X^2$, $X^4$, $X^5$, $X^6$, $X^7$, and $X^8$ are H;
$X^4$ is OH, and $X^1$, $X^2$, $X^3$, $X^5$, $X^6$, $X^7$, and $X^8$ are H;
$X^5$ is OH, and $X^1$, $X^2$, $X^3$, $X^4$, $X^6$, $X^7$, and $X^8$ are H;
$X^6$ is OH, and $X^1$, $X^2$, $X^3$, $X^4$, $X^5$, $X^7$, and $X^8$ are H;
$X^7$ is OH, and $X^1$, $X^2$, $X^3$, $X^4$, $X^5$, $X^6$, and $X^8$ are H;
$X^8$ is OH, and $X^1$, $X^2$, $X^3$, $X^4$, $X^5$, $X^6$, and $X^7$ are H;
$X^1$ and $X^2$ are OH, and $X^3$, $X^4$, $X^5$, $X^6$, $X^7$, and $X^8$ are H;
$X^1$ and $X^5$ are OH, and $X^2$, $X^3$, $X^4$, $X^6$, $X^7$, and $X^8$ are H;
$X^1$ and $X^7$ are OH, and $X^2$, $X^3$, $X^4$, $X^5$, $X^6$, and $X^8$ are H;
$X^1$ and $X^8$ are OH, and $X^2$, $X^3$, $X^4$, $X^5$, $X^6$, and $X^7$ are H;
$X^2$ and $X^3$ are OH, and $X^1$, $X^4$, $X^5$, $X^6$, $X^7$, and $X^8$ are H;
$X^2$ and $X^4$ are OH, and $X^1$, $X^3$, $X^5$, $X^6$, $X^7$, and $X^8$ are H;
$X^2$ and $X^5$ are OH, and $X^1$, $X^3$, $X^4$, $X^6$, $X^7$, and $X^8$ are H;
$X^2$ and $X^6$ are OH, and $X^1$, $X^3$, $X^4$, $X^5$, $X^7$, and $X^8$ are H (urolithin A);
$X^2$ and $X^7$ are OH, and $X^1$, $X^3$, $X^4$, $X^5$, $X^6$, and $X^8$ are H;
$X^3$ and $X^4$ are OH, and $X^1$, $X^2$, $X^5$, $X^6$, $X^7$, and $X^8$ are H;
$X^3$ and $X^5$ are OH, and $X^1$, $X^2$, $X^4$, $X^6$, $X^7$, and $X^8$ are H;
$X^3$ and $X^6$ are OH, and $X^1$, $X^2$, $X^4$, $X^5$, $X^7$, and $X^8$ are H;
$X^5$ and $X^6$ are OH, and $X^1$, $X^2$, $X^3$, $X^4$, $X^7$, and $X^8$ are H;
$X^5$ and $X^8$ are OH, and $X^1$, $X^2$, $X^3$, $X^4$, $X^6$, and $X^7$ are H;
$X^6$ and $X^7$ are OH, and $X^1$, $X^2$, $X^3$, $X^4$, $X^5$, and $X^8$ are H;
$X^1$, $X^2$, and $X^5$ are OH, and $X^3$, $X^4$, $X^6$, $X^7$, and $X^8$ are H;
$X^1$, $X^2$, and $X^6$ are OH, and $X^3$, $X^4$, $X^5$, $X^7$, and $X^8$ are H;
$X^1$, $X^5$, and $X^8$ are OH, and $X^2$, $X^3$, $X^4$, $X^6$, and $X^7$ are H;
$X^2$, $X^4$, and $X^6$ are OH, and $X^1$, $X^3$, $X^5$, $X^7$, and $X^8$ are H;
$X^2$, $X^4$, and $X^7$ are OH, and $X^1$, $X^3$, $X^5$, $X^6$, and $X^8$ are H;
$X^2$, $X^6$, and $X^7$ are OH, and $X^1$, $X^3$, $X^4$, $X^5$, and $X^8$ are H (urolithin C);
$X^2$, $X^6$, and $X^8$ are OH, and $X^1$, $X^3$, $X^4$, $X^5$, and $X^7$ are H;
$X^2$, $X^7$, and $X^8$ are OH, and $X^1$, $X^3$, $X^4$, $X^5$, and $X^6$ are H;
$X^1$, $X^2$, $X^5$, and $X^6$ are OH, and $X^3$, $X^4$, $X^7$, and $X^8$ are H;
$X^1$, $X^2$, $X^5$, and $X^7$ are OH, and $X^3$, $X^4$, $X^6$, and $X^8$ are H;
$X^1$, $X^2$, $X^6$, and $X^7$ are OH, and $X^3$, $X^4$, $X^5$, and $X^8$ are H (urolithin D);
$X^1$, $X^6$, $X^7$, and $X^8$ are OH, and $X^2$, $X^3$, $X^4$, and $X^5$ are H;
$X^2$, $X^3$, $X^6$, and $X^7$ are OH, and $X^1$, $X^4$, $X^5$, and $X^8$ are H;
$X^2$, $X^4$, $X^5$, and $X^8$ are OH, and $X^1$, $X^3$, $X^6$, and $X^7$ are H;
$X^2$, $X^4$, $X^6$, and $X^7$ are OH, and $X^1$, $X^3$, $X^5$, and $X^8$ are H;
$X^1$, $X^2$, $X^4$, $X^5$, and $X^7$ are OH, and $X^3$, $X^6$, and $X^8$ are H;
$X^1$, $X^2$, $X^6$, $X^7$, and $X^8$ are OH, and $X^3$, $X^4$, and $X^5$ are H; or
$X^1$, $X^2$, $X^3$, $X^6$, $X^7$, and $X^8$ are OH, and $X^4$ and $X^5$ are H.

In certain embodiments, the invention relates to any one of the aforementioned compounds, wherein at least two of $X^1$, $X^2$, $X^3$, $X^4$, $X^5$, $X^6$, $X^7$, and $X^8$ are OH.

In certain embodiments, the invention relates to any one of the aforementioned compounds, wherein at least three of $X^1$, $X^2$, $X^3$, $X^4$, $X^5$, $X^6$, $X^7$, and $X^8$ are OH.

In certain embodiments, the invention relates to any one of the aforementioned compounds, wherein at least four of $X^1$, $X^2$, $X^3$, $X^4$, $X^5$, $X^6$, $X^7$, and $X^8$ are OH.

In certain embodiments, the invention relates to any one of the aforementioned compounds, wherein at least five of $X^1$, $X^2$, $X^3$, $X^4$, $X^5$, $X^6$, $X^7$, and $X^8$ are OH.

In certain embodiments, the invention relates to any one of the aforementioned compounds, wherein at least six of $X^1$, $X^2$, $X^3$, $X^4$, $X^5$, $X^6$, $X^7$, and $X^8$ are OH.

In certain embodiments, the invention relates to any one of the aforementioned compounds, wherein at least seven of $X^1$, $X^2$, $X^3$, $X^4$, $X^5$, $X^6$, $X^7$, and $X^8$ are OH.

In certain embodiments, the invention relates to any one of the aforementioned compounds, wherein $X^1$, $X^2$, $X^3$, $X^4$, $X^5$, $X^6$, $X^7$, and $X^8$ are OH.

In certain embodiments, the invention relates to any one of the aforementioned compounds, wherein $X^1$ and $X^3$ are OH; and $X^2$, $X^4$, $X^5$, $X^6$, $X^7$, and $X^8$ are H.

In certain embodiments, the invention relates to any one of the aforementioned compounds, wherein $X^1$ and $X^4$ are OH; and $X^2$, $X^3$, $X^5$, $X^6$, $X^7$, and $X^8$ are H.

In certain embodiments, the invention relates to any one of the aforementioned compounds, wherein $X^1$ and $X^6$ are OH; and $X^2$, $X^3$, $X^4$, $X^5$, $X^7$, and $X^8$ are H.

In certain embodiments, the invention relates to any one of the aforementioned compounds, wherein $X^2$ and $X^8$ are OH; and $X^1$, $X^3$, $X^4$, $X^5$, $X^6$, and $X^7$ are H.

In certain embodiments, the invention relates to any one of the aforementioned compounds, wherein $X^3$ and $X^7$ are OH; and $X^1$, $X^2$, $X^4$, $X^5$, $X^6$, and $X^8$ are H.

In certain embodiments, the invention relates to any one of the aforementioned compounds, wherein $X^3$ and $X^8$ are OH; and $X^1$, $X^2$, $X^4$, $X^5$, $X^6$, and $X^7$ are H.

In certain embodiments, the invention relates to any one of the aforementioned compounds, wherein $X^4$ and $X^5$ are OH; and $X^1$, $X^2$, $X^3$, $X^6$, $X^7$, and $X^8$ are H.

In certain embodiments, the invention relates to any one of the aforementioned compounds, wherein $X^4$ and $X^6$ are OH; and $X^1$, $X^2$, $X^3$, $X^5$, $X^7$, and $X^8$ are H.

In certain embodiments, the invention relates to any one of the aforementioned compounds, wherein $X^4$ and $X^7$ are OH; and $X^1$, $X^2$, $X^3$, $X^5$, $X^6$, and $X^8$ are H.

In certain embodiments, the invention relates to any one of the aforementioned compounds, wherein $X^4$ and $X^8$ are OH; and $X^1$, $X^2$, $X^3$, $X^5$, $X^6$, and $X^7$ are H.

In certain embodiments, the invention relates to any one of the aforementioned compounds, wherein $X^5$ and $X^7$ are OH; and $X^1$, $X^2$, $X^3$, $X^4$, $X^6$, and $X^8$ are H.

In certain embodiments, the invention relates to any one of the aforementioned compounds, wherein $X^6$ and $X^8$ are OH; and $X^1$, $X^2$, $X^3$, $X^4$, $X^5$, and $X^7$ are H.

In certain embodiments, the invention relates to any one of the aforementioned compounds, wherein $X^7$ and $X^8$ are OH; and $X^1$, $X^2$, $X^3$, $X^4$, $X^5$, and $X^6$ are H.

In certain embodiments, the invention relates to any one of the aforementioned compounds, wherein $X^1$, $X^2$, and $X^3$ are OH; and $X^4$, $X^5$, $X^6$, $X^7$, and $X^8$ are H.

In certain embodiments, the invention relates to any one of the aforementioned compounds, wherein $X^1$, $X^2$, and $X^4$ are OH; and $X^3$, $X^5$, $X^6$, $X^7$, and $X^8$ are H.

In certain embodiments, the invention relates to any one of the aforementioned compounds, wherein $X^1$, $X^2$, and $X^7$ are OH; and $X^3$, $X^4$, $X^5$, $X^6$, and $X^8$ are H.

In certain embodiments, the invention relates to any one of the aforementioned compounds, wherein $X^1$, $X^2$, and $X^8$ are OH; and $X^3$, $X^4$, $X^5$, $X^6$, and $X^7$ are H.

In certain embodiments, the invention relates to any one of the aforementioned compounds, wherein $X^1$, $X^3$, and $X^4$ are OH; and $X^2$, $X^5$, $X^6$, $X^7$, and $X^8$ are H.

In certain embodiments, the invention relates to any one of the aforementioned compounds, wherein $X^1$, $X^3$, and $X^5$ are OH; and $X^2$, $X^4$, $X^6$, $X^7$, and $X^8$ are H.

In certain embodiments, the invention relates to any one of the aforementioned compounds, wherein $X^1$, $X^3$, and $X^6$ are OH; and $X^2$, $X^4$, $X^5$, $X^7$, and $X^8$ are H.

In certain embodiments, the invention relates to any one of the aforementioned compounds, wherein $X^1$, $X^3$, and $X^7$ are OH; and $X^2$, $X^4$, $X^5$, $X^6$, and $X^8$ are H.

In certain embodiments, the invention relates to any one of the aforementioned compounds, wherein $X^1$, $X^3$, and $X^8$ are OH; and $X^2$, $X^4$, $X^5$, $X^6$, and $X^7$ are H.

In certain embodiments, the invention relates to any one of the aforementioned compounds, wherein $X^1$, $X^4$, and $X^5$ are OH; and $X^2$, $X^3$, $X^6$, $X^7$, and $X^8$ are H.

In certain embodiments, the invention relates to any one of the aforementioned compounds, wherein $X^1$, $X^4$, and $X^6$ are OH; and $X^2$, $X^3$, $X^5$, $X^7$, and $X^8$ are H.

In certain embodiments, the invention relates to any one of the aforementioned compounds, wherein $X^1$, $X^4$, and $X^7$ are OH; and $X^2$, $X^3$, $X^5$, $X^6$, and $X^8$ are H.

In certain embodiments, the invention relates to any one of the aforementioned compounds, wherein $X^1$, $X^4$, and $X^8$ are OH; and $X^2$, $X^3$, $X^5$, $X^6$, and $X^7$ are H.

In certain embodiments, the invention relates to any one of the aforementioned compounds, wherein $X^1$, $X^5$, and $X^6$ are OH; and $X^2$, $X^3$, $X^4$, $X^7$, and $X^8$ are H.

In certain embodiments, the invention relates to any one of the aforementioned compounds, wherein $X^1$, $X^5$, and $X^7$ are OH; and $X^2$, $X^3$, $X^4$, $X^6$, and $X^8$ are H.

In certain embodiments, the invention relates to any one of the aforementioned compounds, wherein $X^1$, $X^6$, and $X^7$ are OH; and $X^2$, $X^3$, $X^4$, $X^5$, and $X^8$ are H.

In certain embodiments, the invention relates to any one of the aforementioned compounds, wherein $X^1$, $X^6$, and $X^8$ are OH; and $X^2$, $X^3$, $X^4$, $X^5$, and $X^7$ are H.

In certain embodiments, the invention relates to any one of the aforementioned compounds, wherein $X^1$, $X^7$, and $X^8$ are OH; and $X^2$, $X^3$, $X^4$, $X^5$, and $X^6$ are H.

In certain embodiments, the invention relates to any one of the aforementioned compounds, wherein $X^2$, $X^3$, and $X^4$ are OH; and $X^1$, $X^5$, $X^6$, $X^7$, and $X^8$ are H.

In certain embodiments, the invention relates to any one of the aforementioned compounds, wherein $X^2$, $X^3$, and $X^5$ are OH; and $X^1$, $X^4$, $X^6$, $X^7$, and $X^8$ are H.

In certain embodiments, the invention relates to any one of the aforementioned compounds, wherein $X^2$, $X^3$, and $X^6$ are OH; and $X^1$, $X^4$, $X^5$, $X^7$, and $X^8$ are H.

In certain embodiments, the invention relates to any one of the aforementioned compounds, wherein $X^2$, $X^3$, and $X^7$ are OH; and $X^1$, $X^4$, $X^5$, $X^6$, and $X^8$ are H.

In certain embodiments, the invention relates to any one of the aforementioned compounds, wherein $X^2$, $X^3$, and $X^8$ are OH; and $X^1$, $X^4$, $X^5$, $X^6$, and $X^7$ are H.

In certain embodiments, the invention relates to any one of the aforementioned compounds, wherein $X^2$, $X^4$, and $X^5$ are OH; and $X^1$, $X^3$, $X^6$, $X^7$, and $X^8$ are H.

In certain embodiments, the invention relates to any one of the aforementioned compounds, wherein $X^2$, $X^4$, and $X^8$ are OH; and $X^1$, $X^3$, $X^5$, $X^6$, and $X^7$ are H.

In certain embodiments, the invention relates to any one of the aforementioned compounds, wherein $X^2$, $X^5$, and $X^6$ are OH; and $X^1$, $X^3$, $X^4$, $X^7$, and $X^8$ are H.

In certain embodiments, the invention relates to any one of the aforementioned compounds, wherein $X^2$, $X^5$, and $X^7$ are OH; and $X^1$, $X^3$, $X^4$, $X^6$, and $X^8$ are H.

In certain embodiments, the invention relates to any one of the aforementioned compounds, wherein $X^2$, $X^5$, and $X^8$ are OH; and $X^1$, $X^3$, $X^4$, $X^6$, and $X^7$ are H.

In certain embodiments, the invention relates to any one of the aforementioned compounds, wherein $X^3$, $X^4$, and $X^5$ are OH; and $X^1$, $X^2$, $X^6$, $X^7$, and $X^8$ are H.

In certain embodiments, the invention relates to any one of the aforementioned compounds, wherein $X^3$, $X^4$, and $X^6$ are OH; and $X^1$, $X^2$, $X^5$, $X^7$, and $X^8$ are H.

In certain embodiments, the invention relates to any one of the aforementioned compounds, wherein $X^3$, $X^4$, and $X^7$ are OH; and $X^1$, $X^2$, $X^5$, $X^6$, and $X^8$ are H.

In certain embodiments, the invention relates to any one of the aforementioned compounds, wherein $X^3$, $X^4$, and $X^8$ are OH; and $X^1$, $X^2$, $X^5$, $X^6$, and $X^7$ are H.

In certain embodiments, the invention relates to any one of the aforementioned compounds, wherein $X^3$, $X^5$, and $X^6$ are OH; and $X^1$, $X^2$, $X^4$, $X^7$, and $X^8$ are H.

In certain embodiments, the invention relates to any one of the aforementioned compounds, wherein $X^3$, $X^5$, and $X^7$ are OH; and $X^1$, $X^2$, $X^4$, $X^6$, and $X^8$ are H.

In certain embodiments, the invention relates to any one of the aforementioned compounds, wherein $X^3$, $X^5$, and $X^8$ are OH; and $X^1$, $X^2$, $X^4$, $X^6$, and $X^7$ are H.

In certain embodiments, the invention relates to any one of the aforementioned compounds, wherein $X^3$, $X^6$, and $X^7$ are OH; and $X^1$, $X^2$, $X^4$, $X^5$, and $X^8$ are H.

In certain embodiments, the invention relates to any one of the aforementioned compounds, wherein $X^3$, $X^6$, and $X^8$ are OH; and $X^1$, $X^2$, $X^4$, $X^5$, and $X^7$ are H.

In certain embodiments, the invention relates to any one of the aforementioned compounds, wherein $X^3$, $X^7$, and $X^8$ are OH; and $X^1$, $X^2$, $X^4$, $X^5$, and $X^6$ are H.

In certain embodiments, the invention relates to any one of the aforementioned compounds, wherein $X^4$, $X^5$, and $X^6$ are OH; and $X^1$, $X^2$, $X^3$, $X^7$, and $X^8$ are H.

In certain embodiments, the invention relates to any one of the aforementioned compounds, wherein $X^4$, $X^5$, and $X^7$ are OH; and $X^1$, $X^2$, $X^3$, $X^6$, and $X^8$ are H.

In certain embodiments, the invention relates to any one of the aforementioned compounds, wherein $X^4$, $X^5$, and $X^8$ are OH; and $X^1$, $X^2$, $X^3$, $X^6$, and $X^7$ are H.

In certain embodiments, the invention relates to any one of the aforementioned compounds, wherein $X^4$, $X^6$, and $X^7$ are OH; and $X^1$, $X^2$, $X^3$, $X^5$, and $X^8$ are H.

In certain embodiments, the invention relates to any one of the aforementioned compounds, wherein $X^4$, $X^6$, and $X^8$ are OH; and $X^1$, $X^2$, $X^3$, $X^5$, and $X^7$ are H.

In certain embodiments, the invention relates to any one of the aforementioned compounds, wherein $X^4$, $X^7$, and $X^8$ are OH; and $X^1$, $X^2$, $X^3$, $X^5$, and $X^6$ are H.

In certain embodiments, the invention relates to any one of the aforementioned compounds, wherein $X^5$, $X^6$, and $X^7$ are OH; and $X^1$, $X^2$, $X^3$, $X^4$, and $X^8$ are H.

In certain embodiments, the invention relates to any one of the aforementioned compounds, wherein $X^5$, $X^6$, and $X^8$ are OH; and $X^1$, $X^2$, $X^3$, $X^4$, and $X^7$ are H.

In certain embodiments, the invention relates to any one of the aforementioned compounds, wherein $X^5$, $X^7$, and $X^8$ are OH; and $X^1$, $X^2$, $X^3$, $X^4$, and $X^6$ are H.

In certain embodiments, the invention relates to any one of the aforementioned compounds, wherein $X^6$, $X^7$, and $X^8$ are OH; and $X^1$, $X^2$, $X^3$, $X^4$, and $X^5$ are H.

In certain embodiments, the invention relates to any one of the aforementioned compounds, wherein $X^1$, $X^2$, $X^3$, and $X^4$ are OH; and $X^5$, $X^6$, $X^7$, and $X^8$ are H.

In certain embodiments, the invention relates to any one of the aforementioned compounds, wherein $X^1$, $X^2$, $X^3$, and $X^5$ are OH; and $X^4$, $X^6$, $X^7$, and $X^8$ are H.

In certain embodiments, the invention relates to any one of the aforementioned compounds, wherein $X^1$, $X^2$, $X^3$, and $X^6$ are OH; and $X^4$, $X^5$, $X^7$, and $X^8$ are H.

In certain embodiments, the invention relates to any one of the aforementioned compounds, wherein $X^1$, $X^2$, $X^3$, and $X^7$ are OH; and $X^4$, $X^5$, $X^6$, and $X^8$ are H.

In certain embodiments, the invention relates to any one of the aforementioned compounds, wherein $X^1$, $X^2$, $X^3$, and $X^8$ are OH; and $X^4$, $X^5$, $X^6$, and $X^7$ are H.

In certain embodiments, the invention relates to any one of the aforementioned compounds, wherein $X^1$, $X^2$, $X^4$, and $X^5$ are OH; and $X^3$, $X^6$, $X^7$, and $X^8$ are H.

In certain embodiments, the invention relates to any one of the aforementioned compounds, wherein $X^1$, $X^2$, $X^4$, and $X^6$ are OH; and $X^3$, $X^5$, $X^7$, and $X^8$ are H.

In certain embodiments, the invention relates to any one of the aforementioned compounds, wherein $X^1$, $X^2$, $X^4$, and $X^7$ are OH; and $X^3$, $X^5$, $X^6$, and $X^8$ are H.

In certain embodiments, the invention relates to any one of the aforementioned compounds, wherein $X^1$, $X^2$, $X^4$, and $X^8$ are OH; and $X^3$, $X^5$, $X^6$, and $X^7$ are H.

In certain embodiments, the invention relates to any one of the aforementioned compounds, wherein $X^1$, $X^2$, $X^5$, and $X^8$ are OH; and $X^3$, $X^4$, $X^6$, and $X^7$ are H.

In certain embodiments, the invention relates to any one of the aforementioned compounds, wherein $X^1$, $X^2$, $X^6$, and $X^8$ are OH; and $X^3$, $X^4$, $X^5$, and $X^7$ are H.

In certain embodiments, the invention relates to any one of the aforementioned compounds, wherein $X^1$, $X^2$, $X^7$, and $X^8$ are OH; and $X^3$, $X^4$, $X^5$, and $X^6$ are H.

In certain embodiments, the invention relates to any one of the aforementioned compounds, wherein $X^1$, $X^3$, $X^4$, and $X^5$ are OH; and $X^2$, $X^6$, $X^7$, and $X^8$ are H.

In certain embodiments, the invention relates to any one of the aforementioned compounds, wherein $X^1$, $X^3$, $X^4$, and $X^6$ are OH; and $X^2$, $X^5$, $X^7$, and $X^8$ are H.

In certain embodiments, the invention relates to any one of the aforementioned compounds, wherein $X^1$, $X^3$, $X^4$, and $X^7$ are OH; and $X^2$, $X^5$, $X^6$, and $X^8$ are H.

In certain embodiments, the invention relates to any one of the aforementioned compounds, wherein $X^1$, $X^3$, $X^4$, and $X^8$ are OH; and $X^2$, $X^5$, $X^6$, and $X^7$ are H.

In certain embodiments, the invention relates to any one of the aforementioned compounds, wherein $X^1$, $X^3$, $X^5$, and $X^6$ are OH; and $X^2$, $X^4$, $X^7$, and $X^8$ are H.

In certain embodiments, the invention relates to any one of the aforementioned compounds, wherein $X^1$, $X^3$, $X^5$, and $X^7$ are OH; and $X^2$, $X^4$, $X^6$, and $X^8$ are H.

In certain embodiments, the invention relates to any one of the aforementioned compounds, wherein $X^1$, $X^3$, $X^5$, and $X^8$ are OH; and $X^2$, $X^4$, $X^6$, and $X^7$ are H.

In certain embodiments, the invention relates to any one of the aforementioned compounds, wherein $X^1$, $X^3$, $X^6$, and $X^7$ are OH; and $X^2$, $X^4$, $X^5$, and $X^8$ are H.

In certain embodiments, the invention relates to any one of the aforementioned compounds, wherein $X^1$, $X^3$, $X^6$, and $X^8$ are OH; and $X^2$, $X^4$, $X^5$, and $X^7$ are H.

In certain embodiments, the invention relates to any one of the aforementioned compounds, wherein $X^1$, $X^3$, $X^7$, and $X^8$ are OH; and $X^2$, $X^4$, $X^5$, and $X^6$ are H.

In certain embodiments, the invention relates to any one of the aforementioned compounds, wherein $X^1$, $X^4$, $X^5$, and $X^6$ are OH; and $X^2$, $X^3$, $X^7$, and $X^8$ are H.

In certain embodiments, the invention relates to any one of the aforementioned compounds, wherein $X^1$, $X^4$, $X^5$, and $X^7$ are OH; and $X^2$, $X^3$, $X^6$, and $X^8$ are H.

In certain embodiments, the invention relates to any one of the aforementioned compounds, wherein $X^1$, $X^4$, $X^5$, and $X^8$ are OH; and $X^2$, $X^3$, $X^6$, and $X^7$ are H.

In certain embodiments, the invention relates to any one of the aforementioned compounds, wherein $X^1$, $X^4$, $X^6$, and $X^7$ are OH; and $X^2$, $X^3$, $X^5$, and $X^8$ are H.

In certain embodiments, the invention relates to any one of the aforementioned compounds, wherein $X^1$, $X^4$, $X^6$, and $X^8$ are OH; and $X^2$, $X^3$, $X^5$, and $X^7$ are H.

In certain embodiments, the invention relates to any one of the aforementioned compounds, wherein $X^1$, $X^4$, $X^7$, and $X^8$ are OH; and $X^2$, $X^3$, $X^5$, and $X^6$ are H.

In certain embodiments, the invention relates to any one of the aforementioned compounds, wherein $X^1$, $X^5$, $X^6$, and $X^7$ are OH; and $X^2$, $X^3$, $X^4$, and $X^8$ are H.

In certain embodiments, the invention relates to any one of the aforementioned compounds, wherein $X^1$, $X^5$, $X^6$, and $X^8$ are OH; and $X^2$, $X^3$, $X^4$, and $X^7$ are H.

In certain embodiments, the invention relates to any one of the aforementioned compounds, wherein $X^1$, $X^5$, $X^7$, and $X^8$ are OH; and $X^2$, $X^3$, $X^4$, and $X^6$ are H.

In certain embodiments, the invention relates to any one of the aforementioned compounds, wherein $X^2$, $X^3$, $X^4$, and $X^5$ are OH; and $X^1$, $X^6$, $X^7$, and $X^8$ are H.

In certain embodiments, the invention relates to any one of the aforementioned compounds, wherein $X^2$, $X^3$, $X^4$, and $X^6$ are OH; and $X^1$, $X^5$, $X^7$, and $X^8$ are H.

In certain embodiments, the invention relates to any one of the aforementioned compounds, wherein $X^2$, $X^3$, $X^4$, and $X^7$ are OH; and $X^1$, $X^5$, $X^6$, and $X^8$ are H.

In certain embodiments, the invention relates to any one of the aforementioned compounds, wherein $X^2$, $X^3$, $X^4$, and $X^8$ are OH; and $X^1$, $X^5$, $X^6$, and $X^7$ are H.

In certain embodiments, the invention relates to any one of the aforementioned compounds, wherein $X^2$, $X^3$, $X^5$, and $X^6$ are OH; and $X^1$, $X^4$, $X^7$, and $X^8$ are H.

In certain embodiments, the invention relates to any one of the aforementioned compounds, wherein $X^2$, $X^3$, $X^5$, and $X^7$ are OH; and $X^1$, $X^4$, $X^6$, and $X^8$ are H.

In certain embodiments, the invention relates to any one of the aforementioned compounds, wherein $X^2$, $X^3$, $X^5$, and $X^8$ are OH; and $X^1$, $X^4$, $X^6$, and $X^7$ are H.

In certain embodiments, the invention relates to any one of the aforementioned compounds, wherein $X^2$, $X^3$, $X^6$, and $X^8$ are OH; and $X^1$, $X^4$, $X^5$, and $X^7$ are H.

In certain embodiments, the invention relates to any one of the aforementioned compounds, wherein $X^2$, $X^3$, $X^7$, and $X^8$ are OH; and $X^1$, $X^4$, $X^6$, and $X^7$ are H.

In certain embodiments, the invention relates to any one of the aforementioned compounds, wherein $X^2$, $X^4$, $X^5$, and $X^6$ are OH; and $X^1$, $X^3$, $X^7$, and $X^8$ are H.

In certain embodiments, the invention relates to any one of the aforementioned compounds, wherein $X^2$, $X^4$, $X^5$, and $X^7$ are OH; and $X^1$, $X^3$, $X^6$, and $X^8$ are H.

In certain embodiments, the invention relates to any one of the aforementioned compounds, wherein $X^2$, $X^4$, $X^6$, and $X^8$ are OH; and $X^1$, $X^3$, $X^5$, and $X^7$ are H.

In certain embodiments, the invention relates to any one of the aforementioned compounds, wherein $X^2$, $X^4$, $X^7$, and $X^8$ are OH; and $X^1$, $X^3$, $X^5$, and $X^6$ are H.

In certain embodiments, the invention relates to any one of the aforementioned compounds, wherein $X^2$, $X^5$, $X^6$, and $X^7$ are OH; and $X^1$, $X^3$, $X^4$, and $X^8$ are H.

In certain embodiments, the invention relates to any one of the aforementioned compounds, wherein $X^2$, $X^5$, $X^6$, and $X^8$ are OH; and $X^1$, $X^3$, $X^4$, and $X^7$ are H.

In certain embodiments, the invention relates to any one of the aforementioned compounds, wherein $X^2$, $X^5$, $X^7$, and $X^8$ are OH; and $X^1$, $X^3$, $X^4$, and $X^6$ are H.

In certain embodiments, the invention relates to any one of the aforementioned compounds, wherein $X^2$, $X^6$, $X^7$, and $X^8$ are OH; and $X^1$, $X^3$, $X^4$, and $X^5$ are H.

In certain embodiments, the invention relates to any one of the aforementioned compounds, wherein $X^3$, $X^4$, $X^5$, and $X^6$ are OH; and $X^1$, $X^2$, $X^7$, and $X^8$ are H.

In certain embodiments, the invention relates to any one of the aforementioned compounds, wherein $X^3$, $X^4$, $X^5$, and $X^7$ are OH; and $X^1$, $X^2$, $X^6$, and $X^8$ are H.

In certain embodiments, the invention relates to any one of the aforementioned compounds, wherein $X^3$, $X^4$, $X^5$, and $X^8$ are OH; and $X^1$, $X^2$, $X^6$, and $X^7$ are H.

In certain embodiments, the invention relates to any one of the aforementioned compounds, wherein $X^3$, $X^4$, $X^6$, and $X^7$ are OH; and $X^1$, $X^2$, $X^5$, and $X^8$ are H.

In certain embodiments, the invention relates to any one of the aforementioned compounds, wherein $X^3$, $X^4$, $X^6$, and $X^8$ are OH; and $X^1$, $X^2$, $X^5$, and $X^7$ are H.

In certain embodiments, the invention relates to any one of the aforementioned compounds, wherein $X^3$, $X^4$, $X^7$, and $X^8$ are OH; and $X^1$, $X^2$, $X^5$, and $X^6$ are H.

In certain embodiments, the invention relates to any one of the aforementioned compounds, wherein $X^3$, $X^5$, $X^6$, and $X^7$ are OH; and $X^1$, $X^2$, $X^4$, and $X^8$ are H.

In certain embodiments, the invention relates to any one of the aforementioned compounds, wherein $X^3$, $X^5$, $X^6$, and $X^8$ are OH; and $X^1$, $X^2$, $X^4$, and $X^7$ are H.

In certain embodiments, the invention relates to any one of the aforementioned compounds, wherein $X^3$, $X^5$, $X^7$, and $X^8$ are OH; and $X^1$, $X^2$, $X^4$, and $X^6$ are H.

In certain embodiments, the invention relates to any one of the aforementioned compounds, wherein $X^3$, $X^6$, $X^7$, and $X^8$ are OH; and $X^1$, $X^2$, $X^4$, and $X^5$ are H.

In certain embodiments, the invention relates to any one of the aforementioned compounds, wherein $X^4$, $X^5$, $X^6$, and $X^7$ are OH; and $X^1$, $X^2$, $X^3$, and $X^8$ are H.

In certain embodiments, the invention relates to any one of the aforementioned compounds, wherein $X^4$, $X^5$, $X^6$, and $X^8$ are OH; and $X^1$, $X^2$, $X^3$, and $X^7$ are H.

In certain embodiments, the invention relates to any one of the aforementioned compounds, wherein $X^4$, $X^5$, $X^7$, and $X^8$ are OH; and $X^1$, $X^2$, $X^3$, and $X^6$ are H.

In certain embodiments, the invention relates to any one of the aforementioned compounds, wherein $X^4$, $X^6$, $X^7$, and $X^8$ are OH; and $X^1$, $X^2$, $X^3$, and $X^5$ are H.

In certain embodiments, the invention relates to any one of the aforementioned compounds, wherein $X^5$, $X^6$, $X^7$, and $X^8$ are OH; and $X^1$, $X^2$, $X^3$, and $X^4$ are H.

In certain embodiments, the invention relates to any one of the aforementioned compounds, wherein $X^1$, $X^2$, $X^3$, $X^4$, and $X^5$ are OH; and $X^6$, $X^7$, and $X^8$ are H.

In certain embodiments, the invention relates to any one of the aforementioned compounds, wherein $X^1$, $X^2$, $X^3$, $X^4$, and $X^6$ are OH; and $X^5$, $X^7$, and $X^8$ are H.

In certain embodiments, the invention relates to any one of the aforementioned compounds, wherein $X^1$, $X^2$, $X^3$, $X^4$, and $X^7$ are OH; and $X^5$, $X^6$, and $X^8$ are H.

In certain embodiments, the invention relates to any one of the aforementioned compounds, wherein $X^1$, $X^2$, $X^3$, $X^4$, and $X^8$ are OH; and $X^5$, $X^6$, and $X^7$ are H.

In certain embodiments, the invention relates to any one of the aforementioned compounds, wherein $X^1$, $X^2$, $X^3$, $X^5$, and $X^6$ are OH; and $X^4$, $X^7$, and $X^8$ are H.

In certain embodiments, the invention relates to any one of the aforementioned compounds, wherein $X^1$, $X^2$, $X^3$, $X^5$, and $X^7$ are OH; and $X^4$, $X^6$, and $X^8$ are H.

In certain embodiments, the invention relates to any one of the aforementioned compounds, wherein $X^1$, $X^2$, $X^3$, $X^5$, and $X^8$ are OH; and $X^4$, $X^6$, and $X^7$ are H.

In certain embodiments, the invention relates to any one of the aforementioned compounds, wherein $X^1$, $X^2$, $X^3$, $X^6$, and $X^7$ are OH; and $X^4$, $X^5$, and $X^8$ are H.

In certain embodiments, the invention relates to any one of the aforementioned compounds, wherein $X^1$, $X^2$, $X^3$, $X^6$, and $X^8$ are OH; and $X^4$, $X^5$, and $X^7$ are H.

In certain embodiments, the invention relates to any one of the aforementioned compounds, wherein $X^1$, $X^2$, $X^3$, $X^7$, and $X^8$ are OH; and $X^4$, $X^5$, and $X^6$ are H.

In certain embodiments, the invention relates to any one of the aforementioned compounds, wherein $X^1$, $X^2$, $X^4$, $X^5$, and $X^6$ are OH; and $X^3$, $X^7$, and $X^8$ are H.

In certain embodiments, the invention relates to any one of the aforementioned compounds, wherein $X^1$, $X^2$, $X^4$, $X^5$, and $X^8$ are OH; and $X^3$, $X^6$, and $X^7$ are H.

In certain embodiments, the invention relates to any one of the aforementioned compounds, wherein $X^1$, $X^2$, $X^4$, $X^6$, and $X^7$ are OH; and $X^3$, $X^5$, and $X^8$ are H.

In certain embodiments, the invention relates to any one of the aforementioned compounds, wherein $X^1$, $X^2$, $X^4$, $X^6$, and $X^8$ are OH; and $X^3$, $X^5$, and $X^7$ are H.

In certain embodiments, the invention relates to any one of the aforementioned compounds, wherein $X^1$, $X^2$, $X^4$, $X^7$, and $X^8$ are OH; and $X^3$, $X^5$, and $X^6$ are H.

In certain embodiments, the invention relates to any one of the aforementioned compounds, wherein $X^1$, $X^2$, $X^5$, $X^6$, and $X^7$ are OH; and $X^3$, $X^4$, and $X^8$ are H.

In certain embodiments, the invention relates to any one of the aforementioned compounds, wherein $X^1$, $X^2$, $X^5$, $X^6$, and $X^8$ are OH; and $X^3$, $X^4$, and $X^7$ are H.

In certain embodiments, the invention relates to any one of the aforementioned compounds, wherein $X^1$, $X^2$, $X^5$, $X^7$, and $X^8$ are OH; and $X^3$, $X^4$, and $X^6$ are H.

In certain embodiments, the invention relates to any one of the aforementioned compounds, wherein $X^1$, $X^3$, $X^4$, $X^5$, and $X^6$ are OH; and $X^2$, $X^7$, and $X^8$ are H.

In certain embodiments, the invention relates to any one of the aforementioned compounds, wherein $X^1$, $X^3$, $X^4$, $X^5$, and $X^7$ are OH; and $X^2$, $X^6$, and $X^8$ are H.

In certain embodiments, the invention relates to any one of the aforementioned compounds, wherein $X^1$, $X^3$, $X^4$, $X^5$, and $X^8$ are OH; and $X^2$, $X^6$, and $X^7$ are H.

In certain embodiments, the invention relates to any one of the aforementioned compounds, wherein $X^1$, $X^3$, $X^4$, $X^6$, and $X^7$ are OH; and $X^2$, $X^5$, and $X^8$ are H.

In certain embodiments, the invention relates to any one of the aforementioned compounds, wherein $X^1$, $X^3$, $X^4$, $X^6$, and $X^8$ are OH; and $X^2$, $X^5$, and $X^7$ are H.

In certain embodiments, the invention relates to any one of the aforementioned compounds, wherein $X^1$, $X^3$, $X^4$, $X^7$, and $X^8$ are OH; and $X^2$, $X^5$, and $X^7$ are H.

In certain embodiments, the invention relates to any one of the aforementioned compounds, wherein $X^1$, $X^3$, $X^5$, $X^6$, and $X^7$ are OH; and $X^2$, $X^4$, and $X^8$ are H.

In certain embodiments, the invention relates to any one of the aforementioned compounds, wherein $X^1$, $X^3$, $X^5$, $X^6$, and $X^8$ are OH; and $X^2$, $X^4$, and $X^7$ are H.

In certain embodiments, the invention relates to any one of the aforementioned compounds, wherein $X^1$, $X^3$, $X^5$, $X^7$, and $X^8$ are OH; and $X^2$, $X^4$, and $X^6$ are H.

In certain embodiments, the invention relates to any one of the aforementioned compounds, wherein $X^1$, $X^3$, $X^6$, $X^7$, and $X^8$ are OH; and $X^2$, $X^4$, and $X^5$ are H.

In certain embodiments, the invention relates to any one of the aforementioned compounds, wherein $X^1$, $X^4$, $X^5$, $X^6$, and $X^7$ are OH; and $X^2$, $X^3$, and $X^8$ are H.

In certain embodiments, the invention relates to any one of the aforementioned compounds, wherein $X^1$, $X^4$, $X^5$, $X^6$, and $X^8$ are OH; and $X^2$, $X^3$, and $X^7$ are H.

In certain embodiments, the invention relates to any one of the aforementioned compounds, wherein $X^1$, $X^4$, $X^5$, $X^7$, and $X^8$ are OH; and $X^2$, $X^3$, and $X^6$ are H.

In certain embodiments, the invention relates to any one of the aforementioned compounds, wherein $X^1$, $X^4$, $X^6$, $X^7$, and $X^8$ are OH; and $X^2$, $X^3$, and $X^5$ are H.

In certain embodiments, the invention relates to any one of the aforementioned compounds, wherein $X^1$, $X^5$, $X^6$, $X^7$, and $X^8$ are OH; and $X^2$, $X^3$, and $X^4$ are H.

In certain embodiments, the invention relates to any one of the aforementioned compounds, wherein $X^2$, $X^3$, $X^4$, $X^5$, and $X^6$ are OH; and $X^1$, $X^7$, and $X^8$ are H.

In certain embodiments, the invention relates to any one of the aforementioned compounds, wherein $X^2$, $X^3$, $X^4$, $X^5$, and $X^7$ are OH; and $X^1$, $X^6$, and $X^8$ are H.

In certain embodiments, the invention relates to any one of the aforementioned compounds, wherein $X^2$, $X^3$, $X^4$, $X^5$, and $X^8$ are OH; and $X^1$, $X^6$, and $X^7$ are H.

In certain embodiments, the invention relates to any one of the aforementioned compounds, wherein $X^2$, $X^3$, $X^4$, $X^6$, and $X^7$ are OH; and $X^1$, $X^5$, and $X^8$ are H.

In certain embodiments, the invention relates to any one of the aforementioned compounds, wherein $X^2$, $X^3$, $X^4$, $X^6$, and $X^8$ are OH; and $X^1$, $X^5$, and $X^7$ are H.

In certain embodiments, the invention relates to any one of the aforementioned compounds, wherein $X^2$, $X^3$, $X^4$, $X^7$, and $X^8$ are OH; and $X^1$, $X^5$, and $X^6$ are H.

In certain embodiments, the invention relates to any one of the aforementioned compounds, wherein $X^2$, $X^3$, $X^5$, $X^6$, and $X^7$ are OH; and $X^1$, $X^4$, and $X^8$ are H.

In certain embodiments, the invention relates to any one of the aforementioned compounds, wherein $X^2$, $X^3$, $X^5$, $X^6$, and $X^8$ are OH; and $X^1$, $X^4$, and $X^7$ are H.

In certain embodiments, the invention relates to any one of the aforementioned compounds, wherein $X^2$, $X^3$, $X^5$, $X^7$, and $X^8$ are OH; and $X^1$, $X^4$, and $X^6$ are H.

In certain embodiments, the invention relates to any one of the aforementioned compounds, wherein $X^2$, $X^3$, $X^6$, $X^7$, and $X^8$ are OH; and $X^1$, $X^4$, and $X^5$ are H.

In certain embodiments, the invention relates to any one of the aforementioned compounds, wherein $X^2$, $X^4$, $X^5$, $X^6$, and $X^7$ are OH; and $X^1$, $X^3$, and $X^8$ are H.

In certain embodiments, the invention relates to any one of the aforementioned compounds, wherein $X^2$, $X^4$, $X^5$, $X^6$, and $X^8$ are OH; and $X^1$, $X^3$, and $X^7$ are H.

In certain embodiments, the invention relates to any one of the aforementioned compounds, wherein $X^2$, $X^4$, $X^5$, $X^7$, and $X^8$ are OH; and $X^1$, $X^3$, and $X^6$ are H.

In certain embodiments, the invention relates to any one of the aforementioned compounds, wherein $X^2$, $X^4$, $X^6$, $X^7$, and $X^8$ are OH; and $X^1$, $X^3$, and $X^5$ are H.

In certain embodiments, the invention relates to any one of the aforementioned compounds, wherein $X^2$, $X^5$, $X^6$, $X^7$, and $X^8$ are OH; and $X^1$, $X^3$, and $X^5$ are H.

In certain embodiments, the invention relates to any one of the aforementioned compounds, wherein $X^3$, $X^4$, $X^5$, $X^6$, and $X^7$ are OH; and $X^1$, $X^2$, and $X^8$ are H.

In certain embodiments, the invention relates to any one of the aforementioned compounds, wherein $X^3$, $X^4$, $X^5$, $X^6$, and $X^8$ are OH; and $X^1$, $X^2$, and $X^7$ are H.

In certain embodiments, the invention relates to any one of the aforementioned compounds, wherein $X^3$, $X^4$, $X^5$, $X^7$, and $X^8$ are OH; and $X^1$, $X^2$, and $X^6$ are H.

In certain embodiments, the invention relates to any one of the aforementioned compounds, wherein $X^3$, $X^4$, $X^6$, $X^7$, and $X^8$ are OH; and $X^1$, $X^2$, and $X^5$ are H.

In certain embodiments, the invention relates to any one of the aforementioned compounds, wherein $X^3$, $X^5$, $X^6$, $X^7$, and $X^8$ are OH; and $X^1$, $X^2$, and $X^4$ are H.

In certain embodiments, the invention relates to any one of the aforementioned compounds, wherein $X^4$, $X^5$, $X^6$, $X^7$, and $X^8$ are OH; and $X^1$, $X^2$, and $X^3$ are H.

In certain embodiments, the invention relates to any one of the aforementioned compounds, wherein $X^1$, $X^2$, $X^3$, $X^4$, $X^5$, and $X^6$ are OH; and $X^7$ and $X^8$ are H.

In certain embodiments, the invention relates to any one of the aforementioned compounds, wherein $X^1$, $X^2$, $X^3$, $X^4$, $X^5$, and $X^7$ are OH; and $X^6$ and $X^8$ are H.

In certain embodiments, the invention relates to any one of the aforementioned compounds, wherein $X^1$, $X^2$, $X^3$, $X^4$, $X^5$, and $X^8$ are OH; and $X^6$ and $X^7$ are H.

In certain embodiments, the invention relates to any one of the aforementioned compounds, wherein $X^1$, $X^2$, $X^3$, $X^4$, $X^6$, and $X^7$ are OH; and $X^5$ and $X^8$ are H.

In certain embodiments, the invention relates to any one of the aforementioned compounds, wherein $X^1$, $X^2$, $X^3$, $X^4$, $X^6$, and $X^8$ are OH; and $X^5$ and $X^7$ are H.

In certain embodiments, the invention relates to any one of the aforementioned compounds, wherein $X^1$, $X^2$, $X^3$, $X^4$, $X^7$, and $X^8$ are OH; and $X^5$ and $X^6$ are H.

In certain embodiments, the invention relates to any one of the aforementioned compounds, wherein $X^1$, $X^2$, $X^3$, $X^5$, $X^6$, and $X^7$ are OH; and $X^4$ and $X^8$ are H.

In certain embodiments, the invention relates to any one of the aforementioned compounds, wherein $X^1$, $X^2$, $X^3$, $X^5$, $X^6$, and $X^8$ are OH; and $X^4$ and $X^7$ are H.

In certain embodiments, the invention relates to any one of the aforementioned compounds, wherein $X^1$, $X^2$, $X^3$, $X^5$, $X^7$, and $X^8$ are OH; and $X^4$ and $X^6$ are H.

In certain embodiments, the invention relates to any one of the aforementioned compounds, wherein $X^1$, $X^2$, $X^4$, $X^5$, $X^6$, and $X^7$ are OH; and $X^3$ and $X^8$ are H.

In certain embodiments, the invention relates to any one of the aforementioned compounds, wherein $X^1$, $X^2$, $X^4$, $X^5$, $X^6$, and $X^8$ are OH; and $X^3$ and $X^7$ are H.

In certain embodiments, the invention relates to any one of the aforementioned compounds, wherein $X^1$, $X^2$, $X^4$, $X^5$, $X^7$, and $X^8$ are OH; and $X^3$ and $X^6$ are H.

In certain embodiments, the invention relates to any one of the aforementioned compounds, wherein $X^1$, $X^2$, $X^4$, $X^6$, $X^7$, and $X^8$ are OH; and $X^3$ and $X^5$ are H.

In certain embodiments, the invention relates to any one of the aforementioned compounds, wherein $X^1$, $X^2$, $X^5$, $X^6$, $X^7$, and $X^8$ are OH; and $X^3$ and $X^4$ are H.

In certain embodiments, the invention relates to any one of the aforementioned compounds, wherein $X^1$, $X^3$, $X^4$, $X^5$, $X^6$, and $X^7$ are OH; and $X^2$ and $X^8$ are H.

In certain embodiments, the invention relates to any one of the aforementioned compounds, wherein $X^1$, $X^3$, $X^4$, $X^5$, $X^6$, and $X^8$ are OH; and $X^2$ and $X^7$ are H.

In certain embodiments, the invention relates to any one of the aforementioned compounds, wherein $X^1$, $X^3$, $X^4$, $X^5$, $X^7$, and $X^8$ are OH; and $X^2$ and $X^6$ are H.

In certain embodiments, the invention relates to any one of the aforementioned compounds, wherein $X^1$, $X^3$, $X^4$, $X^6$, $X^7$, and $X^8$ are OH; and $X^2$ and $X^5$ are H.

In certain embodiments, the invention relates to any one of the aforementioned compounds, wherein $X^1$, $X^3$, $X^5$, $X^6$, $X^7$, and $X^8$ are OH; and $X^2$ and $X^4$ are H.

In certain embodiments, the invention relates to any one of the aforementioned compounds, wherein $X^1$, $X^4$, $X^5$, $X^6$, $X^7$, and $X^8$ are OH; and $X^2$ and $X^3$ are H.

In certain embodiments, the invention relates to any one of the aforementioned compounds, wherein $X^2$, $X^3$, $X^4$, $X^5$, $X^6$, and $X^7$ are OH; and $X^1$ and $X^8$ are H.

In certain embodiments, the invention relates to any one of the aforementioned compounds, wherein $X^2$, $X^3$, $X^4$, $X^5$, $X^6$, and $X^8$ are OH; and $X^1$ and $X^7$ are H.

In certain embodiments, the invention relates to any one of the aforementioned compounds, wherein $X^2$, $X^3$, $X^4$, $X^5$, $X^7$, and $X^8$ are OH; and $X^1$ and $X^6$ are H.

In certain embodiments, the invention relates to any one of the aforementioned compounds, wherein $X^2$, $X^3$, $X^4$, $X^6$, $X^7$, and $X^8$ are OH; and $X^1$ and $X^5$ are H.

In certain embodiments, the invention relates to any one of the aforementioned compounds, wherein $X^2$, $X^3$, $X^5$, $X^6$, $X^7$, and $X^8$ are OH; and $X^1$ and $X^4$ are H.

In certain embodiments, the invention relates to any one of the aforementioned compounds, wherein $X^2$, $X^4$, $X^5$, $X^6$, $X^7$, and $X^8$ are OH; and $X^1$ and $X^3$ are H.

In certain embodiments, the invention relates to any one of the aforementioned compounds, wherein $X^3$, $X^4$, $X^5$, $X^6$, $X^7$, and $X^8$ are OH; and $X^1$ and $X^2$ are H.

In certain embodiments, the invention relates to any one of the aforementioned compounds, wherein $X^1$, $X^2$, $X^3$, $X^4$, $X^5$, $X^6$, and $X^7$ are OH; and $X^8$ is H.

In certain embodiments, the invention relates to any one of the aforementioned compounds, wherein $X^1$, $X^2$, $X^3$, $X^4$, $X^5$, $X^6$, and $X^8$ are OH; and $X^7$ is H.

In certain embodiments, the invention relates to any one of the aforementioned compounds, wherein $X^1$, $X^2$, $X^3$, $X^4$, $X^5$, $X^7$, and $X^8$ are OH; and $X^6$ is H.

In certain embodiments, the invention relates to any one of the aforementioned compounds, wherein $X^1$, $X^2$, $X^3$, $X^4$, $X^6$, $X^7$, and $X^8$ are OH; and $X^5$ is H.

In certain embodiments, the invention relates to any one of the aforementioned compounds, wherein $X^1$, $X^2$, $X^3$, $X^5$, $X^6$, $X^7$, and $X^8$ are OH; and $X^4$ is H.

In certain embodiments, the invention relates to any one of the aforementioned compounds, wherein $X^1$, $X^2$, $X^4$, $X^5$, $X^6$, $X^7$, and $X^8$ are OH; and $X^3$ is H.

In certain embodiments, the invention relates to any one of the aforementioned compounds, wherein $X^1$, $X^3$, $X^4$, $X^5$, $X^6$, $X^7$, and $X^8$ are OH; and $X^2$ is H.

In certain embodiments, the invention relates to any one of the aforementioned compounds, wherein $X^2$, $X^3$, $X^4$, $X^5$, $X^6$, $X^7$, and $X^8$ are OH; and $X^1$ is H.

In certain embodiments, the invention relates to a compound of Formula III

Formula III wherein
R$^1$, R$^2$, R$^3$, R$^4$, R$^5$, R$^6$, R$^7$, and R$^8$ are independently selected from the group consisting of H and OR;
R is H, substituted or unsubstituted alkyl, substituted or unsubstituted aryl, a substituted or unsubstituted monosaccharide, or a substituted or unsubstituted oligosaccharide; and
with the proviso that the compound is not a compound of Formula III wherein
R$^1$, R$^2$, R$^3$, R$^4$, R$^5$, R$^6$, R$^7$, and R$^8$ are H;
R$^1$ is OR, and R$^2$, R$^3$, R$^4$, R$^5$, R$^6$, R$^7$, and R$^8$ are H;
R$^2$ is OR, and R$^1$, R$^3$, R$^4$, R$^5$, R$^6$, R$^7$, and R$^8$ are H;
R$^3$ is OR, and R$^1$, R$^2$, R$^4$, R$^5$, R$^6$, R$^7$, and R$^8$ are H;
R$^4$ is OR, and R$^1$, R$^2$, R$^3$, R$^5$, R$^6$, R$^7$, and R$^8$ are H;
R$^5$ is OR, and R$^1$, R$^2$, R$^3$, R$^4$, R$^6$, R$^7$, and R$^8$ are H;
R$^6$ is OR, and R$^1$, R$^2$, R$^3$, R$^4$, R$^5$, R$^7$, and R$^8$ are H;
R$^7$ is OR, and R$^1$, R$^2$, R$^3$, R$^4$, R$^5$, R$^6$, and R$^8$ are H;
R$^8$ is OR, and R$^1$, R$^2$, R$^3$, R$^4$, R$^5$, R$^6$, and R$^7$ are H;
R$^1$ and R$^2$ are OR, and R$^3$, R$^4$, R$^5$, R$^6$, R$^7$, and R$^8$ are H;
R$^1$ and R$^5$ are OR, and R$^2$, R$^3$, R$^4$, R$^6$, R$^7$, and R$^8$ are H;
R$^1$ and R$^7$ are OR, and R$^2$, R$^3$, R$^4$, R$^5$, R$^6$, and R$^8$ are H;
R$^1$ and R$^8$ are OR, and R$^2$, R$^3$, R$^4$, R$^5$, R$^6$, and R$^7$ are H;
R$^2$ and R$^3$ are OR, and R$^1$, R$^4$, R$^5$, R$^6$, R$^7$, and R$^8$ are H;
R$^2$ and R$^4$ are OR, and R$^1$, R$^3$, R$^5$, R$^6$, R$^7$, and R$^8$ are H;
R$^2$ and R$^5$ are OR, and R$^1$, R$^3$, R$^4$, R$^6$, R$^7$, and R$^8$ are H;
R$^2$ and R$^6$ are OR, and R$^1$, R$^3$, R$^4$, R$^5$, R$^7$, and R$^8$ are H;
R$^2$ and R$^7$ are OR, and R$^1$, R$^3$, R$^4$, R$^5$, R$^6$, and R$^8$ are H;
R$^2$ and R$^8$ are OR, and R$^1$, R$^3$, R$^4$, R$^5$, R$^6$, and R$^7$ are H;
R$^3$ and R$^4$ are OR, and R$^1$, R$^2$, R$^5$, R$^6$, R$^7$, and R$^8$ are H;
R$^3$ and R$^5$ are OR, and R$^1$, R$^2$, R$^4$, R$^6$, R$^7$, and R$^8$ are H;
R$^3$ and R$^6$ are OR, and R$^1$, R$^2$, R$^4$, R$^5$, R$^7$, and R$^8$ are H;
R$^3$ and R$^7$ are OR, and R$^1$, R$^2$, R$^4$, R$^5$, R$^6$, and R$^8$ are H;
R$^3$ and R$^8$ are OR, and R$^1$, R$^2$, R$^4$, R$^5$, R$^6$, and R$^7$ are H;
R$^4$ and R$^8$ are OR, and R$^1$, R$^2$, R$^3$, R$^5$, R$^6$, and R$^7$ are H;
R$^5$ and R$^6$ are OR, and R$^1$, R$^2$, R$^3$, R$^4$, R$^7$, and R$^8$ are H;
R$^5$ and R$^7$ are OR, and R$^1$, R$^2$, R$^3$, R$^4$, R$^6$, and R$^8$ are H;
R$^5$ and R$^8$ are OR, and R$^1$, R$^2$, R$^3$, R$^4$, R$^6$, and R$^7$ are H;
R$^6$ and R$^7$ are OR, and R$^1$, R$^2$, R$^3$, R$^4$, R$^5$, and R$^8$ are H;
R$^6$ and R$^8$ are OR, and R$^1$, R$^2$, R$^3$, R$^4$, R$^5$, and R$^7$ are H;
R$^1$, R$^2$, and R$^3$ are OR, and R$^4$, R$^5$, R$^6$, R$^7$, and R$^8$ are H;
R$^1$, R$^2$, and R$^5$ are OR, and R$^3$, R$^4$, R$^6$, R$^7$, and R$^8$ are H;
R$^1$, R$^2$, and R$^6$ are OR, and R$^3$, R$^4$, R$^5$, R$^7$, and R$^8$ are H;
R$^1$, R$^2$, and R$^6$ are OR, and R$^3$, R$^4$, R$^5$, R$^6$, and R$^7$ are H;
R$^1$, R$^2$, and R$^8$ are OR, and R$^2$, R$^3$, R$^4$, R$^6$, and R$^7$ are H;
R$^1$, R$^7$, and R$^8$ are OR, and R$^2$, R$^3$, R$^4$, R$^5$, and R$^6$ are H;
R$^2$, R$^3$, and R$^4$ are OR, and R$^2$, R$^3$, R$^6$, R$^7$, and R$^6$ are H;
R$^2$, R$^4$, and R$^6$ are OR, and R$^1$, R$^3$, R$^6$, R$^7$, and R$^8$ are H;
R$^2$, R$^4$, and R$^7$ are OR, and R$^1$, R$^3$, R$^5$, R$^6$, and R$^8$ are H;
R$^2$, R$^5$, and R$^8$ are OR, and R$^1$, R$^3$, R$^4$, R$^6$, and R$^7$ are H;
R$^2$, R$^6$, and R$^7$ are OR, and R$^1$, R$^3$, R$^4$, R$^5$, and R$^8$ are H;
R$^2$, R$^6$, and R$^8$ are OR, and R$^1$, R$^3$, R$^4$, R$^5$, and R$^7$ are H;
R$^2$, R$^7$, and R$^8$ are OR, and R$^1$, R$^3$, R$^4$, R$^5$, and R$^6$ are H;
R$^3$, R$^5$, and R$^8$ are OR, and R$^1$, R$^2$, R$^4$, R$^6$, and R$^7$ are H;
R$^3$, R$^7$, and R$^8$ are OR, and R$^1$, R$^2$, R$^4$, R$^5$, and R$^6$ are H;
R$^6$, R$^7$, and R$^8$ are OR, and R$^1$, R$^2$, R$^3$, R$^4$, and R$^5$ are H;
R$^1$, R$^2$, R$^5$, and R$^6$ are OR, and R$^3$, R$^4$, R$^7$, and R$^8$ are H;
R$^1$, R$^2$, R$^5$, and R$^7$ are OR, and R$^3$, R$^4$, R$^6$, and R$^8$ are H;
R$^1$, R$^2$, R$^6$, and R$^7$ are OR, and R$^3$, R$^4$, R$^5$, and R$^8$ are H;
R$^1$, R$^6$, R$^7$, and R$^8$ are OR, and R$^2$, R$^3$, R$^4$, and R$^5$ are H;
R$^2$, R$^3$, R$^4$, and R$^6$ are OR, and R$^1$, R$^5$, R$^7$, and R$^8$ are H;
R$^2$, R$^3$, R$^5$, and R$^7$ are OR, and R$^1$, R$^4$, R$^6$, and R$^8$ are H;
R$^2$, R$^3$, R$^6$, and R$^7$ are OR, and R$^1$, R$^4$, R$^5$, and R$^8$ are H;
R$^2$, R$^4$, R$^5$, and R$^8$ are OR, and R$^1$, R$^3$, R$^6$, and R$^7$ are H;
R$^2$, R$^4$, R$^6$, and R$^7$ are OR, and R$^1$, R$^3$, R$^5$, and R$^8$ are H;
R$^2$, R$^5$, R$^6$, and R$^7$ are OR, and R$^1$, R$^3$, R$^4$, and R$^8$ are H;
R$^2$, R$^6$, R$^7$, and R$^8$ are OR, and R$^1$, R$^3$, R$^4$, and R$^5$ are H;
R$^1$, R$^2$, R$^4$, R$^5$, and R$^7$ are OR, and R$^3$, R$^6$, and R$^8$ are H;
R$^1$, R$^2$, R$^6$, R$^7$, and R$^8$ are OR, and R$^3$, R$^4$, and R$^5$ are H;
R$^2$, R$^3$, R$^4$, R$^5$, and R$^7$ are OR, and R$^1$, R$^6$, and R$^8$ are H;
R$^2$, R$^3$, R$^6$, R$^7$, and R$^8$ are OR, and R$^1$, R$^4$, and R$^5$ are H;
R$^2$, R$^4$, R$^6$, R$^7$, and R$^8$ are OR, and R$^1$, R$^3$, and R$^5$ are H;
R$^2$, R$^5$, R$^6$, R$^7$, and R$^8$ are OR, and R$^1$, R$^3$, and R$^4$ are H;
R$^1$, R$^2$, R$^3$, R$^6$, R$^7$, and R$^8$ are OR, and R$^4$ and R$^5$ are H;
R$^2$, R$^3$, R$^4$, R$^6$, R$^7$, and R$^8$ are OR, and R$^1$ and R$^5$ are H; and
R$^2$, R$^4$, R$^5$, R$^6$, R$^7$, and R$^8$ are OR, and R$^1$ and R$^3$ are H.

In certain embodiments, the invention relates to any one of the aforementioned compounds, wherein at least two of R$^1$, R$^2$, R$^3$, R$^4$, R$^5$, R$^6$, R$^7$, and R$^8$ are OR.

In certain embodiments, the invention relates to any one of the aforementioned compounds, wherein at least three of R$^1$, R$^2$, R$^3$, R$^4$, R$^5$, R$^6$, R$^7$, and R$^8$ are OR.

In certain embodiments, the invention relates to any one of the aforementioned compounds, wherein at least four of R$^1$, R$^2$, R$^3$, R$^4$, R$^5$, R$^6$, R$^7$, and R$^8$ are OR.

In certain embodiments, the invention relates to any one of the aforementioned compounds, wherein at least five of R$^1$, R$^2$, R$^3$, R$^4$, R$^5$, R$^6$, R$^7$, and R$^8$ are OR.

In certain embodiments, the invention relates to any one of the aforementioned compounds, wherein at least six of R$^1$, R$^2$, R$^3$, R$^4$, R$^5$, R$^6$, R$^7$, and R$^8$ are OR.

In certain embodiments, the invention relates to any one of the aforementioned compounds, wherein at least seven of R$^1$, R$^2$, R$^3$, R$^4$, R$^5$, R$^6$, R$^7$, and R$^8$ are OR.

In certain embodiments, the invention relates to any one of the aforementioned compounds, wherein R$^1$, R$^2$, R$^3$, R$^4$, R$^5$, R$^6$, R$^7$, and R$^8$ are OR.

In certain embodiments, the invention relates to any one of the aforementioned compounds, wherein R$^1$ and R$^3$ are OR; and R$^2$, R$^4$, R$^5$, R$^6$, R$^7$, and R$^8$ are H.

In certain embodiments, the invention relates to any one of the aforementioned compounds, wherein R$^1$ and R$^4$ are OR; and R$^2$, R$^3$, R$^5$, R$^6$, R$^7$, and R$^8$ are H.

In certain embodiments, the invention relates to any one of the aforementioned compounds, wherein R$^1$ and R$^6$ are OR; and R$^2$, R$^3$, R$^4$, R$^5$, R$^7$, and R$^8$ are H.

In certain embodiments, the invention relates to any one of the aforementioned compounds, wherein R$^4$ and R$^5$ are OR; and R$^1$, R$^2$, R$^3$, R$^6$, R$^7$, and R$^8$ are H.

In certain embodiments, the invention relates to any one of the aforementioned compounds, wherein R$^4$ and R$^6$ are OR; and R$^1$, R$^2$, R$^3$, R$^5$, R$^7$, and R$^8$ are H.

In certain embodiments, the invention relates to any one of the aforementioned compounds, wherein R$^4$ and R$^7$ are OR; and R$^1$, R$^2$, R$^3$, R$^5$, R$^6$, and R$^8$ are H.

In certain embodiments, the invention relates to any one of the aforementioned compounds, wherein R$^7$ and R$^8$ are OR; and R$^1$, R$^2$, R$^3$, R$^4$, R$^5$, and R$^6$ are H.

In certain embodiments, the invention relates to any one of the aforementioned compounds, wherein R$^1$, R$^2$, and R$^4$ are OR; and R$^3$, R$^5$, R$^6$, R$^7$, and R$^8$ are H.

In certain embodiments, the invention relates to any one of the aforementioned compounds, wherein R$^1$, R$^2$, and R$^7$ are OR; and R$^3$, R$^4$, R$^5$, R$^6$, and R$^8$ are H.

In certain embodiments, the invention relates to any one of the aforementioned compounds, wherein R$^1$, R$^3$, and R$^4$ are OR; and R$^2$, R$^5$, R$^6$, R$^7$, and R$^8$ are H.

In certain embodiments, the invention relates to any one of the aforementioned compounds, wherein R$^1$, R$^3$, and R$^5$ are OR; and R$^2$, R$^4$, R$^6$, R$^7$, and R$^8$ are H.

In certain embodiments, the invention relates to any one of the aforementioned compounds, wherein R$^1$, R$^3$, and R$^6$ are OR; and R$^2$, R$^4$, R$^5$, R$^7$, and R$^8$ are H.

In certain embodiments, the invention relates to any one of the aforementioned compounds, wherein $R^1$, $R^3$, and $R^7$ are OR; and $R^2$, $R^4$, $R^5$, $R^6$, and $R^8$ are H.

In certain embodiments, the invention relates to any one of the aforementioned compounds, wherein $R^1$, $R^3$, and $R^8$ are OR; and $R^2$, $R^4$, $R^5$, $R^6$, and $R^7$ are H.

In certain embodiments, the invention relates to any one of the aforementioned compounds, wherein $R^1$, $R^4$, and $R^5$ are OR; and $R^2$, $R^3$, $R^6$, $R^7$, and $R^8$ are H.

In certain embodiments, the invention relates to any one of the aforementioned compounds, wherein $R^1$, $R^4$, and $R^6$ are OR; and $R^2$, $R^3$, $R^5$, $R^7$, and $R^8$ are H.

In certain embodiments, the invention relates to any one of the aforementioned compounds, wherein $R^1$, $R^4$, and $R^7$ are OR; and $R^2$, $R^3$, $R^5$, $R^6$, and $R^8$ are H.

In certain embodiments, the invention relates to any one of the aforementioned compounds, wherein $R^1$, $R^4$, and $R^8$ are OR; and $R^2$, $R^3$, $R^5$, $R^6$, and $R^7$ are H.

In certain embodiments, the invention relates to any one of the aforementioned compounds, wherein $R^1$, $R^5$, and $R^6$ are OR; and $R^2$, $R^3$, $R^4$, $R^7$, and $R^8$ are H.

In certain embodiments, the invention relates to any one of the aforementioned compounds, wherein $R^1$, $R^5$, and $R^7$ are OR; and $R^2$, $R^3$, $R^4$, $R^6$, and $R^8$ are H.

In certain embodiments, the invention relates to any one of the aforementioned compounds, wherein $R^1$, $R^6$, and $R^7$ are OR; and $R^2$, $R^3$, $R^4$, $R^5$, and $R^8$ are H.

In certain embodiments, the invention relates to any one of the aforementioned compounds, wherein $R^1$, $R^6$, and $R^8$ are OR; and $R^2$, $R^3$, $R^4$, $R^5$, and $R^7$ are H.

In certain embodiments, the invention relates to any one of the aforementioned compounds, wherein $R^2$, $R^3$, and $R^5$ are OR; and $R^1$, $R^4$, $R^6$, $R^7$, and $R^8$ are H.

In certain embodiments, the invention relates to any one of the aforementioned compounds, wherein $R^2$, $R^3$, and $R^6$ are OR; and $R^1$, $R^4$, $R^5$, $R^7$, and $R^8$ are H.

In certain embodiments, the invention relates to any one of the aforementioned compounds, wherein $R^2$, $R^3$, and $R^7$ are OR; and $R^1$, $R^4$, $R^5$, $R^6$, and $R^8$ are H.

In certain embodiments, the invention relates to any one of the aforementioned compounds, wherein $R^2$, $R^3$, and $R^8$ are OR; and $R^1$, $R^4$, $R^5$, $R^6$, and $R^7$ are H.

In certain embodiments, the invention relates to any one of the aforementioned compounds, wherein $R^2$, $R^4$, and $R^5$ are OR; and $R^1$, $R^3$, $R^6$, $R^7$, and $R^8$ are H.

In certain embodiments, the invention relates to any one of the aforementioned compounds, wherein $R^2$, $R^4$, and $R^8$ are OR; and $R^1$, $R^3$, $R^5$, $R^6$, and $R^7$ are H.

In certain embodiments, the invention relates to any one of the aforementioned compounds, wherein $R^2$, $R^5$, and $R^6$ are OR; and $R^1$, $R^3$, $R^4$, $R^7$, and $R^8$ are H.

In certain embodiments, the invention relates to any one of the aforementioned compounds, wherein $R^2$, $R^5$, and $R^7$ are OR; and $R^1$, $R^3$, $R^4$, $R^6$, and $R^8$ are H.

In certain embodiments, the invention relates to any one of the aforementioned compounds, wherein $R^3$, $R^4$, and $R^5$ are OR; and $R^1$, $R^2$, $R^6$, $R^7$, and $R^8$ are H.

In certain embodiments, the invention relates to any one of the aforementioned compounds, wherein $R^3$, $R^4$, and $R^6$ are OR; and $R^1$, $R^2$, $R^5$, $R^7$, and $R^8$ are H.

In certain embodiments, the invention relates to any one of the aforementioned compounds, wherein $R^3$, $R^4$, and $R^7$ are OR; and $R^1$, $R^2$, $R^5$, $R^6$, and $R^8$ are H.

In certain embodiments, the invention relates to any one of the aforementioned compounds, wherein $R^3$, $R^4$, and $R^8$ are OR; and $R^1$, $R^2$, $R^5$, $R^6$, and $R^7$ are H.

In certain embodiments, the invention relates to any one of the aforementioned compounds, wherein $R^3$, $R^5$, and $R^6$ are OR; and $R^1$, $R^2$, $R^4$, $R^7$, and $R^8$ are H.

In certain embodiments, the invention relates to any one of the aforementioned compounds, wherein $R^3$, $R^5$, and $R^7$ are OR; and $R^1$, $R^2$, $R^4$, $R^6$, and $R^8$ are H.

In certain embodiments, the invention relates to any one of the aforementioned compounds, wherein $R^3$, $R^6$, and $R^7$ are OR; and $R^1$, $R^2$, $R^4$, $R^5$, and $R^8$ are H.

In certain embodiments, the invention relates to any one of the aforementioned compounds, wherein $R^3$, $R^6$, and $R^8$ are OR; and $R^1$, $R^2$, $R^4$, $R^5$, and $R^7$ are H.

In certain embodiments, the invention relates to any one of the aforementioned compounds, wherein $R^4$, $R^5$, and $R^6$ are OR; and $R^1$, $R^2$, $R^3$, $R^7$, and $R^8$ are H.

In certain embodiments, the invention relates to any one of the aforementioned compounds, wherein $R^4$, $R^5$, and $R^7$ are OR; and $R^1$, $R^2$, $R^3$, $R^6$, and $R^8$ are H.

In certain embodiments, the invention relates to any one of the aforementioned compounds, wherein $R^4$, $R^5$, and $R^8$ are OR; and $R^1$, $R^2$, $R^3$, $R^6$, and $R^7$ are H.

In certain embodiments, the invention relates to any one of the aforementioned compounds, wherein $R^4$, $R^6$, and $R^7$ are OR; and $R^1$, $R^2$, $R^3$, $R^5$, and $R^8$ are H.

In certain embodiments, the invention relates to any one of the aforementioned compounds, wherein $R^4$, $R^6$, and $R^8$ are OR; and $R^1$, $R^2$, $R^3$, $R^5$, and $R^7$ are H.

In certain embodiments, the invention relates to any one of the aforementioned compounds, wherein $R^4$, $R^7$, and $R^8$ are OR; and $R^1$, $R^2$, $R^3$, $R^5$, and $R^6$ are H.

In certain embodiments, the invention relates to any one of the aforementioned compounds, wherein $R^5$, $R^6$, and $R^7$ are OR; and $R^1$, $R^2$, $R^3$, $R^4$, and $R^8$ are H.

In certain embodiments, the invention relates to any one of the aforementioned compounds, wherein $R^5$, $R^6$, and $R^8$ are OR; and $R^1$, $R^2$, $R^3$, $R^4$, and $R^7$ are H.

In certain embodiments, the invention relates to any one of the aforementioned compounds, wherein $R^5$, $R^7$, and $R^8$ are OR; and $R^1$, $R^2$, $R^3$, $R^4$, and $R^6$ are H.

In certain embodiments, the invention relates to any one of the aforementioned compounds, wherein $R^1$, $R^2$, $R^3$, and $R^4$ are OR; and $R^5$, $R^6$, $R^7$, and $R^8$ are H.

In certain embodiments, the invention relates to any one of the aforementioned compounds, wherein $R^1$, $R^2$, $R^3$, and $R^5$ are OR; and $R^4$, $R^6$, $R^7$, and $R^8$ are H.

In certain embodiments, the invention relates to any one of the aforementioned compounds, wherein $R^1$, $R^2$, $R^3$, and $R^6$ are OR; and $R^4$, $R^5$, $R^7$, and $R^8$ are H.

In certain embodiments, the invention relates to any one of the aforementioned compounds, wherein $R^1$, $R^2$, $R^3$, and $R^7$ are OR; and $R^4$, $R^5$, $R^6$, and $R^8$ are H.

In certain embodiments, the invention relates to any one of the aforementioned compounds, wherein $R^1$, $R^2$, $R^3$, and $R^8$ are OR; and $R^4$, $R^5$, $R^6$, and $R^7$ are H.

In certain embodiments, the invention relates to any one of the aforementioned compounds, wherein $R^1$, $R^2$, $R^4$, and $R^5$ are OR; and $R^3$, $R^6$, $R^7$, and $R^8$ are H.

In certain embodiments, the invention relates to any one of the aforementioned compounds, wherein $R^1$, $R^2$, $R^4$, and $R^6$ are OR; and $R^3$, $R^5$, $R^7$, and $R^8$ are H.

In certain embodiments, the invention relates to any one of the aforementioned compounds, wherein $R^1$, $R^2$, $R^4$, and $R^7$ are OR; and $R^3$, $R^5$, $R^6$, and $R^8$ are H.

In certain embodiments, the invention relates to any one of the aforementioned compounds, wherein $R^1$, $R^2$, $R^4$, and $R^8$ are OR; and $R^3$, $R^5$, $R^6$, and $R^7$ are H.

In certain embodiments, the invention relates to any one of the aforementioned compounds, wherein $R^1$, $R^2$, $R^5$, and $R^8$ are OR; and $R^3$, $R^4$, $R^6$, and $R^7$ are H.

In certain embodiments, the invention relates to any one of the aforementioned compounds, wherein $R^1$, $R^2$, $R^6$, and $R^8$ are OR; and $R^3$, $R^4$, $R^5$, and $R^7$ are H.

In certain embodiments, the invention relates to any one of the aforementioned compounds, wherein $R^1$, $R^2$, $R^7$, and $R^8$ are OR; and $R^3$, $R^4$, $R^5$, and $R^6$ are H.

In certain embodiments, the invention relates to any one of the aforementioned compounds, wherein $R^1$, $R^3$, $R^4$, and $R^5$ are OR; and $R^2$, $R^6$, $R^7$, and $R^8$ are H.

In certain embodiments, the invention relates to any one of the aforementioned compounds, wherein $R^1$, $R^3$, $R^4$, and $R^6$ are OR; and $R^2$, $R^5$, $R^7$, and $R^8$ are H.

In certain embodiments, the invention relates to any one of the aforementioned compounds, wherein $R^1$, $R^3$, $R^4$, and $R^7$ are OR; and $R^2$, $R^5$, $R^6$, and $R^8$ are H.

In certain embodiments, the invention relates to any one of the aforementioned compounds, wherein $R^1$, $R^3$, $R^4$, and $R^8$ are OR; and $R^2$, $R^5$, $R^6$, and $R^7$ are H.

In certain embodiments, the invention relates to any one of the aforementioned compounds, wherein $R^1$, $R^3$, $R^5$, and $R^6$ are OR; and $R^2$, $R^4$, $R^7$, and $R^8$ are H.

In certain embodiments, the invention relates to any one of the aforementioned compounds, wherein $R^1$, $R^3$, $R^5$, and $R^7$ are OR; and $R^2$, $R^4$, $R^6$, and $R^8$ are H.

In certain embodiments, the invention relates to any one of the aforementioned compounds, wherein $R^1$, $R^3$, $R^5$, and $R^8$ are OR; and $R^2$, $R^4$, $R^6$, and $R^7$ are H.

In certain embodiments, the invention relates to any one of the aforementioned compounds, wherein $R^1$, $R^3$, $R^6$, and $R^7$ are OR; and $R^2$, $R^4$, $R^5$, and $R^8$ are H.

In certain embodiments, the invention relates to any one of the aforementioned compounds, wherein $R^1$, $R^3$, $R^6$, and $R^8$ are OR; and $R^2$, $R^4$, $R^5$, and $R^7$ are H.

In certain embodiments, the invention relates to any one of the aforementioned compounds, wherein $R^1$, $R^3$, $R^7$, and $R^8$ are OR; and $R^2$, $R^4$, $R^5$, and $R^6$ are H.

In certain embodiments, the invention relates to any one of the aforementioned compounds, wherein $R^1$, $R^4$, $R^5$, and $R^6$ are OR; and $R^2$, $R^3$, $R^7$, and $R^8$ are H.

In certain embodiments, the invention relates to any one of the aforementioned compounds, wherein $R^1$, $R^4$, $R^5$, and $R^7$ are OR; and $R^2$, $R^3$, $R^6$, and $R^8$ are H.

In certain embodiments, the invention relates to any one of the aforementioned compounds, wherein $R^1$, $R^4$, $R^5$, and $R^8$ are OR; and $R^2$, $R^3$, $R^6$, and $R^7$ are H.

In certain embodiments, the invention relates to any one of the aforementioned compounds, wherein $R^1$, $R^4$, $R^6$, and $R^7$ are OR; and $R^2$, $R^3$, $R^5$, and $R^8$ are H.

In certain embodiments, the invention relates to any one of the aforementioned compounds, wherein $R^1$, $R^4$, $R^6$, and $R^8$ are OR; and $R^2$, $R^3$, $R^5$, and $R^7$ are H.

In certain embodiments, the invention relates to any one of the aforementioned compounds, wherein $R^1$, $R^4$, $R^7$, and $R^8$ are OR; and $R^2$, $R^3$, $R^5$, and $R^6$ are H.

In certain embodiments, the invention relates to any one of the aforementioned compounds, wherein $R^1$, $R^5$, $R^6$, and $R^7$ are OR; and $R^2$, $R^3$, $R^4$, and $R^8$ are H.

In certain embodiments, the invention relates to any one of the aforementioned compounds, wherein $R^1$, $R^5$, $R^6$, and $R^8$ are OR; and $R^2$, $R^3$, $R^4$, and $R^7$ are H.

In certain embodiments, the invention relates to any one of the aforementioned compounds, wherein $R^1$, $R^5$, $R^7$, and $R^8$ are OR; and $R^2$, $R^3$, $R^4$, and $R^6$ are H.

In certain embodiments, the invention relates to any one of the aforementioned compounds, wherein $R^2$, $R^3$, $R^4$, and $R^5$ are OR; and $R^1$, $R^6$, $R^7$, and $R^8$ are H.

In certain embodiments, the invention relates to any one of the aforementioned compounds, wherein $R^2$, $R^3$, $R^4$, and $R^7$ are OR; and $R^1$, $R^5$, $R^6$, and $R^8$ are H.

In certain embodiments, the invention relates to any one of the aforementioned compounds, wherein $R^2$, $R^3$, $R^4$, and $R^8$ are OR; and $R^1$, $R^5$, $R^6$, and $R^7$ are H.

In certain embodiments, the invention relates to any one of the aforementioned compounds, wherein $R^2$, $R^3$, $R^5$, and $R^6$ are OR; and $R^1$, $R^4$, $R^7$, and $R^8$ are H.

In certain embodiments, the invention relates to any one of the aforementioned compounds, wherein $R^2$, $R^3$, $R^5$, and $R^8$ are OR; and $R^1$, $R^4$, $R^6$, and $R^7$ are H.

In certain embodiments, the invention relates to any one of the aforementioned compounds, wherein $R^2$, $R^3$, $R^6$, and $R^8$ are OR; and $R^1$, $R^4$, $R^5$, and $R^7$ are H.

In certain embodiments, the invention relates to any one of the aforementioned compounds, wherein $R^2$, $R^3$, $R^7$, and $R^8$ are OR; and $R^1$, $R^4$, $R^6$, and $R^7$ are H.

In certain embodiments, the invention relates to any one of the aforementioned compounds, wherein $R^2$, $R^4$, $R^5$, and $R^6$ are OR; and $R^1$, $R^3$, $R^7$, and $R^8$ are H.

In certain embodiments, the invention relates to any one of the aforementioned compounds, wherein $R^2$, $R^4$, $R^5$, and $R^7$ are OR; and $R^1$, $R^3$, $R^6$, and $R^8$ are H.

In certain embodiments, the invention relates to any one of the aforementioned compounds, wherein $R^2$, $R^4$, $R^6$, and $R^8$ are OR; and $R^1$, $R^3$, $R^5$, and $R^7$ are H.

In certain embodiments, the invention relates to any one of the aforementioned compounds, wherein $R^2$, $R^4$, $R^7$, and $R^8$ are OR; and $R^1$, $R^3$, $R^5$, and $R^6$ are H.

In certain embodiments, the invention relates to any one of the aforementioned compounds, wherein $R^2$, $R^5$, $R^6$, and $R^8$ are OR; and $R^1$, $R^3$, $R^4$, and $R^7$ are H.

In certain embodiments, the invention relates to any one of the aforementioned compounds, wherein $R^2$, $R^5$, $R^7$, and $R^8$ are OR; and $R^1$, $R^3$, $R^4$, and $R^6$ are H.

In certain embodiments, the invention relates to any one of the aforementioned compounds, wherein $R^3$, $R^4$, $R^5$, and $R^6$ are OR; and $R^1$, $R^2$, $R^7$, and $R^8$ are H.

In certain embodiments, the invention relates to any one of the aforementioned compounds, wherein $R^3$, $R^4$, $R^5$, and $R^7$ are OR; and $R^1$, $R^2$, $R^6$, and $R^8$ are H.

In certain embodiments, the invention relates to any one of the aforementioned compounds, wherein $R^3$, $R^4$, $R^5$, and $R^8$ are OR; and $R^1$, $R^2$, $R^6$, and $R^7$ are H.

In certain embodiments, the invention relates to any one of the aforementioned compounds, wherein $R^3$, $R^4$, $R^6$, and $R^7$ are OR; and $R^1$, $R^2$, $R^5$, and $R^8$ are H.

In certain embodiments, the invention relates to any one of the aforementioned compounds, wherein $R^3$, $R^4$, $R^6$, and $R^8$ are OR; and $R^1$, $R^2$, $R^5$, and $R^7$ are H.

In certain embodiments, the invention relates to any one of the aforementioned compounds, wherein $R^3$, $R^4$, $R^7$, and $R^8$ are OR; and $R^1$, $R^2$, $R^5$, and $R^6$ are H.

In certain embodiments, the invention relates to any one of the aforementioned compounds, wherein $R^3$, $R^5$, $R^6$, and $R^7$ are OR; and $R^1$, $R^2$, $R^4$, and $R^8$ are H.

In certain embodiments, the invention relates to any one of the aforementioned compounds, wherein $R^3$, $R^5$, $R^6$, and $R^8$ are OR; and $R^1$, $R^2$, $R^4$, and $R^7$ are H.

In certain embodiments, the invention relates to any one of the aforementioned compounds, wherein $R^3$, $R^5$, $R^7$, and $R^8$ are OR; and $R^1$, $R^2$, $R^4$, and $R^6$ are H.

In certain embodiments, the invention relates to any one of the aforementioned compounds, wherein $R^3$, $R^6$, $R^7$, and $R^8$ are OR; and $R^1$, $R^2$, $R^4$, and $R^5$ are H.

In certain embodiments, the invention relates to any one of the aforementioned compounds, wherein $R^4$, $R^5$, $R^6$, and $R^7$ are OR; and $R^1$, $R^2$, $R^3$, and $R^8$ are H.

In certain embodiments, the invention relates to any one of the aforementioned compounds, wherein $R^4$, $R^5$, $R^6$, and $R^8$ are OR; and $R^1$, $R^2$, $R^3$, and $R^7$ are H.

In certain embodiments, the invention relates to any one of the aforementioned compounds, wherein $R^4$, $R^5$, $R^7$, and $R^8$ are OR; and $R^1$, $R^2$, $R^3$, and $R^6$ are H.

In certain embodiments, the invention relates to any one of the aforementioned compounds, wherein $R^4$, $R^6$, $R^7$, and $R^8$ are OR; and $R^1$, $R^2$, $R^3$, and $R^5$ are H.

In certain embodiments, the invention relates to any one of the aforementioned compounds, wherein $R^5$, $R^6$, $R^7$, and $R^8$ are OR; and $R^1$, $R^2$, $R^3$, and $R^4$ are H.

In certain embodiments, the invention relates to any one of the aforementioned compounds, wherein $R^1$, $R^2$, $R^3$, $R^4$, and $R^5$ are OR; and $R^6$, $R^7$, and $R^8$ are H.

In certain embodiments, the invention relates to any one of the aforementioned compounds, wherein $R^1$, $R^2$, $R^3$, $R^4$, and $R^6$ are OR; and $R^5$, $R^7$, and $R^8$ are H.

In certain embodiments, the invention relates to any one of the aforementioned compounds, wherein $R^1$, $R^2$, $R^3$, $R^4$, and $R^7$ are OR; and $R^5$, $R^6$, and $R^8$ are H.

In certain embodiments, the invention relates to any one of the aforementioned compounds, wherein $R^1$, $R^2$, $R^3$, $R^4$, and $R^8$ are OR; and $R^5$, $R^6$, and $R^7$ are H.

In certain embodiments, the invention relates to any one of the aforementioned compounds, wherein $R^1$, $R^2$, $R^3$, $R^5$, and $R^6$ are OR; and $R^4$, $R^7$, and $R^8$ are H.

In certain embodiments, the invention relates to any one of the aforementioned compounds, wherein $R^1$, $R^2$, $R^3$, $R^5$, and $R^7$ are OR; and $R^4$, $R^6$, and $R^8$ are H.

In certain embodiments, the invention relates to any one of the aforementioned compounds, wherein $R^1$, $R^2$, $R^3$, $R^5$, and $R^8$ are OR; and $R^4$, $R^6$, and $R^7$ are H.

In certain embodiments, the invention relates to any one of the aforementioned compounds, wherein $R^1$, $R^2$, $R^3$, $R^6$, and $R^7$ are OR; and $R^4$, $R^5$, and $R^8$ are H.

In certain embodiments, the invention relates to any one of the aforementioned compounds, wherein $R^1$, $R^2$, $R^3$, $R^6$, and $R^8$ are OR; and $R^4$, $R^5$, and $R^7$ are H.

In certain embodiments, the invention relates to any one of the aforementioned compounds, wherein $R^1$, $R^2$, $R^3$, $R^7$, and $R^8$ are OR; and $R^4$, $R^5$, and $R^6$ are H.

In certain embodiments, the invention relates to any one of the aforementioned compounds, wherein $R^1$, $R^2$, $R^4$, $R^5$, and $R^6$ are OR; and $R^3$, $R^7$, and $R^8$ are H.

In certain embodiments, the invention relates to any one of the aforementioned compounds, wherein $R^1$, $R^2$, $R^4$, $R^5$, and $R^8$ are OR; and $R^3$, $R^6$, and $R^7$ are H.

In certain embodiments, the invention relates to any one of the aforementioned compounds, wherein $R^1$, $R^2$, $R^4$, $R^6$, and $R^7$ are OR; and $R^3$, $R^5$, and $R^8$ are H.

In certain embodiments, the invention relates to any one of the aforementioned compounds, wherein $R^1$, $R^2$, $R^4$, $R^6$, and $R^8$ are OR; and $R^3$, $R^5$, and $R^7$ are H.

In certain embodiments, the invention relates to any one of the aforementioned compounds, wherein $R^1$, $R^2$, $R^4$, $R^7$, and $R^8$ are OR; and $R^3$, $R^5$, and $R^6$ are H.

In certain embodiments, the invention relates to any one of the aforementioned compounds, wherein $R^1$, $R^2$, $R^5$, $R^6$, and $R^7$ are OR; and $R^3$, $R^4$, and $R^8$ are H.

In certain embodiments, the invention relates to any one of the aforementioned compounds, wherein $R^1$, $R^2$, $R^5$, $R^6$, and $R^8$ are OR; and $R^3$, $R^4$, and $R^7$ are H.

In certain embodiments, the invention relates to any one of the aforementioned compounds, wherein $R^1$, $R^2$, $R^5$, $R^7$, and $R^8$ are OR; and $R^3$, $R^4$, and $R^6$ are H.

In certain embodiments, the invention relates to any one of the aforementioned compounds, wherein $R^1$, $R^3$, $R^4$, $R^5$, and $R^6$ are OR; and $R^2$, $R^7$, and $R^8$ are H.

In certain embodiments, the invention relates to any one of the aforementioned compounds, wherein $R^1$, $R^3$, $R^4$, $R^5$, and $R^7$ are OR; and $R^2$, $R^6$, and $R^8$ are H.

In certain embodiments, the invention relates to any one of the aforementioned compounds, wherein $R^1$, $R^3$, $R^4$, $R^5$, and $R^8$ are OR; and $R^2$, $R^6$, and $R^7$ are H.

In certain embodiments, the invention relates to any one of the aforementioned compounds, wherein $R^1$, $R^3$, $R^4$, $R^6$, and $R^7$ are OR; and $R^2$, $R^5$, and $R^8$ are H.

In certain embodiments, the invention relates to any one of the aforementioned compounds, wherein $R^1$, $R^3$, $R^4$, $R^6$, and $R^8$ are OR; and $R^2$, $R^5$, and $R^7$ are H.

In certain embodiments, the invention relates to any one of the aforementioned compounds, wherein $R^1$, $R^3$, $R^4$, $R^7$, and $R^8$ are OR; and $R^2$, $R^5$, and $R^6$ are H.

In certain embodiments, the invention relates to any one of the aforementioned compounds, wherein $R^1$, $R^3$, $R^5$, $R^6$, and $R^7$ are OR; and $R^2$, $R^4$, and $R^8$ are H.

In certain embodiments, the invention relates to any one of the aforementioned compounds, wherein $R^1$, $R^3$, $R^5$, $R^6$, and $R^8$ are OR; and $R^2$, $R^4$, and $R^7$ are H.

In certain embodiments, the invention relates to any one of the aforementioned compounds, wherein $R^1$, $R^3$, $R^5$, $R^7$, and $R^8$ are OR; and $R^2$, $R^4$, and $R^6$ are H.

In certain embodiments, the invention relates to any one of the aforementioned compounds, wherein $R^1$, $R^3$, $R^6$, $R^7$, and $R^8$ are OR; and $R^2$, $R^4$, and $R^5$ are H.

In certain embodiments, the invention relates to any one of the aforementioned compounds, wherein $R^1$, $R^4$, $R^5$, $R^6$, and $R^7$ are OR; and $R^2$, $R^3$, and $R^8$ are H.

In certain embodiments, the invention relates to any one of the aforementioned compounds, wherein $R^1$, $R^4$, $R^5$, $R^6$, and $R^8$ are OR; and $R^2$, $R^3$, and $R^7$ are H.

In certain embodiments, the invention relates to any one of the aforementioned compounds, wherein $R^1$, $R^4$, $R^5$, $R^7$, and $R^8$ are OR; and $R^2$, $R^3$, and $R^6$ are H.

In certain embodiments, the invention relates to any one of the aforementioned compounds, wherein $R^1$, $R^4$, $R^6$, $R^7$, and $R^8$ are OR; and $R^2$, $R^3$, and $R^6$ are H.

In certain embodiments, the invention relates to any one of the aforementioned compounds, wherein $R^1$, $R^5$, $R^6$, $R^7$, and $R^8$ are OR; and $R^2$, $R^3$, and $R^4$ are H.

In certain embodiments, the invention relates to any one of the aforementioned compounds, wherein $R^2$, $R^3$, $R^4$, $R^5$, and $R^6$ are OR; and $R^1$, $R^7$, and $R^8$ are H.

In certain embodiments, the invention relates to any one of the aforementioned compounds, wherein $R^2$, $R^3$, $R^4$, $R^5$, and $R^8$ are OR; and $R^1$, $R^6$, and $R^7$ are H.

In certain embodiments, the invention relates to any one of the aforementioned compounds, wherein $R^2$, $R^3$, $R^4$, $R^6$, and $R^7$ are OR; and $R^1$, $R^5$, and $R^8$ are H.

In certain embodiments, the invention relates to any one of the aforementioned compounds, wherein $R^2$, $R^3$, $R^4$, $R^6$, and $R^8$ are OR; and $R^1$, $R^5$, and $R^7$ are H.

In certain embodiments, the invention relates to any one of the aforementioned compounds, wherein $R^2$, $R^3$, $R^4$, $R^7$, and $R^8$ are OR; and $R^1$, $R^5$, and $R^6$ are H.

In certain embodiments, the invention relates to any one of the aforementioned compounds, wherein $R^2$, $R^3$, $R^5$, $R^6$, and $R^7$ are OR; and $R^1$, $R^4$, and $R^8$ are H.

In certain embodiments, the invention relates to any one of the aforementioned compounds, wherein $R^2$, $R^3$, $R^5$, $R^6$, and $R^8$ are OR; and $R^1$, $R^4$, and $R^7$ are H.

In certain embodiments, the invention relates to any one of the aforementioned compounds, wherein $R^2$, $R^3$, $R^5$, $R^7$, and $R^8$ are OR; and $R^1$, $R^4$, and $R^6$ are H.

In certain embodiments, the invention relates to any one of the aforementioned compounds, wherein $R^2$, $R^4$, $R^5$, $R^6$, and $R^7$ are OR; and $R^1$, $R^3$, and $R^8$ are H.

In certain embodiments, the invention relates to any one of the aforementioned compounds, wherein $R^2$, $R^4$, $R^5$, $R^6$, and $R^8$ are OR; and $R^1$, $R^3$, and $R^7$ are H.

In certain embodiments, the invention relates to any one of the aforementioned compounds, wherein $R^2$, $R^4$, $R^5$, $R^7$, and $R^8$ are OR; and $R^1$, $R^3$, and $R^6$ are H.

In certain embodiments, the invention relates to any one of the aforementioned compounds, wherein $R^3$, $R^4$, $R^5$, $R^6$, and $R^7$ are OR; and $R^1$, $R^2$, and $R^8$ are H.

In certain embodiments, the invention relates to any one of the aforementioned compounds, wherein $R^3$, $R^4$, $R^5$, $R^6$, and $R^8$ are OR; and $R^1$, $R^2$, and $R^7$ are H.

In certain embodiments, the invention relates to any one of the aforementioned compounds, wherein $R^3$, $R^4$, $R^5$, $R^7$, and $R^8$ are OR; and $R^1$, $R^2$, and $R^6$ are H.

In certain embodiments, the invention relates to any one of the aforementioned compounds, wherein $R^3$, $R^4$, $R^6$, $R^7$, and $R^8$ are OR; and $R^1$, $R^2$, and $R^5$ are H.

In certain embodiments, the invention relates to any one of the aforementioned compounds, wherein $R^3$, $R^5$, $R^6$, $R^7$, and $R^8$ are OR; and $R^1$, $R^2$, and $R^4$ are H.

In certain embodiments, the invention relates to any one of the aforementioned compounds, wherein $R^4$, $R^5$, $R^6$, $R^7$, and $R^8$ are OR; and $R^1$, $R^2$, and $R^3$ are H.

In certain embodiments, the invention relates to any one of the aforementioned compounds, wherein $R^1$, $R^2$, $R^3$, $R^4$, $R^5$, and $R^6$ are OR; and $R^7$ and $R^8$ are H.

In certain embodiments, the invention relates to any one of the aforementioned compounds, wherein $R^1$, $R^2$, $R^3$, $R^4$, $R^5$, and $R^7$ are OR; and $R^6$ and $R^8$ are H.

In certain embodiments, the invention relates to any one of the aforementioned compounds, wherein $R^1$, $R^2$, $R^3$, $R^4$, $R^5$, and $R^8$ are OR; and $R^6$ and $R^7$ are H.

In certain embodiments, the invention relates to any one of the aforementioned compounds, wherein $R^1$, $R^2$, $R^3$, $R^4$, $R^6$, and $R^7$ are OR; and $R^5$ and $R^8$ are H.

In certain embodiments, the invention relates to any one of the aforementioned compounds, wherein $R^1$, $R^2$, $R^3$, $R^4$, $R^6$, and $R^8$ are OR; and $R^5$ and $R^7$ are H.

In certain embodiments, the invention relates to any one of the aforementioned compounds, wherein $R^1$, $R^2$, $R^3$, $R^4$, $R^7$, and $R^8$ are OR; and $R^5$ and $R^6$ are H.

In certain embodiments, the invention relates to any one of the aforementioned compounds, wherein $R^1$, $R^2$, $R^3$, $R^5$, $R^6$, and $R^7$ are OR; and $R^4$ and $R^8$ are H.

In certain embodiments, the invention relates to any one of the aforementioned compounds, wherein $R^1$, $R^2$, $R^3$, $R^5$, $R^6$, and $R^8$ are OR; and $R^4$ and $R^7$ are H.

In certain embodiments, the invention relates to any one of the aforementioned compounds, wherein $R^1$, $R^2$, $R^3$, $R^5$, $R^7$, and $R^8$ are OR; and $R^4$ and $R^6$ are H.

In certain embodiments, the invention relates to any one of the aforementioned compounds, wherein $R^1$, $R^2$, $R^4$, $R^5$, $R^6$, and $R^7$ are OR; and $R^3$ and $R^8$ are H.

In certain embodiments, the invention relates to any one of the aforementioned compounds, wherein $R^1$, $R^2$, $R^4$, $R^5$, $R^6$, and $R^8$ are OR; and $R^3$ and $R^7$ are H.

In certain embodiments, the invention relates to any one of the aforementioned compounds, wherein $R^1$, $R^2$, $R^4$, $R^5$, $R^7$, and $R^8$ are OR; and $R^3$ and $R^6$ are H.

In certain embodiments, the invention relates to any one of the aforementioned compounds, wherein $R^1$, $R^2$, $R^4$, $R^6$, $R^7$, and $R^8$ are OR; and $R^3$ and $R^5$ are H.

In certain embodiments, the invention relates to any one of the aforementioned compounds, wherein $R^1$, $R^2$, $R^5$, $R^6$, $R^7$, and $R^8$ are OR; and $R^3$ and $R^4$ are H.

In certain embodiments, the invention relates to any one of the aforementioned compounds, wherein $R^1$, $R^3$, $R^4$, $R^5$, $R^6$, and $R^7$ are OR; and $R^2$ and $R^8$ are H.

In certain embodiments, the invention relates to any one of the aforementioned compounds, wherein $R^1$, $R^3$, $R^4$, $R^5$, $R^6$, and $R^8$ are OR; and $R^2$ and $R^7$ are H.

In certain embodiments, the invention relates to any one of the aforementioned compounds, wherein $R^1$, $R^3$, $R^4$, $R^5$, $R^7$, and $R^8$ are OR; and $R^2$ and $R^6$ are H.

In certain embodiments, the invention relates to any one of the aforementioned compounds, wherein $R^1$, $R^3$, $R^4$, $R^6$, $R^7$, and $R^8$ are OR; and $R^2$ and $R^5$ are H.

In certain embodiments, the invention relates to any one of the aforementioned compounds, wherein $R^1$, $R^3$, $R^5$, $R^6$, $R^7$, and $R^8$ are OR; and $R^2$ and $R^4$ are H.

In certain embodiments, the invention relates to any one of the aforementioned compounds, wherein $R^1$, $R^4$, $R^5$, $R^6$, $R^7$, and $R^8$ are OR; and $R^2$ and $R^3$ are H.

In certain embodiments, the invention relates to any one of the aforementioned compounds, wherein $R^2$, $R^3$, $R^4$, $R^5$, $R^6$, and $R^7$ are OR; and $R^1$ and $R^8$ are H.

In certain embodiments, the invention relates to any one of the aforementioned compounds, wherein $R^2$, $R^3$, $R^4$, $R^5$, $R^6$, and $R^8$ are OR; and $R^1$ and $R^7$ are H.

In certain embodiments, the invention relates to any one of the aforementioned compounds, wherein $R^2$, $R^3$, $R^4$, $R^5$, $R^7$, and $R^8$ are OR; and $R^1$ and $R^6$ are H.

In certain embodiments, the invention relates to any one of the aforementioned compounds, wherein $R^2$, $R^3$, $R^5$, $R^6$, $R^7$, and $R^8$ are OR; and $R^1$ and $R^4$ are H.

In certain embodiments, the invention relates to any one of the aforementioned compounds, wherein $R^3$, $R^4$, $R^5$, $R^6$, $R^7$, and $R^8$ are OR; and $R^1$ and $R^2$ are H.

In certain embodiments, the invention relates to any one of the aforementioned compounds, wherein $R^1$, $R^2$, $R^3$, $R^4$, $R^5$, $R^6$, and $R^7$ are OR; and $R^8$ is H.

In certain embodiments, the invention relates to any one of the aforementioned compounds, wherein $R^1$, $R^2$, $R^3$, $R^4$, $R^5$, $R^6$, and $R^8$ are OR; and $R^7$ is H.

In certain embodiments, the invention relates to any one of the aforementioned compounds, wherein $R^1$, $R^2$, $R^3$, $R^4$, $R^5$, $R^7$, and $R^8$ are OR; and $R^6$ is H.

In certain embodiments, the invention relates to any one of the aforementioned compounds, wherein $R^1$, $R^2$, $R^3$, $R^4$, $R^6$, $R^7$, and $R^8$ are OR; and $R^5$ is H.

In certain embodiments, the invention relates to any one of the aforementioned compounds, wherein $R^1$, $R^2$, $R^3$, $R^5$, $R^6$, $R^7$, and $R^8$ are OR; and $R^4$ is H.

In certain embodiments, the invention relates to any one of the aforementioned compounds, wherein $R^1$, $R^2$, $R^4$, $R^5$, $R^6$, $R^7$, and $R^8$ are OR; and $R^3$ is H.

In certain embodiments, the invention relates to any one of the aforementioned compounds, wherein $R^1$, $R^3$, $R^4$, $R^5$, $R^6$, $R^7$, and $R^8$ are OR; and $R^2$ is H.

In certain embodiments, the invention relates to any one of the aforementioned compounds, wherein $R^2$, $R^3$, $R^4$, $R^5$, $R^6$, $R^7$, and $R^8$ are OR; and $R^1$ is H.

In certain embodiments, the invention relates to any one of the aforementioned compounds, wherein R is H.

As used herein, the term "urolithin precursor" refers to ellagic acid and any ellagitannin capable of being converted to one or more urolithins following administration to an animal. In certain embodiments, a "urolithin precursor" is a compound of Formula IV:

Formula VI

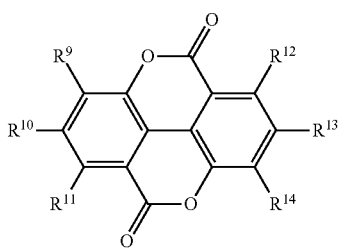

wherein
$R^9$, $R^{10}$, $R^{11}$, $R^{12}$, $R^{13}$, and $R^{14}$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a compound of Formula V

Formula V

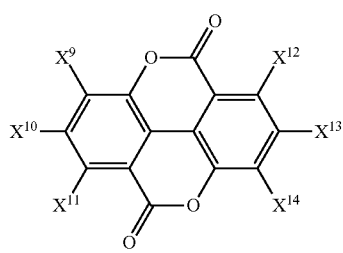

wherein
$X^9$, $X^{10}$, $X^{11}$, $X^{12}$, $X^{13}$, and $X^{14}$ are independently selected from the group consisting of H and OH; and with the proviso that the compound is not a compound of Formula V wherein
$X^9$, $X^{10}$, $X^{11}$, $X^{12}$, $X^{13}$, and $X^{14}$ are H;
$X^{10}$ is OH, and $X^9$, $X^{11}$, $X^{12}$, $X^{13}$, and $X^{14}$ are H;
$X^9$ and $X^{12}$ are OH, and $X^{10}$, $X^{11}$, $X^{13}$, and $X^{14}$ are H;
$X^9$ and $X^{13}$ are OH, and $X^{10}$, $X^{11}$, $X^{12}$, and $X^{14}$ are H;
$X^9$ and $X^{14}$ are OH, and $X^{10}$, $X^{11}$, $X^{12}$, and $X^{13}$ are H;
$X^{10}$ and $X^{13}$ are OH, and $X^9$, $X^{11}$, $X^{12}$, and $X^{14}$ are H;
$X^{10}$, $X^{11}$, and $X^{13}$ are OH, and $X^9$, $X^{12}$, and $X^{14}$ are H;
$X^9$, $X^{10}$, $X^{12}$, and $X^{14}$ are OH, and $X^{11}$ and $X^{13}$ are H;
$X^9$, $X^{10}$, $X^{13}$, and $X^{14}$ are OH, and $X^{11}$ and $X^{12}$ are H (ellagic acid);
$X^9$, $X^{10}$, $X^{11}$, $X^{13}$, and $X^{14}$ are OH, and $X^{12}$ is H; and
$X^9$, $X^{10}$, $X^{11}$, $X^{12}$, $X^{13}$, and $X^{14}$ are OH.

In certain embodiments, the invention relates to any one of the aforementioned compounds, wherein at least one of $X^9$, $X^{10}$, $X^{11}$, $X^{12}$, $X^{13}$, and $X^{14}$ is OH.

In certain embodiments, the invention relates to any one of the aforementioned compounds, wherein at least two of $X^9$, $X^{10}$, $X^{11}$, $X^{12}$, $X^{13}$, and $X^{14}$ are OH.

In certain embodiments, the invention relates to any one of the aforementioned compounds, wherein at least three of $X^9$, $X^{10}$, $X^{11}$, $X^{12}$, $X^{13}$, and $X^{14}$ are OH.

In certain embodiments, the invention relates to any one of the aforementioned compounds, wherein at least four of $X^9$, $X^{10}$, $X^{11}$, $X^{12}$, $X^{13}$, and $X^{14}$ are OH.

In certain embodiments, the invention relates to any one of the aforementioned compounds, wherein five of $X^9$, $X^{10}$, $X^{11}$, $X^{12}$, $X^{13}$, and $X^{14}$ are OH.

In certain embodiments, the invention relates to any one of the aforementioned compounds, wherein $X^9$ is OH; and $X^{10}$, $X^{11}$, $X^{12}$, $X^{13}$, and $X^{14}$ are H.

In certain embodiments, the invention relates to any one of the aforementioned compounds, wherein $X^{11}$ is OH; and $X^9$, $X^{10}$, $X^{12}$, $X^{13}$, and $X^{14}$ are H.

In certain embodiments, the invention relates to any one of the aforementioned compounds, wherein $X^9$ and $X^{10}$ are OH; and $X^{11}$, $X^{12}$, $X^{13}$, and $X^{14}$ are H.

In certain embodiments, the invention relates to any one of the aforementioned compounds, wherein $X^9$ and $X^{11}$ are OH; and $X^{10}$, $X^{12}$, $X^{13}$, and $X^{14}$ are H.

In certain embodiments, the invention relates to any one of the aforementioned compounds, wherein $X^{10}$ and $X^{11}$ are OH; and $X^9$, $X^{12}$, $X^{13}$, and $X^{14}$ are H.

In certain embodiments, the invention relates to any one of the aforementioned compounds, wherein $X^{10}$ and $X^{12}$ are OH; and $X^9$, $X^{11}$, $X^{13}$, and $X^{14}$ are H.

In certain embodiments, the invention relates to any one of the aforementioned compounds, wherein $X^{11}$ and $X^{12}$ are OH; and $X^9$, $X^{10}$, $X^{13}$, and $X^{14}$ are H.

In certain embodiments, the invention relates to any one of the aforementioned compounds, wherein $X^9$, $X^{10}$, and $X^{11}$ are OH; and $X^{12}$, $X^{13}$, and $X^{14}$ are H.

In certain embodiments, the invention relates to any one of the aforementioned compounds, wherein $X^9$, $X^{10}$, and $X^{12}$ are OH; and $X^{11}$, $X^{13}$, and $X^{14}$ are H.

In certain embodiments, the invention relates to any one of the aforementioned compounds, wherein $X^9$, $X^{10}$, and $X^{13}$ are OH; and $X^{11}$, $X^{12}$, and $X^{14}$ are H.

In certain embodiments, the invention relates to any one of the aforementioned compounds, wherein $X^9$, $X^{10}$, and $X^{14}$ are OH; and $X^{11}$, $X^{12}$, and $X^{13}$ are H.

In certain embodiments, the invention relates to any one of the aforementioned compounds, wherein $X^9$, $X^{11}$, and $X^{12}$ are OH; and $X^{10}$, $X^{13}$, and $X^{14}$ are H.

In certain embodiments, the invention relates to any one of the aforementioned compounds, wherein $X^9$, $X^{11}$, and $X^{13}$ are OH; and $X^{10}$, $X^{12}$, and $X^{14}$ are H.

In certain embodiments, the invention relates to any one of the aforementioned compounds, wherein $X^9$, $X^{11}$, and $X^{14}$ are OH; and $X^{10}$, $X^{12}$, and $X^{13}$ are H.

In certain embodiments, the invention relates to any one of the aforementioned compounds, wherein $X^9$, $X^{12}$, and $X^{13}$ are OH; and $X^{10}$, $X^{11}$, and $X^{14}$ are H.

In certain embodiments, the invention relates to any one of the aforementioned compounds, wherein $X^{10}$, $X^{11}$, and $X^{12}$ are OH; and $X^9$, $X^{13}$, and $X^{14}$ are H.

In certain embodiments, the invention relates to any one of the aforementioned compounds, wherein $X^9$, $X^{10}$, $X^{11}$, and $X^{12}$ are OH; and $X^{13}$ and $X^{14}$ are H.

In certain embodiments, the invention relates to any one of the aforementioned compounds, wherein $X^9$, $X^{10}$, $X^{11}$, and $X^{13}$ are OH; and $X^{12}$ and $X^{14}$ are H.

In certain embodiments, the invention relates to any one of the aforementioned compounds, wherein $X^9$, $X^{10}$, $X^{11}$, and $X^{14}$ are OH; and $X^{12}$ and $X^{13}$ are H.

In certain embodiments, the invention relates to any one of the aforementioned compounds, wherein $X^9$, $X^{10}$, $X^{12}$, and $X^{13}$ are OH; and $X^{11}$ and $X^{14}$ are H.

In certain embodiments, the invention relates to any one of the aforementioned compounds, wherein $X^9$, $X^{11}$, $X^{12}$, and $X^{13}$ are OH; and $X^{10}$ and $X^{14}$ are H.

In certain embodiments, the invention relates to any one of the aforementioned compounds, wherein $X^9$, $X^{11}$, $X^{12}$, and $X^{14}$ are OH; and $X^{10}$ and $X^{13}$ are H.

In certain embodiments, the invention relates to any one of the aforementioned compounds, wherein $X^{10}$, $X^{11}$, $X^{12}$, and $X^{13}$ are OH; and $X^9$ and $X^{14}$ are H.

In certain embodiments, the invention relates to any one of the aforementioned compounds, wherein $X^9$, $X^{10}$, $X^{11}$, $X^{12}$, and $X^{13}$ are OH; and $X^{14}$ is H.

In certain embodiments, the invention relates to any one of the aforementioned compounds, wherein $X^9$, $X^{10}$, $X^{11}$, $X^{12}$, and $X^{14}$ are OH; and $X^{13}$ is H.

In certain embodiments, the invention relates to a compound of Formula VI

Formula VI wherein
$R^9$, $R^{10}$, $R^{11}$, $R^{12}$, $R^{13}$, and $R^{14}$ are independently selected from the group consisting of H and OR;
R is H, substituted or unsubstituted alkyl, substituted or unsubstituted aryl, a substituted or unsubstituted monosaccharide, or a substituted or unsubstituted oligosaccharide; and
with the proviso that the compound is not a compound of Formula VI wherein
$R^9$, $R^{10}$, $R^{11}$, $R^{12}$, $R^{13}$, and $R^{14}$ are H;
$R^{10}$ is OR, and $R^9$, $R^{11}$, $R^{12}$, $R^{13}$, and $R^{14}$ are H;
$R^9$ and $R^{12}$ are OR, and $R^{10}$, $R^{11}$, $R^{13}$, and $R^{14}$ are H;
$R^9$ and $R^{13}$ are OR, and $R^{10}$, $R^{11}$, $R^{12}$, and $R^{14}$ are H;
$R^9$ and $R^{14}$ are OR, and $R^{10}$, $R^{11}$, $R^{12}$, and $R^{13}$ are H;
$R^{10}$ and $R^{13}$ are OR, and $R^9$, $R^{11}$, $R^{12}$, and $R^{14}$ are H;
$R^9$, $R^{10}$, and $R^{13}$ are OR, and $R^{11}$, $R^{12}$, and $R^{14}$ are H;
$R^9$, $R^{10}$, and $R^{14}$ are OR, and $R^{11}$, $R^{12}$, and $R^{13}$ are H;
$R^{10}$, $R^{11}$, and $R^{13}$ are OR, and $R^9$, $R^{12}$, and $R^{14}$ are H;
$R^9$, $R^{10}$, $R^{12}$, and $R^{13}$ are OR, and $R^{11}$ and $R^{14}$ are H;
$R^9$, $R^{10}$, $R^{12}$, and $R^{14}$ are OR, and $R^{11}$ and $R^{13}$ are H;
$R^9$, $R^{10}$, $R^{13}$, and $R^{14}$ are OR, and $R^{11}$ and $R^{12}$ are H;
$R^{10}$, $R^{11}$, $R^{12}$, and $R^{13}$ are OR, and $R^9$ and $R^{14}$ are H;
$R^9$, $R^{10}$, $R^{11}$, $R^{12}$, and $R^{13}$ are OR, and $R^{14}$ is H;
$R^9$, $R^{10}$, $R^{11}$, $R^{13}$, and $R^{14}$ are OR, and $R^{12}$ is H; and
$R^9$, $R^{10}$, $R^{11}$, $R^{12}$, $R^{13}$, and $R^{14}$ are OR.

In certain embodiments, the invention relates to any one of the aforementioned compounds, wherein at least one of $R^9$, $R^{10}$, $R^{11}$, $R^{12}$, $R^{13}$, and $R^{14}$ is OR.

In certain embodiments, the invention relates to any one of the aforementioned compounds, wherein at least two of $R^9$, $R^{10}$, $R^{11}$, $R^{12}$, $R^{13}$, and $R^{14}$ are OR.

In certain embodiments, the invention relates to any one of the aforementioned compounds, wherein at least three of $R^9$, $R^{10}$, $R^{11}$, $R^{12}$, $R^{13}$, and $R^{14}$ are OR.

In certain embodiments, the invention relates to any one of the aforementioned compounds, wherein at least four of $R^9$, $R^{10}$, $R^{11}$, $R^{12}$, $R^{13}$, and $R^{14}$ are OR.

In certain embodiments, the invention relates to any one of the aforementioned compounds, wherein five of $R^9$, $R^{10}$, $R^{11}$, $R^{12}$, $R^{13}$, and $R^{14}$ are OR.

In certain embodiments, the invention relates to any one of the aforementioned compounds, wherein $R^9$ is OR; and $R^{10}$, $R^{11}$, $R^{12}$, $R^{13}$, and $R^{14}$ are H.

In certain embodiments, the invention relates to any one of the aforementioned compounds, wherein $R^{11}$ is OR; and $R^9$, $R^{10}$, $R^{12}$, $R^{13}$, and $R^{14}$ are H.

In certain embodiments, the invention relates to any one of the aforementioned compounds, wherein $R^9$ and $R^{10}$ are OR; and $R^{11}$, $R^{12}$, $R^{13}$, and $R^{14}$ are H.

In certain embodiments, the invention relates to any one of the aforementioned compounds, wherein $R^9$ and $R^{11}$ are OR; and $R^{10}$, $R^{12}$, $R^{13}$, and $R^{14}$ are H.

In certain embodiments, the invention relates to any one of the aforementioned compounds, wherein $R^{10}$ and $R^{11}$ are OR; and $R^9$, $R^{12}$, $R^{13}$, and $R^{14}$ are H.

In certain embodiments, the invention relates to any one of the aforementioned compounds, wherein $R^{10}$ and $R^{12}$ are OR; and $R^9$, $R^{11}$, $R^{13}$, and $R^{14}$ are H.

In certain embodiments, the invention relates to any one of the aforementioned compounds, wherein $R^{11}$ and $R^{12}$ are OR; and $R^9$, $R^{10}$, $R^{13}$, and $R^{14}$ are H.

In certain embodiments, the invention relates to any one of the aforementioned compounds, wherein $R^9$, $R^{10}$, and $R^{11}$ are OR; and $R^{12}$, $R^{13}$, and $R^{14}$ are H.

In certain embodiments, the invention relates to any one of the aforementioned compounds, wherein $R^9$, $R^{10}$, and $R^{12}$ are OR; and $R^{11}$, $R^{13}$, and $R^{14}$ are H.

In certain embodiments, the invention relates to any one of the aforementioned compounds, wherein $R^9$, $R^{11}$, and $R^{12}$ are OR; and $R^{10}$, $R^{13}$, and $R^{14}$ are H.

In certain embodiments, the invention relates to any one of the aforementioned compounds, wherein $R^9$, $R^{11}$, and $R^{13}$ are OR; and $R^{10}$, $R^{12}$, and $R^{14}$ are H.

In certain embodiments, the invention relates to any one of the aforementioned compounds, wherein $R^9$, $R^{11}$, and $R^{14}$ are OR; and $R^{10}$, $R^{12}$, and $R^{13}$ are H.

In certain embodiments, the invention relates to any one of the aforementioned compounds, wherein $R^9$, $R^{12}$, and $R^{13}$ are OR; and $R^{10}$, $R^{11}$, and $R^{14}$ are H.

In certain embodiments, the invention relates to any one of the aforementioned compounds, wherein $R^{10}$, $R^{11}$, and $R^{12}$ are OR; and $R^9$, $R^{13}$, and $R^{14}$ are H.

In certain embodiments, the invention relates to any one of the aforementioned compounds, wherein $R^9$, $R^{10}$, $R^{11}$, and $R^{12}$ are OR; and $R^{13}$ and $R^{14}$ are H.

In certain embodiments, the invention relates to any one of the aforementioned compounds, wherein $R^9$, $R^{10}$, $R^{11}$, and $R^{13}$ are OR; and $R^{12}$ and $R^{14}$ are H.

In certain embodiments, the invention relates to any one of the aforementioned compounds, wherein $R^9$, $R^{10}$, $R^{11}$, and $R^{14}$ are OR; and $R^{12}$ and $R^{13}$ are H.

In certain embodiments, the invention relates to any one of the aforementioned compounds, wherein $R^9$, $R^{11}$, $R^{12}$, and $R^{14}$ are OR; and $R^{10}$ and $R^{13}$ are H.

In certain embodiments, the invention relates to any one of the aforementioned compounds, wherein $R^9$, $R^{10}$, $R^{11}$, $R^{12}$, and $R^{14}$ are OR; and $R^{13}$ is H.

In certain embodiments, the invention relates to any one of the aforementioned compounds, wherein R is H.

In one embodiment, a urolithin precursor is punicalagin (PA). In one embodiment, a urolithin precursor is punicalin (PB). See, for example, FIG. 2. In one embodiment, a urolithin precursor is ellagic acid (EA). In one embodiment, a urolithin precursor is provided as an isolated urolithin precursor, e.g., isolated from a natural food source or prepared by total synthesis. Isolated urolithin precursors are usually purified from natural sources or synthesized de novo; some urolithin precursors, including EA, are commercially available from suppliers, such as Sigma Aldrich.

Also in accordance with the invention, precursors of urolithins also include natural foods containing ellagitannins and ellagic acid, especially natural foods that are rich in ellagitannins, ellagic acid, or both ellagitannins and ellagic acid. Such foods include without limitation certain berries, grapes, pomegranates, rose hips, and nuts. In one embodiment, the natural food is pomegranate.

Additionally, precursors of urolithins include processed foods and drinks prepared from such natural foods. The processed food can take any form, including, for example, jams, jellies, preserves, pastes, spreads, juices, wines, extracts, concentrates, and the like. In one embodiment, the processed food is pomegranate juice.

In one embodiment, a urolithin precursor is provided as an extract, e.g., a fruit extract.

In one embodiment, a urolithin precursor is provided as a concentrate, e.g., a fruit concentrate or fruit juice concentrate.

In one embodiment, the urolithin precursor is an isolated urolithin precursor.

In one embodiment, the urolithin precursor is a purified urolithin precursor.

In one embodiment, the urolithin precursor is selected from the group consisting of ellagic acid, an ellagitannin, and any combination thereof.

In one embodiment, the urolithin precursor is ellagic acid.

In one embodiment, the urolithin precursor is an ellagitannin.

In one embodiment, the ellagitannin is selected from the group consisting of castalagin, castalin, casuarictin, chebulagic acid, chebulinic acid, gemin D, grandinin, pedunculagin, punicalagin, punicalin, roburin A, strictinin, tellimagrandin I, tellimagrandin II, terflavin A, terflavin B, tergallagin, Lambertianin C, Sanguiin H-6, Sanguiin H-10, and vescalagin.

Ellagitannins

Among the more than 500 hydrolysable tannins hitherto characterized, ellagitannins, which produce ellagic acid upon hydrolysis, constitute the largest group; the remaining group is gallotannins (galloylglucoses). The ellagitannins include: (1) monomeric ellagitannins, (2) C-glycosidic ellagitannins with an open-chain glucose core, (3) condensates of C-glycosidic tannins with flavan-3-ol (complex tannin), (4) oligomers which are produced through intermolecular C—O or C—C bonds between monomers, and (5) other ellagitannins. Unlike the condensed tannins that are widespread throughout the plant kingdom, ellagitannins have been found only in dicotyledoneous angiosperms. Among the plant families rich in ellagitannins are the Myrtaceae, Lythraceae, Onagraceae, Melastomataceae, and Combretaceae. These families belong to the order Myrtales according to the plant classification systems of New Engler, Cronquist, and APGII (angiosperm phylogeny group).

Ellagitannins are characterized by the presence of one or more hexahydroxydiphenoyl (HHDP) unit(s) on a glucopyranose core. The HHDP group is biosynthetically formed through intramolecular, oxidative C—C bond formation between neighboring galloyl groups in galloylglucoses. They are easily hydrolyzed, either enzymatically or with acid, to liberate a stable ellagic acid as the dilactone form of hexahydroxydiphenoic acid. In addition to the HHDP group, other constituent acyl units in ellagitannins include a galloyl group and HHDP metabolites such as valoneoyl, dehydrohexahydroxydiphenoyl (DHHDP), and chebuloyl groups. Referring to Table 2, variations in the number and position of these acyl units on the glucose core provide a variety of analogs such as tellimagrandin I (1), and II (2), pedunculagin (6), casuarictin (7), chebulagic acid (14), and chebulinic acid (15).

TABLE 2

Representative Monomeric Ellagitannins

| No. | Name | Key | Structure |
|---|---|---|---|
| 1 | Tellimagrandin I | $R^1$ = OH; $R^2$ = $R^3$ = G | 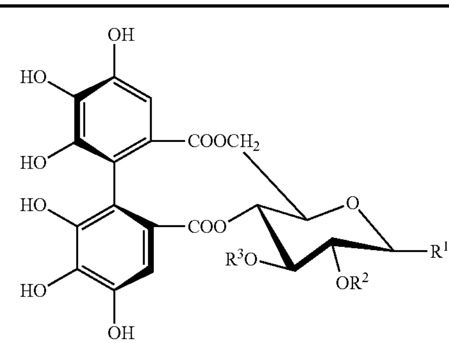 |
| 2 | Tellimagrandin II | $R^1$ = (β)-OG; $R^2$ = $R^3$ = G | |
| 3 | Strictinin | $R^1$ = (β)-OG; $R^2$ = $R^3$ = H | |
| 4 | Gemin D | $R^1$ = OH; $R^2$ = H; $R^3$ = G | |
| 5 | 4,6-(S)-HHDP glucose | $R^1$ = OH; $R^2$ = $R^3$ = H | |

TABLE 2-continued

Representative Monomeric Ellagitannins

| No. | Name | Key |
|---|---|---|
| 6 | Pedunculagin | $R^1$ = OH; $R^2$ = $R^3$ = (S)-HHDP |
| 7 | Casuarictin | $R^1$ = (β)-OG; $R^2$ = $R^3$ = (S)-HHDP |
| 8 | 2,3-(S)-HHDP glucose | $R^1$ = OH; $R^2$ = $R^3$ = H |

| No. | Name | Key |
|---|---|---|
| 9 | Punicalagin | $R^1$ = $R^2$ = (S)-HHDP |
| 10 | Punicalin | $R^1$ = $R^2$ = H |
| 11 | Tergallagin | $R^1$ = $R^2$ = T |

| No. | Name | Key |
|---|---|---|
| 12 | Terflavin A | $R^1$ = $R^2$ = (S)-HHDP |
| 13 | Terflavin B | $R^1$ = $R^2$ = H |

TABLE 2-continued

Representative Monomeric Ellagitannins

| No. | Name | Key |
|-----|------|-----|
| 14 | Chebulagic acid | $R^1 = R^2 = $ (R)-HHDP |
| 15 | Chebulinic acid | $R^1 = R^2 = $ G |

TABLE 2-continued

Representative Monomeric Ellagitannins

| No. | Name | Key | Structure |
|---|---|---|---|
| | | Val = [structure shown] | |

Table 3 presents a representative list of natural sources of monomeric ellagitannins 1-15.

TABLE 3

Representative Natural Sources of Monomeric Ellagitannins 1-15

| Plant Source | Ellagitannin Monomers Found in Myrtales |
|---|---|
| Trapaceae | |
| Trapa japonica | 1, 4, 6, 7 |
| Melastomataceae | 6, 7 |
| Bredia tuberculata | 3, 7 |
| Heterocentron roseum | 3, 7 |
| Melastoma malabathricum | 3, 6, 7 |
| M. normale | 3, 6, 7 |
| Tibouchina semidecandra | 6, 7, 8 |
| Myrtaceae | |
| Callistemon lanceolatus | 4, 6, 8 |
| Eucalyptus alba | 1, 4, 6, 8 |
| E. consideniana | 1, 3, 4, 6 |
| E. globulus | 1 |
| E. rostrata | 1 |
| E. viminalis | 1, 2, 4, 6 |
| Myrtus communis | 1, 2 |
| Pimenta dioica | 2, 3, 5, 6 |
| Syzygium aqueum | 2, 6, 7 |
| S. aromaticum | 1, 2, 3, 4, 7 |
| Onagraceae | |
| Epilobium angustifolium | 1, 3, 4, 6 |
| Oenothera erythrosepala | 1, 4 |
| O. laciniata | 1 |
| O. tetraptera | 1, 2, 4 |

TABLE 3-continued

Representative Natural Sources of Monomeric Ellagitannins 1-15

| Plant Source | Ellagitannin Monomers Found in Myrtales |
|---|---|
| Combretaceae | |
| Combretum glutinosum | 8, 9, 10 |
| C. molle | 9, 10 |
| Quisqualis indica | 1, 2, 6, 8, 9, 10 |
| Terminalia arborea | 8, 9, 10, 14, 15 |
| T. arjuna | 8, 9, 10 |
| T. brachystemma | 9 |
| T. calamansanai | 1, 2, 8, 9, 10 |
| T. catappa | 1, 8, 9, 10, 11, 12, 13, 14, 15 |
| T. chebula | 9, 10, 12, 13, 14, 15 |
| T. citrina | 9, 14 |
| T. macroptera | 8, 9, 12, 13 |
| T. myriocarpa | 8, 9 |
| T. triflora | 10 |
| Punicaceae | |
| Punica granatum | 1, 3, 6, 8, 9, 10 |

C-Glycosidic ellagitannins have been found in many plant families, including Lythraceae, Myrtaceae, Combretaceae, Melastomataceae, and Punicaceae, as well as Fagaceae, Betulaceae, Casuarinaceae, Rosaceae, Theaceae, and Elaeagnaceae. They are categorized into two types: castalagin-type, which contain a flavogalloyl unit participating in the C-glucosidic linkage, such as castalagin (16) and its C-1 epimer, vescalagin (18), and casuarinin-type, which contain an HHDP unit, such as casuarinin (20) and stachyurin (21).

TABLE 4

Representative C-Glycosidic Ellagitannins[a]

| No. | Name | Key | Structure |
|---|---|---|---|
| 16 | Castalagin | $R^1$ = H; $R^2$ = OH; $R^3$ = $R^4$ = (S)-HHDP | 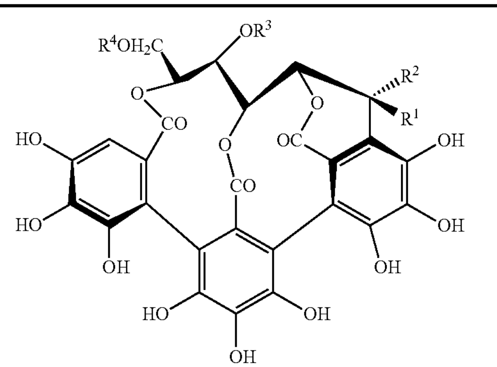 |
| 17 | Castalin | $R^1$ = $R^3$ = $R^4$ = H ; $R^2$ = OH | |
| 18 | Vescalagin | $R^1$ = OH; $R^2$ = H; $R^3$ = $R^4$ = (S)-HHDP | |
| 19 | Grandinin | $R^1$ = L; $R^2$ = H; $R^3$ = $R^4$ = (S)-HHDP | |

TABLE 4-continued

Representative C-Glycosidic Ellagitannins[a]

| No. | Name | Key | Structure |
|-----|------|-----|-----------|
| 20 | Casuarinin | $R^1$ = H; $R^2$ = OH; $R^3$ = G | 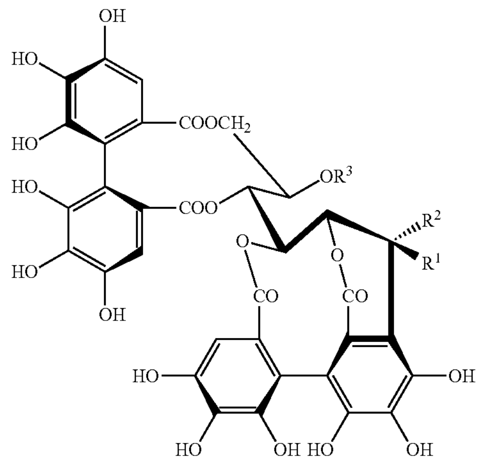 |
| 21 | Stachyurin | $R^1$ = OH; $R^2$ = H; $R^3$ = G | |
| 22 | Casuariin | $R^1$ = $R^3$ = H; $R^2$ = OH | |
| 23 | 5-desgalloystachyurin | $R^1$ = OH; $R^2$ = $R^3$ = H | |
| 29 | Lagerstroemin | $R^1$ = H; $R^2$ = OH; $R^3$ = Val | |

| 24 | Punicacortein A | $R^1$ = $R^4$ = H; $R^2$ = OH; $R^3$ = G | |
| 25 | Epi-Punicacortein A | $R^1$ = OH; $R^2$ = $R^4$ = H; $R^3$ = G | |
| 26 | Punicacortein B | $R^1$ = $R^3$ = H; $R^2$ = OH; $R^4$ = G | |

| 27 | Punicacortein C | $R^1$ = H; $R^2$ = OH | |
| 28 | Punicacortein D | $R^1$ = OH; $R^2$ = H | |

[a] G, (S)-HHDP, and Val have the same meanings as in TABLE 2.

Table 5 presents a representative list of natural sources of C-glycosidic ellagitannins 16-28.

TABLE 5

Representative Natural Sources of C-Glycosidic Ellagitannins 16-28

| Family | Plant species | C-Glycosidic Ellagitannins Found in Myrtales |
|---|---|---|
| Combretaceae | Anogeissus acuminata | 16, 17, 18, 19 |
| | Anogeissus leiocarpus | 16 |
| | Lumnitzera racemosa | 16 |
| | Terminalia arjuna | 16, 20, 22 |
| | Terminalia macroptera | 27 |
| | Terminalia arborea | 28 |
| | Thiloa glaucocarpa | 16, 18, 20, 21 |
| Lythraceae | Lagerstroemia flos-reginea | 16, 18, 20, 21, 22, 23, 24, 29 |
| | Lagerstroemia speciosa | 16, 18, 19, 29 |
| Melastomataceae | Osbeckia chinensis | 20, 22, 25 |
| | Tibouchina semidecandra | 16, 18, 20 |
| Myrtaceae | Callistemon lanceolatus | 20 |
| | Eucalyptus alba | 21, 22 |
| | Eugenia grandis | 16, 18 |
| | Kunzea ambigua | 20 |
| | Melaleuca squarrosa | 20, 21 |
| | Pimenta dioica | 20, 22 16, 18, |
| | Siphoneugena densiflora | 16, 20 |
| | Syzygium aqueum | 16, 18, 19 |
| | Syzygium aromaticum | 20, 22 |
| Punicaceae | Punica granatum | 20, 22, 25, 26, 27, 28 |
| Trapaceae | Trapa japonica | 20 |

Complex tannins (flavono-ellagitannins) are characterized by a unique C—C condensed structure of C-glycosidic tannins (vescalagin-type or stachyurin-type) with flavan-3-ol (catechin or epicatechin). Unlike the C-glycosidic tannins, these tannins have been found in a rather limited number of plant species belonging to the Combretaceae, Myrtaceae, Melastomataceae, Fagaceae, and Theaceae families. Table 6 presents a representative list of complex ellagitannins.

TABLE 6

Representative Complex Ellagitannins

Acutissimin A
Guajavin A
Guajavin B
Guavin A
Guavin C
Guavin D
Malabathrin A
Malabathrin E
Malabathrin F
Mongolicain A
Mongolicain B
Psidinin A
Psidinin B
Psidinin C
Stenophyllanin A Oligomeric ellagitannins are common among many plant families, including the Fagaceae, Rosaceae, Coriariaceae, Onagraceae, Melastomataceae, Myrtaceae, and Lythraceae. This class of tannins is divided into three sub-groups based on structural features: (1) oligomers that contain a valoneoyl group or its equivalent, formed by intermolecular C—O bonds between an HHDP group and a galloyl group of a neighboring monomer; (2) macrocyclic oligomers formed by two C—O bonds; and (3) C-glycosidic tannin oligomers produced by intermolecular C—C bond formation between C-1 of one monomer and the aromatic ring of another. Table 7 presents a representative list of oligomeric ellagitannins.

TABLE 7

Representative Oligomeric Ellagitannins

C-glycosidic Ellagitannin Dimers from Combretaceae

Anogeissinin
Anogeissusin A
Anogeissusin B
Castamollinin

Other Ellagitannin Oligomers

Alienanin B
Benzylcation
Casuarictin
Casuglaunin B
Cowaniin
Cuphiin D1
Cuphiin D2
Eugeniflorin D1
Eugeniflorin D2
Melasquanin A
Melasquanin B
Melasquanin C
Melasquanin D
Melastoflorin A
Melastoflorin B
Melastoflorin C
Melastoflorin D
Nobotanin B
Nobotanin E
Nobotanin F
Nobotanin K
Oenothein A
Oenothein B
Oenotherin T1
Oenotherin T2
Pterocaryanin C
Reginin A
Reginin B
Reginin C
Reginin D
Stachyurin
Woodfordin C
Woodfordin D Table 8 provides a representative list of other ellagitannins.

TABLE 8

Representative Other Ellagitannins

Acalyphidin D1
Agrimoniin
Ascorgeraniin (Elaeocarpusin)
Camelliatannin A
Camelliatannin B
Camelliatannin E
Camelliatannin F
Camelliin B
Coriariin A
Dehydrogeraniin
Eucalbanin B
Eucalbanin C
Euphorbin E
Eurobustin C
Furosinin
Gemin A
Geraniin
Geraniinic Acid B
Geraniinic Acid C
Heterophylliin E
Hirtellin A
Hirtellin B
Hirtellin C
Laevigatin B
Laevigatin C
Laevigatin E
Liquidambin TABLE 8-continued Representative Other Ellagitannins Melastoflorin A
Phyllanthusiin A
Phyllanthusiin B
Phyllanthusiin C
Potentillin
Putranjivain A
Repandusinic acid
Roshenin A
Roshenin B
Rugosin D
Rugosin E
Rugosin F
Rugosin G
Tamarixinin A
Tamarixinin B
Tamarixinin C
Terchebin
Trapanin B Table 9 provides yet another representative list of ellagitannins, including common known natural sources for some of them.

TABLE 9

Representative Ellagitannins

| Name | Source(s) |
|---|---|
| 2-O-galloyl-punicalin | |
| Casaurictin | Rhu tree, Stachyrus plant |
| Castalagin & Vecalagin | Pomegranate bark |
| Castalin | |
| Casuarictin | T. japonica |
| Casuariin | Banaba tree leaves |
| Casuarinin | Banaba tree leaves |
| Casuarinin | Pomegranate |
| Chebulagic acid | T. chebula |
| Chebulinic acid | T. chebula |
| Corilagin | Pomegranate |
| Cornusiin A | |
| Cornusiin C | |
| Cornusiin E | |
| Epipunicacortein A | Banaba tree leaves |
| Flosin B | Banaba tree leaves |
| Gemin D | T. japonica |
| Granatin A | Pomegranate |
| Granatin B | Pomegranate |
| Grandinin | |
| Lagerstroemin | Banaba tree leaves |
| Lambertianin A | |
| Lambertianin C | Raspberries |
| Pedunculagin | Pomegrante bark, and pericarp |
| Punicacortein A | Pomegranate |
| Punicacortein B | Pomegranate |
| Punicacortein C | Pomegranate |
| Punicacortein D | Pomegranate |
| Punicafolin | Pomegranate |
| Punicalagin | Pomegranate |
| Punicalin | Pomegranate |
| Punigluconin | Pomegranate |
| Roburin A | |
| Roburin B | |
| Roburin C | |
| Roburin D | |
| Roburin E | |
| Rubusuaviin C | Tea leaves |
| Sanguiin H-4 | Muscadine grapes |
| Sanguiin H-5 | Muscadine grapes |
| Sanguiin H-6 | Raspberries, Sanguisorba |
| Sanguiin H-10 | |
| Sanguiin H-11 | |
| Stachyurin | Banaba tree leaves |
| Strictinin | |
| Tellimagrandin I | Pomegranate |
| Tellimigrandin II | Pomegranate |

TABLE 9-continued

Representative Ellagitannins

| Name | Source(s) |
|---|---|
| Terchebulin | |
| Terflavin A | |
| Terflavin B | |
| Tergallagin | T. catappa |
| Terminalin/Gallagyldilacton | Pomegranate |

Unfortunately, for the most part ellagitannins are poorly absorbed by the human gut. However, a number of metabolites derived from ellagitannins are absorbed by the human gut, including certain metabolites ultimately formed in the gut by commensal microorganisms (i.e., intestinal microflora).

Ellagitannins release ellagic acid under physiological conditions in vivo, and ellagic acid is then gradually metabolized by the gut microflora in the intestine to produce urolithin A (UA), urolithin B, urolithin C, and urolithin D. Once the metabolites are absorbed, they are further metabolized to produce urolithin glucuronides and/or sulfates, to give a combination of metabolites secreted in the bile.

Ellagic acid is normally found in relatively low amounts in plant tissues. Ellagic acid is thought to be derived from ellagitannins, which when broken down form hexahydroxydiphenic acid, which spontaneously converts to ellagic acid. Some additional sources of ellagic acid are shown in Table 10.

TABLE 10

Representative Sources of Ellagic Acid

| Fruit | Quantity |
|---|---|
| Acai | 55.4 ± 1.39 mg/L fresh pulp |
| Umbu | 314 mg/100 g dry weight (commercial) |
| Camu-camu | 490 mg/100 g dry weight |
| Cagaita | 289 mg/100 g dry weight (commercial) |
| Araca | 262 mg/100 g dry weight |
| | 218 mg/100 g dry weight (commercial) |
| Cambuci | 240 mg/100 g dry weight |
| | 512 mg/100 g dry weight (commercial) |
| Muscadine Grapes | 219 mg/100 g dry weight |

Pomegranate (Punica granatum) fruits are ancient medicinal foods which have been used for centuries in folk medicine. They are consumed fresh and as juice, which is an excellent source of ellagitannins and ellagic acid. Ellagitannins in pomegranate fruit husk and juice include punicalin, punicalagin, corilagin, casuarinin, terminalin/gallagyldilacton, pedunculagin, tellimagrandin, granatin A, and granatin B. Other parts of the pomegranate plant contain additional ellagitannins, including punicafolin, punicacortein A, punicacortein B, punicacortein C, punicacortein D, and punigluconin. Commercial juices contain gallagyl-type ellagitannins, including punicalagin isomers (1500-1900 mg/L), undefined hydrolyzable tannins (400-500 mg/L), and ellagic acid and its glycosides (120-260 mg/L). Gil et al. (2000) J. Agric. Food Chem. 48:4581-4589. Punicalagins, ellagitannins in which gallagic and ellagic acids are linked to a glucose molecule, are abundant in pomegranate peel. Punicalagin isomers and ellagic acid derivatives are not present in the aril juice, but during industrial juice processing they are extracted from the husk and membrane surrounding the arils and released in large quantities into the juice.

Urolithins are metabolites of ellagic acid, punicalagin (PA), punicalin (PB), tellimagrandin (TL), and other ellagitannins. Ellagic acid (EA) is abundant in pomegranate juice. Gil et al. (2000) *J. Agric. Food Chem.* 48:4581-4589. The ellagitannin tellimagrandin (TL) has been previously isolated from pomegranate and other plants. Structural formulas for UA, PA, PB, EA, and TL are presented in FIG. 2.

Figure 3:
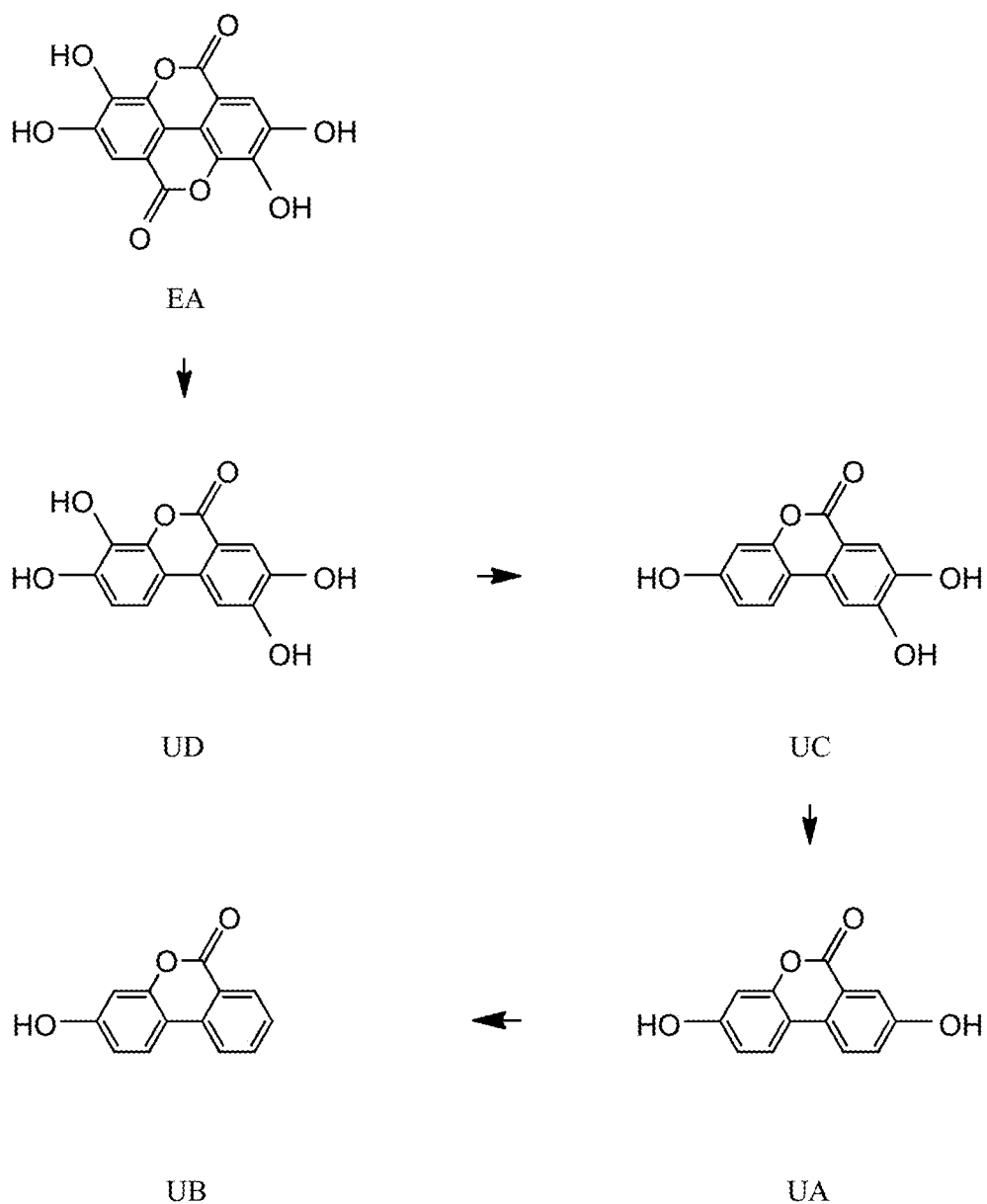
FIG. 3 depicts ellagic acid (EA) and its metabolites, urolithin D (UD), urolithin C (UC), urolithin A (UA), and urolithin B (UB), which are produced by intestinal microflora in mammals, including humans.

As mentioned above, ellagitannins generally are not absorbed in the gut. Rather, they release EA in the gut, which is only poorly absorbed in the stomach and small intestine. EA is largely metabolized by unidentified bacteria in the intestinal lumen to produce urolithins. Microbial metabolism starts in the small intestine and the first metabolites produced retain four phenolic hydroxyls (urolithin D, four hydroxyl groups), and these are further metabolized along the intestinal tract to remove hydroxyl units leading to urolithin C (three hydroxyls), urolithin A (two hydroxyls) and B (one hydroxyl) in the distal parts of the colon (FIG. 3). The absorbed metabolites are conjugated with glucuronic acid (one or two units), and/or methyl ethers (when orthodihydroxyl groupings are present). Urolithin A and B conjugates are the main metabolites detected in plasma and urine, although some trihydroxy derivatives (hydroxyl-UA) or EA-dimethyl ether glucuronide have also been detected in smaller amounts. The tetrahydroxy-urolithins, trihydroxy-urolithins, and EA derivatives generally are not detected in peripheral plasma, but they are absorbed in the small intestine and they are transported to the liver where they are further metabolized and excreted with bile to the small intestine establishing an enterohepatic circulation that is responsible for the relatively long life of urolithins in plasma and urine.

In addition to natural food sources, many papers have appeared on the biosynthesis, isolation, and biological activity of tannins, especially ellagitannins, over the last twenty years. Access to pure ellagitannins by isolation from natural sources may be cumbersome and yield only relatively small quantities of pure natural products. See, for example, Okuda et al., (1982) *Chem Pharm Bull.* 30:4230-4233; Okuda et al. (1982) *Chem Pharm Bull.* 30:234-4236. It is therefore notable that methods for total synthesis of many ellagitannins are known. See, for example, Khanbabaee, K., Strategies for the synthesis of ellagitannins, In: Chemistry and Biology of Ellagitannins, Ed. S. Quideau, World Scientific Publishing, Singapore, 2009, pp. 152-202, including references cited therein.

Methods of Increasing Autophagy, Increasing Longevity, and Treating or Preventing Diseases and Disorders Using Urolithins and Related Compounds In certain embodiments, the invention provides methods of increasing or enhancing autophagy, both in vivo and in vitro, methods of increasing longevity, and methods of treating or preventing various diseases and conditions using urolithins and precursors thereof. In particular embodiments, a disease or disorder treated or prevented according to the present invention is a disease or disorder associated with reduced autophagy, or which would benefit from increased autophagy, including but not limited to any of the diseases and conditions described herein.

An aspect of the invention is a method of treating or preventing a disease or condition associated with, or characterized by, reduced or decreased autophagy, or which would benefit from increased autophagy. The method includes the step of administering to a subject in need thereof a therapeutically effective amount of a urolithin or precursor thereof. In particular embodiments, any of the urolithins or precursors thereof described herein may be used to practice any aspect of the invention.

As used herein, unless the context makes clear otherwise, "treat," and similar words such as "treatment," "treated," "treating," etc., indicates an approach for obtaining beneficial or desired results, including clinical results. Treatment can involve optionally either the reduction or amelioration of symptoms of the disease or condition, or the delaying of the progression of the disease or condition. In some embodiments, treatment is achieved by reducing the duration of the disease or condition. Administration of a compound described herein may, in some embodiments, treat one or more of such symptoms.

As used herein, unless the context makes clear otherwise, "prevent," and similar words such as "prevention," "prevented," "preventing," etc., indicates an approach for preventing, inhibiting, or reducing the likelihood of the onset or recurrence of a disease or condition. It also refers to preventing, inhibiting, or reducing the likelihood of the occurrence or recurrence of the symptoms of a disease or condition, or optionally an approach for delaying the onset or recurrence of a disease or condition or delaying the occurrence or recurrence of the symptoms of a disease or condition. As used herein, "prevent" and similar words also includes reducing the intensity, effect, symptoms or burden of a disease or condition prior to onset or recurrence of the disease or condition.

An aspect of the invention is a method of increasing autophagy in a cell, comprising the step of contacting a cell with an effective amount of a urolithin or a precursor thereof to increase autophagy in the cell. In particular embodiments, the cell is present within a subject, e.g., a mammal. In addition, the invention includes a method of increasing autophagy in a cell, wherein the cell is present in a subject, e.g., a mammal, comprising the step of providing to the subject an effective amount of a urolithin or a precursor thereof to increase autophagy in the cell.

An aspect of the invention is a method of increasing autophagy in a cell, comprising the step of contacting a cell with an effective amount of a urolithin, or a precursor thereof, to increase autophagy in the cell.

In particular embodiments, a urolithin is a compound having a structure set forth in Formula I, Formula II, or Formula III, including any one of the specific compounds of Formula II or Formula III described herein. An "effective amount" as used herein refers to an amount that is sufficient to achieve or realize a specified or desired biological effect. For example, an effective amount of a urolithin to increase autophagy in a cell is an amount of a urolithin that is sufficient to increase autophagy in the cell.

An increase in autophagy in a cell can be measured using any suitable assay for measuring autophagy. For example, autophagy formation can be determined by using the fluorescent dye monodansylcadaverine (MDC) (Sigma-Aldrich, 30432). This dye selectively labels autophagic vacuoles. Biederbick A et al. (1995) *Eur. J. Cell. Biol.* 66:3-14. Autophagy may also be determined by examining the change in the ratio of the proteins involved in autophagy, such as LC3-II to LC3-I, for example, using Western blot analysis. With such a method, an increase in the LC3-II/LC3-I ratio in a treated cell above the baseline, untreated cells LC3-II/LC3-I ratio, would be considered as an increase in autophagy. Examination of other protein levels such as p62 may also help in the confirmation. For the purposes of calculating the percent (%) increase in autophagy in a cell, the ratio of LC3-II/LC3-I at baseline (B-Ratio) and the ratio of LC3-II/LC3-I during treatment (T-Ratio) may be employed. The percent (%) increase can be determined mathematically, for example, by the formula 100×[((T-Ratio)−(B-Ratio))/(B-Ratio)].

Autophagy is said to be increased in a cell if it is measurably greater than autophagy that is or would be present in an untreated or placebo control cell. In one embodiment autophagy is said to be increased in a cell if it is greater by a statistically significant amount or degree than autophagy that is or would be present in an untreated or placebo control cell. In certain embodiments, the increase in autophagy is an increase of at least 5%, at least 10%, at least 15%, at least 20%, at least 25%, at least 30%, at least 40%, at least 50%, at least 60%, at least 70%, at least 80%, at least 90%, at least 100%, at least 150%, at least 200%, at least 300%, at least 400%, at least 500%, at least 600%, at least 700%, at least 800%, at least 900%, at least 1,000% or greater than 1,000%, as compared to the level of autophagy present in an untreated cell or a cell treated with a placebo.

In certain embodiments, the increase in autophagy is an increase of 5-500%, 10-500%, 15-500%, 20-500%, 25-500%, 30-500%, 40-500%, 50-500%, 60-500%, at least 70-500%, 80-500%, 90-500%, 100-500%, 150-500%, 200-500%, 300-500%, or 400-500%, 5-1,000%, 10-500%, 15-1,000%, 20-1,000%, 25-1,000%, 30-1,000%, 40-1,000%, 50-1,000%, 60-1,000%, at least 70-1,000%, 80-1,000%, 90-1,000%, 100-1,000%, 150-1,000%, 200-1,000%, 300-1,000%, 400-1,000%, 500-1,000%, 600-1,000%, 700-1,000%, 800-1,000% or 900-1,000%, as compared to the level of autophagy present in an untreated cell or a cell treated with a placebo.

In one embodiment, the autophagy is mitophagy.

In one embodiment, the urolithin is an isolated urolithin.

In one embodiment, the urolithin is a purified urolithin.

In one embodiment, the urolithin is selected from the group consisting of urolithin A, urolithin B, urolithin C, urolithin D, and any combination thereof.

In one embodiment, the urolithin is urolithin A.

In one embodiment, the urolithin is urolithin B.

In one embodiment, the urolithin is urolithin C.

In one embodiment, the urolithin is urolithin D.

In certain embodiments, the urolithin is a compound of Formula I, Formula II, or Formula III, including any one of the specific compounds of these formulas described herein.

In one embodiment, the urolithin precursor is an isolated urolithin precursor.

In one embodiment, the urolithin precursor is a purified urolithin precursor.

In certain embodiments, the urolithin precursor is a compound of Formula IV, Formula V, or Formula VI, including any one of the specific compounds of these formulas described herein.

In one embodiment, the urolithin precursor is selected from the group consisting of ellagic acid, an ellagitannin, and any combination thereof.

In one embodiment, the urolithin precursor is ellagic acid.

In one embodiment, the urolithin precursor is an ellagitannin.

In one embodiment, the ellagitannin is selected from the group consisting of castalagin, castalin, casuarictin, chebulagic acid, chebulinic acid, gemin D, grandinin, pedunculagin, punicalagin, punicalin, roburin A, strictinin, tellimagrandin I, tellimagrandin II, terflavin A, terflavin B, tergallagin, Lambertianin C, Sanguiin H-6, Sanguiin H-10, and vescalagin.

In one embodiment, the cell is selected from the group consisting of: embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells. In one embodiment, the cell is selected from the group consisting of: endothelial cells, cells of the central and peripheral nervous system (neurons (all types) and glial cells (microglia, astroglia and oligodendrocytes, Schwann cells), keratinocytes (skin cells), retinal cells, immune cells, also hair cells and follicule stem cells, and cancer stem cells. In certain embodiments, the cells are embryonic stem cells. In certain embodiments, the cells are induced pluripotent stem cells. In certain embodiments, the cells are adult stem cells. In certain embodiments, the cells are hematopoietic stem cells. In certain embodiments the cells are cancer cells. In certain embodiments, the cells are present in an isolated organ or bloc of organs, such as an organ or bloc of organs harvested for transplantation or maintained ex vivo. In certain embodiments, the cells are present in a tissue or tissue slice. In various embodiments, the cells are contacted with the urolithin or precursor thereof in vivo, ex vivo, or in vitro.

An aspect of the invention is a method of increasing longevity in an animal, comprising the step of administering to an animal in need thereof an effective amount of a urolithin or a precursor thereof to increase autophagy in the animal, thereby increasing longevity of the animal.

The term "longevity" as used herein with reference to longevity of an animal refers to the lifespan of an individual organism. Although longevity can be measured in an individual organism, it is common to measure and compare mean or median longevity of populations of individual organisms. For example, longevity may be measured and compared as mean survival in an experimental treatment group and a suitably selected untreated or placebo control group. Longevity may also be considered in populations of individuals affected with a health condition in need of autophagy. Treatment of such individuals shall increase their longevity as compared to their untreated counterparts. In one embodiment, longevity is actual longevity. In one embodiment, longevity is actuarial longevity.

The term "longevity" as used herein with reference to longevity of eukaryotic cells in vitro refers to the lifespan of an individual cell. Although longevity can be measured for an individual cell, it is common to measure and compare mean or median longevity of populations of individual cells. For example, longevity may be measured and compared in terms of mean survival in an experimental treatment group and a suitably selected untreated or placebo control group. The term "longevity" also refers to the lifespan of a cell that is subjected to certain metabolic stresses. In one embodiment, metabolic stresses are due to nutrient deprivation, growth factor depletion, or hypoxia. For example, treatment of metabolically stressed cells by a urolithin or a precursor, either directly in vitro, ex vivo or in vivo by administration to a subject, would lead to an increase in the longevity of these metabolically stressed cells and in the case of ex vivo and in vivo treatment, an increased longevity of these metabolically stressed cells would improve the function of tissues which they comprise.

In one embodiment, longevity is said to be increased when it is at least 5 percent longer than untreated control. In various specific embodiments, longevity is said to be increased when it is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 percent longer than untreated control. In certain embodiments, longevity is increased by at least 10 percent compared to untreated control. In certain embodiments, longevity is increased by at least 20 percent compared to untreated control. In certain embodiments, longevity is increased by at least 30 percent compared to untreated control. In certain embodiments, longevity is increased by at least 40 percent compared to untreated control. In certain embodiments, longevity is increased by at least 50 percent compared to untreated control.

In one embodiment, longevity is said to be increased when it is at least 5 percent longer than placebo control. In various specific embodiments, longevity is said to be increased when it is at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 percent longer than placebo control. In certain embodiments, longevity is increased by at least 10 percent compared to placebo control. In certain embodiments, longevity is increased by at least 20 percent compared to placebo control. In certain embodiments, longevity is increased by at least 30 percent compared to placebo control. In certain embodiments, longevity is increased by at least 40 percent compared to placebo control. In certain embodiments, longevity is increased by at least 50 percent compared to placebo control.

In one embodiment, longevity is said to be increased when it is longer, by a statistically significant difference, compared to untreated control. In one embodiment, the statistical significance of the difference is $p \leq 0.05$. In one embodiment, the statistical significance of the difference is $p \leq 0.01$. In one embodiment, the statistical significance of the difference is $p \leq 0.005$. In one embodiment, the statistical significance of the difference is $p \leq 0.001$.

In one embodiment, longevity is said to be increased when it is longer, by a statistically significant difference, compared to placebo control. In one embodiment, the statistical significance of the difference is $p \leq 0.05$. In one embodiment, the statistical significance of the difference is $p \leq 0.01$. In one embodiment, the statistical significance of the difference is $p \leq 0.005$. In one embodiment, the statistical significance of the difference is $p \leq 0.001$.

An animal is any multicellular eukaryote belonging to the kingdom Animalia. In one embodiment an animal is an invertebrate, for example a nematode (e.g., *C. elegans*) or a fruit fly (e.g., *D. melanogaster*). In one embodiment, an animal is a vertebrate, for example a fish or a mammal. In one embodiment, an animal is a mammal. In one embodiment, an animal is a primate. In one embodiment, an animal is a human. In certain embodiments, an animal is a domestic animal, such as a dog or a cat. In certain embodiments, an animal is a livestock, such as a horse, a cow, or a sheep.

In one embodiment, the urolithin is an isolated urolithin.

In one embodiment, the urolithin is a purified urolithin.

In one embodiment, the urolithin is selected from the group consisting of urolithin A, urolithin B, urolithin C, urolithin D, and any combination thereof.

In one embodiment, the urolithin is urolithin A.
In one embodiment, the urolithin is urolithin B.
In one embodiment, the urolithin is urolithin C.
In one embodiment, the urolithin is urolithin D.

In certain embodiments, the urolithin is a compound of Formula I, Formula II, or Formula III, including any one of the specific compounds of these formulas described herein.

In one embodiment, the urolithin precursor is an isolated urolithin precursor.

In one embodiment, the urolithin precursor is a purified urolithin precursor.

In certain embodiments, the urolithin precursor is a compound of Formula IV, Formula V, or Formula VI, including any one of the specific compounds of these formulas described herein.

In one embodiment, the urolithin precursor is selected from the group consisting of ellagic acid, an ellagitannin, and any combination thereof.

In one embodiment, the urolithin precursor is ellagic acid.

In one embodiment, the urolithin precursor is an ellagitannin.

In one embodiment, the ellagitannin is selected from the group consisting of castalagin, castalin, casuarictin, chebulagic acid, chebulinic acid, gemin D, grandinin, pedunculagin, punicalagin, punicalin, roburin A, strictinin, tellimagrandin I, tellimagrandin II, terflavin A, terflavin B, tergallagin, Lambertianin C, Sanguiin H-6, Sanguiin H-10, and vescalagin.

An aspect of the invention is a method of increasing longevity of eukaryotic cells in vitro, the method comprising the step of contacting eukaryotic cells in vitro with an effective amount of a urolithin to increase autophagy in the cells, thereby increasing longevity of the eukaryotic cells in vitro.

In accordance with the invention, urolithins can be used as a cell culture reagent to help promote the growth and preservation of cells and tissues in culture. It is believed urolithin has the potential to keep primary cells and tissues alive for extended periods of time, which means that they could be used for a wide range of in vitro applications, including: (i) routine cell culture in research labs of cell lines, primary cells of any origin (i.e., recently isolated from humans or animals); and (ii) tissues or organs that are maintained in culture. For both cells and tissues maintained in culture, this could also have in vitro diagnostic applications as well as therapeutic applications, such as: tissue expansion, protection during transport (for transplantation into humans), for cell therapy applications using primary cells which need to be stored frozen, so may be part of a special solution for cell freezing. The invention includes a method of culturing or preserving cells or tissue, comprising growing or culturing the cells or tissue in a culture medium comprising a urolithin. Cell culture media suitable for culturing and growing various cells and tissues are known in the art and commercially available.

Urolithins and precursors thereof may also find use as positive controls when testing for autophagy and improved mitochondrial function in a cell, tissue, or organism. For example, a urolithin can be used separately or included as part of a kit useful to examine mitochondrial function or longevity-related pathways such as the mTOR pathway.

In one embodiment, the autophagy is mitophagy.
In one embodiment, the urolithin is an isolated urolithin.
In one embodiment, the urolithin is a purified urolithin.
In one embodiment, the urolithin is selected from the group consisting of urolithin A, urolithin B, urolithin C, urolithin D, and any combination thereof.
In one embodiment, the urolithin is urolithin A.
In one embodiment, the urolithin is urolithin B.
In one embodiment, the urolithin is urolithin C.
In one embodiment, the urolithin is urolithin D.

In certain embodiments, the urolithin is a compound of Formula I, Formula II, or Formula III, including any one of the specific compounds of these formulas described herein.

In one embodiment, the urolithin precursor is an isolated urolithin precursor.

In one embodiment, the urolithin precursor is a purified urolithin precursor.

In certain embodiments, the urolithin precursor is a compound of Formula IV, Formula V, or Formula VI, including any one of the specific compounds of these formulas described herein.

In one embodiment, the urolithin precursor is selected from the group consisting of ellagic acid, an ellagitannin, and any combination thereof.

In one embodiment, the urolithin precursor is ellagic acid.

In one embodiment, the urolithin precursor is an ellagitannin.

In one embodiment, the ellagitannin is selected from the group consisting of castalagin, castalin, casuarictin, chebulagic acid, chebulinic acid, gemin D, grandinin, pedunculagin, punicalagin, punicalin, roburin A, strictinin, tellimagrandin I, tellimagrandin II, terflavin A, terflavin B, tergallagin, Lambertianin C, Sanguiin H-6, Sanguiin H-10, and vescalagin.

In one embodiment, the eukaryotic cells are eukaryotic cells in primary culture.

In one embodiment, the eukaryotic cells are part of a cell line.

In one embodiment, the eukaryotic cells are selected from the group consisting of: embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells. In certain embodiments, the cells are embryonic stem cells. In certain embodiments, the cells are induced pluripotent stem cells. In one embodiment, the cell is selected from the group consisting of: endothelial cells, cells of the central and peripheral nervous system (neurons (all types) and glial cells (microglia, astroglia and oligodendrocytes, Schwann cells), keratinocytes (skin cells), retinal cells, immune cells, also hair cells and follicle stem cells, and cancer stem cells. In certain embodiments, the cells are adult stem cells. In certain embodiments, the cells are hematopoietic stem cells. In certain embodiments the cells are cancer cells.

In certain embodiments, the cell is present in an isolated tissue or organ or portion or sample thereof. In certain embodiments, the cells are present in an isolated organ or bloc of organs, such as an organ or bloc of organs harvested for transplantation or maintained ex vivo. In certain embodiments, the cells are present in a tissue or tissue slice.

In particular embodiments, the cell is present in a primary culture, i.e., a "primary cell." As used herein, "primary culture" refers to cells cultured directly from a tissue or a subject. In one embodiment, a primary culture includes two or more types of cells. In one embodiment, a primary culture includes a single type of cell, e.g., endothelial cells. Cells in primary culture often can have only a limited number of passages or divisions.

In particular embodiments, the cell is present in a cell line. As used herein, a "cell line" refers to an established, immortalized, and genetically homogeneous population of cells derived from a eukaryotic animal and maintained in vitro. In one embodiment, a cell line is derived from a mammal. In one embodiment, a cell line is derived from a human. Cell lines of many types are available from a number of commercial suppliers, including, for example, American Type Culture Collection (ATCC), Manassas, Virginia.

In certain embodiments, the invention relates to a method of increasing autophagy in a cell, comprising contacting the cell with an effective amount of a compound selected from the group consisting of: a compound of Formula II, a compound of Formula III, a compound of Formula V, a compound of Formula VI, urolithin A, urolithin B, urolithin C, urolithin D, and ellagic acid, thereby increasing autophagy in the cell.

In certain embodiments, the invention relates to any one of the aforementioned methods, wherein the autophagy is mitophagy.

In certain embodiments, the invention relates to any one of the aforementioned methods, wherein the compound is urolithin A.

In certain embodiments, the invention relates to any one of the aforementioned methods, wherein the compound is urolithin B.

In certain embodiments, the invention relates to any one of the aforementioned methods, wherein the compound is urolithin C.

In certain embodiments, the invention relates to any one of the aforementioned methods, wherein the compound is urolithin D.

In certain embodiments, the invention relates to any one of the aforementioned methods, wherein the compound is ellagic acid.

In certain embodiments, the invention relates to any one of the aforementioned methods, wherein the cell is selected from the group consisting of: embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells.

In certain embodiments, the invention relates to a method of increasing longevity in an animal, comprising administering to an animal in need thereof an effective amount of a compound selected from the group consisting of: a compound of Formula II, a compound of Formula III, a compound of Formula V, a compound of Formula VI, urolithin A, urolithin B, urolithin C, urolithin D, and ellagic acid, thereby increasing longevity of the animal.

In certain embodiments, the invention relates to any one of the aforementioned methods, wherein the compound is urolithin A.

In certain embodiments, the invention relates to any one of the aforementioned methods, wherein the compound is urolithin B.

In certain embodiments, the invention relates to any one of the aforementioned methods, wherein the compound is urolithin C.

In certain embodiments, the invention relates to any one of the aforementioned methods, wherein the compound is urolithin D.

In certain embodiments, the invention relates to any one of the aforementioned methods, wherein the compound is ellagic acid.

In certain embodiments, the invention relates to any one of the aforementioned methods, wherein the animal is a mammal.

In certain embodiments, the invention relates to any one of the aforementioned methods, wherein the mammal is a human.

In certain embodiments, the invention relates to a method of increasing longevity of eukaryotic cells in vitro, comprising contacting eukaryotic cells in vitro with an effective amount of a compound selected from the group consisting of: a compound of Formula II, a compound of Formula III, a compound of Formula V, a compound of Formula VI, urolithin A, urolithin B, urolithin C, urolithin D, and ellagic acid, thereby increasing longevity of the eukaryotic cells in vitro.

In certain embodiments, the invention relates to any one of the aforementioned methods, wherein the compound is urolithin A.

In certain embodiments, the invention relates to any one of the aforementioned methods, wherein the compound is urolithin B.

In certain embodiments, the invention relates to any one of the aforementioned methods, wherein the compound is urolithin C.

In certain embodiments, the invention relates to any one of the aforementioned methods, wherein the compound is urolithin D.

In certain embodiments, the invention relates to any one of the aforementioned methods, wherein the compound is ellagic acid.

In certain embodiments, the invention relates to any one of the aforementioned methods, wherein the eukaryotic cells are eukaryotic cells in primary culture.

In certain embodiments, the invention relates to any one of the aforementioned methods, wherein the eukaryotic cells are part of a cell line.

In certain embodiments, the invention relates to any one of the aforementioned methods, wherein the eukaryotic cells are cells selected from the group consisting of: embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells.

In certain embodiments, the invention relates to any one of the aforementioned methods, wherein the eukaryotic cells are cells selected from the group consisting of: embryonic stem cells, induced pluripotent stem cells, and adult stem cells.

In certain embodiments, the invention relates to a method of increasing autophagy in a cell, comprising contacting the cell with an effective amount of a compound of Formula I, thereby increasing autophagy in the cell;
wherein the compound of Formula I is

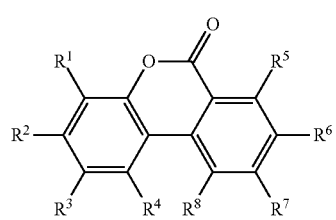

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to any one of the aforementioned methods, wherein the autophagy is mitophagy.

In certain embodiments, the invention relates to any one of the aforementioned methods, wherein the cell is selected from the group consisting of: embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells.

In certain embodiments, the invention relates to a method of increasing longevity in an animal, comprising administering to an animal in need thereof an effective amount of a compound of Formula I, thereby increasing longevity of the animal,
wherein the compound of Formula I is

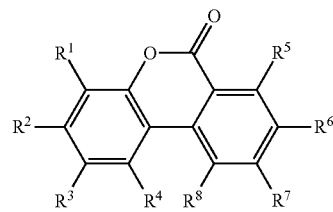

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to any one of the aforementioned methods, wherein the animal is a mammal.

In certain embodiments, the invention relates to any one of the aforementioned methods, wherein the mammal is a human.

In certain embodiments, the invention relates to a method of increasing longevity of eukaryotic cells in vitro, comprising contacting eukaryotic cells in vitro with an effective amount of a compound of Formula I, thereby increasing longevity of the eukaryotic cells in vitro,
wherein the compound of Formula I is

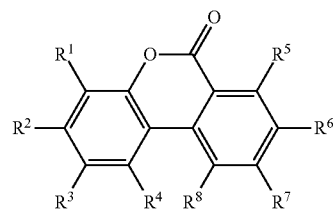

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to any one of the aforementioned methods, wherein the eukaryotic cells are eukaryotic cells in primary culture.

In certain embodiments, the invention relates to any one of the aforementioned methods, wherein the eukaryotic cells are part of a cell line.

In certain embodiments, the invention relates to any one of the aforementioned methods, wherein the eukaryotic cells are cells selected from the group consisting of: embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells.

In certain embodiments, the invention relates to any one of the aforementioned methods, wherein the eukaryotic cells are cells selected from the group consisting of: embryonic stem cells, induced pluripotent stem cells, and adult stem cells.

In certain embodiments, the invention relates to any one of the aforementioned methods, wherein $R^1$, $R^2$, $R^3$, $R^4$, $R^5$, $R^6$, $R^7$, and $R^8$ are H.

In certain embodiments, the invention relates to any one of the aforementioned methods, wherein at least one of $R^1$, $R^2$, $R^3$, $R^4$, $R^5$, $R^6$, $R^7$, and $R^8$ is OR.

In certain embodiments, the invention relates to any one of the aforementioned methods, wherein at least two of $R^1$, $R^2$, $R^3$, $R^4$, $R^5$, $R^6$, $R^7$, and $R^8$ are OR.

In certain embodiments, the invention relates to any one of the aforementioned methods, wherein at least three of $R^1$, $R^2$, $R^3$, $R^4$, $R^5$, $R^6$, $R^7$, and $R^8$ are OR.

In certain embodiments, the invention relates to any one of the aforementioned methods, wherein at least four of $R^1$, $R^2$, $R^3$, $R^4$, $R^5$, $R^6$, $R^7$, and $R^8$ are OR.

In certain embodiments, the invention relates to any one of the aforementioned methods, wherein at least five of $R^1$, $R^2$, $R^3$, $R^4$, $R^5$, $R^6$, $R^7$, and $R^8$ are OR.

In certain embodiments, the invention relates to any one of the aforementioned methods, wherein at least six of $R^1$, $R^2$, $R^3$, $R^4$, $R^5$, $R^6$, $R^7$, and $R^8$ are OR.

In certain embodiments, the invention relates to any one of the aforementioned methods, wherein at least seven of $R^1$, $R^2$, $R^3$, $R^4$, $R^5$, $R^6$, $R^7$, and $R^8$ are OR.

In certain embodiments, the invention relates to any one of the aforementioned methods, wherein $R^1$, $R^2$, $R^3$, $R^4$, $R^5$, $R^6$, $R^7$, and $R^8$ are OR.

In certain embodiments, the invention relates to any one of the aforementioned methods, wherein $R^1$ is OR; and $R^2$, $R^3$, $R^4$, $R^5$, $R^6$, $R^7$, and $R^8$ are H.

In certain embodiments, the invention relates to any one of the aforementioned methods, wherein $R^2$ is OR; and $R^1$, $R^3$, $R^4$, $R^5$, $R^6$, $R^7$, and $R^8$ are H.

In certain embodiments, the invention relates to any one of the aforementioned methods, wherein $R^3$ is OR; and $R^1$, $R^2$, $R^4$, $R^5$, $R^6$, $R^7$, and $R^8$ are H.

In certain embodiments, the invention relates to any one of the aforementioned methods, wherein $R^4$ is OR; and $R^1$, $R^2$, $R^3$, $R^5$, $R^6$, $R^7$, and $R^8$ are H.

In certain embodiments, the invention relates to any one of the aforementioned methods, wherein $R^5$ is OR; and $R^1$, $R^2$, $R^3$, $R^4$, $R^6$, $R^7$, and $R^8$ are H.

In certain embodiments, the invention relates to any one of the aforementioned methods, wherein $R^6$ is OR; and $R^1$, $R^2$, $R^3$, $R^4$, $R^5$, $R^7$, and $R^8$ are H.

In certain embodiments, the invention relates to any one of the aforementioned methods, wherein $R^7$ is OR; and $R^1$, $R^2$, $R^3$, $R^4$, $R^5$, $R^6$, and $R^8$ are H.

In certain embodiments, the invention relates to any one of the aforementioned methods, wherein $R^8$ is OR; and $R^1$, $R^2$, $R^3$, $R^4$, $R^5$, $R^6$, and $R^7$ are H.

In certain embodiments, the invention relates to any one of the aforementioned methods, wherein $R^1$ and $R^2$ are OR; and $R^3$, $R^4$, $R^5$, $R^6$, $R^7$, and $R^8$ are H.

In certain embodiments, the invention relates to any one of the aforementioned methods, wherein $R^1$ and $R^3$ are OR; and $R^2$, $R^4$, $R^5$, $R^6$, $R^7$, and $R^8$ are H.

In certain embodiments, the invention relates to any one of the aforementioned methods, wherein $R^1$ and $R^4$ are OR; and $R^2$, $R^3$, $R^5$, $R^6$, $R^7$, and $R^8$ are H.

In certain embodiments, the invention relates to any one of the aforementioned methods, wherein $R^1$ and $R^5$ are OR; and $R^2$, $R^3$, $R^4$, $R^6$, $R^7$, and $R^8$ are H.

In certain embodiments, the invention relates to any one of the aforementioned methods, wherein $R^1$ and $R^6$ are OR; and $R^2$, $R^3$, $R^4$, $R^5$, $R^7$, and $R^8$ are H.

In certain embodiments, the invention relates to any one of the aforementioned methods, wherein $R^1$ and $R^7$ are OR; and $R^2$, $R^3$, $R^4$, $R^5$, $R^6$, and $R^8$ are H.

In certain embodiments, the invention relates to any one of the aforementioned methods, wherein $R^1$ and $R^8$ are OR; and $R^2$, $R^3$, $R^4$, $R^5$, $R^6$, and $R^7$ are H.

In certain embodiments, the invention relates to any one of the aforementioned methods, wherein $R^2$ and $R^3$ are OR; and $R^1$, $R^4$, $R^5$, $R^6$, $R^7$, and $R^8$ are H.

In certain embodiments, the invention relates to any one of the aforementioned methods, wherein $R^2$ and $R^4$ are OR; and $R^1$, $R^3$, $R^5$, $R^6$, $R^7$, and $R^8$ are H.

In certain embodiments, the invention relates to any one of the aforementioned methods, wherein $R^2$ and $R^5$ are OR; and $R^1$, $R^3$, $R^4$, $R^6$, $R^7$, and $R^8$ are H.

In certain embodiments, the invention relates to any one of the aforementioned methods, wherein $R^2$ and $R^6$ are OR; and $R^1$, $R^3$, $R^4$, $R^5$, $R^7$, and $R^8$ are H.

In certain embodiments, the invention relates to any one of the aforementioned methods, wherein $R^2$ and $R^7$ are OR; and $R^1$, $R^3$, $R^4$, $R^5$, $R^6$, and $R^8$ are H.

In certain embodiments, the invention relates to any one of the aforementioned methods, wherein $R^2$ and $R^8$ are OR; and $R^1$, $R^3$, $R^4$, $R^5$, $R^6$, and $R^7$ are H.

In certain embodiments, the invention relates to any one of the aforementioned methods, wherein $R^3$ and $R^4$ are OR; and $R^1$, $R^2$, $R^5$, $R^6$, $R^7$, and $R^8$ are H.

In certain embodiments, the invention relates to any one of the aforementioned methods, wherein $R^3$ and $R^5$ are OR; and $R^1$, $R^2$, $R^4$, $R^6$, $R^7$, and $R^8$ are H.

In certain embodiments, the invention relates to any one of the aforementioned methods, wherein $R^3$ and $R^6$ are OR; and $R^1$, $R^2$, $R^4$, $R^5$, $R^7$, and $R^8$ are H.

In certain embodiments, the invention relates to any one of the aforementioned methods, wherein $R^3$ and $R^7$ are OR; and $R^1$, $R^2$, $R^4$, $R^5$, $R^6$, and $R^8$ are H.

In certain embodiments, the invention relates to any one of the aforementioned methods, wherein $R^3$ and $R^8$ are OR; and $R^1$, $R^2$, $R^4$, $R^5$, $R^6$, and $R^7$ are H.

In certain embodiments, the invention relates to any one of the aforementioned methods, wherein $R^4$ and $R^5$ are OR; and $R^1$, $R^2$, $R^3$, $R^6$, $R^7$, and $R^8$ are H.

In certain embodiments, the invention relates to any one of the aforementioned methods, wherein $R^4$ and $R^6$ are OR; and $R^1$, $R^2$, $R^3$, $R^5$, $R^7$, and $R^8$ are H.

In certain embodiments, the invention relates to any one of the aforementioned methods, wherein $R^4$ and $R^7$ are OR; and $R^1$, $R^2$, $R^3$, $R^5$, $R^6$, and $R^8$ are H.

In certain embodiments, the invention relates to any one of the aforementioned methods, wherein $R^4$ and $R^8$ are OR; and $R^1$, $R^2$, $R^3$, $R^5$, $R^6$, and $R^7$ are H.

In certain embodiments, the invention relates to any one of the aforementioned methods, wherein $R^5$ and $R^6$ are OR; and $R^1$, $R^2$, $R^3$, $R^4$, $R^7$, and $R^8$ are H.

In certain embodiments, the invention relates to any one of the aforementioned methods, wherein $R^5$ and $R^7$ are OR; and $R^1$, $R^2$, $R^3$, $R^4$, $R^6$, and $R^8$ are H.

In certain embodiments, the invention relates to any one of the aforementioned methods, wherein $R^5$ and $R^8$ are OR; and $R^1$, $R^2$, $R^3$, $R^4$, $R^6$, and $R^7$ are H.

In certain embodiments, the invention relates to any one of the aforementioned methods, wherein $R^6$ and $R^7$ are OR; and $R^1$, $R^2$, $R^3$, $R^4$, $R^5$, and $R^8$ are H.

In certain embodiments, the invention relates to any one of the aforementioned methods, wherein $R^6$ and $R^8$ are OR; and $R^1$, $R^2$, $R^3$, $R^4$, $R^5$, and $R^7$ are H.

In certain embodiments, the invention relates to any one of the aforementioned methods, wherein $R^7$ and $R^8$ are OR; and $R^1$, $R^2$, $R^3$, $R^4$, $R^5$, and $R^6$ are H.

In certain embodiments, the invention relates to any one of the aforementioned methods, wherein $R^1$, $R^2$, and $R^3$ are OR; and $R^4$, $R^5$, $R^6$, $R^7$, and $R^8$ are H.

In certain embodiments, the invention relates to any one of the aforementioned methods, wherein $R^1$, $R^2$, and $R^4$ are OR; and $R^3$, $R^5$, $R^6$, $R^7$, and $R^8$ are H.

In certain embodiments, the invention relates to any one of the aforementioned methods, wherein $R^1$, $R^2$, and $R^5$ are OR; and $R^3$, $R^4$, $R^6$, $R^7$, and $R^8$ are H.

In certain embodiments, the invention relates to any one of the aforementioned methods, wherein $R^1$, $R^2$, and $R^6$ are OR; and $R^3$, $R^4$, $R^5$, $R^7$, and $R^8$ are H.

In certain embodiments, the invention relates to any one of the aforementioned methods, wherein $R^1$, $R^2$, and $R^7$ are OR; and $R^3$, $R^4$, $R^5$, $R^6$, and $R^8$ are H.

In certain embodiments, the invention relates to any one of the aforementioned methods, wherein $R^1$, $R^2$, and $R^8$ are OR; and $R^3$, $R^4$, $R^5$, $R^6$, and $R^7$ are H.

In certain embodiments, the invention relates to any one of the aforementioned methods, wherein $R^1$, $R^3$, and $R^4$ are OR; and $R^2$, $R^5$, $R^6$, $R^7$, and $R^8$ are H.

In certain embodiments, the invention relates to any one of the aforementioned methods, wherein $R^1$, $R^3$, and $R^5$ are OR; and $R^2$, $R^4$, $R^6$, $R^7$, and $R^8$ are H.

In certain embodiments, the invention relates to any one of the aforementioned methods, wherein $R^1$, $R^3$, and $R^6$ are OR; and $R^2$, $R^4$, $R^5$, $R^7$, and $R^8$ are H.

In certain embodiments, the invention relates to any one of the aforementioned methods, wherein $R^1$, $R^3$, and $R^7$ are OR; and $R^2$, $R^4$, $R^5$, $R^6$, and $R^8$ are H.

In certain embodiments, the invention relates to any one of the aforementioned methods, wherein $R^1$, $R^3$, and $R^8$ are OR; and $R^2$, $R^4$, $R^5$, $R^6$, and $R^7$ are H.

In certain embodiments, the invention relates to any one of the aforementioned methods, wherein $R^1$, $R^4$, and $R^5$ are OR; and $R^2$, $R^3$, $R^6$, $R^7$, and $R^8$ are H.

In certain embodiments, the invention relates to any one of the aforementioned methods, wherein $R^1$, $R^4$, and $R^6$ are OR; and $R^2$, $R^3$, $R^5$, $R^7$, and $R^8$ are H.

In certain embodiments, the invention relates to any one of the aforementioned methods, wherein $R^1$, $R^4$, and $R^7$ are OR; and $R^2$, $R^3$, $R^5$, $R^6$, and $R^8$ are H.

In certain embodiments, the invention relates to any one of the aforementioned methods, wherein $R^1$, $R^4$, and $R^8$ are OR; and $R^2$, $R^3$, $R^5$, $R^6$, and $R^7$ are H.

In certain embodiments, the invention relates to any one of the aforementioned methods, wherein $R^1$, $R^5$, and $R^6$ are OR; and $R^2$, $R^3$, $R^4$, $R^7$, and $R^8$ are H.

In certain embodiments, the invention relates to any one of the aforementioned methods, wherein $R^1$, $R^5$, and $R^7$ are OR; and $R^2$, $R^3$, $R^4$, $R^6$, and $R^8$ are H.

In certain embodiments, the invention relates to any one of the aforementioned methods, wherein $R^1$, $R^5$, and $R^8$ are OR; and $R^2$, $R^3$, $R^4$, $R^6$, and $R^7$ are H.

In certain embodiments, the invention relates to any one of the aforementioned methods, wherein $R^1$, $R^6$, and $R^7$ are OR; and $R^2$, $R^3$, $R^4$, $R^5$, and $R^8$ are H.

In certain embodiments, the invention relates to any one of the aforementioned methods, wherein $R^1$, $R^6$, and $R^8$ are OR; and $R^2$, $R^3$, $R^4$, $R^5$, and $R^7$ are H.

In certain embodiments, the invention relates to any one of the aforementioned methods, wherein $R^1$, $R^7$, and $R^8$ are OR; and $R^2$, $R^3$, $R^4$, $R^5$, and $R^7$ are H.

In certain embodiments, the invention relates to any one of the aforementioned methods, wherein $R^2$, $R^3$, and $R^4$ are OR; and $R^1$, $R^5$, $R^6$, $R^7$, and $R^8$ are H.

In certain embodiments, the invention relates to any one of the aforementioned methods, wherein $R^2$, $R^3$, and $R^5$ are OR; and $R^1$, $R^4$, $R^6$, $R^7$, and $R^8$ are H.

In certain embodiments, the invention relates to any one of the aforementioned methods, wherein $R^2$, $R^3$, and $R^6$ are OR; and $R^1$, $R^4$, $R^5$, $R^7$, and $R^8$ are H.

In certain embodiments, the invention relates to any one of the aforementioned methods, wherein $R^2$, $R^3$, and $R^7$ are OR; and $R^1$, $R^4$, $R^5$, $R^6$, and $R^8$ are H.

In certain embodiments, the invention relates to any one of the aforementioned methods, wherein $R^2$, $R^3$, and $R^8$ are OR; and $R^1$, $R^4$, $R^5$, $R^6$, and $R^7$ are H.

In certain embodiments, the invention relates to any one of the aforementioned methods, wherein $R^2$, $R^4$, and $R^5$ are OR; and $R^1$, $R^3$, $R^6$, $R^7$, and $R^8$ are H.

In certain embodiments, the invention relates to any one of the aforementioned methods, wherein $R^2$, $R^4$, and $R^6$ are OR; and $R^1$, $R^3$, $R^5$, $R^7$, and $R^8$ are H.

In certain embodiments, the invention relates to any one of the aforementioned methods, wherein $R^2$, $R^4$, and $R^7$ are OR; and $R^1$, $R^3$, $R^5$, $R^6$, and $R^8$ are H.

In certain embodiments, the invention relates to any one of the aforementioned methods, wherein $R^2$, $R^4$, and $R^8$ are OR; and $R^1$, $R^3$, $R^5$, $R^6$, and $R^7$ are H.

In certain embodiments, the invention relates to any one of the aforementioned methods, wherein $R^2$, $R^5$, and $R^6$ are OR; and $R^1$, $R^3$, $R^4$, $R^7$, and $R^8$ are H.

In certain embodiments, the invention relates to any one of the aforementioned methods, wherein $R^2$, $R^5$, and $R^7$ are OR; and $R^1$, $R^3$, $R^4$, $R^6$, and $R^8$ are H.

In certain embodiments, the invention relates to any one of the aforementioned methods, wherein $R^2$, $R^5$, and $R^8$ are OR; and $R^1$, $R^3$, $R^4$, $R^7$, and $R^8$ are H.

In certain embodiments, the invention relates to any one of the aforementioned methods, wherein $R^2$, $R^6$, and $R^7$ are OR; and $R^1$, $R^3$, $R^4$, $R^5$, and $R^8$ are H.

In certain embodiments, the invention relates to any one of the aforementioned methods, wherein $R^2$, $R^6$, and $R^8$ are OR; and $R^1$, $R^3$, $R^4$, $R^5$, and $R^7$ are H.

In certain embodiments, the invention relates to any one of the aforementioned methods, wherein $R^2$, $R^7$, and $R^8$ are OR; and $R^1$, $R^3$, $R^4$, $R^5$, and $R^6$ are H.

In certain embodiments, the invention relates to any one of the aforementioned methods, wherein $R^3$, $R^4$, and $R^5$ are OR; and $R^1$, $R^2$, $R^6$, $R^7$, and $R^8$ are H.

In certain embodiments, the invention relates to any one of the aforementioned methods, wherein $R^3$, $R^4$, and $R^6$ are OR; and $R^1$, $R^2$, $R^5$, $R^7$, and $R^8$ are H.

In certain embodiments, the invention relates to any one of the aforementioned methods, wherein $R^3$, $R^4$, and $R^7$ are OR; and $R^1$, $R^2$, $R^5$, $R^6$, and $R^8$ are H.

In certain embodiments, the invention relates to any one of the aforementioned methods, wherein $R^3$, $R^4$, and $R^8$ are OR; and $R^1$, $R^2$, $R^5$, $R^6$, and $R^7$ are H.

In certain embodiments, the invention relates to any one of the aforementioned methods, wherein $R^3$, $R^5$, and $R^6$ are OR; and $R^1$, $R^2$, $R^4$, $R^7$, and $R^8$ are H.

In certain embodiments, the invention relates to any one of the aforementioned methods, wherein $R^3$, $R^5$, and $R^7$ are OR; and $R^1$, $R^2$, $R^4$, $R^6$, and $R^8$ are H.

In certain embodiments, the invention relates to any one of the aforementioned methods, wherein $R^3$, $R^5$, and $R^8$ are OR; and $R^1$, $R^2$, $R^4$, $R^6$, and $R^7$ are H.

In certain embodiments, the invention relates to any one of the aforementioned methods, wherein $R^3$, $R^6$, and $R^7$ are OR; and $R^1$, $R^2$, $R^4$, $R^5$, and $R^8$ are H.

In certain embodiments, the invention relates to any one of the aforementioned methods, wherein $R^3$, $R^6$, and $R^8$ are OR; and $R^1$, $R^2$, $R^4$, $R^5$, and $R^7$ are H.

In certain embodiments, the invention relates to any one of the aforementioned methods, wherein $R^3$, $R^7$, and $R^8$ are OR; and $R^1$, $R^2$, $R^4$, $R^5$, and $R^6$ are H.

In certain embodiments, the invention relates to any one of the aforementioned methods, wherein $R^4$, $R^5$, and $R^6$ are OR; and $R^1$, $R^2$, $R^3$, $R^7$, and $R^8$ are H.

In certain embodiments, the invention relates to any one of the aforementioned methods, wherein $R^4$, $R^5$, and $R^7$ are OR; and $R^1$, $R^2$, $R^3$, $R^6$, and $R^8$ are H.

In certain embodiments, the invention relates to any one of the aforementioned methods, wherein $R^4$, $R^5$, and $R^8$ are OR; and $R^1$, $R^2$, $R^3$, $R^6$, and $R^7$ are H.

In certain embodiments, the invention relates to any one of the aforementioned methods, wherein $R^4$, $R^6$, and $R^7$ are OR; and $R^1$, $R^2$, $R^3$, $R^5$, and $R^8$ are H.

In certain embodiments, the invention relates to any one of the aforementioned methods, wherein $R^4$, $R^6$, and $R^8$ are OR; and $R^1$, $R^2$, $R^3$, $R^5$, and $R^7$ are H.

In certain embodiments, the invention relates to any one of the aforementioned methods, wherein $R^4$, $R^7$, and $R^8$ are OR; and $R^1$, $R^2$, $R^3$, $R^5$, and $R^6$ are H.

In certain embodiments, the invention relates to any one of the aforementioned methods, wherein $R^5$, $R^6$, and $R^7$ are OR; and $R^1$, $R^2$, $R^3$, $R^4$, and $R^8$ are H.

In certain embodiments, the invention relates to any one of the aforementioned methods, wherein $R^5$, $R^6$, and $R^8$ are OR; and $R^1$, $R^2$, $R^3$, $R^4$, and $R^7$ are H.

In certain embodiments, the invention relates to any one of the aforementioned methods, wherein $R^5$, $R^7$, and $R^8$ are OR; and $R^1$, $R^2$, $R^3$, $R^4$, and $R^6$ are H.

In certain embodiments, the invention relates to any one of the aforementioned methods, wherein $R^6$, $R^7$, and $R^8$ are OR; and $R^1$, $R^2$, $R^3$, $R^4$, and $R^5$ are H.

In certain embodiments, the invention relates to any one of the aforementioned methods, wherein $R^1$, $R^2$, $R^3$, and $R^4$ are OR; and $R^5$, $R^6$, $R^7$, and $R^8$ are H.

In certain embodiments, the invention relates to any one of the aforementioned methods, wherein $R^1$, $R^2$, $R^3$, and $R^5$ are OR; and $R^4$, $R^6$, $R^7$, and $R^8$ are H.

In certain embodiments, the invention relates to any one of the aforementioned methods, wherein $R^1$, $R^2$, $R^3$, and $R^6$ are OR; and $R^4$, $R^5$, $R^7$, and $R^8$ are H.

In certain embodiments, the invention relates to any one of the aforementioned methods, wherein $R^1$, $R^2$, $R^3$, and $R^7$ are OR; and $R^4$, $R^5$, $R^6$, and $R^8$ are H.

In certain embodiments, the invention relates to any one of the aforementioned methods, wherein $R^1$, $R^2$, $R^3$, and $R^8$ are OR; and $R^4$, $R^5$, $R^6$, and $R^7$ are H.

In certain embodiments, the invention relates to any one of the aforementioned methods, wherein $R^1$, $R^2$, $R^4$, and $R^5$ are OR; and $R^3$, $R^6$, $R^7$, and $R^8$ are H.

In certain embodiments, the invention relates to any one of the aforementioned methods, wherein $R^1$, $R^2$, $R^4$, and $R^6$ are OR; and $R^3$, $R^5$, $R^7$, and $R^8$ are H.

In certain embodiments, the invention relates to any one of the aforementioned methods, wherein $R^1$, $R^2$, $R^4$, and $R^7$ are OR; and $R^3$, $R^5$, $R^6$, and $R^8$ are H.

In certain embodiments, the invention relates to any one of the aforementioned methods, wherein $R^1$, $R^2$, $R^4$, and $R^8$ are OR; and $R^3$, $R^5$, $R^6$, and $R^7$ are H.

In certain embodiments, the invention relates to any one of the aforementioned methods, wherein $R^1$, $R^2$, $R^5$, and $R^6$ are OR; and $R^3$, $R^4$, $R^7$, and $R^8$ are H.

In certain embodiments, the invention relates to any one of the aforementioned methods, wherein $R^1$, $R^2$, $R^5$, and $R^7$ are OR; and $R^3$, $R^4$, $R^6$, and $R^8$ are H.

In certain embodiments, the invention relates to any one of the aforementioned methods, wherein $R^1$, $R^2$, $R^5$, and $R^8$ are OR; and $R^3$, $R^4$, $R^6$, and $R^7$ are H.

In certain embodiments, the invention relates to any one of the aforementioned methods, wherein $R^1$, $R^2$, $R^6$, and $R^7$ are OR; and $R^3$, $R^4$, $R^5$, and $R^8$ are H.

In certain embodiments, the invention relates to any one of the aforementioned methods, wherein $R^1$, $R^2$, $R^6$, and $R^8$ are OR; and $R^3$, $R^4$, $R^5$, and $R^7$ are H.

In certain embodiments, the invention relates to any one of the aforementioned methods, wherein $R^1$, $R^2$, $R^7$, and $R^8$ are OR; and $R^3$, $R^4$, $R^5$, and $R^6$ are H.

In certain embodiments, the invention relates to any one of the aforementioned methods, wherein $R^1$, $R^3$, $R^4$, and $R^5$ are OR; and $R^2$, $R^6$, $R^7$, and $R^8$ are H.

In certain embodiments, the invention relates to any one of the aforementioned methods, wherein $R^1$, $R^3$, $R^4$, and $R^6$ are OR; and $R^2$, $R^5$, $R^7$, and $R^8$ are H.

In certain embodiments, the invention relates to any one of the aforementioned methods, wherein $R^1$, $R^3$, $R^4$, and $R^7$ are OR; and $R^2$, $R^5$, $R^6$, and $R^8$ are H.

In certain embodiments, the invention relates to any one of the aforementioned methods, wherein $R^1$, $R^3$, $R^4$, and $R^8$ are OR; and $R^2$, $R^5$, $R^6$, and $R^7$ are H.

In certain embodiments, the invention relates to any one of the aforementioned methods, wherein $R^1$, $R^3$, $R^5$, and $R^6$ are OR; and $R^2$, $R^4$, $R^7$, and $R^8$ are H.

In certain embodiments, the invention relates to any one of the aforementioned methods, wherein $R^1$, $R^3$, $R^5$, and $R^7$ are OR; and $R^2$, $R^4$, $R^6$, and $R^8$ are H.

In certain embodiments, the invention relates to any one of the aforementioned methods, wherein $R^1$, $R^3$, $R^5$, and $R^8$ are OR; and $R^2$, $R^4$, $R^6$, and $R^7$ are H.

In certain embodiments, the invention relates to any one of the aforementioned methods, wherein $R^1$, $R^3$, $R^6$, and $R^7$ are OR; and $R^2$, $R^4$, $R^5$, and $R^8$ are H.

In certain embodiments, the invention relates to any one of the aforementioned methods, wherein $R^1$, $R^3$, $R^7$, and $R^8$ are OR; and $R^2$, $R^4$, $R^5$, and $R^6$ are H.

In certain embodiments, the invention relates to any one of the aforementioned methods, wherein $R^1$, $R^4$, $R^5$, and $R^6$ are OR; and $R^2$, $R^3$, $R^7$, and $R^8$ are H.

In certain embodiments, the invention relates to any one of the aforementioned methods, wherein $R^1$, $R^4$, $R^5$, and $R^7$ are OR; and $R^2$, $R^3$, $R^6$, and $R^8$ are H.

In certain embodiments, the invention relates to any one of the aforementioned methods, wherein $R^1$, $R^4$, $R^5$, and $R^8$ are OR; and $R^2$, $R^3$, $R^6$, and $R^7$ are H.

In certain embodiments, the invention relates to any one of the aforementioned methods, wherein $R^1$, $R^4$, $R^6$, and $R^7$ are OR; and $R^2$, $R^3$, $R^5$, and $R^8$ are H.

In certain embodiments, the invention relates to any one of the aforementioned methods, wherein $R^1$, $R^4$, $R^6$, and $R^8$ are OR; and $R^2$, $R^3$, $R^5$, and $R^7$ are H.

In certain embodiments, the invention relates to any one of the aforementioned methods, wherein $R^1$, $R^4$, $R^7$, and $R^8$ are OR; and $R^2$, $R^3$, $R^5$, and $R^6$ are H.

In certain embodiments, the invention relates to any one of the aforementioned methods, wherein $R^1$, $R^5$, $R^6$, and $R^7$ are OR; and $R^2$, $R^3$, $R^4$, and $R^8$ are H.

In certain embodiments, the invention relates to any one of the aforementioned methods, wherein $R^1$, $R^5$, $R^6$, and $R^8$ are OR; and $R^2$, $R^3$, $R^4$, and $R^7$ are H.

In certain embodiments, the invention relates to any one of the aforementioned methods, wherein $R^1$, $R^5$, $R^7$, and $R^8$ are OR; and $R^2$, $R^3$, $R^4$, and $R^6$ are H.

In certain embodiments, the invention relates to any one of the aforementioned methods, wherein $R^1$, $R^6$, $R^7$, and $R^8$ are OR; and $R^2$, $R^3$, $R^4$, and $R^5$ are H.

In certain embodiments, the invention relates to any one of the aforementioned methods, wherein $R^2$, $R^3$, $R^4$, and $R^5$ are OR; and $R^1$, $R^6$, $R^7$, and $R^8$ are H.

In certain embodiments, the invention relates to any one of the aforementioned methods, wherein $R^2$, $R^3$, $R^4$, and $R^6$ are OR; and $R^1$, $R^5$, $R^7$, and $R^8$ are H.

In certain embodiments, the invention relates to any one of the aforementioned methods, wherein $R^2$, $R^3$, $R^4$, and $R^7$ are OR; and $R^1$, $R^5$, $R^6$, and $R^8$ are H.

In certain embodiments, the invention relates to any one of the aforementioned methods, wherein $R^2$, $R^3$, $R^4$, and $R^8$ are OR; and $R^1$, $R^5$, $R^6$, and $R^7$ are H.

In certain embodiments, the invention relates to any one of the aforementioned methods, wherein $R^2$, $R^3$, $R^5$, and $R^6$ are OR; and $R^1$, $R^4$, $R^7$, and $R^8$ are H.

In certain embodiments, the invention relates to any one of the aforementioned methods, wherein $R^2$, $R^3$, $R^5$, and $R^7$ are OR; and $R^1$, $R^4$, $R^6$, and $R^8$ are H.

In certain embodiments, the invention relates to any one of the aforementioned methods, wherein $R^2$, $R^3$, $R^5$, and $R^8$ are OR; and $R^1$, $R^4$, $R^6$, and $R^7$ are H.

In certain embodiments, the invention relates to any one of the aforementioned methods, wherein $R^2$, $R^3$, $R^6$, and $R^7$ are OR; and $R^1$, $R^4$, $R^5$, and $R^8$ are H.

In certain embodiments, the invention relates to any one of the aforementioned methods, wherein $R^2$, $R^3$, $R^6$, and $R^8$ are OR; and $R^1$, $R^4$, $R^5$, and $R^7$ are H.

In certain embodiments, the invention relates to any one of the aforementioned methods, wherein $R^2$, $R^3$, $R^7$, and $R^8$ are OR; and $R^1$, $R^4$, $R^6$, and $R^7$ are H.

In certain embodiments, the invention relates to any one of the aforementioned methods, wherein $R^2$, $R^4$, $R^5$, and $R^6$ are OR; and $R^1$, $R^3$, $R^7$, and $R^8$ are H.

In certain embodiments, the invention relates to any one of the aforementioned methods, wherein $R^2$, $R^4$, $R^5$, and $R^7$ are OR; and $R^1$, $R^3$, $R^6$, and $R^8$ are H.

In certain embodiments, the invention relates to any one of the aforementioned methods, wherein $R^2$, $R^4$, $R^5$, and $R^8$ are OR; and $R^1$, $R^3$, $R^6$, and $R^7$ are H.

In certain embodiments, the invention relates to any one of the aforementioned methods, wherein $R^2$, $R^4$, $R^6$, and $R^7$ are OR; and $R^1$, $R^3$, $R^5$, and $R^8$ are H.

In certain embodiments, the invention relates to any one of the aforementioned methods, wherein $R^2$, $R^4$, $R^6$, and $R^8$ are OR; and $R^1$, $R^3$, $R^5$, and $R^7$ are H.

In certain embodiments, the invention relates to any one of the aforementioned methods, wherein $R^2$, $R^4$, $R^7$, and $R^8$ are OR; and $R^1$, $R^3$, $R^5$, and $R^6$ are H.

In certain embodiments, the invention relates to any one of the aforementioned methods, wherein $R^2$, $R^5$, $R^6$, and $R^7$ are OR; and $R^1$, $R^3$, $R^4$, and $R^8$ are H.

In certain embodiments, the invention relates to any one of the aforementioned methods, wherein $R^2$, $R^5$, $R^6$, and $R^8$ are OR; and $R^1$, $R^3$, $R^4$, and $R^7$ are H.

In certain embodiments, the invention relates to any one of the aforementioned methods, wherein $R^2$, $R^5$, $R^7$, and $R^8$ are OR; and $R^1$, $R^3$, $R^4$, and $R^6$ are H.

In certain embodiments, the invention relates to any one of the aforementioned methods, wherein $R^2$, $R^6$, $R^7$, and $R^8$ are OR; and $R^1$, $R^3$, $R^4$, and $R^5$ are H.

In certain embodiments, the invention relates to any one of the aforementioned methods, wherein $R^3$, $R^4$, $R^5$, and $R^6$ are OR; and $R^1$, $R^2$, $R^7$, and $R^8$ are H.

In certain embodiments, the invention relates to any one of the aforementioned methods, wherein $R^3$, $R^4$, $R^5$, and $R^7$ are OR; and $R^1$, $R^2$, $R^6$, and $R^8$ are H.

In certain embodiments, the invention relates to any one of the aforementioned methods, wherein $R^3$, $R^4$, $R^5$, and $R^8$ are OR; and $R^1$, $R^2$, $R^6$, and $R^7$ are H.

In certain embodiments, the invention relates to any one of the aforementioned methods, wherein $R^3$, $R^4$, $R^6$, and $R^7$ are OR; and $R^1$, $R^2$, $R^5$, and $R^8$ are H.

In certain embodiments, the invention relates to any one of the aforementioned methods, wherein $R^3$, $R^4$, $R^6$, and $R^8$ are OR; and $R^1$, $R^2$, $R^5$, and $R^7$ are H.

In certain embodiments, the invention relates to any one of the aforementioned methods, wherein $R^3$, $R^4$, $R^7$, and $R^8$ are OR; and $R^1$, $R^2$, $R^5$, and $R^6$ are H.

In certain embodiments, the invention relates to any one of the aforementioned methods, wherein $R^3$, $R^5$, $R^6$, and $R^7$ are OR; and $R^1$, $R^2$, $R^4$, and $R^8$ are H.

In certain embodiments, the invention relates to any one of the aforementioned methods, wherein $R^3$, $R^5$, $R^6$, and $R^8$ are OR; and $R^1$, $R^2$, $R^4$, and $R^7$ are H.

In certain embodiments, the invention relates to any one of the aforementioned methods, wherein $R^3$, $R^5$, $R^7$, and $R^8$ are OR; and $R^1$, $R^2$, $R^4$, and $R^6$ are H.

In certain embodiments, the invention relates to any one of the aforementioned methods, wherein $R^3$, $R^6$, $R^7$, and $R^8$ are OR; and $R^1$, $R^2$, $R^4$, and $R^5$ are H.

In certain embodiments, the invention relates to any one of the aforementioned methods, wherein $R^4$, $R^5$, $R^6$, and $R^7$ are OR; and $R^1$, $R^2$, $R^3$, and $R^8$ are H.

In certain embodiments, the invention relates to any one of the aforementioned methods, wherein $R^4$, $R^5$, $R^6$, and $R^8$ are OR; and $R^1$, $R^2$, $R^3$, and $R^7$ are H.

In certain embodiments, the invention relates to any one of the aforementioned methods, wherein $R^4$, $R^5$, $R^7$, and $R^8$ are OR; and $R^1$, $R^2$, $R^3$, and $R^6$ are H.

In certain embodiments, the invention relates to any one of the aforementioned methods, wherein $R^4$, $R^6$, $R^7$, and $R^8$ are OR; and $R^1$, $R^2$, $R^3$, and $R^5$ are H.

In certain embodiments, the invention relates to any one of the aforementioned methods, wherein $R^5$, $R^6$, $R^7$, and $R^8$ are OR; and $R^1$, $R^2$, $R^3$, and $R^4$ are H.

In certain embodiments, the invention relates to any one of the aforementioned methods, wherein $R^1$, $R^2$, $R^3$, $R^4$, and $R^5$ are OR; and $R^6$, $R^7$, and $R^8$ are H.

In certain embodiments, the invention relates to any one of the aforementioned methods, wherein $R^1$, $R^2$, $R^3$, $R^4$, and $R^6$ are OR; and $R^5$, $R^7$, and $R^8$ are H.

In certain embodiments, the invention relates to any one of the aforementioned methods, wherein $R^1$, $R^2$, $R^3$, $R^4$, and $R^7$ are OR; and $R^5$, $R^6$, and $R^8$ are H.

In certain embodiments, the invention relates to any one of the aforementioned methods, wherein $R^1$, $R^2$, $R^3$, $R^4$, and $R^8$ are OR; and $R^5$, $R^6$, and $R^7$ are H.

In certain embodiments, the invention relates to any one of the aforementioned methods, wherein $R^1$, $R^2$, $R^3$, $R^5$, and $R^6$ are OR; and $R^4$, $R^7$, and $R^8$ are H.

In certain embodiments, the invention relates to any one of the aforementioned methods, wherein $R^1$, $R^2$, $R^3$, $R^5$, and $R^7$ are OR; and $R^4$, $R^6$, and $R^8$ are H.

In certain embodiments, the invention relates to any one of the aforementioned methods, wherein $R^1$, $R^2$, $R^3$, $R^5$, and $R^8$ are OR; and $R^4$, $R^6$, and $R^7$ are H.

In certain embodiments, the invention relates to any one of the aforementioned methods, wherein $R^1$, $R^2$, $R^3$, $R^6$, and $R^7$ are OR; and $R^4$, $R^5$, and $R^8$ are H.

In certain embodiments, the invention relates to any one of the aforementioned methods, wherein $R^1$, $R^2$, $R^3$, $R^6$, and $R^8$ are OR; and $R^4$, $R^5$, and $R^7$ are H.

In certain embodiments, the invention relates to any one of the aforementioned methods, wherein $R^1$, $R^2$, $R^3$, $R^7$, and $R^8$ are OR; and $R^4$, $R^5$, and $R^6$ are H.

In certain embodiments, the invention relates to any one of the aforementioned methods, wherein $R^1$, $R^2$, $R^4$, $R^5$, and $R^6$ are OR; and $R^3$, $R^7$, and $R^8$ are H.

In certain embodiments, the invention relates to any one of the aforementioned methods, wherein $R^1$, $R^2$, $R^4$, $R^5$, and $R^7$ are OR; and $R^3$, $R^6$, and $R^8$ are H.

In certain embodiments, the invention relates to any one of the aforementioned methods, wherein $R^1$, $R^2$, $R^4$, $R^5$, and $R^8$ are OR; and $R^3$, $R^6$, and $R^7$ are H.

In certain embodiments, the invention relates to any one of the aforementioned methods, wherein $R^1$, $R^2$, $R^4$, $R^6$, and $R^7$ are OR; and $R^3$, $R^5$, and $R^8$ are H.

In certain embodiments, the invention relates to any one of the aforementioned methods, wherein $R^1$, $R^2$, $R^4$, $R^6$, and $R^8$ are OR; and $R^3$, $R^5$, and $R^7$ are H.

In certain embodiments, the invention relates to any one of the aforementioned methods, wherein $R^1$, $R^2$, $R^4$, $R^7$, and $R^8$ are OR; and $R^3$, $R^5$, and $R^6$ are H.

In certain embodiments, the invention relates to any one of the aforementioned methods, wherein $R^1$, $R^2$, $R^5$, $R^6$, and $R^7$ are OR; and $R^3$, $R^4$, and $R^8$ are H.

In certain embodiments, the invention relates to any one of the aforementioned methods, wherein $R^1$, $R^2$, $R^5$, $R^6$, and $R^8$ are OR; and $R^3$, $R^4$, and $R^7$ are H.

In certain embodiments, the invention relates to any one of the aforementioned methods, wherein $R^1$, $R^2$, $R^5$, $R^7$, and $R^8$ are OR; and $R^3$, $R^4$, and $R^6$ are H.

In certain embodiments, the invention relates to any one of the aforementioned methods, wherein $R^1$, $R^2$, $R^6$, $R^7$, and $R^8$ are OR; and $R^3$, $R^4$, and $R^5$ are H.

In certain embodiments, the invention relates to any one of the aforementioned methods, wherein $R^1$, $R^3$, $R^4$, $R^5$, and $R^6$ are OR; and $R^2$, $R^7$, and $R^8$ are H.

In certain embodiments, the invention relates to any one of the aforementioned methods, wherein $R^1$, $R^3$, $R^4$, $R^5$, and $R^7$ are OR; and $R^2$, $R^6$, and $R^8$ are H.

In certain embodiments, the invention relates to any one of the aforementioned methods, wherein $R^1$, $R^3$, $R^4$, $R^5$, and $R^8$ are OR; and $R^2$, $R^6$, and $R^7$ are H.

In certain embodiments, the invention relates to any one of the aforementioned methods, wherein $R^1$, $R^3$, $R^4$, $R^6$, and $R^7$ are OR; and $R^2$, $R^5$, and $R^8$ are H.

In certain embodiments, the invention relates to any one of the aforementioned methods, wherein $R^1$, $R^3$, $R^4$, $R^6$, and $R^8$ are OR; and $R^2$, $R^5$, and $R^7$ are H.

In certain embodiments, the invention relates to any one of the aforementioned methods, wherein $R^1$, $R^3$, $R^4$, $R^7$, and $R^8$ are OR; and $R^2$, $R^5$, and $R^7$ are H.

In certain embodiments, the invention relates to any one of the aforementioned methods, wherein $R^1$, $R^3$, $R^5$, $R^6$, and $R^7$ are OR; and $R^2$, $R^4$, and $R^8$ are H.

In certain embodiments, the invention relates to any one of the aforementioned methods, wherein $R^1$, $R^3$, $R^5$, $R^6$, and $R^8$ are OR; and $R^2$, $R^4$, and $R^7$ are H.

In certain embodiments, the invention relates to any one of the aforementioned methods, wherein $R^1$, $R^3$, $R^5$, $R^7$, and $R^8$ are OR; and $R^2$, $R^4$, and $R^6$ are H.

In certain embodiments, the invention relates to any one of the aforementioned methods, wherein $R^1$, $R^3$, $R^6$, $R^7$, and $R^8$ are OR; and $R^2$, $R^4$, and $R^5$ are H.

In certain embodiments, the invention relates to any one of the aforementioned methods, wherein $R^1$, $R^4$, $R^5$, $R^6$, and $R^7$ are OR; and $R^2$, $R^3$, and $R^8$ are H.

In certain embodiments, the invention relates to any one of the aforementioned methods, wherein $R^1$, $R^4$, $R^5$, $R^6$, and $R^8$ are OR; and $R^2$, $R^3$, and $R^7$ are H.

In certain embodiments, the invention relates to any one of the aforementioned methods, wherein $R^1$, $R^4$, $R^5$, $R^7$, and $R^8$ are OR; and $R^2$, $R^3$, and $R^6$ are H.

In certain embodiments, the invention relates to any one of the aforementioned methods, wherein $R^1$, $R^4$, $R^6$, $R^7$, and $R^8$ are OR; and $R^2$, $R^3$, and $R^6$ are H.

In certain embodiments, the invention relates to any one of the aforementioned methods, wherein $R^1$, $R^5$, $R^6$, $R^7$, and $R^8$ are OR; and $R^2$, $R^3$, and $R^4$ are H.

In certain embodiments, the invention relates to any one of the aforementioned methods, wherein $R^2$, $R^3$, $R^4$, $R^5$, and $R^6$ are OR; and $R^1$, $R^7$, and $R^8$ are H.

In certain embodiments, the invention relates to any one of the aforementioned methods, wherein $R^2$, $R^3$, $R^4$, $R^5$, and $R^7$ are OR; and $R^1$, $R^6$, and $R^8$ are H.

In certain embodiments, the invention relates to any one of the aforementioned methods, wherein $R^2$, $R^3$, $R^4$, $R^5$, and $R^8$ are OR; and $R^1$, $R^6$, and $R^7$ are H.

In certain embodiments, the invention relates to any one of the aforementioned methods, wherein $R^2$, $R^3$, $R^4$, $R^6$, and $R^7$ are OR; and $R^1$, $R^5$, and $R^8$ are H.

In certain embodiments, the invention relates to any one of the aforementioned methods, wherein $R^2$, $R^3$, $R^4$, $R^6$, and $R^8$ are OR; and $R^1$, $R^5$, and $R^7$ are H.

In certain embodiments, the invention relates to any one of the aforementioned methods, wherein $R^2$, $R^3$, $R^4$, $R^7$, and $R^8$ are OR; and $R^1$, $R^5$, and $R^6$ are H.

In certain embodiments, the invention relates to any one of the aforementioned methods, wherein $R^2$, $R^3$, $R^5$, $R^6$, and $R^7$ are OR; and $R^1$, $R^4$, and $R^8$ are H.

In certain embodiments, the invention relates to any one of the aforementioned methods, wherein $R^2$, $R^3$, $R^5$, $R^6$, and $R^8$ are OR; and $R^1$, $R^4$, and $R^7$ are H.

In certain embodiments, the invention relates to any one of the aforementioned methods, wherein $R^2$, $R^3$, $R^5$, $R^7$, and $R^8$ are OR; and $R^1$, $R^4$, and $R^6$ are H.

In certain embodiments, the invention relates to any one of the aforementioned methods, wherein $R^2$, $R^3$, $R^6$, $R^7$, and $R^8$ are OR; and $R^1$, $R^4$, and $R^5$ are H.

In certain embodiments, the invention relates to any one of the aforementioned methods, wherein $R^2$, $R^4$, $R^5$, $R^6$, and $R^7$ are OR; and $R^1$, $R^3$, and $R^8$ are H.

In certain embodiments, the invention relates to any one of the aforementioned methods, wherein $R^2$, $R^4$, $R^5$, $R^6$, and $R^8$ are OR; and $R^1$, $R^3$, and $R^7$ are H.

In certain embodiments, the invention relates to any one of the aforementioned methods, wherein $R^2$, $R^4$, $R^5$, $R^7$, and $R^8$ are OR; and $R^1$, $R^3$, and $R^6$ are H.

In certain embodiments, the invention relates to any one of the aforementioned methods, wherein $R^2$, $R^4$, $R^6$, $R^7$, and $R^8$ are OR; and $R^1$, $R^3$, and $R^5$ are H.

In certain embodiments, the invention relates to any one of the aforementioned methods, wherein $R^2$, $R^5$, $R^6$, $R^7$, and $R^8$ are OR; and $R^1$, $R^3$, and $R^4$ are H.

In certain embodiments, the invention relates to any one of the aforementioned methods, wherein $R^3$, $R^4$, $R^5$, $R^6$, and $R^7$ are OR; and $R^1$, $R^2$, and $R^8$ are H.

In certain embodiments, the invention relates to any one of the aforementioned methods, wherein $R^3$, $R^4$, $R^5$, $R^6$, and $R^8$ are OR; and $R^1$, $R^2$, and $R^7$ are H.

In certain embodiments, the invention relates to any one of the aforementioned methods, wherein $R^3$, $R^4$, $R^5$, $R^7$, and $R^8$ are OR; and $R^1$, $R^2$, and $R^6$ are H.

In certain embodiments, the invention relates to any one of the aforementioned methods, wherein $R^3$, $R^4$, $R^6$, $R^7$, and $R^8$ are OR; and $R^1$, $R^2$, and $R^5$ are H.

In certain embodiments, the invention relates to any one of the aforementioned methods, wherein $R^3$, $R^5$, $R^6$, $R^7$, and $R^8$ are OR; and $R^1$, $R^2$, and $R^4$ are H.

In certain embodiments, the invention relates to any one of the aforementioned methods, wherein $R^4$, $R^5$, $R^6$, $R^7$, and $R^8$ are OR; and $R^1$, $R^2$, and $R^3$ are H.

In certain embodiments, the invention relates to any one of the aforementioned methods, wherein $R^1$, $R^2$, $R^3$, $R^4$, $R^5$, and $R^6$ are OR; and $R^7$ and $R^8$ are H.

In certain embodiments, the invention relates to any one of the aforementioned methods, wherein $R^1$, $R^2$, $R^3$, $R^4$, $R^5$, and $R^7$ are OR; and $R^6$ and $R^8$ are H.

In certain embodiments, the invention relates to any one of the aforementioned methods, wherein $R^1$, $R^2$, $R^3$, $R^4$, $R^5$, and $R^8$ are OR; and $R^6$ and $R^7$ are H.

In certain embodiments, the invention relates to any one of the aforementioned methods, wherein $R^1$, $R^2$, $R^3$, $R^4$, $R^6$, and $R^7$ are OR; and $R^5$ and $R^8$ are H.

In certain embodiments, the invention relates to any one of the aforementioned methods, wherein $R^1$, $R^2$, $R^3$, $R^4$, $R^6$, and $R^8$ are OR; and $R^5$ and $R^7$ are H.

In certain embodiments, the invention relates to any one of the aforementioned methods, wherein $R^1$, $R^2$, $R^3$, $R^4$, $R^7$, and $R^8$ are OR; and $R^5$ and $R^6$ are H.

In certain embodiments, the invention relates to any one of the aforementioned methods, wherein $R^1$, $R^2$, $R^3$, $R^5$, $R^6$, and $R^7$ are OR; and $R^4$ and $R^8$ are H.

In certain embodiments, the invention relates to any one of the aforementioned methods, wherein $R^1$, $R^2$, $R^3$, $R^5$, $R^6$, and $R^8$ are OR; and $R^4$ and $R^7$ are H.

In certain embodiments, the invention relates to any one of the aforementioned methods, wherein $R^1$, $R^2$, $R^3$, $R^5$, $R^7$, and $R^8$ are OR; and $R^4$ and $R^6$ are H.

In certain embodiments, the invention relates to any one of the aforementioned methods, wherein $R^1$, $R^2$, $R^3$, $R^6$, $R^7$, and $R^8$ are OR; and $R^4$ and $R^5$ are H.

In certain embodiments, the invention relates to any one of the aforementioned methods, wherein $R^1$, $R^2$, $R^4$, $R^5$, $R^6$, and $R^7$ are OR; and $R^3$ and $R^8$ are H.

In certain embodiments, the invention relates to any one of the aforementioned methods, wherein $R^1$, $R^2$, $R^4$, $R^5$, $R^6$, and $R^8$ are OR; and $R^3$ and $R^7$ are H.

In certain embodiments, the invention relates to any one of the aforementioned methods, wherein $R^1$, $R^2$, $R^4$, $R^5$, $R^7$, and $R^8$ are OR; and $R^3$ and $R^6$ are H.

In certain embodiments, the invention relates to any one of the aforementioned methods, wherein $R^1$, $R^2$, $R^4$, $R^6$, $R^7$, and $R^8$ are OR; and $R^3$ and $R^5$ are H.

In certain embodiments, the invention relates to any one of the aforementioned methods, wherein $R^1$, $R^2$, $R^5$, $R^6$, $R^7$, and $R^8$ are OR; and $R^3$ and $R^4$ are H.

In certain embodiments, the invention relates to any one of the aforementioned methods, wherein $R^1$, $R^3$, $R^4$, $R^5$, $R^6$, and $R^7$ are OR; and $R^2$ and $R^8$ are H.

In certain embodiments, the invention relates to any one of the aforementioned methods, wherein $R^1$, $R^3$, $R^4$, $R^5$, $R^6$, and $R^8$ are OR; and $R^2$ and $R^7$ are H.

In certain embodiments, the invention relates to any one of the aforementioned methods, wherein $R^1$, $R^3$, $R^4$, $R^5$, $R^7$, and $R^8$ are OR; and $R^2$ and $R^6$ are H.

In certain embodiments, the invention relates to any one of the aforementioned methods, wherein $R^1$, $R^3$, $R^4$, $R^6$, $R^7$, and $R^8$ are OR; and $R^2$ and $R^5$ are H.

In certain embodiments, the invention relates to any one of the aforementioned methods, wherein $R^1$, $R^3$, $R^5$, $R^6$, $R^7$, and $R^8$ are OR; and $R^2$ and $R^4$ are H.

In certain embodiments, the invention relates to any one of the aforementioned methods, wherein $R^1$, $R^4$, $R^5$, $R^6$, $R^7$, and $R^8$ are OR; and $R^2$ and $R^3$ are H.

In certain embodiments, the invention relates to any one of the aforementioned methods, wherein $R^2$, $R^3$, $R^4$, $R^5$, $R^6$, and $R^7$ are OR; and $R^1$, and $R^8$ are H.

In certain embodiments, the invention relates to any one of the aforementioned methods, wherein $R^2$, $R^3$, $R^4$, $R^5$, $R^6$, and $R^8$ are OR; and $R^1$ and $R^7$ are H.

In certain embodiments, the invention relates to any one of the aforementioned methods, wherein $R^2$, $R^3$, $R^4$, $R^5$, $R^7$, and $R^8$ are OR; and $R^1$ and $R^6$ are H.

In certain embodiments, the invention relates to any one of the aforementioned methods, wherein $R^2$, $R^3$, $R^4$, $R^6$, $R^7$, and $R^8$ are OR; and $R^1$ and $R^5$ are H.

In certain embodiments, the invention relates to any one of the aforementioned methods, wherein $R^2$, $R^3$, $R^5$, $R^6$, $R^7$, and $R^8$ are OR; and $R^1$ and $R^4$ are H.

In certain embodiments, the invention relates to any one of the aforementioned methods, wherein $R^2$, $R^4$, $R^5$, $R^6$, $R^7$, and $R^8$ are OR; and $R^1$ and $R^3$ are H.

In certain embodiments, the invention relates to any one of the aforementioned methods, wherein $R^3$, $R^4$, $R^5$, $R^6$, $R^7$, and $R^8$ are OR; and $R^1$ and $R^2$ are H.

In certain embodiments, the invention relates to any one of the aforementioned methods, wherein $R^1$, $R^2$, $R^3$, $R^4$, $R^5$, $R^6$, and $R^7$ are OR; and $R^8$ is H.

In certain embodiments, the invention relates to any one of the aforementioned methods, wherein $R^1$, $R^2$, $R^3$, $R^4$, $R^5$, $R^6$, and $R^8$ are OR; and $R^7$ is H.

In certain embodiments, the invention relates to any one of the aforementioned methods, wherein $R^1$, $R^2$, $R^3$, $R^4$, $R^5$, $R^7$, and $R^8$ are OR; and $R^6$ is H.

In certain embodiments, the invention relates to any one of the aforementioned methods, wherein $R^1$, $R^2$, $R^3$, $R^4$, $R^6$, $R^7$, and $R^8$ are OR; and $R^5$ is H.

In certain embodiments, the invention relates to any one of the aforementioned methods, wherein $R^1$, $R^2$, $R^3$, $R^5$, $R^6$, $R^7$, and $R^8$ are OR; and $R^4$ is H.

In certain embodiments, the invention relates to any one of the aforementioned methods, wherein $R^1$, $R^2$, $R^4$, $R^5$, $R^6$, $R^7$, and $R^8$ are OR; and $R^3$ is H.

In certain embodiments, the invention relates to any one of the aforementioned methods, wherein $R^1$, $R^3$, $R^4$, $R^5$, $R^6$, $R^7$, and $R^8$ are OR; and $R^2$ is H.

In certain embodiments, the invention relates to any one of the aforementioned methods, wherein $R^2$, $R^3$, $R^4$, $R^5$, $R^6$, $R^7$, and $R^8$ are OR; and $R^1$ is H.

In certain embodiments, the invention relates to any one of the aforementioned methods, wherein R is H.

In certain embodiments, the invention relates to a method of increasing autophagy in a cell, comprising contacting the cell with an effective amount of a compound of Formula IV, thereby increasing autophagy in the cell;

wherein the compound of Formula IV is

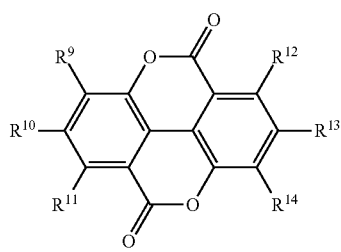

Formula IV wherein
$R^9$, $R^{10}$, $R^{11}$, $R^{12}$, $R^{13}$, and $R^{14}$ are independently selected from the group consisting of H and OR; and R is H, substituted or unsubstituted alkyl, substituted or unsubstituted aryl, a substituted or unsubstituted monosaccharide, or a substituted or unsubstituted oligosaccharide.

In certain embodiments, the invention relates to any one of the aforementioned methods, wherein the autophagy is mitophagy.

In certain embodiments, the invention relates to any one of the aforementioned methods, wherein the cell is selected from the group consisting of: embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells.

In certain embodiments, the invention relates to a method of increasing longevity in an animal, comprising administering to an animal in need thereof an effective amount of a compound of Formula IV, thereby increasing longevity of the animal, wherein the compound of Formula IV is

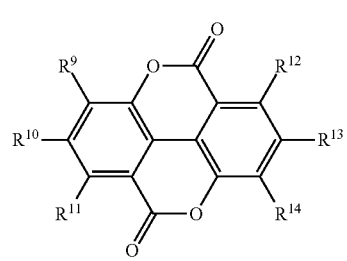

Formula IV wherein
$R^9$, $R^{10}$, $R^{11}$, $R^{12}$, $R^{13}$, and $R^{14}$ are independently selected from the group consisting of H and OR; and R is H, substituted or unsubstituted alkyl, substituted or unsubstituted aryl, a substituted or unsubstituted monosaccharide, or a substituted or unsubstituted oligosaccharide.

In certain embodiments, the invention relates to any one of the aforementioned methods, wherein the animal is a mammal.

In certain embodiments, the invention relates to any one of the aforementioned methods, wherein the mammal is a human.

In certain embodiments, the invention relates to a method of increasing longevity of eukaryotic cells in vitro, comprising contacting eukaryotic cells in vitro with an effective amount of a compound of Formula IV, thereby increasing longevity of the eukaryotic cells in vitro, wherein the compound of Formula IV is

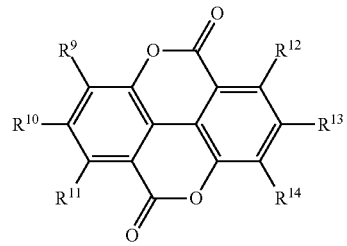

Formula IV wherein
$R^9$, $R^{10}$, $R^{11}$, $R^{12}$, $R^{13}$, and $R^{14}$ are independently selected from the group consisting of H and OR; and R is H, substituted or unsubstituted alkyl, substituted or unsubstituted aryl, a substituted or unsubstituted monosaccharide, or a substituted or unsubstituted oligosaccharide.

In certain embodiments, the invention relates to any one of the aforementioned methods, wherein the eukaryotic cells are eukaryotic cells in primary culture.

In certain embodiments, the invention relates to any one of the aforementioned methods, wherein the eukaryotic cells are part of a cell line.

In certain embodiments, the invention relates to any one of the aforementioned methods, wherein the eukaryotic cells are cells selected from the group consisting of: embryonic stem cells, induced pluripotent stem cells, adult stem cells, differentiated cells, blood cells, hematopoietic cells, epithelial cells, exocrine cells, endocrine cells, connective tissue cells, adipose cells, bone cells, smooth muscle cells, striated muscle cells, nerve cells, sensory cells, cardiac cells, hepatic cells, gastric cells, intestinal cells, pulmonary cells, kidney cells, and germ cells.

In certain embodiments, the invention relates to any one of the aforementioned methods, wherein the eukaryotic cells are cells selected from the group consisting of: embryonic stem cells, induced pluripotent stem cells, and adult stem cells.

In certain embodiments, the invention relates to any one of the aforementioned methods, wherein $R^9$, $R^{10}$, $R^{11}$, $R^{12}$, $R^{13}$, and $R^{14}$ are H.

In certain embodiments, the invention relates to any one of the aforementioned methods, wherein at least one of $R^9$, $R^{10}$, $R^{11}$, $R^{12}$, $R^{13}$, and $R^{14}$ is OR.

In certain embodiments, the invention relates to any one of the aforementioned methods, wherein at least two of $R^9$, $R^{10}$, $R^{11}$, $R^{12}$, $R^{13}$, and $R^{14}$ are OR.

In certain embodiments, the invention relates to any one of the aforementioned methods, wherein at least three of $R^9$, $R^{10}$, $R^{11}$, $R^{12}$, $R^{13}$, and $R^{14}$ are OR.

In certain embodiments, the invention relates to any one of the aforementioned methods, wherein at least four of $R^9$, $R^{10}$, $R^{11}$, $R^{12}$, $R^{13}$, and $R^{14}$ are OR.

In certain embodiments, the invention relates to any one of the aforementioned methods, wherein five of $R^9$, $R^{10}$, $R^{11}$, $R^{12}$, $R^{13}$, and $R^{14}$ are OR.

In certain embodiments, the invention relates to any one of the aforementioned methods, wherein $R^9$, $R^{10}$, $R^{11}$, $R^{12}$, $R^{13}$, and $R^{14}$ are OR.

In certain embodiments, the invention relates to any one of the aforementioned methods, wherein $R^9$ is OR; and $R^{10}$, $R^{11}$, $R^{12}$, $R^{13}$, and $R^{14}$ are H.

In certain embodiments, the invention relates to any one of the aforementioned methods, wherein $R^{10}$ is OR; and $R^9$, $R^{11}$, $R^{12}$, $R^{13}$, and $R^{14}$ are H.

In certain embodiments, the invention relates to any one of the aforementioned methods, wherein $R^{11}$ is OR; and $R^9$, $R^{10}$, $R^{12}$, $R^{13}$, and $R^{14}$ are H.

In certain embodiments, the invention relates to any one of the aforementioned methods, wherein $R^9$ and $R^{10}$ are OR; and $R^{11}$, $R^{12}$, $R^{13}$, and $R^{14}$ are H.

In certain embodiments, the invention relates to any one of the aforementioned methods, wherein $R^9$ and $R^{11}$ are OR; and $R^{10}$, $R^{12}$, $R^{13}$, and $R^{14}$ are H.

In certain embodiments, the invention relates to any one of the aforementioned methods, wherein $R^9$ and $R^{12}$ are OR; and $R^{10}$, $R^{11}$, $R^{13}$, and $R^{14}$ are H.

In certain embodiments, the invention relates to any one of the aforementioned methods, wherein $R^9$ and $R^{13}$ are OR; and $R^{10}$, $R^{11}$, $R^{12}$, and $R^{14}$ are H.

In certain embodiments, the invention relates to any one of the aforementioned methods, wherein $R^9$ and $R^{14}$ are OR; and $R^{10}$, $R^{11}$, $R^{12}$, and $R^{13}$ are H.

In certain embodiments, the invention relates to any one of the aforementioned methods, wherein $R^{10}$ and $R^{11}$ are OR; and $R^9$, $R^{12}$, $R^{13}$, and $R^{14}$ are H.

In certain embodiments, the invention relates to any one of the aforementioned methods, wherein $R^{10}$ and $R^{12}$ are OR; and $R^9$, $R^{11}$, $R^{13}$, and $R^{14}$ are H.

In certain embodiments, the invention relates to any one of the aforementioned methods, wherein $R^{10}$ and $R^{13}$ are OR; and $R^9$, $R^{11}$, $R^{12}$, and $R^{14}$ are H.

In certain embodiments, the invention relates to any one of the aforementioned methods, wherein $R^{11}$ and $R^{12}$ are OR; and $R^9$, $R^{10}$, $R^{13}$, and $R^{14}$ are H.

In certain embodiments, the invention relates to any one of the aforementioned methods, wherein $R^9$, $R^{10}$, and $R^{11}$ are OR; and $R^{12}$, $R^{13}$, and $R^{14}$ are H.

In certain embodiments, the invention relates to any one of the aforementioned methods, wherein $R^9$, $R^{10}$, and $R^{12}$ are OR; and $R^{11}$, $R^{13}$, and $R^{14}$ are H.

In certain embodiments, the invention relates to any one of the aforementioned methods, wherein $R^9$, $R^{10}$, and $R^{13}$ are OR; and $R^{11}$, $R^{12}$, and $R^{14}$ are H.

In certain embodiments, the invention relates to any one of the aforementioned methods, wherein $R^9$, $R^{10}$, and $R^{14}$ are OR; and $R^{11}$, $R^{12}$, and $R^{13}$ are H.

In certain embodiments, the invention relates to any one of the aforementioned methods, wherein $R^9$, $R^{11}$, and $R^{12}$ are OR; and $R^{10}$, $R^{13}$, and $R^{14}$ are H.

In certain embodiments, the invention relates to any one of the aforementioned methods, wherein $R^9$, $R^{11}$, and $R^{13}$ are OR; and $R^{10}$, $R^{12}$, and $R^{14}$ are H.

In certain embodiments, the invention relates to any one of the aforementioned methods, wherein $R^9$, $R^{11}$, and $R^{14}$ are OR; and $R^{10}$, $R^{12}$, and $R^{13}$ are H.

In certain embodiments, the invention relates to any one of the aforementioned methods, wherein $R^9$, $R^{12}$, and $R^{13}$ are OR; and $R^{10}$, $R^{11}$, and $R^{14}$ are H.

In certain embodiments, the invention relates to any one of the aforementioned methods, wherein $R^{10}$, $R^{11}$, and $R^{12}$ are OR; and $R^9$, $R^{13}$, and $R^{14}$ are H.

In certain embodiments, the invention relates to any one of the aforementioned methods, wherein $R^{10}$, $R^{11}$, and $R^{13}$ are OR; and $R^9$, $R^{12}$, and $R^{14}$ are H.

In certain embodiments, the invention relates to any one of the aforementioned methods, wherein $R^9$, $R^{10}$, $R^{11}$, and $R^{12}$ are OR; and $R^{13}$ and $R^{14}$ are H.

In certain embodiments, the invention relates to any one of the aforementioned methods, wherein $R^9$, $R^{10}$, $R^{11}$, and $R^{13}$ are OR; and $R^{12}$ and $R^{14}$ are H.

In certain embodiments, the invention relates to any one of the aforementioned methods, wherein $R^9$, $R^{10}$, $R^{11}$, and $R^{14}$ are OR; and $R^{12}$ and $R^{13}$ are H.

In certain embodiments, the invention relates to any one of the aforementioned methods, wherein $R^9$, $R^{10}$, $R^{12}$, and $R^{13}$ are OR; and $R^{11}$ and $R^{14}$ are H.

In certain embodiments, the invention relates to any one of the aforementioned methods, wherein $R^9$, $R^{10}$, $R^{12}$, and $R^{14}$ are OR; and $R^{11}$ and $R^{13}$ are H.

In certain embodiments, the invention relates to any one of the aforementioned methods, wherein $R^9$, $R^{10}$, $R^{13}$, and $R^{14}$ are OR; and $R^{11}$ and $R^{12}$ are H.

In certain embodiments, the invention relates to any one of the aforementioned methods, wherein $R^9$, $R^{11}$, $R^{12}$, and $R^{13}$ are OR; and $R^{10}$ and $R^{14}$ are H.

In certain embodiments, the invention relates to any one of the aforementioned methods, wherein $R^9$, $R^{11}$, $R^{12}$, and $R^{14}$ are OR; and $R^{10}$ and $R^{13}$ are H.

In certain embodiments, the invention relates to any one of the aforementioned methods, wherein $R^{10}$, $R^{11}$, $R^{12}$, and $R^{13}$ are OR; and $R^9$ and $R^{14}$ are H.

In certain embodiments, the invention relates to any one of the aforementioned methods, wherein $R^9$, $R^{10}$, $R^{11}$, $R^{12}$, and $R^{13}$ are OR; and $R^{14}$ is H.

In certain embodiments, the invention relates to any one of the aforementioned methods, wherein $R^9$, $R^{10}$, $R^{11}$, $R^{12}$, and $R^{14}$ are OR; and $R^{13}$ is H.

In certain embodiments, the invention relates to any one of the aforementioned methods, wherein $R^9$, $R^{10}$, $R^{11}$, $R^{13}$, and $R^{14}$ are OR; and $R^{12}$ is H.

In certain embodiments, the invention relates to any one of the aforementioned methods, wherein R is H.

In certain embodiments, the invention relates to a method of treating or preventing metabolic stress, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the metabolic stress.

In certain embodiments, the invention relates to a method of treating or preventing cardiovascular disease, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the cardiovascular disease.

In certain embodiments, the invention relates to a method of treating or preventing cardiomyopathy, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the cardiomyopathy.

In certain embodiments, the invention relates to a method of improving muscle function, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby improving muscle function.

In certain embodiments, the invention relates to a method of treating or preventing sarcopenia, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the sarcopenia.

In certain embodiments, the invention relates to a method of treating or preventing muscle degenerative disease, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the muscle degenerative disease.

In certain embodiments, the invention relates to a method of treating or preventing Duchenne muscular dystrophy, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the Duchenne muscular dystrophy.

In certain embodiments, the invention relates to a method of treating or preventing alcoholic liver disease, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the alcoholic liver disease.

In certain embodiments, the invention relates to a method of treating or preventing nonalcoholic fatty liver disease, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the nonalcoholic fatty liver disease.

In certain embodiments, the invention relates to a method of treating or preventing drug-induced liver injury, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the drug-induced liver injury.

In certain embodiments, the invention relates to a method of treating or preventing α1-antitrypsin deficiency, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the α1-antitrypsin deficiency.

In certain embodiments, the invention relates to a method of treating or preventing ischemia-reperfusion injury, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the ischemia/reperfusion injury.

In certain embodiments, the invention relates to a method of treating or preventing inflammation, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the inflammation.

In certain embodiments, the invention relates to a method of treating or preventing inflammatory bowel disease, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the inflammatory bowel disease.

In certain embodiments, the invention relates to a method of treating or preventing Crohn's disease, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the Crohn's disease.

In certain embodiments, the invention relates to a method of treating or preventing obesity, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the obesity.

In certain embodiments, the invention relates to a method of treating or preventing metabolic syndrome, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the metabolic syndrome.

In certain embodiments, the invention relates to a method of treating or preventing type II diabetes mellitus, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the type II diabetes mellitus.

In certain embodiments, the invention relates to a method of treating or preventing hyperlipidemia, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the hyperlipidemia.

In certain embodiments, the invention relates to a method of treating or preventing osteoarthritis, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the osteoarthritis.

In certain embodiments, the invention relates to a method of treating or preventing neurodegenerative disease, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the neurodegenerative disease.

In certain embodiments, the invention relates to a method of treating or preventing Alzheimer's disease, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the Alzheimer's disease.

In certain embodiments, the invention relates to a method of treating or preventing Parkinson's disease, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the Parkinson's disease.

In certain embodiments, the invention relates to a method of treating or preventing amyotrophic lateral sclerosis (ALS), comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the ALS.

In certain embodiments, the invention relates to a method of treating or preventing cancer, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the cancer.

In certain embodiments, the invention relates to a method of treating or preventing cognitive disorder, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the cognitive disorder.

In certain embodiments, the invention relates to a method of treating or preventing mood disorder, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the mood disorder.

In certain embodiments, the invention relates to a method of treating or preventing stress, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby treating or preventing the stress.

In certain embodiments, the invention relates to a method of improving activity during aging, comprising administering a therapeutically effective amount of a compound selected from the group consisting of: a compound of Formula II, a compound of Formula III, a compound of Formula V, a compound of Formula VI, urolithin A, urolithin B, urolithin C, urolithin D, and ellagic acid, to a subject in need thereof, thereby improving activity during aging.

In certain embodiments, the invention relates to any one of the aforementioned methods, wherein the compound is a compound of Formula II as defined herein.

In certain embodiments, the invention relates to any one of the aforementioned methods, wherein the compound is a compound of Formula III as defined herein.

In certain embodiments, the invention relates to any one of the aforementioned methods, wherein the compound is a compound of Formula V as defined herein.

In certain embodiments, the invention relates to any one of the aforementioned methods, wherein the compound is a compound of Formula VI as defined herein.

In certain embodiments, the invention relates to any one of the aforementioned methods, wherein the compound is urolithin A.

In certain embodiments, the invention relates to any one of the aforementioned methods, wherein the compound is urolithin B.

In certain embodiments, the invention relates to any one of the aforementioned methods, wherein the compound is urolithin C.

In certain embodiments, the invention relates to any one of the aforementioned methods, wherein the compound is urolithin D.

In certain embodiments, the invention relates to any one of the aforementioned methods, wherein the compound is ellagic acid.

In certain embodiments, the invention relates to a method of treating or preventing metabolic stress, comprising administering a therapeutically effective amount of a compound of Formula I to a subject in need thereof, thereby treating or preventing the metabolic stress, wherein the compound of Formula I is

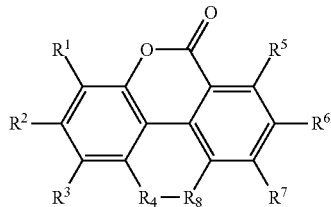

Formula I wherein
- $R^1$, $R^2$, $R^3$, $R^4$, $R^5$, $R^6$, $R^7$, and $R^8$ are independently selected from the group consisting of H and OR; and
- R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing cardiovascular disease, comprising administering a therapeutically effective amount of a compound of Formula I to a subject in need thereof, thereby treating or preventing the cardiovascular disease, wherein the compound of Formula I is

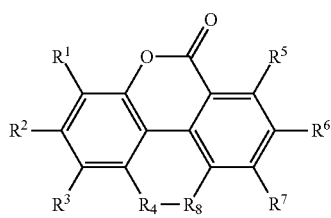

Formula I wherein
- $R^1$, $R^2$, $R^3$, $R^4$, $R^5$, $R^6$, $R^7$, and $R^8$ are independently selected from the group consisting of H and OR; and
- R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing cardiomyopathy, comprising administering a therapeutically effective amount of a compound of Formula I to a subject in need thereof, thereby treating or preventing the cardiomyopathy, wherein the compound of Formula I is

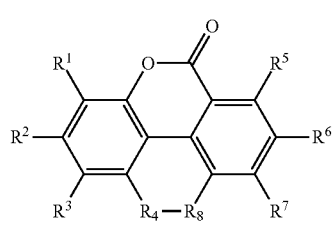

Formula I wherein
- $R^1$, $R^2$, $R^3$, $R^4$, $R^5$, $R^6$, $R^7$, and $R^8$ are independently selected from the group consisting of H and OR; and
- R is H, substituted or unsubstituted alkyl, substituted or unsubstituted aryl, a substituted or unsubstituted monosaccharide, or a substituted or unsubstituted oligosaccharide.

In certain embodiments, the invention relates to a method of improving muscle function, comprising administering a therapeutically effective amount of a compound of Formula I to a subject in need thereof, thereby improving muscle function, wherein the compound of Formula I is

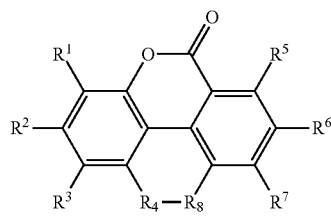

Formula I wherein
- $R^1$, $R^2$, $R^3$, $R^4$, $R^5$, $R^6$, $R^7$, and $R^8$ are independently selected from the group consisting of H and OR; and
- R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing sarcopenia, comprising administering a therapeutically effective amount of a compound of Formula I to a subject in need thereof, thereby treating or preventing the sarcopenia, wherein the compound of Formula I is

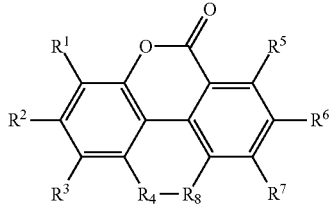

Formula I wherein
- $R^1$, $R^2$, $R^3$, $R^4$, $R^5$, $R^6$, $R^7$, and $R^8$ are independently selected from the group consisting of H and OR; and
- R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing muscle degenerative disease, comprising administering a therapeutically effective amount of a compound of Formula I to a subject in need thereof, thereby treating or preventing the muscle degenerative disease, wherein the compound of Formula I is

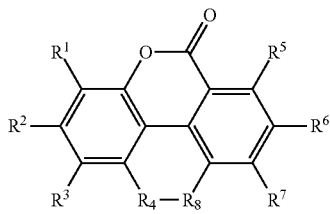

Formula I wherein
- $R^1$, $R^2$, $R^3$, $R^4$, $R^5$, $R^6$, $R^7$, and $R^8$ are independently selected from the group consisting of H and OR; and
- R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing Duchenne muscular dystrophy, comprising administering a therapeutically effective amount of a compound of Formula I to a subject in need thereof, thereby treating or preventing the Duchenne muscular dystrophy, wherein the compound of Formula I is

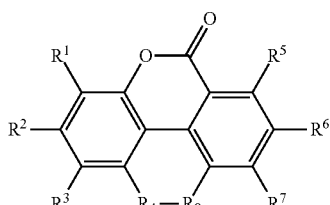

Formula I wherein
- $R^1$, $R^2$, $R^3$, $R^4$, $R^5$, $R^6$, $R^7$, and $R^8$ are independently selected from the group consisting of H and OR; and
- R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing alcoholic liver disease, comprising administering a therapeutically effective amount of a compound of Formula I to a subject in need thereof, thereby treating or preventing the alcoholic liver disease, wherein the compound of Formula I is

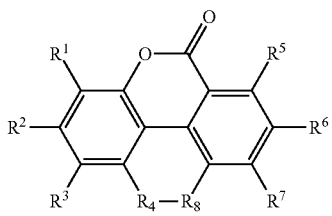

Formula I wherein
- $R^1$, $R^2$, $R^3$, $R^4$, $R^5$, $R^6$, $R^7$, and $R^8$ are independently selected from the group consisting of H and OR; and
- R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing nonalcoholic fatty liver disease, comprising administering a therapeutically effective amount of a compound of Formula I to a subject in need thereof, thereby treating or preventing the nonalcoholic fatty liver disease, wherein the compound of Formula I is

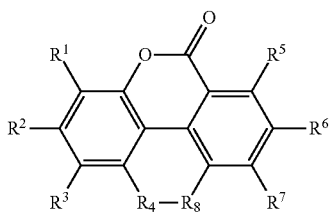

Formula I wherein
- $R^1$, $R^2$, $R^3$, $R^4$, $R^5$, $R^6$, $R^7$, and $R^8$ are independently selected from the group consisting of H and OR; and
- R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing drug-induced liver injury, comprising administering a therapeutically effective amount of a compound of Formula I to a subject in need thereof, thereby treating or preventing the drug-induced liver injury, wherein the compound of Formula I is

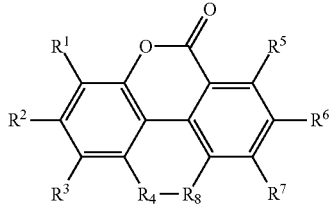

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing α1-antitrypsin deficiency, comprising administering a therapeutically effective amount of a compound of Formula I to a subject in need thereof, thereby treating or preventing the α1-antitrypsin deficiency,
wherein the compound of Formula I is

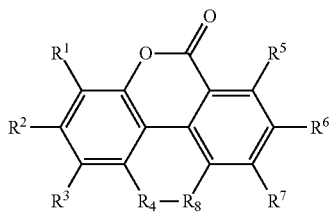

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing ischemia-reperfusion injury, comprising administering a therapeutically effective amount of a compound of Formula I to a subject in need thereof, thereby treating or preventing the ischemia/reperfusion injury,
wherein the compound of Formula I is

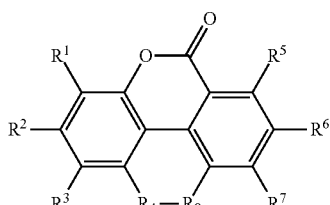

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing inflammation, comprising administering a therapeutically effective amount of a compound of Formula I to a subject in need thereof, thereby treating or preventing the inflammation,
wherein the compound of Formula I is

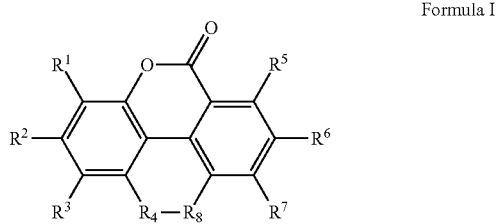

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing inflammatory bowel disease, comprising administering a therapeutically effective amount of a compound of Formula I to a subject in need thereof, thereby treating or preventing the inflammatory bowel disease,
wherein the compound of Formula I is

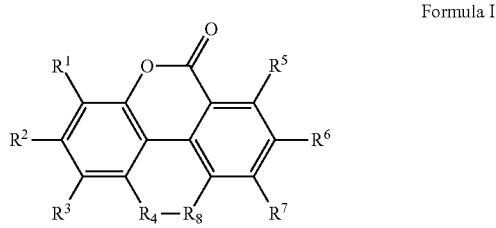

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing Crohn's disease, comprising administering a therapeutically effective amount of a compound of Formula I to a subject in need thereof, thereby treating or preventing the Crohn's disease, wherein the compound of Formula I is

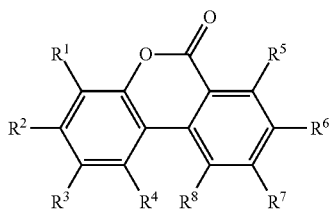

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing obesity, comprising administering a therapeutically effective amount of a compound of Formula I to a subject in need thereof, thereby treating or preventing the obesity,
wherein the compound of Formula I is

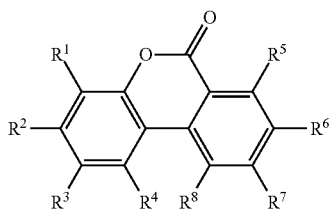

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing metabolic syndrome, comprising administering a therapeutically effective amount of a compound of Formula I to a subject in need thereof, thereby treating or preventing the metabolic syndrome,
wherein the compound of Formula I is

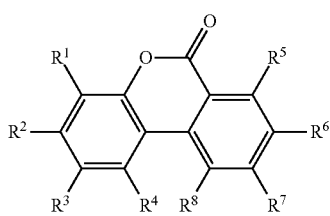

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing type II diabetes mellitus, comprising administering a therapeutically effective amount of a compound of Formula I to a subject in need thereof, thereby treating or preventing the type II diabetes mellitus,
wherein the compound of Formula I is

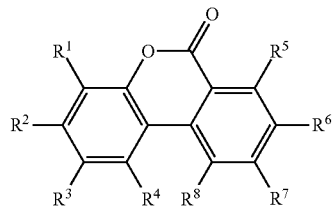

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing hyperlipidemia, comprising administering a therapeutically effective amount of a compound of Formula I to a subject in need thereof, thereby treating or preventing the hyperlipidemia,
wherein the compound of Formula I is

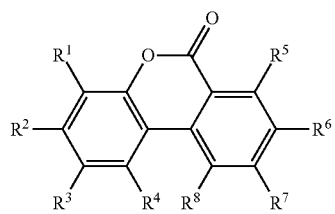

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing osteoarthritis, comprising administering a therapeutically effective amount of a compound of Formula I to a subject in need thereof, thereby treating or preventing the osteoarthritis, wherein the compound of Formula I is

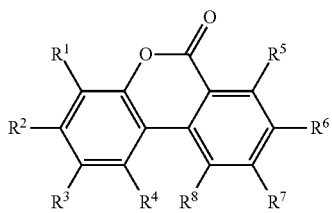

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing neurodegenerative disease, comprising administering a therapeutically effective amount of a compound of Formula I to a subject in need thereof, thereby treating or preventing the neurodegenerative disease,
wherein the compound of Formula I is

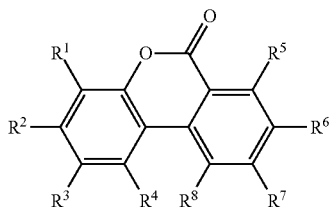

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing Alzheimer's disease, comprising administering a therapeutically effective amount of a compound of Formula I to a subject in need thereof, thereby treating or preventing the Alzheimer's disease,
wherein the compound of Formula I is

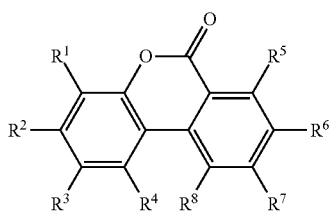

Formula I wherein
$R^1$, $R^2$, $R^3$, $R^4$, $R^5$, $R^6$, $R^7$, and $R^8$ are independently selected from the group consisting of H and OR; and R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing Parkinson's disease, comprising administering a therapeutically effective amount of a compound of Formula I to a subject in need thereof, thereby treating or preventing the Parkinson's disease,
wherein the compound of Formula I is

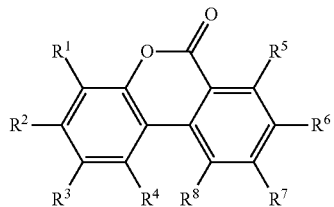

Formula I wherein
$R^1$, $R^2$, $R^3$, $R^4$, $R^5$, $R^6$, $R^7$, and $R^8$ are independently selected from the group consisting of H and OR; and R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing amyotrophic lateral sclerosis (ALS), comprising administering a therapeutically effective amount of a compound of Formula I to a subject in need thereof, thereby treating or preventing the ALS,
wherein the compound of Formula I is

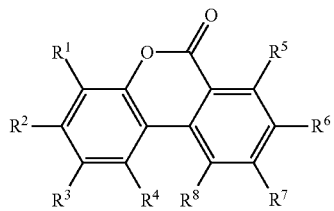

Formula I wherein
$R^1$, $R^2$, $R^3$, $R^4$, $R^5$, $R^6$, $R^7$, and $R^8$ are independently selected from the group consisting of H and OR; and R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing cancer, comprising a therapeutically effective amount of a compound of Formula I to a subject in need thereof, thereby treating or preventing the cancer, wherein the compound of Formula I is

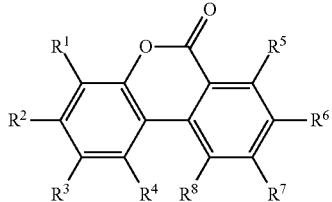

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing cognitive disorder, comprising administering a therapeutically effective amount of a compound of Formula I to a subject in need thereof, thereby treating or preventing the cognitive disorder,
wherein the compound of Formula I is

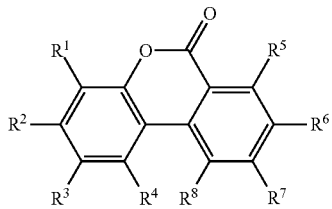

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing mood disorder, comprising administering a therapeutically effective amount of a compound of Formula I to a subject in need thereof, thereby treating or preventing the mood disorder,
wherein the compound of Formula I is

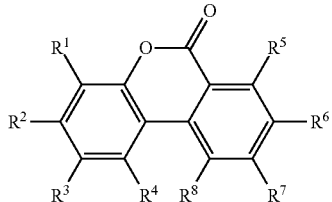

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing stress, comprising administering a therapeutically effective amount of a compound of Formula I to a subject in need thereof, thereby treating or preventing the stress,
wherein the compound of Formula I is

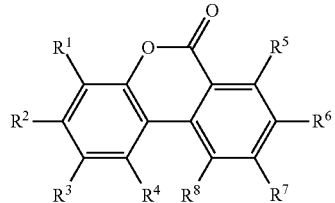

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of improving activity during aging, comprising administering a therapeutically effective amount of a compound of Formula I to a subject in need thereof, thereby improving activity during aging,
wherein the compound of Formula I is

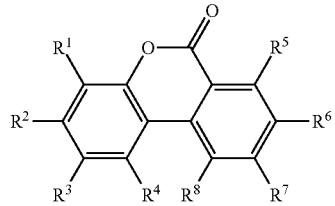

Formula I wherein
$R^1$, $R^2$, $R^3$, $R^4$, $R^5$, $R^6$, $R^7$, and $R^8$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to any one of the aforementioned methods, wherein $R^1$, $R^2$, $R^3$, $R^4$, $R^5$, $R^6$, $R^7$, and $R^8$ are H.

In certain embodiments, the invention relates to any one of the aforementioned methods, wherein at least one of $R^1$, $R^2$, $R^3$, $R^4$, $R^5$, $R^6$, $R^7$, and $R^8$ is OR.

In certain embodiments, the invention relates to any one of the aforementioned methods, wherein at least two of $R^1$, $R^2$, $R^3$, $R^4$, $R^5$, $R^6$, $R^7$, and $R^8$ are OR.

In certain embodiments, the invention relates to any one of the aforementioned methods, wherein at least three of $R^1$, $R^2$, $R^3$, $R^4$, $R^5$, $R^6$, $R^7$, and $R^8$ are OR.

In certain embodiments, the invention relates to any one of the aforementioned methods, wherein at least four of $R^1$, $R^2$, $R^3$, $R^4$, $R^5$, $R^6$, $R^7$, and $R^8$ are OR.

In certain embodiments, the invention relates to any one of the aforementioned methods, wherein at least five of $R^1$, $R^2$, $R^3$, $R^4$, $R^5$, $R^6$, $R^7$, and $R^8$ are OR.

In certain embodiments, the invention relates to any one of the aforementioned methods, wherein at least six of $R^1$, $R^2$, $R^3$, $R^4$, $R^5$, $R^6$, $R^7$, and $R^8$ are OR.

In certain embodiments, the invention relates to any one of the aforementioned methods, wherein at least seven of $R^1$, $R^2$, $R^3$, $R^4$, $R^5$, $R^6$, $R^7$, and $R^8$ are OR.

In certain embodiments, the invention relates to any one of the aforementioned methods, wherein $R^1$, $R^2$, $R^3$, $R^4$, $R^5$, $R^6$, $R^7$, and $R^8$ are OR.

In certain embodiments, the invention relates to any one of the aforementioned methods, wherein $R^1$ is OR; and $R^2$, $R^3$, $R^4$, $R^5$, $R^6$, $R^7$, and $R^8$ are H.

In certain embodiments, the invention relates to any one of the aforementioned methods, wherein $R^2$ is OR; and $R^1$, $R^3$, $R^4$, $R^5$, $R^6$, $R^7$, and $R^8$ are H.

In certain embodiments, the invention relates to any one of the aforementioned methods, wherein $R^3$ is OR; and $R^1$, $R^2$, $R^4$, $R^5$, $R^6$, $R^7$, and $R^8$ are H.

In certain embodiments, the invention relates to any one of the aforementioned methods, wherein $R^4$ is OR; and $R^1$, $R^2$, $R^3$, $R^5$, $R^6$, $R^7$, and $R^8$ are H.

In certain embodiments, the invention relates to any one of the aforementioned methods, wherein $R^5$ is OR; and $R^1$, $R^2$, $R^3$, $R^4$, $R^6$, $R^7$, and $R^8$ are H.

In certain embodiments, the invention relates to any one of the aforementioned methods, wherein $R^6$ is OR; and $R^1$, $R^2$, $R^3$, $R^4$, $R^5$, $R^7$, and $R^8$ are H.

In certain embodiments, the invention relates to any one of the aforementioned methods, wherein $R^7$ is OR; and $R^1$, $R^2$, $R^3$, $R^4$, $R^5$, $R^6$, and $R^8$ are H.

In certain embodiments, the invention relates to any one of the aforementioned methods, wherein $R^8$ is OR; and $R^1$, $R^2$, $R^3$, $R^4$, $R^5$, $R^6$, and $R^7$ are H.

In certain embodiments, the invention relates to any one of the aforementioned methods, wherein $R^1$ and $R^2$ are OR; and $R^3$, $R^4$, $R^5$, $R^6$, $R^7$, and $R^8$ are H.

In certain embodiments, the invention relates to any one of the aforementioned methods, wherein $R^1$ and $R^3$ are OR; and $R^2$, $R^4$, $R^5$, $R^6$, $R^7$, and $R^8$ are H.

In certain embodiments, the invention relates to any one of the aforementioned methods, wherein $R^1$ and $R^4$ are OR; and $R^2$, $R^3$, $R^5$, $R^6$, $R^7$, and $R^8$ are H.

In certain embodiments, the invention relates to any one of the aforementioned methods, wherein $R^1$ and $R^5$ are OR; and $R^2$, $R^3$, $R^4$, $R^6$, $R^7$, and $R^8$ are H.

In certain embodiments, the invention relates to any one of the aforementioned methods, wherein $R^1$ and $R^6$ are OR; and $R^2$, $R^3$, $R^4$, $R^5$, $R^7$, and $R^8$ are H.

In certain embodiments, the invention relates to any one of the aforementioned methods, wherein $R^1$ and $R^7$ are OR; and $R^2$, $R^3$, $R^4$, $R^5$, $R^6$, and $R^8$ are H.

In certain embodiments, the invention relates to any one of the aforementioned methods, wherein $R^1$ and $R^8$ are OR; and $R^2$, $R^3$, $R^4$, $R^5$, $R^6$, and $R^7$ are H.

In certain embodiments, the invention relates to any one of the aforementioned methods, wherein $R^2$ and $R^3$ are OR; and $R^1$, $R^4$, $R^5$, $R^6$, $R^7$, and $R^8$ are H.

In certain embodiments, the invention relates to any one of the aforementioned methods, wherein $R^2$ and $R^4$ are OR; and $R^1$, $R^3$, $R^5$, $R^6$, $R^7$, and $R^8$ are H.

In certain embodiments, the invention relates to any one of the aforementioned methods, wherein $R^2$ and $R^5$ are OR; and $R^1$, $R^3$, $R^4$, $R^6$, $R^7$, and $R^8$ are H.

In certain embodiments, the invention relates to any one of the aforementioned methods, wherein $R^2$ and $R^6$ are OR; and $R^1$, $R^3$, $R^4$, $R^5$, $R^7$, and $R^8$ are H.

In certain embodiments, the invention relates to any one of the aforementioned methods, wherein $R^2$ and $R^7$ are OR; and $R^1$, $R^3$, $R^4$, $R^5$, $R^6$, and $R^8$ are H.

In certain embodiments, the invention relates to any one of the aforementioned methods, wherein $R^2$ and $R^8$ are OR; and $R^1$, $R^3$, $R^4$, $R^5$, $R^6$, and $R^7$ are H.

In certain embodiments, the invention relates to any one of the aforementioned methods, wherein $R^3$ and $R^4$ are OR; and $R^1$, $R^2$, $R^5$, $R^6$, $R^7$, and $R^8$ are H.

In certain embodiments, the invention relates to any one of the aforementioned methods, wherein $R^3$ and $R^5$ are OR; and $R^1$, $R^2$, $R^4$, $R^6$, $R^7$, and $R^8$ are H.

In certain embodiments, the invention relates to any one of the aforementioned methods, wherein $R^3$ and $R^6$ are OR; and $R^1$, $R^2$, $R^4$, $R^5$, $R^7$, and $R^8$ are H.

In certain embodiments, the invention relates to any one of the aforementioned methods, wherein $R^3$ and $R^7$ are OR; and $R^1$, $R^2$, $R^4$, $R^5$, $R^6$, and $R^8$ are H.

In certain embodiments, the invention relates to any one of the aforementioned methods, wherein $R^3$ and $R^8$ are OR; and $R^1$, $R^2$, $R^4$, $R^5$, $R^6$, and $R^7$ are H.

In certain embodiments, the invention relates to any one of the aforementioned methods, wherein $R^4$ and $R^5$ are OR; and $R^1$, $R^2$, $R^3$, $R^6$, $R^7$, and $R^8$ are H.

In certain embodiments, the invention relates to any one of the aforementioned methods, wherein $R^4$ and $R^6$ are OR; and $R^1$, $R^2$, $R^3$, $R^5$, $R^7$, and $R^8$ are H.

In certain embodiments, the invention relates to any one of the aforementioned methods, wherein $R^4$ and $R^7$ are OR; and $R^1$, $R^2$, $R^3$, $R^5$, $R^6$, and $R^8$ are H.

In certain embodiments, the invention relates to any one of the aforementioned methods, wherein $R^4$ and $R^8$ are OR; and $R^1$, $R^2$, $R^3$, $R^5$, $R^6$, and $R^7$ are H.

In certain embodiments, the invention relates to any one of the aforementioned methods, wherein $R^5$ and $R^6$ are OR; and $R^1$, $R^2$, $R^3$, $R^4$, $R^7$, and $R^8$ are H.

In certain embodiments, the invention relates to any one of the aforementioned methods, wherein $R^5$ and $R^7$ are OR; and $R^1$, $R^2$, $R^3$, $R^4$, $R^6$, and $R^8$ are H.

In certain embodiments, the invention relates to any one of the aforementioned methods, wherein $R^5$ and $R^8$ are OR; and $R^1$, $R^2$, $R^3$, $R^4$, $R^6$, and $R^7$ are H.

In certain embodiments, the invention relates to any one of the aforementioned methods, wherein $R^6$ and $R^7$ are OR; and $R^1$, $R^2$, $R^3$, $R^4$, $R^5$, and $R^8$ are H.

In certain embodiments, the invention relates to any one of the aforementioned methods, wherein $R^6$ and $R^8$ are OR; and $R^1$, $R^2$, $R^3$, $R^4$, $R^5$, and $R^7$ are H.

In certain embodiments, the invention relates to any one of the aforementioned methods, wherein $R^7$ and $R^8$ are OR; and $R^1$, $R^2$, $R^3$, $R^4$, $R^5$, and $R^6$ are H.

In certain embodiments, the invention relates to any one of the aforementioned methods, wherein $R^1$, $R^2$, and $R^3$ are OR; and $R^4$, $R^5$, $R^6$, $R^7$, and $R^8$ are H.

In certain embodiments, the invention relates to any one of the aforementioned methods, wherein $R^1$, $R^2$, and $R^4$ are OR; and $R^3$, $R^5$, $R^6$, $R^7$, and $R^8$ are H.

In certain embodiments, the invention relates to any one of the aforementioned methods, wherein $R^1$, $R^2$, and $R^5$ are OR; and $R^3$, $R^4$, $R^6$, $R^7$, and $R^8$ are H.

In certain embodiments, the invention relates to any one of the aforementioned methods, wherein $R^1$, $R^2$, and $R^6$ are OR; and $R^3$, $R^4$, $R^5$, $R^7$, and $R^8$ are H.

In certain embodiments, the invention relates to any one of the aforementioned methods, wherein $R^1$, $R^2$, and $R^7$ are OR; and $R^3$, $R^4$, $R^5$, $R^6$, and $R^8$ are H.

In certain embodiments, the invention relates to any one of the aforementioned methods, wherein $R^1$, $R^2$, and $R^8$ are OR; and $R^3$, $R^4$, $R^5$, $R^6$, and $R^7$ are H.

In certain embodiments, the invention relates to any one of the aforementioned methods, wherein $R^1$, $R^3$, and $R^4$ are OR; and $R^2$, $R^5$, $R^6$, $R^7$, and $R^8$ are H.

In certain embodiments, the invention relates to any one of the aforementioned methods, wherein $R^1$, $R^3$, and $R^5$ are OR; and $R^2$, $R^4$, $R^6$, $R^7$, and $R^8$ are H.

In certain embodiments, the invention relates to any one of the aforementioned methods, wherein $R^1$, $R^3$, and $R^6$ are OR; and $R^2$, $R^4$, $R^5$, $R^7$, and $R^8$ are H.

In certain embodiments, the invention relates to any one of the aforementioned methods, wherein $R^1$, $R^3$, and $R^7$ are OR; and $R^2$, $R^4$, $R^5$, $R^6$, and $R^8$ are H.

In certain embodiments, the invention relates to any one of the aforementioned methods, wherein $R^1$, $R^3$, and $R^8$ are OR; and $R^2$, $R^4$, $R^5$, $R^6$, and $R^7$ are H.

In certain embodiments, the invention relates to any one of the aforementioned methods, wherein $R^1$, $R^4$, and $R^5$ are OR; and $R^2$, $R^3$, $R^6$, $R^7$, and $R^8$ are H.

In certain embodiments, the invention relates to any one of the aforementioned methods, wherein $R^1$, $R^4$, and $R^6$ are OR; and $R^2$, $R^3$, $R^5$, $R^7$, and $R^8$ are H.

In certain embodiments, the invention relates to any one of the aforementioned methods, wherein $R^1$, $R^4$, and $R^7$ are OR; and $R^2$, $R^3$, $R^5$, $R^6$, and $R^8$ are H.

In certain embodiments, the invention relates to any one of the aforementioned methods, wherein $R^1$, $R^4$, and $R^8$ are OR; and $R^2$, $R^3$, $R^5$, $R^6$, and $R^7$ are H.

In certain embodiments, the invention relates to any one of the aforementioned methods, wherein $R^1$, $R^5$, and $R^6$ are OR; and $R^2$, $R^3$, $R^4$, $R^7$, and $R^8$ are H.

In certain embodiments, the invention relates to any one of the aforementioned methods, wherein $R^1$, $R^5$, and $R^7$ are OR; and $R^2$, $R^3$, $R^4$, $R^6$, and $R^8$ are H.

In certain embodiments, the invention relates to any one of the aforementioned methods, wherein $R^1$, $R^5$, and $R^8$ are OR; and $R^2$, $R^3$, $R^4$, $R^6$, and $R^7$ are H.

In certain embodiments, the invention relates to any one of the aforementioned methods, wherein $R^1$, $R^6$, and $R^7$ are OR; and $R^2$, $R^3$, $R^4$, $R^5$, and $R^8$ are H.

In certain embodiments, the invention relates to any one of the aforementioned methods, wherein $R^1$, $R^6$, and $R^8$ are OR; and $R^2$, $R^3$, $R^4$, $R^5$, and $R^7$ are H.

In certain embodiments, the invention relates to any one of the aforementioned methods, wherein $R^1$, $R^7$, and $R^8$ are OR; and $R^2$, $R^3$, $R^4$, $R^5$, and $R^7$ are H.

In certain embodiments, the invention relates to any one of the aforementioned methods, wherein $R^2$, $R^3$, and $R^4$ are OR; and $R^1$, $R^5$, $R^6$, $R^7$, and $R^8$ are H.

In certain embodiments, the invention relates to any one of the aforementioned methods, wherein $R^2$, $R^3$, and $R^5$ are OR; and $R^1$, $R^4$, $R^6$, $R^7$, and $R^8$ are H.

In certain embodiments, the invention relates to any one of the aforementioned methods, wherein $R^2$, $R^3$, and $R^6$ are OR; and $R^1$, $R^4$, $R^5$, $R^7$, and $R^8$ are H.

In certain embodiments, the invention relates to any one of the aforementioned methods, wherein $R^2$, $R^3$, and $R^7$ are OR; and $R^1$, $R^4$, $R^5$, $R^6$, and $R^8$ are H.

In certain embodiments, the invention relates to any one of the aforementioned methods, wherein $R^2$, $R^3$, and $R^8$ are OR; and $R^1$, $R^4$, $R^5$, $R^6$, and $R^7$ are H.

In certain embodiments, the invention relates to any one of the aforementioned methods, wherein $R^2$, $R^4$, and $R^5$ are OR; and $R^1$, $R^3$, $R^6$, $R^7$, and $R^8$ are H.

In certain embodiments, the invention relates to any one of the aforementioned methods, wherein $R^2$, $R^4$, and $R^6$ are OR; and $R^1$, $R^3$, $R^5$, $R^7$, and $R^8$ are H.

In certain embodiments, the invention relates to any one of the aforementioned methods, wherein $R^2$, $R^4$, and $R^7$ are OR; and $R^1$, $R^3$, $R^5$, $R^6$, and $R^8$ are H.

In certain embodiments, the invention relates to any one of the aforementioned methods, wherein $R^2$, $R^4$, and $R^8$ are OR; and $R^1$, $R^3$, $R^5$, $R^6$, and $R^7$ are H.

In certain embodiments, the invention relates to any one of the aforementioned methods, wherein $R^2$, $R^5$, and $R^6$ are OR; and $R^1$, $R^3$, $R^4$, $R^7$, and $R^8$ are H.

In certain embodiments, the invention relates to any one of the aforementioned methods, wherein $R^2$, $R^5$, and $R^7$ are OR; and $R^1$, $R^3$, $R^4$, $R^6$, and $R^8$ are H.

In certain embodiments, the invention relates to any one of the aforementioned methods, wherein $R^2$, $R^5$, and $R^8$ are OR; and $R^1$, $R^3$, $R^4$, $R^7$, and $R^8$ are H.

In certain embodiments, the invention relates to any one of the aforementioned methods, wherein $R^2$, $R^6$, and $R^7$ are OR; and $R^1$, $R^3$, $R^4$, $R^5$, and $R^8$ are H.

In certain embodiments, the invention relates to any one of the aforementioned methods, wherein $R^2$, $R^6$, and $R^8$ are OR; and $R^1$, $R^3$, $R^4$, $R^5$, and $R^7$ are H.

In certain embodiments, the invention relates to any one of the aforementioned methods, wherein $R^2$, $R^7$, and $R^8$ are OR; and $R^1$, $R^3$, $R^4$, $R^5$, and $R^6$ are H.

In certain embodiments, the invention relates to any one of the aforementioned methods, wherein $R^3$, $R^4$, and $R^5$ are OR; and $R^1$, $R^2$, $R^6$, $R^7$, and $R^8$ are H.

In certain embodiments, the invention relates to any one of the aforementioned methods, wherein $R^3$, $R^4$, and $R^6$ are OR; and $R^1$, $R^2$, $R^5$, $R^7$, and $R^8$ are H.

In certain embodiments, the invention relates to any one of the aforementioned methods, wherein $R^3$, $R^4$, and $R^7$ are OR; and $R^1$, $R^2$, $R^5$, $R^6$, and $R^8$ are H.

In certain embodiments, the invention relates to any one of the aforementioned methods, wherein $R^3$, $R^4$, and $R^8$ are OR; and $R^1$, $R^2$, $R^5$, $R^6$, and $R^7$ are H.

In certain embodiments, the invention relates to any one of the aforementioned methods, wherein $R^3$, $R^5$, and $R^6$ are OR; and $R^1$, $R^2$, $R^4$, $R^7$, and $R^8$ are H.

In certain embodiments, the invention relates to any one of the aforementioned methods, wherein $R^3$, $R^5$, and $R^7$ are OR; and $R^1$, $R^2$, $R^4$, $R^6$, and $R^8$ are H.

In certain embodiments, the invention relates to any one of the aforementioned methods, wherein $R^3$, $R^5$, and $R^8$ are OR; and $R^1$, $R^2$, $R^4$, $R^6$, and $R^7$ are H.

In certain embodiments, the invention relates to any one of the aforementioned methods, wherein $R^3$, $R^6$, and $R^7$ are OR; and $R^1$, $R^2$, $R^4$, $R^5$, and $R^8$ are H.

In certain embodiments, the invention relates to any one of the aforementioned methods, wherein $R^3$, $R^6$, and $R^8$ are OR; and $R^1$, $R^2$, $R^4$, $R^5$, and $R^7$ are H.

In certain embodiments, the invention relates to any one of the aforementioned methods, wherein $R^3$, $R^7$, and $R^8$ are OR; and $R^1$, $R^2$, $R^4$, $R^5$, and $R^6$ are H.

In certain embodiments, the invention relates to any one of the aforementioned methods, wherein $R^4$, $R^5$, and $R^6$ are OR; and $R^1$, $R^2$, $R^3$, $R^7$, and $R^8$ are H.

In certain embodiments, the invention relates to any one of the aforementioned methods, wherein $R^4$, $R^5$, and $R^7$ are OR; and $R^1$, $R^2$, $R^3$, $R^6$, and $R^8$ are H.

In certain embodiments, the invention relates to any one of the aforementioned methods, wherein $R^4$, $R^5$, and $R^8$ are OR; and $R^1$, $R^2$, $R^3$, $R^6$, and $R^7$ are H.

In certain embodiments, the invention relates to any one of the aforementioned methods, wherein $R^4$, $R^6$, and $R^7$ are OR; and $R^1$, $R^2$, $R^3$, $R^5$, and $R^8$ are H.

In certain embodiments, the invention relates to any one of the aforementioned methods, wherein $R^4$, $R^6$, and $R^8$ are OR; and $R^1$, $R^2$, $R^3$, $R^5$, and $R^7$ are H.

In certain embodiments, the invention relates to any one of the aforementioned methods, wherein $R^4$, $R^7$, and $R^8$ are OR; and $R^1$, $R^2$, $R^3$, $R^5$, and $R^6$ are H.

In certain embodiments, the invention relates to any one of the aforementioned methods, wherein $R^5$, $R^6$, and $R^7$ are OR; and $R^1$, $R^2$, $R^3$, $R^4$, and $R^8$ are H.

In certain embodiments, the invention relates to any one of the aforementioned methods, wherein $R^5$, $R^6$, and $R^8$ are OR; and $R^1$, $R^2$, $R^3$, $R^4$, and $R^7$ are H.

In certain embodiments, the invention relates to any one of the aforementioned methods, wherein $R^5$, $R^7$, and $R^8$ are OR; and $R^1$, $R^2$, $R^3$, $R^4$, and $R^6$ are H.

In certain embodiments, the invention relates to any one of the aforementioned methods, wherein $R^6$, $R^7$, and $R^8$ are OR; and $R^1$, $R^2$, $R^3$, $R^4$, and $R^5$ are H.

In certain embodiments, the invention relates to any one of the aforementioned methods, wherein $R^1$, $R^2$, $R^3$, and $R^4$ are OR; and $R^5$, $R^6$, $R^7$, and $R^8$ are H.

In certain embodiments, the invention relates to any one of the aforementioned methods, wherein $R^1$, $R^2$, $R^3$, and $R^5$ are OR; and $R^4$, $R^6$, $R^7$, and $R^8$ are H.

In certain embodiments, the invention relates to any one of the aforementioned methods, wherein $R^1$, $R^2$, $R^3$, and $R^6$ are OR; and $R^4$, $R^5$, $R^7$, and $R^8$ are H.

In certain embodiments, the invention relates to any one of the aforementioned methods, wherein $R^1$, $R^2$, $R^3$, and $R^7$ are OR; and $R^4$, $R^5$, $R^6$, and $R^8$ are H.

In certain embodiments, the invention relates to any one of the aforementioned methods, wherein $R^1$, $R^2$, $R^3$, and $R^8$ are OR; and $R^4$, $R^5$, $R^6$, and $R^7$ are H.

In certain embodiments, the invention relates to any one of the aforementioned methods, wherein $R^1$, $R^2$, $R^4$, and $R^5$ are OR; and $R^3$, $R^6$, $R^7$, and $R^8$ are H.

In certain embodiments, the invention relates to any one of the aforementioned methods, wherein $R^1$, $R^2$, $R^4$, and $R^6$ are OR; and $R^3$, $R^5$, $R^7$, and $R^8$ are H.

In certain embodiments, the invention relates to any one of the aforementioned methods, wherein $R^1$, $R^2$, $R^4$, and $R^7$ are OR; and $R^3$, $R^5$, $R^6$, and $R^8$ are H.

In certain embodiments, the invention relates to any one of the aforementioned methods, wherein $R^1$, $R^2$, $R^4$, and $R^8$ are OR; and $R^3$, $R^5$, $R^6$, and $R^7$ are H.

In certain embodiments, the invention relates to any one of the aforementioned methods, wherein $R^1$, $R^2$, $R^5$, and $R^6$ are OR; and $R^3$, $R^4$, $R^7$, and $R^8$ are H.

In certain embodiments, the invention relates to any one of the aforementioned methods, wherein $R^1$, $R^2$, $R^5$, and $R^7$ are OR; and $R^3$, $R^4$, $R^6$, and $R^8$ are H.

In certain embodiments, the invention relates to any one of the aforementioned methods, wherein $R^1$, $R^2$, $R^5$, and $R^8$ are OR; and $R^3$, $R^4$, $R^6$, and $R^7$ are H.

In certain embodiments, the invention relates to any one of the aforementioned methods, wherein $R^1$, $R^2$, $R^6$, and $R^7$ are OR; and $R^3$, $R^4$, $R^5$, and $R^8$ are H.

In certain embodiments, the invention relates to any one of the aforementioned methods, wherein $R^1$, $R^2$, $R^6$, and $R^8$ are OR; and $R^3$, $R^4$, $R^5$, and $R^7$ are H.

In certain embodiments, the invention relates to any one of the aforementioned methods, wherein $R^1$, $R^2$, $R^7$, and $R^8$ are OR; and $R^3$, $R^4$, $R^5$, and $R^6$ are H.

In certain embodiments, the invention relates to any one of the aforementioned methods, wherein $R^1$, $R^3$, $R^4$, and $R^5$ are OR; and $R^2$, $R^6$, $R^7$, and $R^8$ are H.

In certain embodiments, the invention relates to any one of the aforementioned methods, wherein $R^1$, $R^3$, $R^4$, and $R^6$ are OR; and $R^2$, $R^5$, $R^7$, and $R^8$ are H.

In certain embodiments, the invention relates to any one of the aforementioned methods, wherein $R^1$, $R^3$, $R^4$, and $R^7$ are OR; and $R^2$, $R^5$, $R^6$, and $R^8$ are H.

In certain embodiments, the invention relates to any one of the aforementioned methods, wherein $R^1$, $R^3$, $R^4$, and $R^8$ are OR; and $R^2$, $R^5$, $R^6$, and $R^7$ are H.

In certain embodiments, the invention relates to any one of the aforementioned methods, wherein $R^1$, $R^3$, $R^5$, and $R^6$ are OR; and $R^2$, $R^4$, $R^7$, and $R^8$ are H.

In certain embodiments, the invention relates to any one of the aforementioned methods, wherein $R^1$, $R^3$, $R^5$, and $R^7$ are OR; and $R^2$, $R^4$, $R^6$, and $R^8$ are H.

In certain embodiments, the invention relates to any one of the aforementioned methods, wherein $R^1$, $R^3$, $R^5$, and $R^8$ are OR; and $R^2$, $R^4$, $R^6$, and $R^7$ are H.

In certain embodiments, the invention relates to any one of the aforementioned methods, wherein $R^1$, $R^3$, $R^6$, and $R^7$ are OR; and $R^2$, $R^4$, $R^5$, and $R^8$ are H.

In certain embodiments, the invention relates to any one of the aforementioned methods, wherein $R^1$, $R^3$, $R^6$, and $R^8$ are OR; and $R^2$, $R^4$, $R^5$, and $R^7$ are H.

In certain embodiments, the invention relates to any one of the aforementioned methods, wherein $R^1$, $R^3$, $R^7$, and $R^8$ are OR; and $R^2$, $R^4$, $R^5$, and $R^6$ are H.

In certain embodiments, the invention relates to any one of the aforementioned methods, wherein $R^1$, $R^4$, $R^5$, and $R^6$ are OR; and $R^2$, $R^3$, $R^7$, and $R^8$ are H.

In certain embodiments, the invention relates to any one of the aforementioned methods, wherein $R^1$, $R^4$, $R^5$, and $R^7$ are OR; and $R^2$, $R^3$, $R^6$, and $R^8$ are H.

In certain embodiments, the invention relates to any one of the aforementioned methods, wherein $R^1$, $R^4$, $R^5$, and $R^8$ are OR; and $R^2$, $R^3$, $R^6$, and $R^7$ are H.

In certain embodiments, the invention relates to any one of the aforementioned methods, wherein $R^1$, $R^4$, $R^6$, and $R^7$ are OR; and $R^2$, $R^3$, $R^5$, and $R^8$ are H.

In certain embodiments, the invention relates to any one of the aforementioned methods, wherein $R^1$, $R^4$, $R^6$, and $R^8$ are OR; and $R^2$, $R^3$, $R^5$, and $R^7$ are H.

In certain embodiments, the invention relates to any one of the aforementioned methods, wherein $R^1$, $R^4$, $R^7$, and $R^8$ are OR; and $R^2$, $R^3$, $R^5$, and $R^6$ are H.

In certain embodiments, the invention relates to any one of the aforementioned methods, wherein $R^1$, $R^5$, $R^6$, and $R^7$ are OR; and $R^2$, $R^3$, $R^4$, and $R^8$ are H.

In certain embodiments, the invention relates to any one of the aforementioned methods, wherein $R^1$, $R^5$, $R^6$, and $R^8$ are OR; and $R^2$, $R^3$, $R^4$, and $R^7$ are H.

In certain embodiments, the invention relates to any one of the aforementioned methods, wherein $R^1$, $R^5$, $R^7$, and $R^8$ are OR; and $R^2$, $R^3$, $R^4$, and $R^6$ are H.

In certain embodiments, the invention relates to any one of the aforementioned methods, wherein $R^1$, $R^6$, $R^7$, and $R^8$ are OR; and $R^2$, $R^3$, $R^4$, and $R^5$ are H.

In certain embodiments, the invention relates to any one of the aforementioned methods, wherein $R^2$, $R^3$, $R^4$, and $R^5$ are OR; and $R^1$, $R^6$, $R^7$, and $R^8$ are H.

In certain embodiments, the invention relates to any one of the aforementioned methods, wherein $R^2$, $R^3$, $R^4$, and $R^6$ are OR; and $R^1$, $R^5$, $R^7$, and $R^8$ are H.

In certain embodiments, the invention relates to any one of the aforementioned methods, wherein $R^2$, $R^3$, $R^4$, and $R^7$ are OR; and $R^1$, $R^5$, $R^6$, and $R^8$ are H.

In certain embodiments, the invention relates to any one of the aforementioned methods, wherein $R^2$, $R^3$, $R^4$, and $R^8$ are OR; and $R^1$, $R^5$, $R^6$, and $R^7$ are H.

In certain embodiments, the invention relates to any one of the aforementioned methods, wherein $R^2$, $R^3$, $R^5$, and $R^6$ are OR; and $R^1$, $R^4$, $R^7$, and $R^8$ are H.

In certain embodiments, the invention relates to any one of the aforementioned methods, wherein $R^2$, $R^3$, $R^5$, and $R^7$ are OR; and $R^1$, $R^4$, $R^6$, and $R^8$ are H.

In certain embodiments, the invention relates to any one of the aforementioned methods, wherein $R^2$, $R^3$, $R^5$, and $R^8$ are OR; and $R^1$, $R^4$, $R^6$, and $R^7$ are H.

In certain embodiments, the invention relates to any one of the aforementioned methods, wherein $R^2$, $R^3$, $R^6$, and $R^7$ are OR; and $R^1$, $R^4$, $R^5$, and $R^8$ are H.

In certain embodiments, the invention relates to any one of the aforementioned methods, wherein $R^2$, $R^3$, $R^6$, and $R^8$ are OR; and $R^1$, $R^4$, $R^5$, and $R^7$ are H.

In certain embodiments, the invention relates to any one of the aforementioned methods, wherein $R^2$, $R^3$, $R^7$, and $R^8$ are OR; and $R^1$, $R^4$, $R^6$, and $R^7$ are H.

In certain embodiments, the invention relates to any one of the aforementioned methods, wherein $R^2$, $R^4$, $R^5$, and $R^6$ are OR; and $R^1$, $R^3$, $R^7$, and $R^8$ are H.

In certain embodiments, the invention relates to any one of the aforementioned methods, wherein $R^2$, $R^4$, $R^5$, and $R^7$ are OR; and $R^1$, $R^3$, $R^6$, and $R^8$ are H.

In certain embodiments, the invention relates to any one of the aforementioned methods, wherein $R^2$, $R^4$, $R^5$, and $R^8$ are OR; and $R^1$, $R^3$, $R^6$, and $R^7$ are H.

In certain embodiments, the invention relates to any one of the aforementioned methods, wherein $R^2$, $R^4$, $R^6$, and $R^7$ are OR; and $R^1$, $R^3$, $R^5$, and $R^8$ are H.

In certain embodiments, the invention relates to any one of the aforementioned methods, wherein $R^2$, $R^4$, $R^6$, and $R^8$ are OR; and $R^1$, $R^3$, $R^5$, and $R^7$ are H.

In certain embodiments, the invention relates to any one of the aforementioned methods, wherein $R^2$, $R^4$, $R^7$, and $R^8$ are OR; and $R^1$, $R^3$, $R^5$, and $R^6$ are H.

In certain embodiments, the invention relates to any one of the aforementioned methods, wherein $R^2$, $R^5$, $R^6$, and $R^7$ are OR; and $R^1$, $R^3$, $R^4$, and $R^8$ are H.

In certain embodiments, the invention relates to any one of the aforementioned methods, wherein $R^2$, $R^5$, $R^6$, and $R^8$ are OR; and $R^1$, $R^3$, $R^4$, and $R^7$ are H.

In certain embodiments, the invention relates to any one of the aforementioned methods, wherein $R^2$, $R^5$, $R^7$, and $R^8$ are OR; and $R^1$, $R^3$, $R^4$, and $R^6$ are H.

In certain embodiments, the invention relates to any one of the aforementioned methods, wherein $R^2$, $R^6$, $R^7$, and $R^8$ are OR; and $R^1$, $R^3$, $R^4$, and $R^5$ are H.

In certain embodiments, the invention relates to any one of the aforementioned methods, wherein $R^3$, $R^4$, $R^5$, and $R^6$ are OR; and $R^1$, $R^2$, $R^7$, and $R^8$ are H.

In certain embodiments, the invention relates to any one of the aforementioned methods, wherein $R^3$, $R^4$, $R^5$, and $R^7$ are OR; and $R^1$, $R^2$, $R^6$, and $R^8$ are H.

In certain embodiments, the invention relates to any one of the aforementioned methods, wherein $R^3$, $R^4$, $R^5$, and $R^8$ are OR; and $R^1$, $R^2$, $R^6$, and $R^7$ are H.

In certain embodiments, the invention relates to any one of the aforementioned methods, wherein $R^3$, $R^4$, $R^6$, and $R^7$ are OR; and $R^1$, $R^2$, $R^5$, and $R^8$ are H.

In certain embodiments, the invention relates to any one of the aforementioned methods, wherein $R^3$, $R^4$, $R^6$, and $R^8$ are OR; and $R^1$, $R^2$, $R^5$, and $R^7$ are H.

In certain embodiments, the invention relates to any one of the aforementioned methods, wherein $R^3$, $R^4$, $R^7$, and $R^8$ are OR; and $R^1$, $R^2$, $R^5$, and $R^6$ are H.

In certain embodiments, the invention relates to any one of the aforementioned methods, wherein $R^3$, $R^5$, $R^6$, and $R^7$ are OR; and $R^1$, $R^2$, $R^4$, and $R^8$ are H.

In certain embodiments, the invention relates to any one of the aforementioned methods, wherein $R^3$, $R^5$, $R^6$, and $R^8$ are OR; and $R^1$, $R^2$, $R^4$, and $R^7$ are H.

In certain embodiments, the invention relates to any one of the aforementioned methods, wherein $R^3$, $R^5$, $R^7$, and $R^8$ are OR; and $R^1$, $R^2$, $R^4$, and $R^6$ are H.

In certain embodiments, the invention relates to any one of the aforementioned methods, wherein $R^3$, $R^6$, $R^7$, and $R^8$ are OR; and $R^1$, $R^2$, $R^4$, and $R^5$ are H.

In certain embodiments, the invention relates to any one of the aforementioned methods, wherein $R^4$, $R^5$, $R^6$, and $R^7$ are OR; and $R^1$, $R^2$, $R^3$, and $R^8$ are H.

In certain embodiments, the invention relates to any one of the aforementioned methods, wherein $R^4$, $R^5$, $R^6$, and $R^8$ are OR; and $R^1$, $R^2$, $R^3$, and $R^7$ are H.

In certain embodiments, the invention relates to any one of the aforementioned methods, wherein $R^4$, $R^5$, $R^7$, and $R^8$ are OR; and $R^1$, $R^2$, $R^3$, and $R^6$ are H.

In certain embodiments, the invention relates to any one of the aforementioned methods, wherein $R^4$, $R^6$, $R^7$, and $R^8$ are OR; and $R^1$, $R^2$, $R^3$, and $R^5$ are H.

In certain embodiments, the invention relates to any one of the aforementioned methods, wherein $R^5$, $R^6$, $R^7$, and $R^8$ are OR; and $R^1$, $R^2$, $R^3$, and $R^4$ are H.

In certain embodiments, the invention relates to any one of the aforementioned methods, wherein $R^1$, $R^2$, $R^3$, $R^4$, and $R^5$ are OR; and $R^6$, $R^7$, and $R^8$ are H.

In certain embodiments, the invention relates to any one of the aforementioned methods, wherein $R^1$, $R^2$, $R^3$, $R^4$, and $R^6$ are OR; and $R^5$, $R^7$, and $R^8$ are H.

In certain embodiments, the invention relates to any one of the aforementioned methods, wherein $R^1$, $R^2$, $R^3$, $R^4$, and $R^7$ are OR; and $R^5$, $R^6$, and $R^8$ are H.

In certain embodiments, the invention relates to any one of the aforementioned methods, wherein $R^1$, $R^2$, $R^3$, $R^4$, and $R^8$ are OR; and $R^5$, $R^6$, and $R^7$ are H.

In certain embodiments, the invention relates to any one of the aforementioned methods, wherein $R^1$, $R^2$, $R^3$, $R^5$, and $R^6$ are OR; and $R^4$, $R^7$, and $R^8$ are H.

In certain embodiments, the invention relates to any one of the aforementioned methods, wherein $R^1$, $R^2$, $R^3$, $R^5$, and $R^7$ are OR; and $R^4$, $R^6$, and $R^8$ are H.

In certain embodiments, the invention relates to any one of the aforementioned methods, wherein $R^1$, $R^2$, $R^3$, $R^5$, and $R^8$ are OR; and $R^4$, $R^6$, and $R^7$ are H.

In certain embodiments, the invention relates to any one of the aforementioned methods, wherein $R^1$, $R^2$, $R^3$, $R^6$, and $R^7$ are OR; and $R^4$, $R^5$, and $R^8$ are H.

In certain embodiments, the invention relates to any one of the aforementioned methods, wherein $R^1$, $R^2$, $R^3$, $R^6$, and $R^8$ are OR; and $R^4$, $R^5$, and $R^7$ are H.

In certain embodiments, the invention relates to any one of the aforementioned methods, wherein $R^1$, $R^2$, $R^3$, $R^7$, and $R^8$ are OR; and $R^4$, $R^5$, and $R^6$ are H.

In certain embodiments, the invention relates to any one of the aforementioned methods, wherein $R^1$, $R^2$, $R^4$, $R^5$, and $R^6$ are OR; and $R^3$, $R^7$, and $R^8$ are H.

In certain embodiments, the invention relates to any one of the aforementioned methods, wherein $R^1$, $R^2$, $R^4$, $R^5$, and $R^7$ are OR; and $R^3$, $R^6$, and $R^8$ are H.

In certain embodiments, the invention relates to any one of the aforementioned methods, wherein $R^1$, $R^2$, $R^4$, $R^5$, and $R^8$ are OR; and $R^3$, $R^6$, and $R^7$ are H.

In certain embodiments, the invention relates to any one of the aforementioned methods, wherein $R^1$, $R^2$, $R^4$, $R^6$, and $R^7$ are OR; and $R^3$, $R^5$, and $R^8$ are H.

In certain embodiments, the invention relates to any one of the aforementioned methods, wherein $R^1$, $R^2$, $R^4$, $R^6$, and $R^8$ are OR; and $R^3$, $R^5$, and $R^7$ are H.

In certain embodiments, the invention relates to any one of the aforementioned methods, wherein $R^1$, $R^2$, $R^4$, $R^7$, and $R^8$ are OR; and $R^3$, $R^5$, and $R^6$ are H.

In certain embodiments, the invention relates to any one of the aforementioned methods, wherein $R^1$, $R^2$, $R^5$, $R^6$, and $R^7$ are OR; and $R^3$, $R^4$, and $R^8$ are H.

In certain embodiments, the invention relates to any one of the aforementioned methods, wherein $R^1$, $R^2$, $R^5$, $R^6$, and $R^8$ are OR; and $R^3$, $R^4$, and $R^7$ are H.

In certain embodiments, the invention relates to any one of the aforementioned methods, wherein $R^1$, $R^2$, $R^5$, $R^7$, and $R^8$ are OR; and $R^3$, $R^4$, and $R^6$ are H.

In certain embodiments, the invention relates to any one of the aforementioned methods, wherein $R^1$, $R^2$, $R^6$, $R^7$, and $R^8$ are OR; and $R^3$, $R^4$, and $R^5$ are H.

In certain embodiments, the invention relates to any one of the aforementioned methods, wherein $R^1$, $R^3$, $R^4$, $R^5$, and $R^6$ are OR; and $R^2$, $R^7$, and $R^8$ are H.

In certain embodiments, the invention relates to any one of the aforementioned methods, wherein $R^1$, $R^3$, $R^4$, $R^5$, and $R^7$ are OR; and $R^2$, $R^6$, and $R^8$ are H.

In certain embodiments, the invention relates to any one of the aforementioned methods, wherein $R^1$, $R^3$, $R^4$, $R^5$, and $R^8$ are OR; and $R^2$, $R^6$, and $R^7$ are H.

In certain embodiments, the invention relates to any one of the aforementioned methods, wherein $R^1$, $R^3$, $R^4$, $R^6$, and $R^7$ are OR; and $R^2$, $R^5$, and $R^8$ are H.

In certain embodiments, the invention relates to any one of the aforementioned methods, wherein $R^1$, $R^3$, $R^4$, $R^6$, and $R^8$ are OR; and $R^2$, $R^5$, and $R^7$ are H.

In certain embodiments, the invention relates to any one of the aforementioned methods, wherein $R^1$, $R^3$, $R^4$, $R^7$, and $R^8$ are OR; and $R^2$, $R^5$, and $R^7$ are H.

In certain embodiments, the invention relates to any one of the aforementioned methods, wherein $R^1$, $R^3$, $R^5$, $R^6$, and $R^7$ are OR; and $R^2$, $R^4$, and $R^8$ are H.

In certain embodiments, the invention relates to any one of the aforementioned methods, wherein $R^1$, $R^3$, $R^5$, $R^6$, and $R^8$ are OR; and $R^2$, $R^4$, and $R^7$ are H.

In certain embodiments, the invention relates to any one of the aforementioned methods, wherein $R^1$, $R^3$, $R^5$, $R^7$, and $R^8$ are OR; and $R^2$, $R^4$, and $R^6$ are H.

In certain embodiments, the invention relates to any one of the aforementioned methods, wherein $R^1$, $R^3$, $R^6$, $R^7$, and $R^8$ are OR; and $R^2$, $R^4$, and $R^5$ are H.

In certain embodiments, the invention relates to any one of the aforementioned methods, wherein $R^1$, $R^4$, $R^5$, $R^6$, and $R^7$ are OR; and $R^2$, $R^3$, and $R^8$ are H.

In certain embodiments, the invention relates to any one of the aforementioned methods, wherein $R^1$, $R^4$, $R^5$, $R^6$, and $R^8$ are OR; and $R^2$, $R^3$, and $R^7$ are H.

In certain embodiments, the invention relates to any one of the aforementioned methods, wherein $R^1$, $R^4$, $R^5$, $R^7$, and $R^8$ are OR; and $R^2$, $R^3$, and $R^6$ are H.

In certain embodiments, the invention relates to any one of the aforementioned methods, wherein $R^1$, $R^4$, $R^6$, $R^7$, and $R^8$ are OR; and $R^2$, $R^3$, and $R^6$ are H.

In certain embodiments, the invention relates to any one of the aforementioned methods, wherein $R^1$, $R^5$, $R^6$, $R^7$, and $R^8$ are OR; and $R^2$, $R^3$, and $R^4$ are H.

In certain embodiments, the invention relates to any one of the aforementioned methods, wherein $R^2$, $R^3$, $R^4$, $R^5$, and $R^6$ are OR; and $R^1$, $R^7$, and $R^8$ are H.

In certain embodiments, the invention relates to any one of the aforementioned methods, wherein $R^2$, $R^3$, $R^4$, $R^5$, and $R^7$ are OR; and $R^1$, $R^6$, and $R^8$ are H.

In certain embodiments, the invention relates to any one of the aforementioned methods, wherein $R^2$, $R^3$, $R^4$, $R^5$, and $R^8$ are OR; and $R^1$, $R^6$, and $R^7$ are H.

In certain embodiments, the invention relates to any one of the aforementioned methods, wherein $R^2$, $R^3$, $R^4$, $R^6$, and $R^7$ are OR; and $R^1$, $R^5$, and $R^8$ are H.

In certain embodiments, the invention relates to any one of the aforementioned methods, wherein $R^2$, $R^3$, $R^4$, $R^6$, and $R^8$ are OR; and $R^1$, $R^5$, and $R^7$ are H.

In certain embodiments, the invention relates to any one of the aforementioned methods, wherein $R^2$, $R^3$, $R^4$, $R^7$, and $R^8$ are OR; and $R^1$, $R^5$, and $R^6$ are H.

In certain embodiments, the invention relates to any one of the aforementioned methods, wherein $R^2$, $R^3$, $R^5$, $R^6$, and $R^7$ are OR; and $R^1$, $R^4$, and $R^8$ are H.

In certain embodiments, the invention relates to any one of the aforementioned methods, wherein $R^2$, $R^3$, $R^5$, $R^6$, and $R^8$ are OR; and $R^1$, $R^4$, and $R^7$ are H.

In certain embodiments, the invention relates to any one of the aforementioned methods, wherein $R^2$, $R^3$, $R^5$, $R^7$, and $R^8$ are OR; and $R^1$, $R^4$, and $R^6$ are H.

In certain embodiments, the invention relates to any one of the aforementioned methods, wherein $R^2$, $R^3$, $R^6$, $R^7$, and $R^8$ are OR; and $R^1$, $R^4$, and $R^5$ are H.

In certain embodiments, the invention relates to any one of the aforementioned methods, wherein $R^2$, $R^4$, $R^5$, $R^6$, and $R^7$ are OR; and $R^1$, $R^3$, and $R^8$ are H.

In certain embodiments, the invention relates to any one of the aforementioned methods, wherein $R^2$, $R^4$, $R^5$, $R^6$, and $R^8$ are OR; and $R^1$, $R^3$, and $R^7$ are H.

In certain embodiments, the invention relates to any one of the aforementioned methods, wherein $R^2$, $R^4$, $R^5$, $R^7$, and $R^8$ are OR; and $R^1$, $R^3$, and $R^6$ are H.

In certain embodiments, the invention relates to any one of the aforementioned methods, wherein $R^2$, $R^4$, $R^6$, $R^7$, and $R^8$ are OR; and $R^1$, $R^3$, and $R^5$ are H.

In certain embodiments, the invention relates to any one of the aforementioned methods, wherein $R^2$, $R^5$, $R^6$, $R^7$, and $R^8$ are OR; and $R^1$, $R^3$, and $R^4$ are H.

In certain embodiments, the invention relates to any one of the aforementioned methods, wherein $R^3$, $R^4$, $R^5$, $R^6$, and $R^7$ are OR; and $R^1$, $R^2$, and $R^8$ are H.

In certain embodiments, the invention relates to any one of the aforementioned methods, wherein $R^3$, $R^4$, $R^5$, $R^6$, and $R^8$ are OR; and $R^1$, $R^2$, and $R^7$ are H.

In certain embodiments, the invention relates to any one of the aforementioned methods, wherein $R^3$, $R^4$, $R^5$, $R^7$, and $R^8$ are OR; and $R^1$, $R^2$, and $R^6$ are H.

In certain embodiments, the invention relates to any one of the aforementioned methods, wherein $R^3$, $R^4$, $R^6$, $R^7$, and $R^8$ are OR; and $R^1$, $R^2$, and $R^5$ are H.

In certain embodiments, the invention relates to any one of the aforementioned methods, wherein $R^3$, $R^5$, $R^6$, $R^7$, and $R^8$ are OR; and $R^1$, $R^2$, and $R^4$ are H.

In certain embodiments, the invention relates to any one of the aforementioned methods, wherein $R^4$, $R^5$, $R^6$, $R^7$, and $R^8$ are OR; and $R^1$, $R^2$, and $R^3$ are H.

In certain embodiments, the invention relates to any one of the aforementioned methods, wherein $R^1$, $R^2$, $R^3$, $R^4$, $R^5$, and $R^6$ are OR; and $R^7$ and $R^8$ are H.

In certain embodiments, the invention relates to any one of the aforementioned methods, wherein $R^1$, $R^2$, $R^3$, $R^4$, $R^5$, and $R^7$ are OR; and $R^6$ and $R^8$ are H.

In certain embodiments, the invention relates to any one of the aforementioned methods, wherein $R^1$, $R^2$, $R^3$, $R^4$, $R^5$, and $R^8$ are OR; and $R^6$ and $R^7$ are H.

In certain embodiments, the invention relates to any one of the aforementioned methods, wherein $R^1$, $R^2$, $R^3$, $R^4$, $R^6$, and $R^7$ are OR; and $R^5$ and $R^8$ are H.

In certain embodiments, the invention relates to any one of the aforementioned methods, wherein $R^1$, $R^2$, $R^3$, $R^4$, $R^6$, and $R^8$ are OR; and $R^5$ and $R^7$ are H.

In certain embodiments, the invention relates to any one of the aforementioned methods, wherein $R^1$, $R^2$, $R^3$, $R^4$, $R^7$, and $R^8$ are OR; and $R^5$ and $R^6$ are H.

In certain embodiments, the invention relates to any one of the aforementioned methods, wherein $R^1$, $R^2$, $R^3$, $R^5$, $R^6$, and $R^7$ are OR; and $R^4$ and $R^8$ are H.

In certain embodiments, the invention relates to any one of the aforementioned methods, wherein $R^1$, $R^2$, $R^3$, $R^5$, $R^6$, and $R^8$ are OR; and $R^4$ and $R^7$ are H.

In certain embodiments, the invention relates to any one of the aforementioned methods, wherein $R^1$, $R^2$, $R^3$, $R^5$, $R^7$, and $R^8$ are OR; and $R^4$ and $R^6$ are H.

In certain embodiments, the invention relates to any one of the aforementioned methods, wherein $R^1$, $R^2$, $R^3$, $R^6$, $R^7$, and $R^8$ are OR; and $R^4$ and $R^5$ are H.

In certain embodiments, the invention relates to any one of the aforementioned methods, wherein $R^1$, $R^2$, $R^4$, $R^5$, $R^6$, and $R^7$ are OR; and $R^3$ and $R^8$ are H.

In certain embodiments, the invention relates to any one of the aforementioned methods, wherein $R^1$, $R^2$, $R^4$, $R^5$, $R^6$, and $R^8$ are OR; and $R^3$ and $R^7$ are H.

In certain embodiments, the invention relates to any one of the aforementioned methods, wherein $R^1$, $R^2$, $R^4$, $R^5$, $R^7$, and $R^8$ are OR; and $R^3$ and $R^6$ are H.

In certain embodiments, the invention relates to any one of the aforementioned methods, wherein $R^1$, $R^2$, $R^4$, $R^6$, $R^7$, and $R^8$ are OR; and $R^3$ and $R^5$ are H.

In certain embodiments, the invention relates to any one of the aforementioned methods, wherein $R^1$, $R^2$, $R^5$, $R^6$, $R^7$, and $R^8$ are OR; and $R^3$ and $R^4$ are H.

In certain embodiments, the invention relates to any one of the aforementioned methods, wherein $R^1$, $R^3$, $R^4$, $R^5$, $R^6$, and $R^7$ are OR; and $R^2$ and $R^8$ are H.

In certain embodiments, the invention relates to any one of the aforementioned methods, wherein $R^1$, $R^3$, $R^4$, $R^5$, $R^6$, and $R^8$ are OR; and $R^2$ and $R^7$ are H.

In certain embodiments, the invention relates to any one of the aforementioned methods, wherein $R^1$, $R^3$, $R^4$, $R^5$, $R^7$, and $R^8$ are OR; and $R^2$ and $R^6$ are H.

In certain embodiments, the invention relates to any one of the aforementioned methods, wherein $R^1$, $R^3$, $R^4$, $R^6$, $R^7$, and $R^8$ are OR; and $R^2$ and $R^5$ are H.

In certain embodiments, the invention relates to any one of the aforementioned methods, wherein $R^1$, $R^3$, $R^5$, $R^6$, $R^7$, and $R^8$ are OR; and $R^2$ and $R^4$ are H.

In certain embodiments, the invention relates to any one of the aforementioned methods, wherein $R^1$, $R^4$, $R^5$, $R^6$, $R^7$, and $R^8$ are OR; and $R^2$ and $R^3$ are H.

In certain embodiments, the invention relates to any one of the aforementioned methods, wherein $R^2$, $R^3$, $R^4$, $R^5$, $R^6$, and $R^7$ are OR; and $R^1$, and $R^8$ are H.

In certain embodiments, the invention relates to any one of the aforementioned methods, wherein $R^2$, $R^3$, $R^4$, $R^5$, $R^6$, and $R^8$ are OR; and $R^1$ and $R^7$ are H.

In certain embodiments, the invention relates to any one of the aforementioned methods, wherein $R^2$, $R^3$, $R^4$, $R^5$, $R^7$, and $R^8$ are OR; and $R^1$ and $R^6$ are H.

In certain embodiments, the invention relates to any one of the aforementioned methods, wherein $R^2$, $R^3$, $R^4$, $R^6$, $R^7$, and $R^8$ are OR; and $R^1$ and $R^5$ are H.

In certain embodiments, the invention relates to any one of the aforementioned methods, wherein $R^2$, $R^3$, $R^5$, $R^6$, $R^7$, and $R^8$ are OR; and $R^1$ and $R^4$ are H.

In certain embodiments, the invention relates to any one of the aforementioned methods, wherein $R^2$, $R^4$, $R^5$, $R^6$, $R^7$, and $R^8$ are OR; and $R^1$ and $R^3$ are H.

In certain embodiments, the invention relates to any one of the aforementioned methods, wherein $R^3$, $R^4$, $R^5$, $R^6$, $R^7$, and $R^8$ are OR; and $R^1$ and $R^2$ are H.

In certain embodiments, the invention relates to any one of the aforementioned methods, wherein $R^1$, $R^2$, $R^3$, $R^4$, $R^5$, $R^6$, and $R^7$ are OR; and $R^8$ is H.

In certain embodiments, the invention relates to any one of the aforementioned methods, wherein $R^1$, $R^2$, $R^3$, $R^4$, $R^5$, $R^6$, and $R^8$ are OR; and $R^7$ is H.

In certain embodiments, the invention relates to any one of the aforementioned methods, wherein $R^1$, $R^2$, $R^3$, $R^4$, $R^5$, $R^7$, and $R^8$ are OR; and $R^6$ is H.

In certain embodiments, the invention relates to any one of the aforementioned methods, wherein $R^1$, $R^2$, $R^3$, $R^4$, $R^6$, $R^7$, and $R^8$ are OR; and $R^5$ is H.

In certain embodiments, the invention relates to any one of the aforementioned methods, wherein $R^1$, $R^2$, $R^3$, $R^5$, $R^6$, $R^7$, and $R^8$ are OR; and $R^4$ is H.

In certain embodiments, the invention relates to any one of the aforementioned methods, wherein $R^1$, $R^2$, $R^4$, $R^5$, $R^6$, $R^7$, and $R^8$ are OR; and $R^3$ is H.

In certain embodiments, the invention relates to any one of the aforementioned methods, wherein $R^1$, $R^3$, $R^4$, $R^5$, $R^6$, $R^7$, and $R^8$ are OR; and $R^2$ is H.

In certain embodiments, the invention relates to any one of the aforementioned methods, wherein $R^2$, $R^3$, $R^4$, $R^5$, $R^6$, $R^7$, and $R^8$ are OR; and $R^1$ is H.

In certain embodiments, the invention relates to any one of the aforementioned methods, wherein R is H.

In certain embodiments, the invention relates to a method of treating or preventing metabolic stress, comprising administering a therapeutically effective amount of a compound Formula IV to a subject in need thereof, thereby treating or preventing the metabolic stress, wherein the compound of Formula IV is

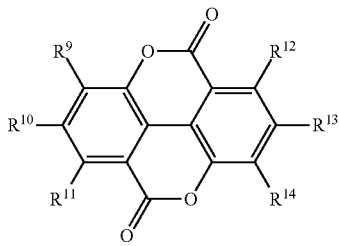

Formula IV wherein
  $R^9, R^{10}, R^{11}, R^{12}, R^{13}$, and $R^{14}$ are independently selected from the group consisting of H and OR; and
  R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing cardiovascular disease, comprising administering a therapeutically effective amount of a compound Formula IV to a subject in need thereof, thereby treating or preventing the cardiovascular disease,
  wherein the compound of Formula IV is

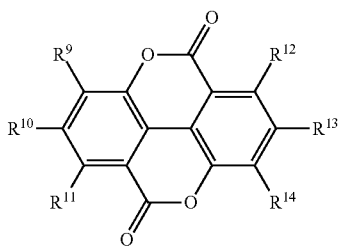

Formula IV wherein
  $R^9, R^{10}, R^{11}, R^{12}, R^{13}$, and $R^{14}$ are independently selected from the group consisting of H and OR; and
  R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing cardiomyopathy, comprising administering a therapeutically effective amount of a compound Formula IV to a subject in need thereof, thereby treating or preventing the cardiomyopathy,
  wherein the compound of Formula IV is

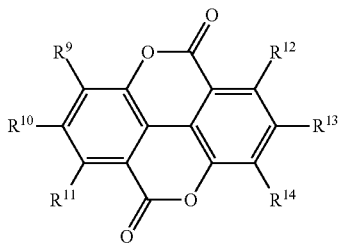

Formula IV wherein
  $R^9, R^{10}, R^{11}, R^{12}, R^{13}$, and $R^{14}$ are independently selected from the group consisting of H and OR; and
  R is H, substituted or unsubstituted alkyl, substituted or unsubstituted aryl, a substituted or unsubstituted monosaccharide, or a substituted or unsubstituted oligosaccharide.

In certain embodiments, the invention relates to a method of improving muscle function, comprising administering a therapeutically effective amount of a compound Formula IV to a subject in need thereof, thereby improving muscle function,
  wherein the compound of Formula IV is

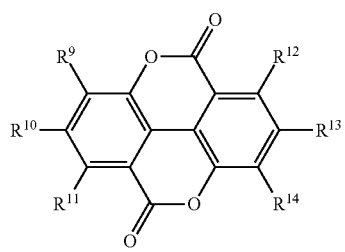

Formula IV wherein
  $R^9, R^{10}, R^{11}, R^{12}, R^{13}$, and $R^{14}$ are independently selected from the group consisting of H and OR; and
  R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing sarcopenia, comprising administering a therapeutically effective amount of a compound Formula IV to a subject in need thereof, thereby treating or preventing the sarcopenia,
  wherein the compound of Formula IV is

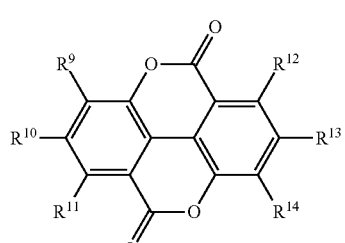

Formula IV wherein
  $R^9, R^{10}, R^{11}, R^{12}, R^{13}$, and $R^{14}$ are independently selected from the group consisting of H and OR; and
  R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing muscle degenerative disease, comprising administering a therapeutically effective amount of a compound Formula IV to a subject in need thereof, thereby treating or preventing the muscle degenerative disease, wherein the compound of Formula IV is

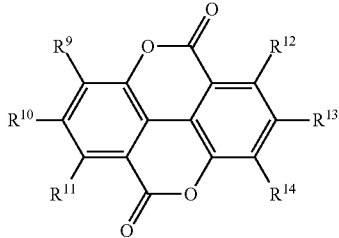

Formula IV wherein
$R^9, R^{10}, R^{11}, R^{12}, R^{13}$, and $R^{14}$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing Duchenne muscular dystrophy, comprising administering a therapeutically effective amount of a compound Formula IV to a subject in need thereof, thereby treating or preventing the Duchenne muscular dystrophy,
wherein the compound of Formula IV is

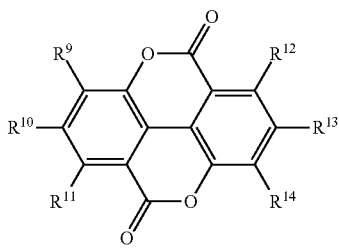

Formula IV wherein
$R^9, R^{10}, R^{11}, R^{12}, R^{13}$, and $R^{14}$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing alcoholic liver disease, comprising administering a therapeutically effective amount of a compound Formula IV to a subject in need thereof, thereby treating or preventing the alcoholic liver disease,
wherein the compound of Formula IV is

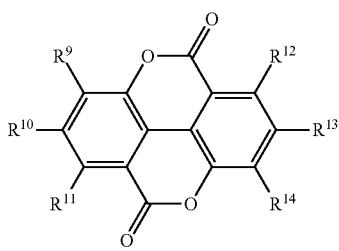

Formula IV wherein
$R^9, R^{10}, R^{11}, R^{12}, R^{13}$, and $R^{14}$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing nonalcoholic fatty liver disease, comprising administering a therapeutically effective amount of a compound Formula IV to a subject in need thereof, thereby treating or preventing the nonalcoholic fatty liver disease,
wherein the compound of Formula IV is

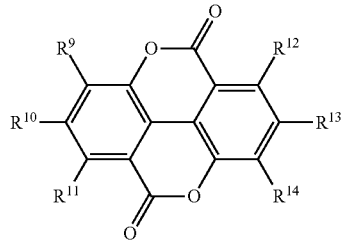

Formula IV wherein
$R^9, R^{10}, R^{11}, R^{12}, R^{13}$, and $R^{14}$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing drug-induced liver injury, comprising administering a therapeutically effective amount of a compound Formula IV to a subject in need thereof, thereby treating or preventing the drug-induced liver injury,
wherein the compound of Formula IV is

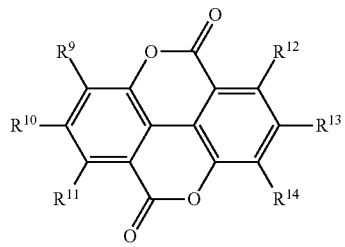

Formula IV wherein
$R^9, R^{10}, R^{11}, R^{12}, R^{13}$, and $R^{14}$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing α1-antitrypsin deficiency, comprising administering a therapeutically effective amount of a compound Formula IV to a subject in need thereof, thereby treating or preventing the α1-antitrypsin deficiency, wherein the compound of Formula IV is

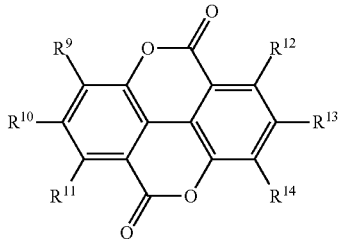

Formula IV wherein
  $R^9, R^{10}, R^{11}, R^{12}, R^{13}$, and $R^{14}$ are independently selected from the group consisting of H and OR; and
  R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing ischemia-reperfusion injury, comprising administering a therapeutically effective amount of a compound Formula IV to a subject in need thereof, thereby treating or preventing the ischemia/reperfusion injury,
  wherein the compound of Formula IV is

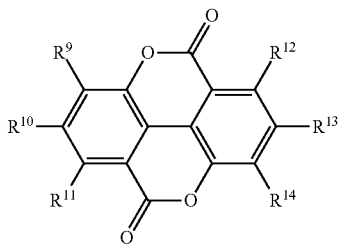

Formula IV wherein
  $R^9, R^{10}, R^{11}, R^{12}, R^{13}$, and $R^{14}$ are independently selected from the group consisting of H and OR; and
  R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing inflammation, comprising administering a therapeutically effective amount of a compound Formula IV to a subject in need thereof, thereby treating or preventing the inflammation,
  wherein the compound of Formula IV is

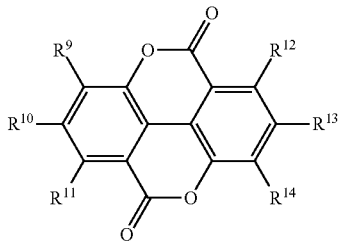

Formula IV wherein
  $R^9, R^{10}, R^{11}, R^{12}, R^{13}$, and $R^{14}$ are independently selected from the group consisting of H and OR; and
  R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing inflammatory bowel disease, comprising administering a therapeutically effective amount of a compound Formula IV to a subject in need thereof, thereby treating or preventing the inflammatory bowel disease,
  wherein the compound of Formula IV is

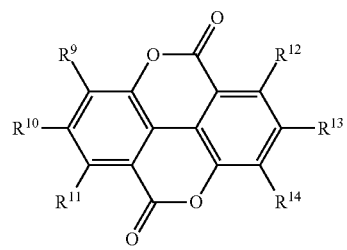

Formula IV wherein
  $R^9, R^{10}, R^{11}, R^{12}, R^{13}$, and $R^{14}$ are independently selected from the group consisting of H and OR; and
  R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing Crohn's disease, comprising administering a therapeutically effective amount of a compound Formula IV to a subject in need thereof, thereby treating or preventing the Crohn's disease,
  wherein the compound of Formula IV is

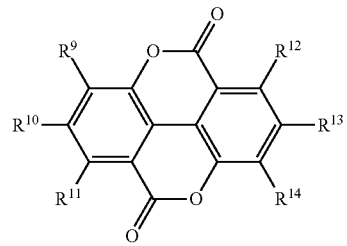

Formula IV wherein
  $R^9, R^{10}, R^{11}, R^{12}, R^{13}$, and $R^{14}$ are independently selected from the group consisting of H and OR; and
  R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing obesity, comprising administering a therapeutically effective amount of a compound Formula IV to a subject in need thereof, thereby treating or preventing the obesity, wherein the compound of Formula IV is

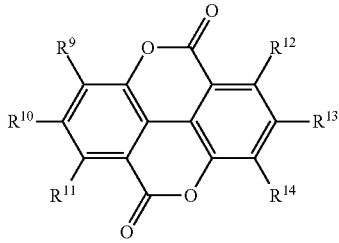

Formula IV wherein
  $R^9, R^{10}, R^{11}, R^{12}, R^{13}$, and $R^{14}$ are independently selected from the group consisting of H and OR; and
  R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing metabolic syndrome, comprising administering a therapeutically effective amount of a compound Formula IV to a subject in need thereof, thereby treating or preventing the metabolic syndrome,
  wherein the compound of Formula IV is

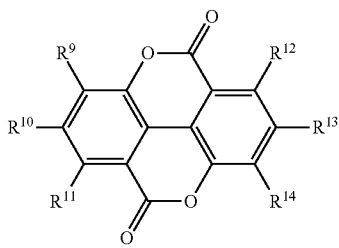

Formula IV wherein
  $R^9, R^{10}, R^{11}, R^{12}, R^{13}$, and $R^{14}$ are independently selected from the group consisting of H and OR; and
  R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing type II diabetes mellitus, comprising administering a therapeutically effective amount of a compound Formula IV to a subject in need thereof, thereby treating or preventing the type II diabetes mellitus,
  wherein the compound of Formula IV is

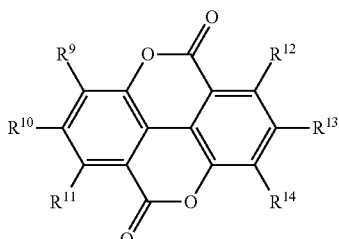

Formula IV wherein
  $R^9, R^{10}, R^{11}, R^{12}, R^{13}$, and $R^{14}$ are independently selected from the group consisting of H and OR; and
  R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing hyperlipidemia, comprising administering a therapeutically effective amount of a compound Formula IV to a subject in need thereof, thereby treating or preventing the hyperlipidemia,
  wherein the compound of Formula IV is

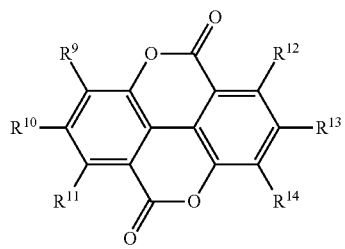

Formula IV wherein
  $R^9, R^{10}, R^{11}, R^{12}, R^{13}$, and $R^{14}$ are independently selected from the group consisting of H and OR; and
  R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing osteoarthritis, comprising administering a therapeutically effective amount of a compound Formula IV to a subject in need thereof, thereby treating or preventing the osteoarthritis,
  wherein the compound of Formula IV is

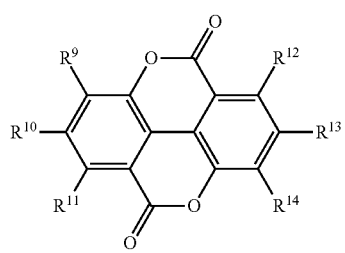

Formula IV wherein
  $R^9, R^{10}, R^{11}, R^{12}, R^{13}$, and $R^{14}$ are independently selected from the group consisting of H and OR; and
  R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing neurodegenerative disease, comprising administering a therapeutically effective amount of a compound Formula IV to a subject in need thereof, thereby treating or preventing the neurodegenerative disease, wherein the compound of Formula IV is

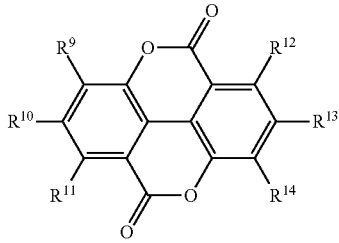

Formula IV wherein
- $R^9, R^{10}, R^{11}, R^{12}, R^{13}$, and $R^{14}$ are independently selected from the group consisting of H and OR; and
- R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing Alzheimer's disease, comprising administering a therapeutically effective amount of a compound Formula IV to a subject in need thereof, thereby treating or preventing the Alzheimer's disease,
wherein the compound of Formula IV is

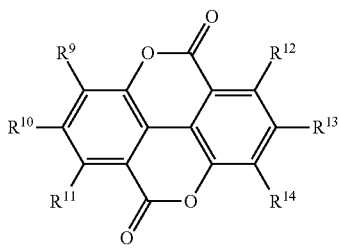

Formula IV wherein
- $R^9, R^{10}, R^{11}, R^{12}, R^{13}$, and $R^{14}$ are independently selected from the group consisting of H and OR; and
- R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing Parkinson's disease, comprising administering a therapeutically effective amount of a compound Formula IV to a subject in need thereof, thereby treating or preventing the Parkinson's disease,
wherein the compound of Formula IV is

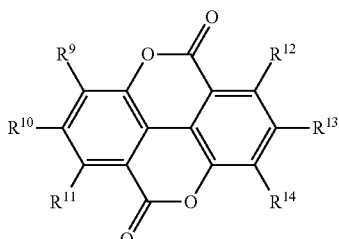

Formula IV wherein
- $R^9, R^{10}, R^{11}, R^{12}, R^{13}$, and $R^{14}$ are independently selected from the group consisting of H and OR; and
- R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing amyotrophic lateral sclerosis (ALS), comprising administering a therapeutically effective amount of a compound Formula IV to a subject in need thereof, thereby treating or preventing the ALS,
wherein the compound of Formula IV is

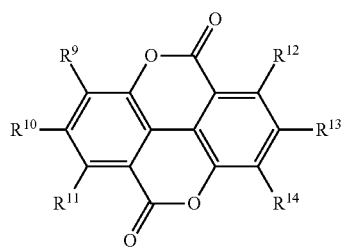

Formula IV wherein
- $R^9, R^{10}, R^{11}, R^{12}, R^{13}$, and $R^{14}$ are independently selected from the group consisting of H and OR; and
- R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing cancer, comprising administering a therapeutically effective amount of a compound Formula IV to a subject in need thereof, thereby treating or preventing the cancer,
wherein the compound of Formula IV is

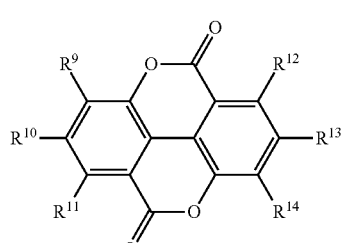

Formula IV wherein
- $R^9, R^{10}, R^{11}, R^{12}, R^{13}$, and $R^{14}$ are independently selected from the group consisting of H and OR; and
- R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing cognitive disorder, comprising administering a therapeutically effective amount of a compound Formula IV to a subject in need thereof, thereby treating or preventing the cognitive disorder, wherein the compound of Formula IV is

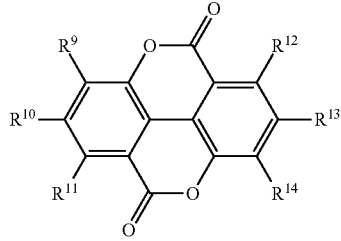

Formula IV wherein
$R^9$, $R^{10}$, $R^{11}$, $R^{12}$, $R^{13}$, and $R^{14}$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing mood disorder, comprising administering a therapeutically effective amount of a compound Formula IV to a subject in need thereof, thereby treating or preventing the mood disorder,
wherein the compound of Formula IV is

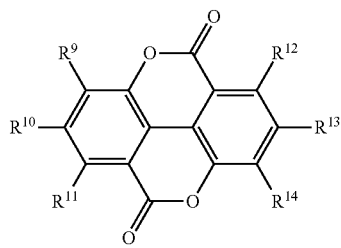

Formula IV wherein
$R^9$, $R^{10}$, $R^{11}$, $R^{12}$, $R^{13}$, and $R^{14}$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of treating or preventing stress, comprising administering a therapeutically effective amount of a compound Formula IV to a subject in need thereof, thereby treating or preventing the stress,
wherein the compound of Formula IV is

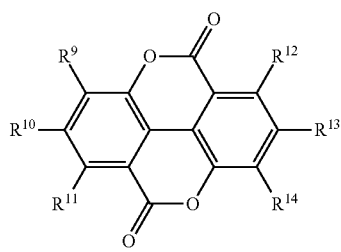

Formula IV wherein
$R^9$, $R^{10}$, $R^{11}$, $R^{12}$, $R^{13}$, and $R^{14}$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to a method of improving activity during aging, comprising administering a therapeutically effective amount of a compound of Formula IV to a subject in need thereof, thereby improving activity during aging,
wherein the compound of Formula IV is

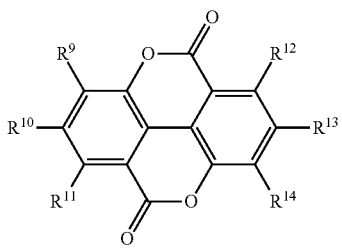

Formula IV wherein
$R^9$, $R^{10}$, $R^{11}$, $R^{12}$, $R^{13}$, and $R^{14}$ are independently selected from the group consisting of H and OR; and
R is H, substituted or unsubstituted alkyl, substituted or unsubstituted aryl, a substituted or unsubstituted monosaccharide, or a substituted or unsubstituted oligosaccharide.

In certain embodiments, the invention relates to any one of the aforementioned methods, wherein $R^9$, $R^{10}$, $R^{11}$, $R^{12}$, $R^{13}$, and $R^{14}$ are H.

In certain embodiments, the invention relates to any one of the aforementioned methods, wherein at least one of $R^9$, $R^{10}$, $R^{11}$, $R^{12}$, $R^{13}$, and $R^{14}$ is OR.

In certain embodiments, the invention relates to any one of the aforementioned methods, wherein at least two of $R^9$, $R^{10}$, $R^{11}$, $R^{12}$, $R^{13}$, and $R^{14}$ are OR.

In certain embodiments, the invention relates to any one of the aforementioned methods, wherein at least three of $R^9$, $R^{10}$, $R^{11}$, $R^{12}$, $R^{13}$, and $R^{14}$ are OR.

In certain embodiments, the invention relates to any one of the aforementioned methods, wherein at least four of $R^9$, $R^{10}$, $R^{11}$, $R^{12}$, $R^{13}$, and $R^{14}$ are OR.

In certain embodiments, the invention relates to any one of the aforementioned methods, wherein five of $R^9$, $R^{10}$, $R^{11}$, $R^{12}$, $R^{13}$, and $R^{14}$ are OR.

In certain embodiments, the invention relates to any one of the aforementioned methods, wherein $R^9$, $R^{10}$, $R^{11}$, $R^{12}$, $R^{13}$, and $R^{14}$ are OR.

In certain embodiments, the invention relates to any one of the aforementioned methods, wherein $R^9$ is OR; and $R^{10}$, $R^{11}$, $R^{12}$, $R^{13}$, and $R^{14}$ are H.

In certain embodiments, the invention relates to any one of the aforementioned methods, wherein $R^{10}$ is OR; and $R^9$, $R^{11}$, $R^{12}$, $R^{13}$, and $R^{14}$ are H.

In certain embodiments, the invention relates to any one of the aforementioned methods, wherein $R^{11}$ is OR; and $R^9$, $R^{10}$, $R^{12}$, $R^{13}$, and $R^{14}$ are H.

In certain embodiments, the invention relates to any one of the aforementioned methods, wherein $R^9$ and $R^{10}$ are OR; and $R^{11}$, $R^{12}$, $R^{13}$, and $R^{14}$ are H.

In certain embodiments, the invention relates to any one of the aforementioned methods, wherein $R^9$ and $R^{11}$ are OR; and $R^{10}$, $R^{12}$, $R^{13}$, and $R^{14}$ are H.

In certain embodiments, the invention relates to any one of the aforementioned methods, wherein $R^9$ and $R^{12}$ are OR; and $R^{10}$, $R^{11}$, $R^{13}$, and $R^{14}$ are H.

In certain embodiments, the invention relates to any one of the aforementioned methods, wherein $R^9$ and $R^{13}$ are OR; and $R^{10}$, $R^{11}$, $R^{12}$, and $R^{14}$ are H.

In certain embodiments, the invention relates to any one of the aforementioned methods, wherein $R^9$ and $R^{14}$ are OR; and $R^{10}$, $R^{11}$, $R^{12}$, and $R^{13}$ are H.

In certain embodiments, the invention relates to any one of the aforementioned methods, wherein $R^{10}$ and $R^{11}$ are OR; and $R^9$, $R^{12}$, $R^{13}$, and $R^{14}$ are H.

In certain embodiments, the invention relates to any one of the aforementioned methods, wherein $R^{10}$ and $R^{12}$ are OR; and $R^9$, $R^{11}$, $R^{13}$, and $R^{14}$ are H.

In certain embodiments, the invention relates to any one of the aforementioned methods, wherein $R^{10}$ and $R^{13}$ are OR; and $R^9$, $R^{11}$, $R^{12}$, and $R^{14}$ are H.

In certain embodiments, the invention relates to any one of the aforementioned methods, wherein $R^{11}$ and $R^{12}$ are OR; and $R^9$, $R^{10}$, $R^{13}$, and $R^{14}$ are H.

In certain embodiments, the invention relates to any one of the aforementioned methods, wherein $R^9$, $R^{10}$, and $R^{11}$ are OR; and $R^{12}$, $R^{13}$, and $R^{14}$ are H.

In certain embodiments, the invention relates to any one of the aforementioned methods, wherein $R^9$, $R^{10}$, and $R^{12}$ are OR; and $R^{11}$, $R^{13}$, and $R^{14}$ are H.

In certain embodiments, the invention relates to any one of the aforementioned methods, wherein $R^9$, $R^{10}$, and $R^{13}$ are OR; and $R^{11}$, $R^{12}$, and $R^{14}$ are H.

In certain embodiments, the invention relates to any one of the aforementioned methods, wherein $R^9$, $R^{10}$, and $R^{14}$ are OR; and $R^{11}$, $R^{12}$, and $R^{13}$ are H.

In certain embodiments, the invention relates to any one of the aforementioned methods, wherein $R^9$, $R^{11}$, and $R^{12}$ are OR; and $R^{10}$, $R^{13}$, and $R^{14}$ are H.

In certain embodiments, the invention relates to any one of the aforementioned methods, wherein $R^9$, $R^{11}$, and $R^{13}$ are OR; and $R^{10}$, $R^{12}$, and $R^{14}$ are H.

In certain embodiments, the invention relates to any one of the aforementioned methods, wherein $R^9$, $R^{11}$, and $R^{14}$ are OR; and $R^{10}$, $R^{12}$, and $R^{13}$ are H.

In certain embodiments, the invention relates to any one of the aforementioned methods, wherein $R^9$, $R^{12}$, and $R^{13}$ are OR; and $R^{10}$, $R^{11}$, and $R^{14}$ are H.

In certain embodiments, the invention relates to any one of the aforementioned methods, wherein $R^{10}$, $R^{11}$, and $R^{12}$ are OR; and $R^9$, $R^{13}$, and $R^{14}$ are H.

In certain embodiments, the invention relates to any one of the aforementioned methods, wherein $R^{10}$, $R^{11}$, and $R^{13}$ are OR; and $R^9$, $R^{12}$, and $R^{14}$ are H.

In certain embodiments, the invention relates to any one of the aforementioned methods, wherein $R^9$, $R^{10}$, $R^{11}$, and $R^{12}$ are OR; and $R^{13}$ and $R^{14}$ are H.

In certain embodiments, the invention relates to any one of the aforementioned methods, wherein $R^9$, $R^{10}$, $R^{11}$, and $R^{13}$ are OR; and $R^{12}$ and $R^{14}$ are H.

In certain embodiments, the invention relates to any one of the aforementioned methods, wherein $R^9$, $R^{10}$, $R^{11}$, and $R^{14}$ are OR; and $R^{12}$ and $R^{13}$ are H.

In certain embodiments, the invention relates to any one of the aforementioned methods, wherein $R^9$, $R^{10}$, $R^{12}$, and $R^{13}$ are OR; and $R^{11}$ and $R^{14}$ are H.

In certain embodiments, the invention relates to any one of the aforementioned methods, wherein $R^9$, $R^{10}$, $R^{12}$, and $R^{14}$ are OR; and $R^{11}$ and $R^{13}$ are H.

In certain embodiments, the invention relates to any one of the aforementioned methods, wherein $R^9$, $R^{10}$, $R^{13}$, and $R^{14}$ are OR; and $R^{11}$ and $R^{12}$ are H.

In certain embodiments, the invention relates to any one of the aforementioned methods, wherein $R^9$, $R^{11}$, $R^{12}$, and $R^{13}$ are OR; and $R^{10}$ and $R^{14}$ are H.

In certain embodiments, the invention relates to any one of the aforementioned methods, wherein $R^9$, $R^{11}$, $R^{12}$, and $R^{14}$ are OR; and $R^{10}$ and $R^{13}$ are H.

In certain embodiments, the invention relates to any one of the aforementioned methods, wherein $R^{10}$, $R^{11}$, $R^{12}$, and $R^{13}$ are OR; and $R^9$ and $R^{14}$ are H.

In certain embodiments, the invention relates to any one of the aforementioned methods, wherein $R^9$, $R^{10}$, $R^{11}$, $R^{12}$, and $R^{13}$ are OR; and $R^{14}$ is H.

In certain embodiments, the invention relates to any one of the aforementioned methods, wherein $R^9$, $R^{10}$, $R^{11}$, $R^{12}$, and $R^{14}$ are OR; and $R^{13}$ is H.

In certain embodiments, the invention relates to any one of the aforementioned methods, wherein $R^9$, $R^{10}$, $R^{11}$, $R^{13}$, and $R^{14}$ are OR; and $R^{12}$ is H.

In certain embodiments, the invention relates to any one of the aforementioned methods, wherein R is H.

Exemplary Compositions

In certain embodiments, the invention relates to a composition comprising any one of the aforementioned compounds, wherein the composition further comprises a pharmaceutically acceptable carrier.

In certain embodiments, the invention relates to a composition comprising a first compound selected from the group consisting of: a compound of Formula I, and a compound of Formula IV; and a second compound selected from the group consisting of rapamycin, resveratrol, metformin, and spermidine.

In certain embodiments, the invention relates to any one of the aforementioned compositions, wherein the first compound is urolithin A.

In certain embodiments, the invention relates to any one of the aforementioned compositions, wherein the first compound is urolithin B.

In certain embodiments, the invention relates to any one of the aforementioned compositions, wherein the first compound is urolithin C.

In certain embodiments, the invention relates to any one of the aforementioned compositions, wherein the first compound is urolithin D.

In certain embodiments, the invention relates to any one of the aforementioned compositions, wherein the first compound is ellagic acid.

In certain embodiments, the invention relates to any one of the aforementioned compositions, wherein the first compound is any of the specific urolithin or urolithin precursor compounds disclosed herein.

In certain embodiments, the invention relates to any one of the aforementioned compositions, wherein the composition further comprises a pharmaceutically acceptable carrier.

Compositions Comprising Urolithins and Other Compounds

An aspect of the invention is a composition, comprising a urolithin or a precursor thereof, and one or more additional compounds that induce autophagy. In certain embodiments, the one or more additional compounds comprises a urolithin or precursor thereof. In certain embodiments, the one or more additional compounds is selected from the group consisting of rapamycin, resveratrol, metformin, and spermidine. In a related embodiment, the one or more additional compounds comprise both a urolithin or precursor thereof and a compound selected from the group consisting of rapamycin, resveratrol, metformin, and spermidine.

In one embodiment, the urolithin is an isolated urolithin.

In one embodiment, the urolithin is a purified urolithin.

In one embodiment, the urolithin is selected from the group consisting of urolithin A, urolithin B, urolithin C, urolithin D, and any combination thereof.

In one embodiment, the urolithin is urolithin A.

In one embodiment, the urolithin is urolithin B.

In one embodiment, the urolithin is urolithin C.

In one embodiment, the urolithin is urolithin D.

In certain embodiments, the urolithin is a compound of Formula I, Formula II, or Formula III, including any one of the specific compounds of these formulas described herein.

In one embodiment, the urolithin precursor is an isolated urolithin precursor.

In one embodiment, the urolithin precursor is a purified urolithin precursor.

In certain embodiments, the urolithin precursor is a compound of Formula IV, Formula V, or Formula VI, including any one of the specific compounds of these formulas described herein.

In one embodiment, the urolithin precursor is selected from the group consisting of ellagic acid, an ellagitannin, and any combination thereof.

In one embodiment, the urolithin precursor is ellagic acid.

In one embodiment, the urolithin precursor is an ellagitannin.

In one embodiment, the ellagitannin is selected from the group consisting of castalagin, castalin, casuarictin, chebulagic acid, chebulinic acid, gemin D, grandinin, pedunculagin, punicalagin, punicalin, roburin A, strictinin, tellimagrandin I, tellimagrandin II, terflavin A, terflavin B, tergallagin, Lambertianin C, Sanguiin H-6, Sanguiin H-10, and vescalagin.

In certain embodiments, the invention relates to a composition comprising a first compound selected from the group consisting of: a compound of Formula II, a compound of Formula III, a compound of Formula V, and a compound of Formula VI; and a second compound selected from the group consisting of rapamycin, resveratrol, metformin, and spermidine.

In one embodiment, the composition further comprises a pharmaceutically acceptable carrier.

Autophagy is known to be strongly induced by caloric restriction (e.g., starvation), and inhibited by the mTOR pathway. Caloric restriction, without malnutrition, has been reported to delay aging and extend lifespan in a number of species, including insects, worms, mice, rats, fish, monkeys, and even humans. See, for example, Fontana L et al. (2004) *Proc Natl Acad Sci USA* 101:6659-6663; Colman R J et al. (2009) *Science* 325:201-204. Additionally, long-term calorie restriction has been reported to be highly effective in reducing the risk of atherosclerosis in humans. Fontana L et al. (supra).

Moreover, inhibition of the mTOR pathway is known to promote autophagy, and inhibitors of the mTOR pathway are known to activate autophagy. Inhibitors of the mTOR pathway are known to include rapamycin, metformin, and resveratrol. Additional agents known to stimulate autophagy, albeit via different mechanism(s), include spermidine, clonidine, rilmenidine, tyramine, morphine, baclofen, mastoparan, propranolol, bupivacain, N-dodecyl lysinamide, tamoxifen, interferon (IFN)-gamma, trehalose and vinblastine. In one embodiment of this aspect, the autophagy inducing compound is selected from the group consisting of Loperamide, Amiodarone, Niguldipine, Pimozide, Nicardipine, Penitrem A, Fluspirilene, and Trifluoerazine and pharmaceutically acceptable salts thereof.

Rapamycin ((3S,6R,7E,9R,10R,12R,14S,15E,17E,19E, 21S,23S,26R,27R,34aS)-9,10,12,13,14,21,22,23,24,25,26, 27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4]-oxaazacyclohentriacontine-1,5,11,28,29(4H,6H,31H)-pentone), also known as sirolimus, is a macrolide immunosuppressant agent. It was approved by the FDA in September 1999 and is marketed under the trade name Rapamune® by Pfizer (formerly by Wyeth). It binds to the cytosolic protein FK-binding protein 12 (FKBP12) to form a complex that inhibits the mTOR pathway by directly binding the mTOR Complex1 (mTORC1). In *C. elegans* and in yeast, rapamycin extends lifespan only under conditions in which autophagy can be induced. Rapamycin was first shown to extend lifespan in eukaryotes in 2006. Powers et al. ((2006) *Genes Dev.* 20:174-184) showed a dose-responsive effect of rapamycin on lifespan extension in yeast cells. Building on this and other work, in a 2009 study, the lifespans of mice fed rapamycin were increased between 28 and 38% from the beginning of treatment, or 9 to 14% in total increased maximum lifespan. Harrison D E et al. (2009) *Nature* 460:392-395. Of particular note, the treatment began in mice aged 20 months, the equivalent of 60 human years.

Metformin (N,N-Dimethylimidodicarbonimidic diamide; rosiglitazone) is a thiazolidinedione compound in a class of oral antidiabetic drugs known as the biguanide class. It is commercially available in the United States as Glucophage, Fortamet, Glumetza, and Riomet, principally for use in the treatment of type 2 (insulin resistant) diabetes mellitus. Dowling R J O et al. (2007) *Cancer Res.* 67:10804-10812 reported that metformin inhibits the mTOR pathway in breast cancer cells.

Resveratrol (3,5,4'-trihydroxy-trans-stilbene) is a natural phenol found in the skin of red grapes and other fruits, and it is an indirect activator of sirtuin 1. It has also been produced by chemical synthesis. Farina A et al. (2006) Nat. Prod. Res. 20:247-252. Resveratrol is available as a nutritional supplement from a number of commercial suppliers. A number of studies have reported that resveratrol extends lifespan in yeast, *C. elegans, Drosophila*, certain fish, and mice. In addition, Brito P M et al. (2009) *Atherosclerosis* 205:126-134 reported that resveratrol inhibits the mTOR pathway.

Baur J A et al. (2006) *Nature* 444:337-342 reported that resveratrol shifts the physiology of middle-aged mice on a high-calorie diet towards that of mice on a standard diet and significantly increases their survival. According to Baur et al., resveratrol produces changes associated with longer lifespan, including increased insulin sensitivity, reduced insulin-like growth factor-1 (IGF-I) levels, increased AMP-activated protein kinase (AMPK) and peroxisome proliferator-activated receptor-gamma coactivator 1α (PGC-1α) activity, increased mitochondrial number, and improved motor function. Parametric analysis of gene set enrichment revealed that resveratrol opposed the effects of the high-calorie diet in 144 out of 153 significantly altered pathways.

Pearson K J et al. (2008) *Cell Metab.* 8:157-168 reported that resveratrol-fed elderly mice show a marked reduction in signs of aging, including reduced albuminuria, decreased inflammation and apoptosis in the vascular endothelium, increased aortic elasticity, greater motor coordination, reduced cataract formation, and preserved bone mineral density.

In addition to resveratrol, other small molecules have been reported to activate sirtuins and extend lifespan in yeast, including butein (3,4,2',4'-tetrahydroxychalcone), piceatannol (3,5,3',4'-tetrahydroxy-trans-stilbene), isoliquiritigenin (4,2',4'-trihydroxychalcone), fisetin (3,7,3',4'-tetrahydroxyflavone), and quercetin (3,5,7,3',4'-pentahydroxyflavone). Howitz K T et al. (2003) *Nature* 425:191-196; Wood, J G et al. (2004) *Nature* 430:686-689, corrigendum *Nature* 431:107.

The effects of various treatments on aging and longevity are commonly assessed on invertebrates, including nematodes (*C. elegans*), yeast, and fruit flies (*Drosophila*). *C. elegans*, in particular, is the most commonly employed in vivo model for determining impact on longevity due to its short lifespan and ease of genetic manipulation. Pharmaceutical interventions found to extend the lifespan of *C. elegans* have also been shown to extend the lifespan of yeast and fruitflies.

Figure 4:
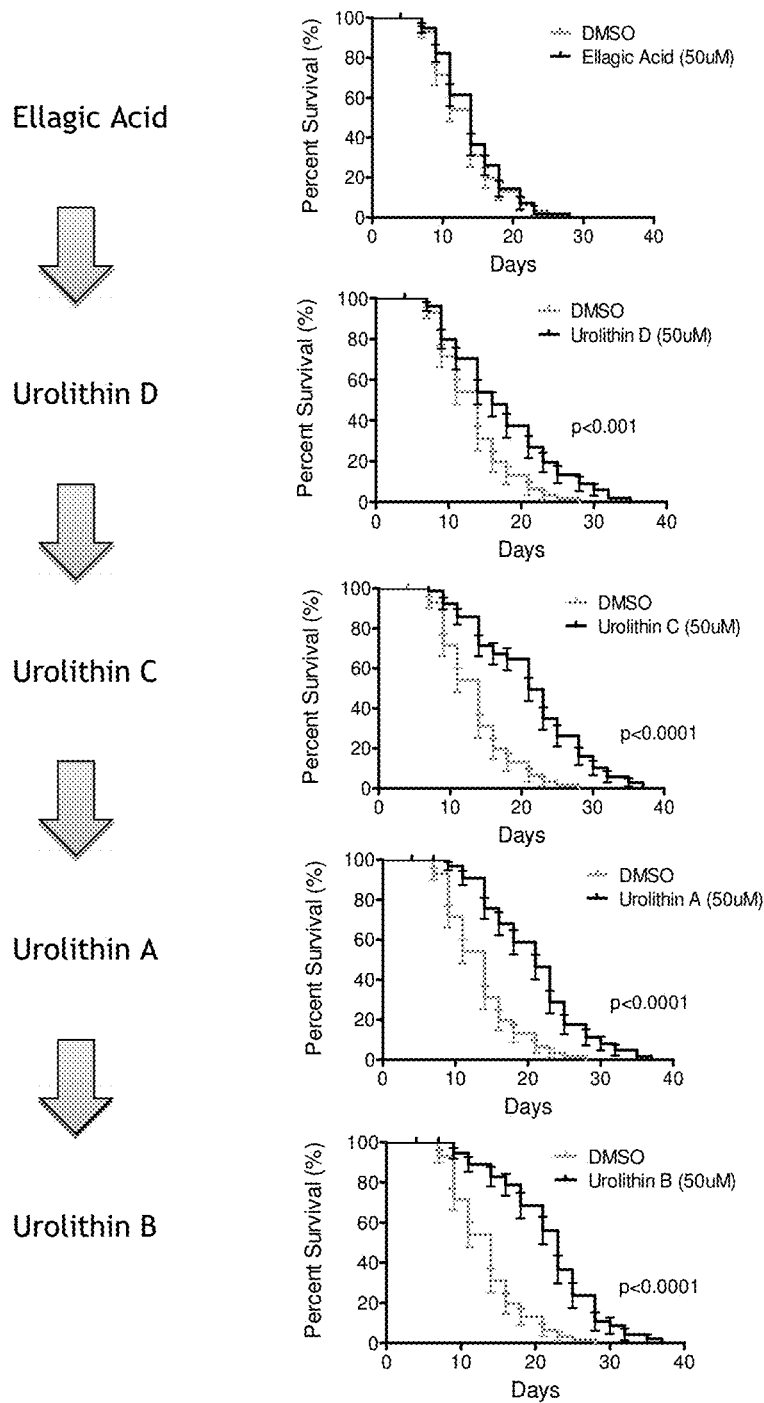
FIG. 4 is a group of five graphs depicting the effect of ellagic acid and urolithins A, B, C, and D on the lifespan of C. elegans. Test agents were present at 50 µM in DMSO. DMSO, dimethylsulfoxide, was the control and vehicle for test agents.

Importantly, in accordance with the instant invention, urolithin A has been found to be unexpectedly more potent, in terms of life extension, than any of rapamycin, resveratrol, metformin, or spermidine. Referring to Table 11, it is clear that urolithins are the most potent among all of the compounds listed, in terms of life extension, increasing mean life extension by 75% versus 27% for metformin, the most potent other compound listed. This illustrates that urolithins show superior effects with respect to their ability to delay the negative consequences linked to aging. The effects of other urolithins have also shown impressive effects on life span extension (FIG. 4). Similar effects are seen across all of the urolithins tested, so the compound class as a whole is expected to show comparable effects.

TABLE 11

Comparison of the Effects of Compounds Active in Extending the Lifespan of *C. elegans*

| Treatment | *C. elegans* | Dose | Mean Life Extension (%) | Reference |
| --- | --- | --- | --- | --- |
| Resveratrol | Genotype: N2 Fed Live *E. coli* (OP50) | 100 μM | 6.2-12.6 | Wood J et al. (2004) *Nature* 430:686-689. |
| Spermidine | Genotype: N2 Fed Live *E. coli* (OP50) | 200 μM | 15 | Eisenberg T et al.; *Nat. Cell Biol.* 11:1305-1314. |
| Rapamycin | Genotype: N2 Fed Live *E. coli* (OP50) | 100 μM | 19 | Robida-Stubbs S et al. (2012) *Cell Metabolism* 15:713-724. |
| Metformin | Genotype: N2 Fed Live *E. coli* (OP50) | 50 μM | 27 | Onken B et al. (2010) *PLoS ONE* 5(1):e8758. |
| Urolithin A | Genotype: N2 Fed Live *E. coli* (OP50) | 10 μM 50 μM | 27.7 75 | This invention |

As indicated above, the invention encompasses methods and compositions combining urolithins, or precursors thereof, with one or more other agents that promote autophagy. Such agents include, without limitation, rapamycin, metformin, resveratrol, spermidine, epigallocatechin gallate, genistein, silibinin, curcumin, clonidine, rilmenidine, tyramine, morphine, baclofen, mastoparan, propranolol, bupivacaine, N-dodecyl lysinamide, tamoxifen, IFN-gamma, trehalose, and vinblastine.

The invention further encompasses methods and compositions combining urolithins, or precursors thereof, with drugs reported to exert mitochondrial toxicity. Such toxic effects have been reported in connection with, for example, valproic acid, antiretrovirals, statins, aspirin, aminoglycoside antibiotics, platinum-containing chemotherapeutic agents, acetaminophen, beta blockers, and steroids. In this setting, a urolithin or urolithin precursor is useful to counteract or treat the mitochondrial toxicity of the drugs reported to exert mitochondrial toxicity.

The invention further encompasses methods and compositions combining urolithins, or precursors thereof, together with one or more agents that are useful for mitochondrial biogenesis. Such compounds include, without limitation, resveratrol, pyrroloquinoline quinone, genistein, hydroxyltyrosol, and quercetin.

The invention further encompasses methods and compositions combining urolithins, or precursors thereof, together with one or more agents that are useful for mitochondrial disorders. Such agents, which may be identified as mitochondrial medications and supplements, include coenzyme Q10 (CoQ10) as ubiquinol, CoQ10 as ubiquinone, riboflavin (vitamin $B_2$), L-creatine, L-arginine, L-carnitine, B50 or B100 (B vitamin complexes), vitamin E, vitamin C, alpha-lipoic acid, and folinic acid (e.g., as leucovorin).

The invention further encompasses methods and compositions combining urolithins, or precursors thereof, together with one or more natural products that are useful in the treatment of disorders of weight management, metabolism, cognition, mood, and mitochondrial diseases.

In connection with disorders of weight management and metabolism, such natural products include, without limitation, 23-oxo-3α-hydroxycycloart-24-en-26-oic acid (diabetes); berberine (diabetes, hypertension, and hypercholesterolemia); mangiferin (dyslipidemia); arabinoxylan (blood glucose management); beta-glucans (weight loss); chromium, fructose, hydroxypropylmethylcellulose, pectins, digestable starch, and konjacmannan (to promote weight loss); alpha-linolenic acid (ALA), beta-glucans, chitosan, guar gum, monacolin K, sterols, stanols, pectins, unsaturated fats, and linoleic acid (for management of blood cholesterol); calcium, chloride, lactulose, and fiber (for improved digestion); folate, choline, zinc, vitamin B6, magnesium, biotin, chromium, vitamin D (for improved metabolism); riboflavin (vitamin B2), vitamin A, copper, and vitamin D (for improved iron utilization); iron, and vitamin B6 (for oxygen transport); and choline (for liver).

In connection with disorders of cognition and mood, such natural products include, without limitation, extract of *Bacopa monnieri*, omega-3 fatty acids, flavonoids, vitamin D, and vitamin E (age-associated cognitive decline); pycnogenol (cognition during stress); omega-3 fatty acids, and *Lactobacillus rhamnosus* bacteria (mood disorders); biotin, folate, magnesium, niacin, thiamin, vitamin B6, vitamin B12, and vitamin C (psychological function); omega-3 fatty acids, curcumin, and vitamin E (traumatic brain injury); choline (seizure-induced memory impairment); omega-3 fatty acids, curcumin, and copper (cognitive decay in Alzheimer's disease); danshensu (cognitive defects secondary to diabetes); flavonoids, vitamin B6, vitamin B12, folate, caffeine, pantothenic acid, iodine, iron, and zinc (for cognitive enhancement); iron, and docosahexaenoic acid (DHA) (for cognitive development); and melatonin (for jet lag and for sleep).

In connection with mitochondrial diseases, such natural products include, without limitation, ethanol extract of *Cassia* seed (liver protection); viniferin (Huntington's disease);

Korean mistletoe (*Viscum album coloratum*) extract (for increasing endurance capacity and reducing fatigue); β-phenylethyl isothiocyanate (PEITC), and epigallocatechin-3-gallate (EGCG) (for cancer); and coenzyme Q10, creatine, lipoic acid, and whey-based cysteine supplement (mitochondrial diseases).

Formulations and Clinical Use

Methods and compositions of the invention are believed to be useful in any of a variety of clinical settings for which increasing autophagy and/or improving mitochondrial function are desirable. Methods and compositions of the invention can be used for the treatment and prevention of diseases and conditions where increasing autophagy and/or improving mitochondrial function are desirable. Non-limiting indications for clinical use include: immune disorders, improving stem cell function, all aging-related health conditions where decline in autophagy with aging and/or increase in defective or suboptimally functioning mitochondria accumulate, e.g., neurodegenerative disease, heart disease, vascular disease, atherosclerosis, macular degeneration, sensory hearing loss, obesity, fatty liver, cancer, and infectious disease. Methods and compositions of the invention are also believed to be useful in the treatment and prevention of ischemia and reperfusion injury (including, for example, stroke, myocardial infarction, cardiac bypass, and organ transplantation). Methods and compositions of the invention are also believed to be useful in the treatment of certain skin disorders, including skin aging, skin inflammation, and psoriasis. Methods and compositions of the invention are also believed to be useful in the treatment of osteoarthritis.

In another aspect, the present invention features a method of enhancing autophagy in a subject with a disease or condition; the method includes administering to the subject an effective amount of a urolithin or a precursor thereof, thereby treating the disease or condition in the subject. In related embodiments, the invention includes methods of treating or preventing any of a variety of diseases or conditions by providing to a subject in need thereof an effective amount of a urolithin or precursor thereof. In particular embodiments, the urolithin or precursor thereof is present in a pharmaceutical composition. In certain embodiments, the pharmaceutical composition comprises one or more additional active agents, such as, e.g., one or more additional urolithin or precursor thereof, or other compound described herein. In particular embodiments, the urolithin or precursor thereof is present in a medical food or beverage, functional food or beverage or nutraceutical. In certain embodiments, the medical food or beverage, functional food or beverage or nutraceutical comprises one or more additional active agents, such as, e.g., one or more additional urolithin or precursor thereof, or other compound described herein.

In certain embodiments, the disease or condition is metabolic stress. In particular embodiments, the disease or disorder is nutrient deprivation, growth factor depletion, or hypoxia.

In certain embodiments, the disease or condition is a heart disease or condition, such as, e.g., cardiac hypertrophy, left ventricular dilation, diminished cardiac output, decreased cardiac function, or Danon disease.

In certain embodiments, the disease or condition is muscular atrophy, e.g., muscle disuse atrophy, skeletal muscular atrophy, or sarcopenia of aging.

In certain embodiments, the disease or condition is a muscle degenerative disorder, such as, e.g., a muscular dystrophy, e.g., Duchenne's muscular dystrophy, or Ulrich myopathy.

In certain embodiments, the disease or condition is a liver disease, such as, e.g., cancer, cirrhosis, α1-antitrypsin deficiency, nonalcoholic fatty liver disease, alcoholic induced liver disease, or drug induced liver injury.

In certain embodiments, the disease or condition is ischemic reperfusion injury. In particular embodiments, the ischemic reperfusion injury is due to liver surgery.

In certain embodiments, the disease or condition is a cardiac infarct.

In certain embodiments, the disease or condition relates to future surgical procedures and prevention or treatment of potential damage to cells and tissue, such as, e.g. angioplasty, heart valve repair, or cardiac bypass surgery.

In certain embodiments, the disease or condition is an inflammatory disease or disorder. In particular embodiments, it is an autoimmune disorder, such as, e.g., lupus erythematosus. In particular embodiments, it is an inflammatory disease or disorder, such as, e.g. psoriasis.

In certain embodiments, the disease or condition is a neurodegenerative disease or disorder, such as, e.g., Parkinson's, Alzheimer's, Huntington's or polyQ disease.

In certain embodiments, the disease or condition is a cancer or tumor.

In one embodiment of this aspect, the disease is caused by misfolded protein aggregates. In another embodiment of this aspect, the disease caused by misfolded protein aggregates is selected from the group including: Alzheimer's disease, Parkinson's disease, amyotrophic lateral sclerosis, Huntington's disease, spinocerebellar ataxia, oculopharyngeal muscular dystrophy, prion diseases, fatal familial insomnia, alpha-1 antitrypsin deficiency, dentatorubral pallidoluysian atrophy, frontal temporal dementia, progressive supranuclear palsy, X-linked spinobulbar muscular atrophy, and neuronal intranuclear hyaline inclusion disease. In a further embodiment of this aspect, the disease associated with misfolded protein aggregates is a chronic disease. In yet another embodiment of this aspect, the disease is cancer.

In addition to their usefulness in extending longevity, methods and compositions of the invention are also believed to be useful for extending health span. As used herein, "health span" (or, equivalently, "healthspan") refers to the period of an individual's life during which they are generally healthy and free from serious or chronic illness. In one embodiment, "health span" (or, equivalently, "healthspan") refers to the period of time during which an individual meets one or more selected measures of health. An increase in health span refers to an extension in the period of health, according to such measures, as compared to the period of health in a control population. An increase in health span can be measured, e.g., by determining the length of time that an individual continues to meet the selected measure(s) of health.

The urolithin or precursor thereof may be administered, alone or together with at least one other agent, to a subject (e.g., a mammal) in any of a variety of ways. For example, the urolithin or precursor thereof can be administered orally or parenterally. Parenterally includes, without limitation, intravenously, intramuscularly, intraperitoneally, subcutaneously, intra-articularly, intrasynovially, intraocularly, intrathecally, topically, or by inhalation. As such, the form of the urolithin or precursor thereof dose can be any of a variety of suitable forms, including neat compounds, natural foods, processed foods, natural juices, concentrates and extracts, injectable solutions, microcapsules, nano-capsules, liposomes, plasters, inhalation forms, nose sprays, nosedrops, eyedrops, sublingual tablets, and sustained-release preparations.

The compounds of this invention can be provided in isolated form. As used herein, the term "isolated" means substantially removed from other compounds or components with which the compound of interest may otherwise be found, for example, as found in nature. In one embodiment, a compound is isolated when it is essentially completely removed from other compounds or components with which the compound of interest may otherwise be found. In one embodiment, a compound is isolated when it is pure.

The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including without limitation oral, buccal, rectal, intravenous, intramuscular, intraperitoneal, intradermal, transdermal, and intratracheal administration. The active agent may be systemic after administration or may be localized by the use of regional administration, intramural administration, or use of an implant that acts to retain the active dose at the site of implantation.

The compounds of the invention can also be formulated as food additives, food ingredients, functional foods, dietary supplements, medical foods, nutraceuticals, or food supplements. In certain embodiments, compounds of the invention can be included into nutraceutical beverages of varying volumes to permit the administration of a daily dose in a convenient format. As a non-limiting example, beverages may deliver effective doses in a final volume ranging from 5 mL to 1,000 mL, delivered as a single dose or multiple doses. In certain embodiments, compositions and methods of the invention are utilized for and in non-human animals. Accordingly, compounds and compositions of the invention may be formulated as veterinary products. Compounds and composition may also be formulated into functional foods for administration to animals, for example, dogs, cats, horses, etc.

In pharmaceutical dosage forms, the compounds may be administered in the form of their pharmaceutically acceptable salts. The term "pharmaceutically acceptable salt" is intended to encompass any and all acceptable salt forms derived from a physiologically acceptable acid or base. The compounds of the present invention may be utilized as the free acid or free base. Alternatively, the compounds of this invention may be used in the form of acid or base addition salts, which may be formed by methods well known in the art.

The compounds may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional, additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier, wherein each dosage unit, for example, mL or L, contains a predetermined amount of the composition containing one or more compounds of the present invention.

Implants for sustained release formulations are well-known in the art. Implants are formulated as microspheres; slabs, etc., with biodegradable or non-biodegradable polymers. For example, polymers of lactic acid and/or glycolic acid form an erodible polymer that is well-tolerated by the host. The implant containing the inhibitory compounds may be placed in proximity to a site of interest, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

For clinical use, the urolithin or urolithin precursor is administered in a therapeutically effective amount. As used herein, an "effective amount" refers to an amount that is sufficient to achieve or realize a specified or desired biological effect. As used herein, a "therapeutically effective amount" refers to an amount sufficient to realize, in a single dose or multiple doses, a desired therapeutic effect. A skilled artisan can determine therapeutically effective amounts based on in vitro, preclinical, or clinical studies, or any combination thereof.

In one embodiment urolithins and their precursors can be delivered by means of natural products. One of these is the pomegranate, which contains ellagitannins and ellagic acid. Pomegranates may be processed in several ways for practicing this invention. Pomegranate juice can vary widely in terms of its polyphenol constituents, particularly punicalagin, the ellagitannin having the highest concentration found in the pomegranate. The starting material (i.e., pomegranates and their variety), the method of juicing, as well as the storage conditions will affect punicalagin levels found in the final juice product. Table 12 below provides examples of juices that have been store bought and of different origins. A large variation in punicalagin from one juice batch to another is observed. For the purpose of practicing this invention it is advantageous that individuals consume a standardized batch of juice that is delivering known and consistent levels of ellagitannins. Presently in the marketplace pomegranate juice is not standardized by ellagitannin levels and dosing is not indicated. Consequently, currently available juices are not suitable for effectively practicing the invention as they do not offer the possibility of consistent dosing by an individual, due to the wide variations of ellagitannins and their concentrations found in the different products.

TABLE 12

Variation of Punicalagin Content in Different Commercially Available Pomegranate Juices

| Commercial Juice | Punicalagins (g/L) |
|---|---|
| 1 | 0.08 |
| 2 | 0.28 |
| 3 | 0.04 |
| 4 | 0.32 |
| 5 | 0.26 |
| 6 | 0.89 |
| 7 | 0.10 |
| 8 | 0.10 |
| 9 | 0.02 |
| 10 | 0.51 |
| 11 | 0.38 |

As described earlier, the consumption of ellagitannins by humans leads to the formation of urolithins by the gut microflora prior to their absorption. It is believed that consumption of ellagitannins holds the potential to modify the microflora of the gut. In one study in rats it was observed that urolithins were found in the urine only following four days of consumption, suggesting that the rats required time to adapt their microflora to metabolize pomegranate tannins to produce the urolithin metabolites. Cerda et al. (2003) *Eur J Nutr* 42:18-28. This finding suggests that optimal dosing of ellagitannins in humans may require a similar period for each individual's microflora to adapt optimally to metabolize consumed ellagitannins or ellagic acid equivalents into urolithins.

With urolithin precursors, including but not limited to ellagitannins and ellagic acid, a minimal treatment period sometimes may be needed prior to observing autophagy or the health benefits, depending on the subject. For example, this pre-treatment period may be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days, or 1, 2, or 3 months.

Additionally, it has been shown that individuals' microflora compositions can vary dramatically and that some individuals may metabolize ellagitannins more completely than others. For instance, following the consumption of pomegranate juice, some individuals may preferentially convert ellagitannins or ellagic acid equivalents into urolithin A, while others may preferentially convert into urolithin C. Also, it has been observed that certain individuals are high converters (i.e., a high level of urolithins are formed in the gut from consumed ellagitannins and ellagic acid equivalents), while others are low converters (i.e., only a low level of urolithins are formed in the gut from consumed ellagitannins and ellagic acid equivalents). These differences in metabolite production from high producer to low producer and variations of urolithin are believed to be due to differences in colonic microflora and the potential requirement for an adaptation period. Cerda et al. (2004) *Eur J Nutr* 43:205-220. Consequently, due to these variations when administering ellagitannins and their equivalents, for certain applications it may be beneficial to administer urolithins directly.

Dosing will generally be daily to weekly. In one embodiment, dosing is at least weekly. For example, a subject may receive one dose once weekly, twice weekly, thrice weekly, or every other day. In one embodiment, dosing is at least daily. For example, a subject may receive one or more doses daily.

It is believed that dosing for greatest efficacy in humans involves extended, daily administration, e.g., when delivering ellagitannins, amounts equivalent to at least 16 ounces (500 mL) of pomegranate juice per day. Extended use is contemplated to include use for 1 month, 2 months, 3 months, 4 months, 5 months, 6 months, or even longer.

For clinical use, a urolithin or precursor may be administered to treat either a chronic or an acute condition. As autophagy is observed to be increased in cells in less than one day, for example after 8 hours, urolithins and their variants of Formula I, Formula II and Formula III may be administered in an acute fashion to treat a condition acutely in need an induction of autophagy. Such instances may include conditions due to reperfusion injuries (for example, organ transplantation), heart attack, stroke, ischemic insult, during surgery (for example, during an angioplasty procedure or replacement of a heart valve), or following a traumatic injury.

For clinical use, a urolithin or precursor thereof will generally be administered in an amount equal or equivalent to 0.2-2000 milligram (mg) of urolithin per kilogram (kg) of body weight of the subject per day. In one embodiment, the urolithin or precursor thereof is administered in a dose equal or equivalent to 2-2000 mg of urolithin per kg body weight of the subject per day. In one embodiment, the urolithin or precursor thereof is administered in a dose equal or equivalent to 20-2000 mg of urolithin per kg body weight of the subject per day. In one embodiment, the urolithin or precursor thereof is administered in a dose equal or equivalent to 50-2000 mg of urolithin per kg body weight of the subject per day. In one embodiment, the urolithin or precursor thereof is administered in a dose equal or equivalent to 100-2000 mg of urolithin per kg body weight of the subject per day. In one embodiment, the urolithin or precursor thereof is administered in a dose equal or equivalent to 200-2000 mg of urolithin per kg body weight of the subject per day. Where a precursor of urolithin is to be administered rather than a urolithin, it is administered in an amount that is equivalent to, i.e., sufficient to deliver, the above-stated amounts of urolithin.

The formulations of urolithin or precursor thereof can be administered to human subjects in therapeutically effective amounts. Typical dose ranges are from about 0.01 microgram/kg to about 2 mg/kg of body weight per day. The dosage of drug to be administered is likely to depend on such variables as the type and extent of the disorder, the overall health status of the particular subject, the specific compound being administered, the excipients used to formulate the compound, and its route of administration. Routine experiments may be used to optimize the dose and dosing frequency for any particular compound.

In one embodiment, the urolithin or precursor thereof is administered at a concentration in the range from about 0.001 microgram/kg to greater than about 500 mg/kg. For example, the concentration may be 0.001 microgram/kg, 0.01 microgram/kg, 0.05 microgram/kg, 0.1 microgram/kg, 0.5 microgram/kg, 1.0 microgram/kg, 10.0 microgram/kg, 50.0 microgram/kg, 100.0 microgram/kg, 500 microgram/kg, 1.0 mg/kg, 5.0 mg/kg, 10.0 mg/kg, 15.0 mg/kg, 20.0 mg/kg, 25.0 mg/kg, 30.0 mg/kg, 35.0 mg/kg, 40.0 mg/kg, 45.0 mg/kg, 50.0 mg/kg, 60.0 mg/kg, 70.0 mg/kg, 80.0 mg/kg, 90.0 mg/kg, 100.0 mg/kg, 150.0 mg/kg, 200.0 mg/kg, 250.0 mg/kg, 300.0 mg/kg, 350.0 mg/kg, 400.0 mg/kg, 450.0 mg/kg, to greater than about 500.0 mg/kg or any incremental value thereof. It is to be understood that all values and ranges between these values and ranges are meant to be encompassed by the present invention.

In one embodiment, the urolithin or precursor thereof is administered at a dosage in the range from about 0.2 milligram/kg/day to greater than about 100 mg/kg/day. For example, the dosage may be 0.2 mg/kg/day to 100 mg/kg/day, 0.2 mg/kg/day to 50 mg/kg/day, 0.2 mg/kg/day to 25 mg/kg/day, 0.2 mg/kg/day to 10 mg/kg/day, 0.2 mg/kg/day to 7.5 mg/kg/day, 0.2 mg/kg/day to 5 mg/kg/day, 0.25 mg/kg/day to 100 mg/kg/day, 0.25 mg/kg/day to 50 mg/kg/day, 0.25 mg/kg/day to 25 mg/kg/day, 0.25 mg/kg/day to 10 mg/kg/day, 0.25 mg/kg/day to 7.5 mg/kg/day, 0.25 mg/kg/day to 5 mg/kg/day, 0.5 mg/kg/day to 50 mg/kg/day, 0.5 mg/kg/day to 25 mg/kg/day, 0.5 mg/kg/day to 20 mg/kg/day, 0.5 mg/kg/day to 15 mg/kg/day, 0.5 mg/kg/day to 10 mg/kg/day, 0.5 mg/kg/day to 7.5 mg/kg/day, 0.5 mg/kg/day to 5 mg/kg/day, 0.75 mg/kg/day to 50 mg/kg/day, 0.75 mg/kg/day to 25 mg/kg/day, 0.75 mg/kg/day to 20 mg/kg/day, 0.75 mg/kg/day to 15 mg/kg/day, 0.75 mg/kg/day to 10 mg/kg/day, 0.75 mg/kg/day to 7.5 mg/kg/day, 0.75 mg/kg/day to 5 mg/kg/day, 1.0 mg/kg/day to 50 mg/kg/day, 1.0 mg/kg/day to 25 mg/kg/day, 1.0 mg/kg/day to 20 mg/kg/day, 1.0 mg/kg/day to 15 mg/kg/day, 1.0 mg/kg/day to 10 mg/kg/day, 1.0 mg/kg/day to 7.5 mg/kg/day, 1.0 mg/kg/day to 5 mg/kg/day, 2 mg/kg/day to 50 mg/kg/day, 2 mg/kg/day to 25 mg/kg/day, 2 mg/kg/day to 20 mg/kg/day, 2 mg/kg/day to 15 mg/kg/day, 2 mg/kg/day to 10 mg/kg/day, 2 mg/kg/day to 7.5 mg/kg/day, or 2 mg/kg/day to 5 mg/kg/day.

In one embodiment, the urolithin or precursor thereof is administered at a dosage in the range from about 0.25 milligram/kg/day to about 25 mg/kg/day. For example, the dosage may be 0.25 mg/kg/day, 0.5 mg/kg/day, 0.75 mg/kg/day, 1.0 mg/kg/day, 1.25 mg/kg/day, 1.5 mg/kg/day, 1.75 mg/kg/day, 2.0 mg/kg/day, 2.25 mg/kg/day, 2.5 mg/kg/day, 2.75 mg/kg/day, 3.0 mg/kg/day, 3.25 mg/kg/day, 3.5 mg/kg/day, 3.75 mg/kg/day, 4.0 mg/kg/day, 4.25 mg/kg/day, 4.5 mg/kg/day, 4.75 mg/kg/day, 5 mg/kg/day, 5.5 mg/kg/day, 6.0 mg/kg/day, 6.5 mg/kg/day, 7.0 mg/kg/day, 7.5 mg/kg/day, 8.0 mg/kg/day, 8.5 mg/kg/day, 9.0 mg/kg/day, 9.5 mg/kg/day, 10 mg/kg/day, 11 mg/kg/day, 12 mg/kg/day, 13 mg/kg/day, 14 mg/kg/day, 15 mg/kg/day, 16 mg/kg/day, 17 mg/kg/day, 18 mg/kg/day, 19 mg/kg/day, 20 mg/kg/day, 21 mg/kg/day, 22 mg/kg/day, 23 mg/kg/day, 24 mg/kg/day, 25 mg/kg/day, 26 mg/kg/day, 27 mg/kg/day, 28 mg/kg/day, 29 mg/kg/day, 30 mg/kg/day, 31 mg/kg/day, 32 mg/kg/day, 33 mg/kg/day, 34 mg/kg/day, 35 mg/kg/day, 36 mg/kg/day, 37 mg/kg/day, 38 mg/kg/day, 39 mg/kg/day, 40 mg/kg/day, 41 mg/kg/day, 42 mg/kg/day, 43 mg/kg/day, 44 mg/kg/day, 45 mg/kg/day, 46 mg/kg/day, 47 mg/kg/day, 48 mg/kg/day, 49 mg/kg/day, or 50 mg/kg/day.

In another embodiment, the urolithin or precursor thereof is administered in concentrations that range from 0.01 micromolar to greater than or equal to 500 micromolar. For example, the dose may be 0.01 micromolar, 0.02 micromolar, 0.05 micromolar, 0.1 micromolar, 0.15 micromolar, 0.2 micromolar, 0.5 micromolar, 0.7 micromolar, 1.0 micromolar, 3.0 micromolar, 5.0 micromolar, 7.0 micromolar, 10.0 micromolar, 15.0 micromolar, 20.0 micromolar, 25.0 micromolar, 30.0 micromolar, 35.0 micromolar, 40.0 micromolar, 45.0 micromolar, 50.0 micromolar, 60.0 micromolar, 70.0 micromolar, 80.0 micromolar, 90.0 micromolar, 100.0 micromolar, 150.0 micromolar, 200.0 micromolar, 250.0 micromolar, 300.0 micromolar, 350.0 micromolar, 400.0 micromolar, 450.0 micromolar, to greater than about 500.0 micromolar or any incremental value thereof. It is to be understood that all values and ranges between these values and ranges are meant to be encompassed by the present invention.

In yet another embodiment, the urolithin or precursor thereof is administered at concentrations that range from 0.10 microgram/mL to 500.0 microgram/mL. For example, the concentration may be 0.10 microgram/mL, 0.50 microgram/mL, 1 microgram/mL, 2.0 microgram/mL, 5.0 microgram/mL, 10.0 microgram/mL, 20 microgram/mL, 25 microgram/mL. 30 microgram/mL, 35 microgram/mL, 40 microgram/mL, 45 microgram/mL, 50 microgram/mL, 60.0 microgram/mL, 70.0 microgram/mL, 80.0 microgram/mL, 90.0 microgram/mL, 100.0 microgram/mL, 150.0 microgram/mL, 200.0 microgram/mL, 250.0 g/mL. 250.0 microgram/mL, 300.0 microgram/mL, 350.0 microgram/mL, 400.0 microgram/mL, 450.0 microgram/mL, to greater than about 500.0 microgram/mL or any incremental value thereof. It is to be understood that all values and ranges between these values and ranges are meant to be encompassed by the present invention.

The term "effective amount" refers to the amount of the urolithin or precursor thereof required to enhance autophagy, e.g., in a disease associated with misfolded protein aggregates. The effective amount of the urolithin or precursor thereof used to enhance autophagy varies depending upon the manner of administration, the age, body weight, and general health of the subject. An effective amount of the urolithin or precursor thereof, as defined herein, may vary according to factors such as the disease state, age, and weight of the subject, and the ability of the urolithin or precursor thereof to elicit a desired response in the subject. Dosage regimens may be adjusted to provide the optimum therapeutic response. An effective amount is also one in which any toxic or detrimental effects (e.g., side effects) of the autophagy inducing compound are outweighed by the therapeutically beneficial effects. For example, a therapeutically effective amount of the urolithin or precursor thereof (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of the urolithin or precursor thereof can include a single treatment or, preferably, can include a series of treatments. In one example, a subject is treated with the urolithin or precursor thereof in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of the urolithin or precursor thereof used for treatment may increase or decrease over the course of a particular treatment.

Non-limiting, illustrative examples of ellagitannin, ellagic acid, and urolithin dosages that may be used are provided in Table 13.

TABLE 13

Ellagitannin/Ellagic Acid/Urolithin Dosing in Mice and Man

|  | Mice | Man |
|---|---|---|
| Punicalagin (mg/kg/d) | 90.00 | 6.56 |
| Punicalagin (moles/kg/day) | 97.65 | 7.11 |
| Ellagic acid (mg/kg/day) | 75.00 | 5.46 |
| Ellagic acid (moles/kg/day) | 22.65 | 1.65 |
| Total Urolithins (mg/kg/day) | 55.00 | 4.01 |
| Urolithin A (moles/kg/day) | 12.49 | 0.91 |
| Urolithin B (moles/kg/day) | 11.66 | 0.85 |
| Urolithin C (moles/kg/day) | 13.42 | 0.98 |
| Urolithin D (moles/kg/day) | 14.25 | 1.04 |

Additional non-limiting, illustrative examples of urolithin doses that may be used are provided in Table 14.

TABLE 14

Urolithin Dosing in Mouse and Human

| Mouse Dose (mg/kg/day) | Human Dose (mg/kg/day) |
|---|---|
| 5 | 0.36 |
| 10 | 0.73 |
| 15 | 1.09 |
| 20 | 1.46 |
| 30 | 2.19 |
| 40 | 2.91 |
| 50 | 3.64 |
| 60 | 4.37 |
| 70 | 5.10 |
| 80 | 5.33 |
| 90 | 6.56 |
| 100 | 7.29 |
| 110 | 8.01 |
| 120 | 8.74 |
| 130 | 9.47 |
| 140 | 10.20 |
| 150 | 10.93 |
| 160 | 11.66 |
| 170 | 12.38 |
| 180 | 13.11 |
| 190 | 13.84 |
| 200 | 14.57 |
| 210 | 15.30 |
| 220 | 16.03 |
| 230 | 16.76 |
| 240 | 17.48 |
| 250 | 18.21 |
| 260 | 18.94 |
| 270 | 19.67 |
| 280 | 20.40 |

TABLE 14-continued

Urolithin Dosing in Mouse and Human

| Mouse Dose (mg/kg/day) | Human Dose (mg/kg/day) |
|---|---|
| 290 | 21.13 |
| 300 | 21.86 |
| 310 | 22.58 |
| 320 | 23.31 |
| 330 | 24.04 |
| 340 | 24.77 |
| 350 | 25.50 |
| 360 | 26.23 |
| 370 | 26.96 |
| 380 | 27.68 |
| 390 | 28.41 |
| 400 | 29.14 |
| 410 | 29.87 |
| 420 | 30.60 |
| 430 | 31.33 |

Additional non-limiting, illustrative examples of urolithin dose ranges that may be used are provided in Table 15.

TABLE 15

Urolithin Dosing in Humans
Human Dose Ranges
(mg/kg/day)

| Low | High |
|---|---|
| 0.2 | 4 |
| 0.2 | 5 |
| 0.2 | 6 |
| 0.2 | 7 |
| 0.2 | 8 |
| 0.2 | 9 |
| 0.2 | 10 |
| 0.2 | 15 |
| 0.2 | 20 |
| 0.2 | 25 |
| 0.2 | 30 |
| 0.2 | 35 |
| 0.2 | 40 |
| 0.5 | 2 |
| 0.5 | 3 |
| 0.5 | 4 |
| 0.5 | 5 |
| 0.5 | 10 |
| 0.5 | 15 |
| 0.5 | 20 |
| 0.5 | 25 |
| 0.5 | 30 |
| 0.5 | 35 |
| 0.5 | 40 |
| 0.75 | 5 |
| 0.75 | 10 |
| 0.75 | 15 |
| 0.75 | 20 |
| 0.75 | 25 |
| 0.75 | 30 |
| 0.75 | 35 |
| 0.75 | 40 |
| 1 | 2 |
| 1 | 3 |
| 1 | 4 |
| 1 | 5 |
| 1 | 6 |
| 1 | 7 |
| 1 | 8 |
| 1 | 9 |
| 1 | 10 |
| 1 | 11 |
| 1 | 12 |
| 1.25 | 4 |
| 1.25 | 5 |

Any dose may be given as a single dose or as divided doses.

In one embodiment, the urolithin or precursor thereof is administered in a dose sufficient to achieve a peak serum level of urolithin and its known metabolites (glucuronides, sulfonates, etc.) of at least 0.001 micromolar ($\mu$M). In one embodiment, the urolithin or precursor thereof is administered in a dose sufficient to achieve a peak serum level of urolithin of at least 0.01 $\mu$M. In one embodiment, the urolithin or precursor thereof is administered in a dose sufficient to achieve a peak serum level of urolithin of at least 0.1 $\mu$M. In one embodiment, the urolithin or precursor thereof is administered in a dose sufficient to achieve a peak serum level of urolithin of at least 1 $\mu$M. In various embodiments, the urolithin or precursor thereof is administered in a dose sufficient to achieve a peak serum level of urolithin of at least 10 $\mu$M, at least 20 $\mu$M, at least 30 $\mu$M, at least 40 $\mu$M, at least 50 $\mu$M, at least 60 $\mu$M, at least 70 $\mu$M, at least 80 $\mu$M, at least 90 $\mu$M, at least 100 $\mu$M, or at least 200 $\mu$M.

In one embodiment, the urolithin or precursor thereof is administered in a dose sufficient to achieve a sustained serum level of urolithin of at least 0.001 micromolar ($\mu$M). In one embodiment, the urolithin or precursor thereof is administered in a dose sufficient to achieve a sustained serum level of urolithin of at least 0.01 $\mu$M. In one embodiment, the urolithin or precursor thereof is administered in a dose sufficient to achieve a sustained serum level of urolithin of at least 0.1 $\mu$M. In one embodiment, the urolithin or precursor thereof is administered in a dose sufficient to achieve a sustained serum level of urolithin of at least 1 $\mu$M. In one embodiment, the urolithin or precursor thereof is administered in a dose sufficient to achieve a sustained serum level of urolithin of at least 10 $\mu$M, the urolithin or precursor thereof is administered in a dose sufficient to achieve a sustained serum level of urolithin of at least 50 $\mu$M. The sustained serum level can be measured using any suitable method, for example, high pressure liquid chromatography (HPLC) or HPLC-MS.

EXAMPLES

Example 1

Urolithin A Synthesis

Urolithin A (4) was prepared in two steps starting from bromide 1 and resorcinol 2. The pure compound was obtained as a pale yellow powder.

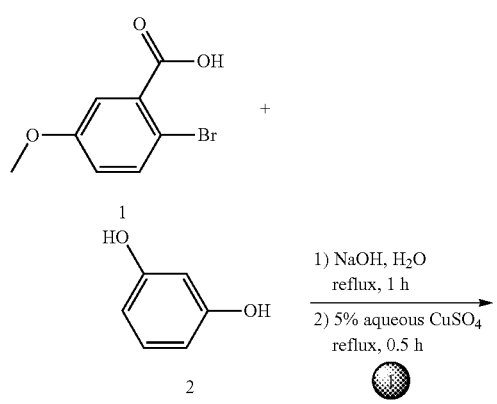

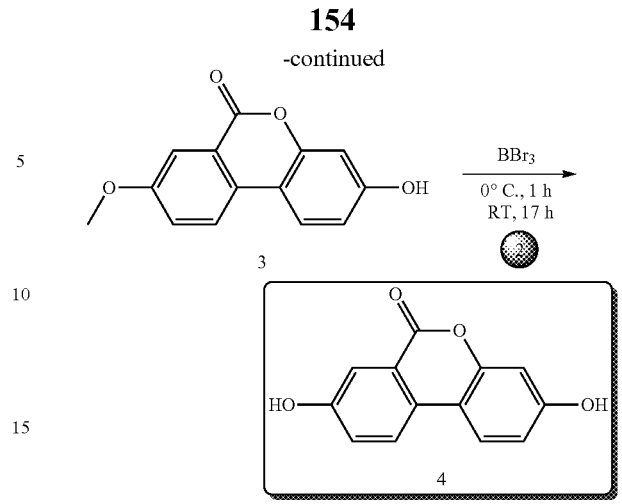

Step 1:

A mixture of 2-bromo-5-methoxybenzoic acid 1 (27.6 g; 119 mmol; 1.0 eq.), resorcinol 2 (26.3 g; 239 mmol; 2.0 eq.) and sodium hydroxide (10.5 g; 263 mmol; 2.2 eq.) in water (120 mL) was heated under reflux for 1 hour. A 5% aqueous solution of copper sulphate (3.88 g of $CuSO_4.5H_2O$ in 50 mL water; 15.5 mmol; 0.1 eq.) was then added and the mixture was refluxed for additional 30 minutes. The mixture was allowed to cool to room temperature and the solid was filtered on a Buchner filter. The residue was washed with cold water to give a pale red solid which was triturated in hot MeOH. The suspension was left overnight at 4° C. The resultant precipitate was filtered and washed with cold MeOH to yield the title compound 3 as a pale brown solid.

Step 2:

To a suspension of 3 (10.0 g; 41 mmol; 1.0 eq.) in dry dichloromethane (100 mL) was added dropwise at 0° C. a 1 M solution of boron tribromide in dry dichloromethane (11.93 mL of pure $BBr_3$ in 110 mL of anhydrous dichloromethane; 124 mmol; 3.0 eq.). The mixture was left at 0° C. for 1 hour and was then allowed to warm up to room temperature. The solution was stirred at that temperature for 17 hours. Then ice was added thoroughly to the mixture. The yellow precipitate was filtered and washed with cold water to give a yellow solid which was heated to reflux in acetic acid for 3 hours. The hot solution was filtered quickly and the precipitate was washed with acetic acid, then with diethyl ether to yield the title compound 4 as a yellow solid. $^1$H and $^{13}$C NMR were in accordance with the structure of 4.

Example 2

Urolithin B Synthesis

Urolithin B (3) was prepared in one step by coupling of resorcinol (1) and 2-bromobenzoic acid (2) following the procedure employed for the preparation of urolithin A in Example 1.

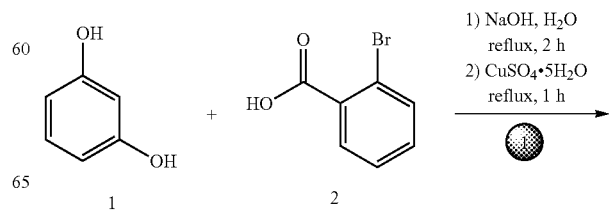

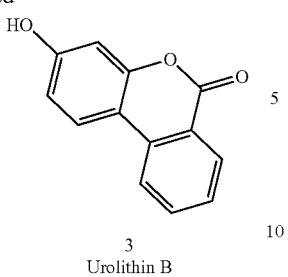

3
Urolithin B

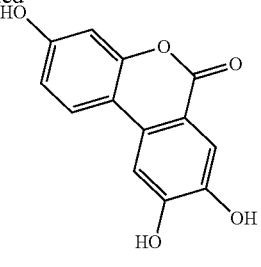

4
Urolithin C

A mixture of resorcinol 1 (8.40 g; 75.6 mmol; 2.0 eq.), 2-bromobenzoic acid (7.60 g; 37.8 mmol; 1.0 eq.) and NaOH (3.34 g; 83.5 mmol; 2.2 eq.) in water (38 mL) was heated at reflux and stirred for 2 hours. Water (30 mL) and CuSO$_4$.5H$_2$O (0.95 g; 3.78 mmol; 0.1 eq.) were added and the mixture was stirred under reflux for an additional 1 hour. The reaction was then cooled to room temperature and the precipitate was filtered. The product was then dissolved in absolute ethanol and concentrated. The crude was dissolved in hot methanol and filtered on paper to afford the title compound. $^1$H and $^{13}$C NMR were in accordance with the structure of 3.

Example 3

Urolithin C Synthesis

Urolithin C (4) was prepared in two steps starting from resorcinol (1) and 2-bromo-4,5-dimethoxybenzoic acid (2) following the procedure above for the preparation of urolithin A in Example 1.

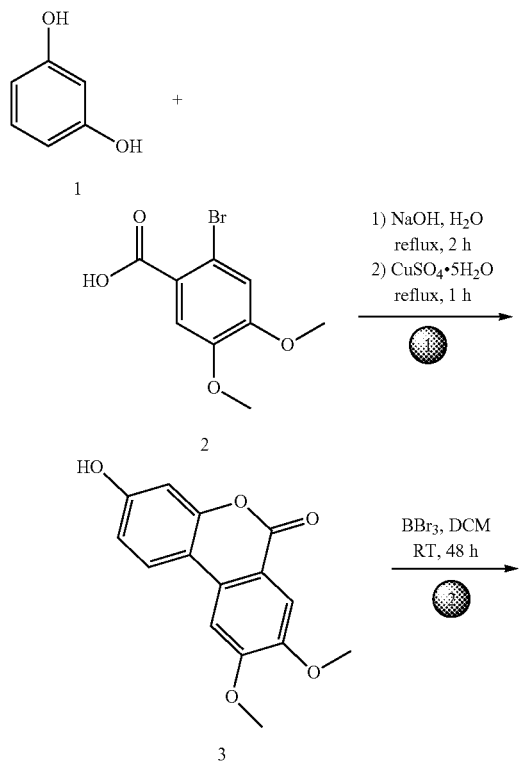

Step 1: Preparation of Compound 3

A mixture of resorcinol 1 (8.00 g; 72.6 mmol; 2.0 eq.), 2-bromo-4,5-dimethoxybenzoic acid 2 (9.50 g; 36.3 mmol; 1.0 eq.) and NaOH (3.20 g; 79.9 mmol; 2.2 eq.) in water (36 mL) was heated at reflux and stirred for 2 hours. Water (20 mL) and CuSO$_4$.5H$_2$O (0.91 g; 3.63 mmol; 0.1 eq.) were added and the mixture was stirred under reflux for an additional 1 hour. The reaction was then cooled down to room temperature and the precipitate was filtered. The product was then dissolved in absolute ethanol and concentrated. The crude was engaged in the next step without further purification.

Step 2: Preparation of Compound 4

A 1M solution of BBr$_3$ in dichloromethane (11 mL; 11.0 mmol; 6.0 eq.) was added dropwise to a solution of intermediate 3 (500 mg; 1.84 mmol; 1.0 eq.) in cold (0° C.) dichloromethane (5 mL). The reaction mixture was stirred at 0° C. during 1 hour and at room temperature for an additional 48 hours. The reaction was then hydrolysed by addition of ice. The precipitate was filtered and washed with ice-cold water until pH 7. The product was then dissolved in absolute ethanol and concentrated. The crude was dried under vacuum in presence of P$_2$O$_5$ to afford the title compound. $^1$H and $^{13}$C NMR were in accordance with the structure of 4.

Example 4

Urolithin D Synthesis

Urolithin D (5) was prepared in three steps starting from 2,3-dimethoxyphenol (1) and 2-bromo-4,5-dimethoxybenzoic acid (2).

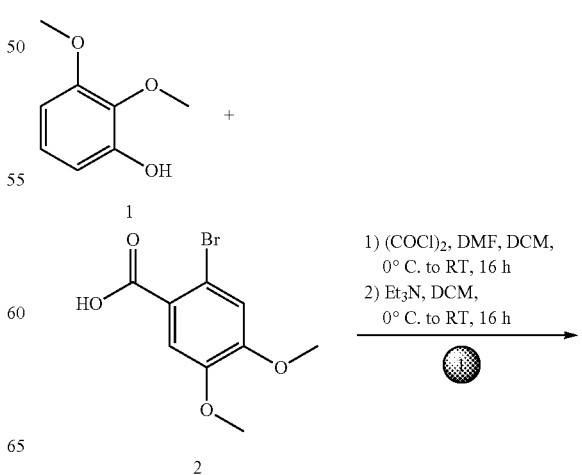

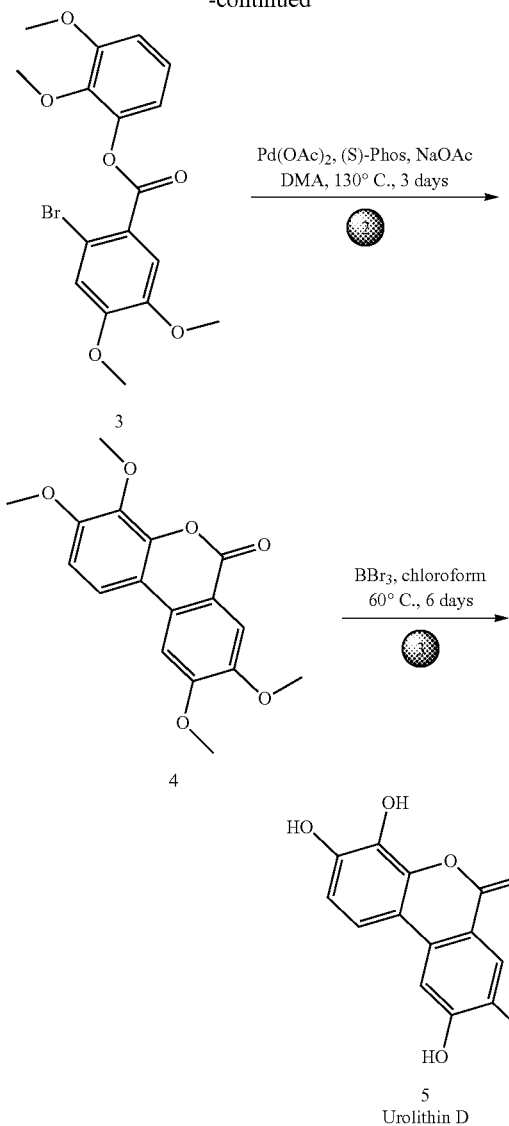

Step 1: Preparation of Compound 3

Oxalyl chloride (1.07 mL; 12.6 mmol; 1.1 eq.) and dimethylformamide (1 drop; cat.) were added to a cold (0° C.) suspension of 2-bromo-4,5-dimethoxybenzoic acid 2 (3.00 g; 11.5 mmol; 1.0 eq.) in dichloromethane (20 mL). After addition, the reaction mixture was stirred for 5 minutes at 0° C. and then for 16 hours at room temperature. The reaction mixture was concentrated under reduced pressure. The resulting oil was solubilized in dichloromethane (10 mL) and cooled to 0° C. 2,3-Methoxyphenol 1 (1.90 g; 12.6 mmol; 1.1 eq.) and triethylamine (2.4 mL; 17.2 mmol; 1.5 eq.) were successively added and the mixture was stirred for 5 minutes. Acetonitrile (10 mL) was finally added and the resulting solution was stirred for 16 hours at room temperature. The reaction was quenched by addition of a saturated solution of ammonium chloride and the layers were separated. The aqueous phase was extracted with dichloromethane and the combined organic layers were dried over sodium sulphate, filtered and concentrated under reduced pressure. The crude was purified by column chromatography on silica gel to yield the title compound 3.

Step 2: Preparation of Compound 4

Sodium acetate (1.79 g; 21.8 mmol; 2.0 eq.), (S)-Phos (451 mg; 1.1 mmol; 0.1 eq.) and palladium diacetate (244 mg; 1.1 mmol; 0.1 eq.) were successively added to a solution of 3 (4.32 g; 10.9 mmol; 1 eq.) in dimethylacetamide (200 mL) under an argon atmosphere. The reaction mixture was stirred at 130° C. for 3 days. The reaction was quenched by addition of water and the mixture was extracted with dichloromethane. The combined organic layers were washed with brine, dried over sodium sulphate, and concentrated under reduced pressure. The remaining dimethylacetamide was eliminated using a Hickman apparatus. The crude dark oil was purified by column chromatography on silica gel to yield the title compound 4.

Step 3: Preparation of Compound 5

Boron tribromide (726 µL; 10.3 mmol; 5.0 eq.) was added to a cold (15° C.) solution of compound 4 (650 mg; 2.0 mmol; 1.0 eq.) in chloroform (7.3 mL). After the addition, the reaction mixture was allowed to reach room temperature and stirred for 15 minutes. The mixture was then heated up to 60° C. and stirred for 4 days. The reaction was quenched by addition of methanol and the mixture was evaporated to dryness. The crude was purified by column chromatography on $C_{18}$ to yield pure compound 5.

Example 5

Urolithins Extend Lifespan in *C. elegans*

*C. elegans* strains were cultured at 20° C. on nematode growth media (NGM) agar plates seeded with *E. coli* strain OP50. Strain used was wild-type Bristol N2 provided by the *Caenorhabditis* Genetics Center (University of Minnesota). All Compounds were dissolved in DMSO. Animals were exposed to compounds from eggs on plates seeded with live OP50 bacteria. Control plates were prepared with the corresponding concentrations of DMSO (0.1%). For lifespan tests, worms were observed using a Nikon SMZ1500 stereomicroscope (Nikon, Melville, NY, USA). Briefly, 10 L4 worms were transferred on plates containing NGM medium with either vehicle alone (DMSO 0.1%) or test compounds dissolved in DMSO (DMSO 0.1%) and seeded with *E. coli* strain OP50. After 3 days (corresponding to day 0), newly developed 60 to 100 L4 worms were used per condition, scored and transferred to fresh plates every 3 days starting from day 1 (young adult worms). All lifespan experiments were performed at 20° C. Animals that crawled off the plate or had an "exploded vulva" phenotype were censored.

Treatment with urolithins A, B, C, and D at a concentration of 50 µM extended the lifespan in *C. elegans* (FIG. 4). Ellagic acid (EA) at the same concentration showed no effects in prolonging the lifespan of the *C. elegans*.

Figure 5:
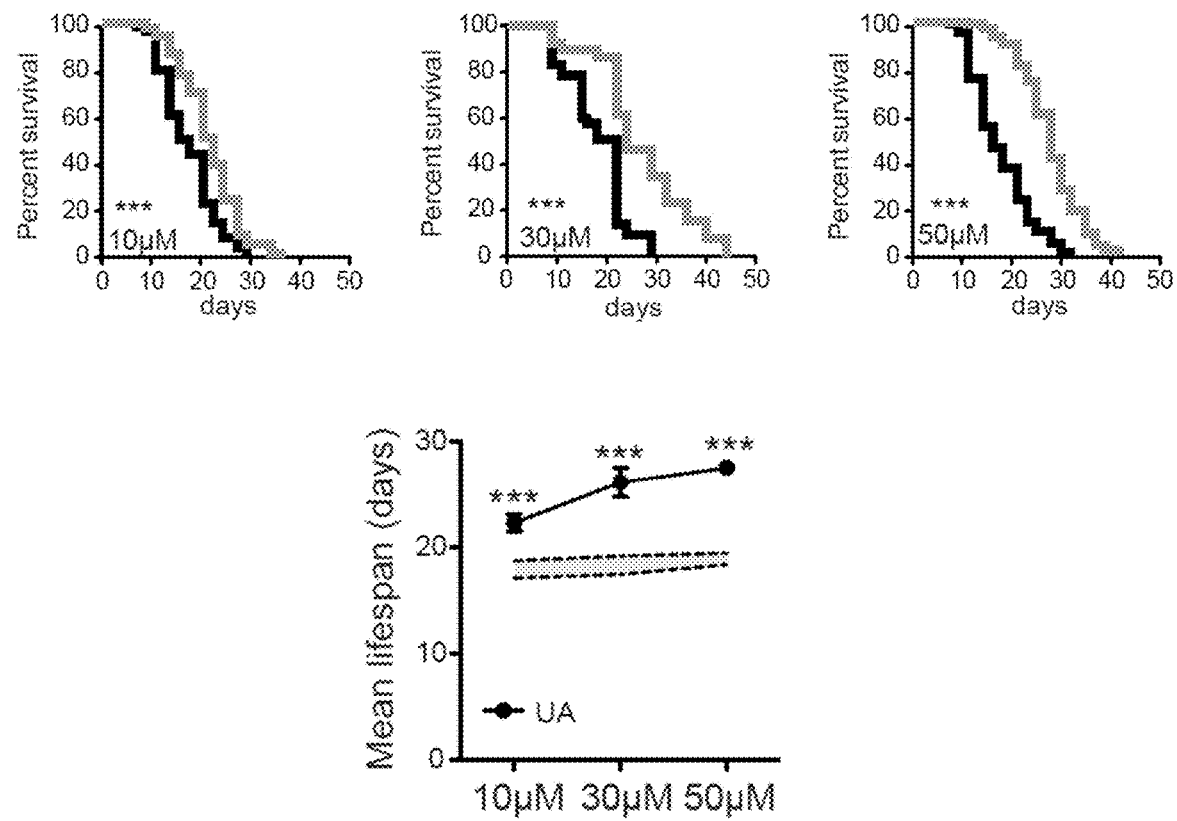
FIG. 5 is a set of graphs depicting longevity of wild-type C. elegans grown in the presence of urolithin A at the concentrations shown.
Figure 6A:
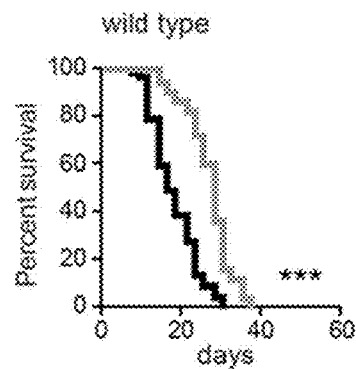
FIGS. 6A-6F are a group of six graphs depicting lifespan analysis of wild-type and indicated mutant strains of C. elegans grown in the absence (black) or presence (grey) of urolithin A at 50 µM.
Figure 6B:
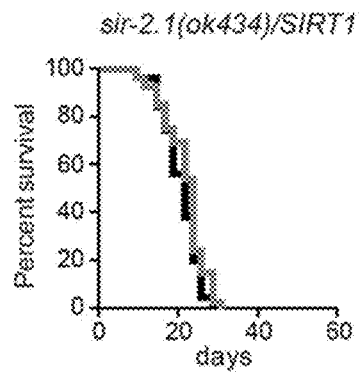
Figure 6C:
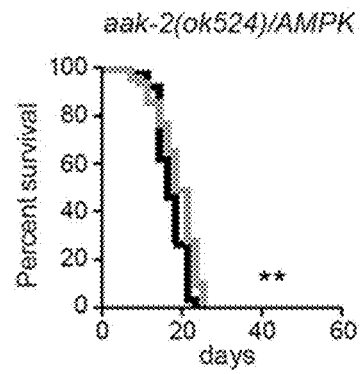
Figure 6D:
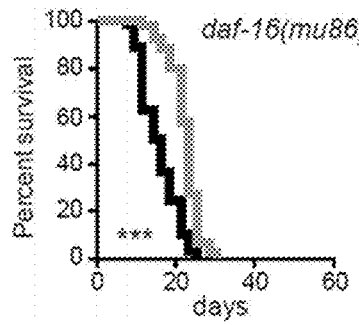
Figure 6E:
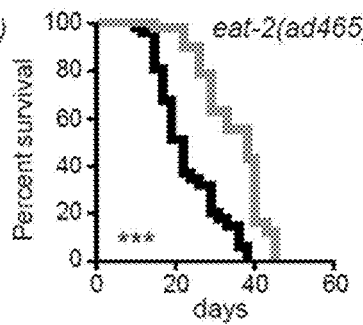
Figure 6F:
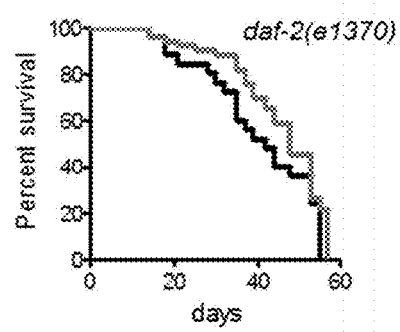

Treatment with urolithin A extended the lifespan in *C. elegans* in a dose-dependent manner (FIG. 5). At a concentration of 10 µM the median lifespan increased by 27.7%, and at a concentration of 50 µM the median lifespan increased by 75%.

Example 6

Urolithin A Activates AMPK/aak-2 and SIRT1/Sir-2.1 to Mediate Longevity

Lifespan assays were performed with (A) wild-type (N2), (B) sir-2.1(ok434) mutant, (C) aak-2(ok524), (D) daf-16 (mu86), (E) eat-2(ad465) and (F) daf-2(e1370) mutant strains of *C. elegans* maintained during their full life on plates supplemented with either 50 µM of urolithin A or with a control treatment and seeded with OP50 bacteria. Control plates without urolithin A contained an equivalent concentration of DMSO. Worm lifespan assays were performed at 20° C. Animals that crawled off the plate or had an "exploded vulva" phenotype were censored.

sir-2.1: sir-2.1 encodes the mammalian homolog of the NAD-dependent deacetylase SIRT1 in C. elegans. SIR-2.1/SIRT1 activity is mediated by $NAD^+$ level and is well described to be involved in longevity regulation in yeast, C. elegans, and Drosophila in response to caloric restriction.

aak-2/AMPK: aak-2 encodes the mammalian homolog of the AMP-dependent kinase AMPK in C. elegans.

daf-16 encodes a FOXO transcription factor.

eat-2 encodes a protein involved in pharyngeal pumping.

daf-2 encodes for the insulin-like growth factor 1 (IGF-1) receptor in C. elegans.

Results are shown in Table 16 and FIGS. 6A-6F. As shown in the figure, urolithin A significantly extended lifespan in wild-type C. elegans by 75%, showing that urolithin A is a pro-longevity compound.

TABLE 16

Lifespan Extension in sir-2.1, aak-2, daf-16, daf-2, and eat-2 Mutant C. elegans

| Genotype | Urolithin/ DMSO conc. | Median lifespan (days) | Lifespan extension compared to control (%) | P-values against control | Death/Censored (trials) |
|---|---|---|---|---|---|
| wild-type (N2) | 1% DMSO 50 µM UA | 16 28 | +75 | $<10^{-3}$ | 37/24 (1) 50/10 (1) |
| sir-2.1 (mu86) | 1% DMSO 50 µM UA | 21 23 | +9.5 | NS | 46/14 (1) 39/21 (1) |
| aak-2 (o524) | 1% DMSO 50 µM UA | 16 18 | +12.5 | 0.003 | 55/5 (1) 43/17 (1) |
| daf-16 | 1% DMSO 50 µM UA | 16 23 | +43.7 | $<10^{-3}$ | 42/18 (1) 49/11 (1) |
| daf-2 | 1% DMSO 50 µM UA | 42 48 | +14.2 | NS | 21/19(1) 39/21 (1) |
| eat-2 | 1% DMSO 50 µM UA | 21 37 | +76.2 | $<10^{-3}$ | 40/20 (1) 26/34 (1) |

Energy Stress—Caloric Restriction Pathway

The sir-2.1 mutant completely suppressed the activity of urolithin A on the extension of median lifespan in C. elegans. This indicates that sir-2.1 is required for the lifespan extension induced by urolithin A and that urolithin A is dependent on sir-2.1 to extend lifespan.

The aak-2 mutant significantly suppressed the lifespan extension phenotype induced by urolithin A from a 75% increase in mean lifespan down to a 12.5% extension. This indicates that aak-2 plays an important role in the lifespan subsequent to urolithin A exposure. This also demonstrates that urolithin A activation of AMPK is a key step in the lifespan extension induced by urolithin A.

Insulin Signaling Pathway

The daf-2 mutant completely suppressed the activity of urolithin A on the extension of median lifespan in C. elegans. This indicates that daf-2 is required for the lifespan extension induced by urolithin A and that urolithin A is dependent on daf-2 to extend lifespan.

Treatment of C. elegans with either rapamycin, resveratrol, or metformin induces an increase in worm mean lifespan, which has been shown to be a result of acting on the autophagy pathway.

It is worth noting that the lifespan extension induced by urolithin A treatment (75%) is much greater than the life extension induced by either resveratrol (12.6%), rapamycin (19%), or metformin (27%) alone.

Example 7

Urolithin a Increases Mitochondrial Activity in C. elegans

C. elegans strains were cultured at 20° C. on nematode growth media (NGM) agar plates seeded with HT115 bacteria and containing 50 µM urolithin A or a corresponding concentration of DMSO as a control. The worms were treated from eggs to the first day of adulthood. The strains used were the SJ4103 (zcIs14[myo-3::GFP(mit)]), which is a stable transgenic line expressing a mitochondrially localized green fluorescent protein (GFP) with a cleavable mitochondrial import signal peptide under the control of the specific body wall muscle promoter myo-3. GFP expression and quantification was carried out according to the protocol previously described. Durieux J et al. (2011) Cell 144:79-91. Worms were treated with 50 µM urolithin A from eggs and GFP was monitored after one day of adulthood. Fluorimetric assays were performed using a Victor X4 multilabel plate reader (Perkin-Elmer Life Science). Eighty worms were picked at random (20 worms per well of a black-walled 96-well plate), and each well was read four times and averaged.

Figure 7:
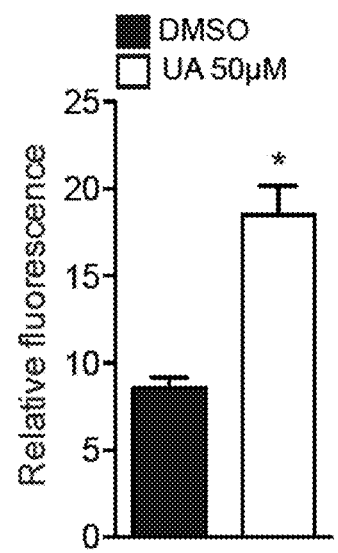
FIG. 7 is a bar graph depicting the effect of urolithin A on mitochondria in muscle of C. elegans. Transgenic C. elegans strain SJ4103 shows fluorescence due to muscle-specific expression of green fluorescent protein (GFP) which is targeted to the mitochondrial membrane. Mitochondria presence in the muscle of the C. elegans is shown by an increase in fluorescence. Results are expressed as mean±SEM. *, p=0.0014 (Student's t-test).

The results in FIG. 7 show that treatment of worms with urolithin A induces the expression of the mitochondrial GFP reporter driven by the muscle-specific myo-3 promoter in C. elegans. This striking increase in GFP expression provides clear evidence that mitochondrial capacity was increased due to the urolithin A. To permit such an increase in observed GFP signal, mitochondria in muscle must either be enlarged or more numerous in these worms.

Example 8

Urolithin A Increases Mitochondrial Function in Aged C. elegans

C. elegans strains were cultured at 20° C. on nematode growth media (NGM) agar plates seeded with E. coli strain OP50. Strain used was wild-type Bristol N2 provided by the Caenorhabditis Genetics Center (University of Minnesota). Urolithin A was dissolved in DMSO. Animals were exposed to compounds from eggs on plates seeded with live OP50 bacteria. Control plates were prepared with the corresponding concentration of DMSO (0.1%).

Measurement of oxygen consumption is a direct indicator of mitochondrial activity. The effect of urolithin A on mitochondrial activity in aged C. elegans (10 days old) was assessed by treating C. elegans with urolithin A for 10 days of adulthood, at which time oxygen consumption was measured using the Seahorse XF24 equipment (Seahorse Bioscience Inc., North Billerica, MA). 250 ten-day-old C. elegans were used per condition. C. elegans were recovered from NGM plates with M9 medium, washed three times in 2 mL M9 to eliminate residual bacteria, and resuspended in 500 µL M9 medium. Worms were transferred into 24-well standard Seahorse plates (#100777-004) (50 worms per well) and oxygen consumption was measured. The basal oxygen consumption of the worms was first measured over 30 minutes at 5-minute intervals (0 min, 5 min, 15 min, 20 min, 25 min, and 30 min) with 5 replicates per interval. Respiration rates were normalized to the exact number of worms per well determined after the completion of the experiment using a stereomicroscope. After determining the basal oxygen consumption, uncoupled oxygen consumption was measured by adding carbonylcyanide-p-(trifluoromethoxy) phenylhydrazone (FCCP) at the 30 minute time point to the media in order assess the maximal oxygen consumption capacity and maximal mitochondrial capacity. Uncoupled oxygen consumption was measured at 5-minute intervals (35 min, 40 min, 45 min, 50 min, 55 min, and 60 min) to permit measuring the mitochondrial function over time.

FCCP is a chemical uncoupling agent that abolishes the obligatory linkage between the respiratory chain and the phosphorylation system which is observed with intact mitochondria. This effect is due to the amphipathic properties of the molecule which dissolves in mitochondrial phospholipid bilayers. This dramatically increases ionic permeability of the mitochondrial membrane and generates dramatic proton leak leading to increase in oxygen consumption due to the quenching by oxygen of the electrons pumped into the respiratory chain in parallel to the proton leak. Since this oxygen consumption is dissociated (uncoupled) to ATP production (oxidative phosphorylation), FCCP increases oxygen consumption while decreasing the generation of energy (ATP) by the mitochondria. Fully uncoupled mitochondria, as achieved with FCCP, display the maximal capacity of their mitochondrial respiratory chain (maximal oxygen consumption) without the "brake" that oxidative phosphorylation and energy production represents.

Figure 8A:
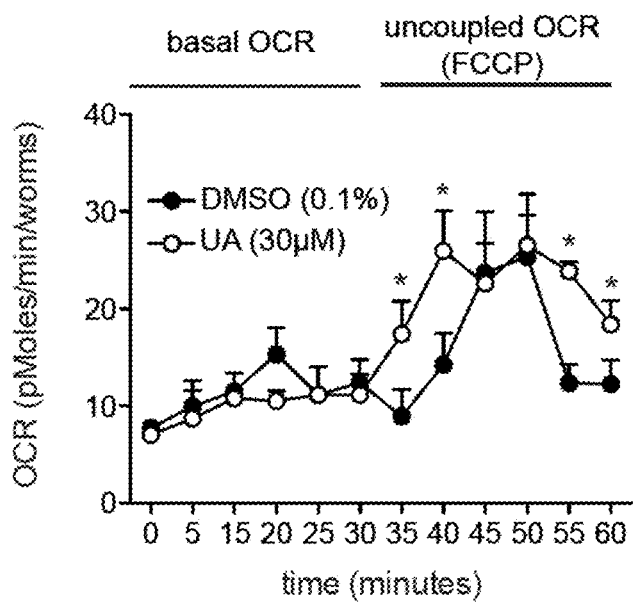
FIGS. 8A-8D are a line graph and three bar graphs depicting effect of urolithin A (UA) on basal and uncoupled respiration in young (one-day-old) and old (ten-day-old) C. elegans.
Figure 8B:
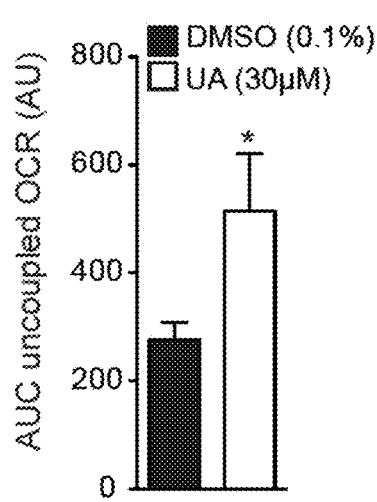
Figure 8C:
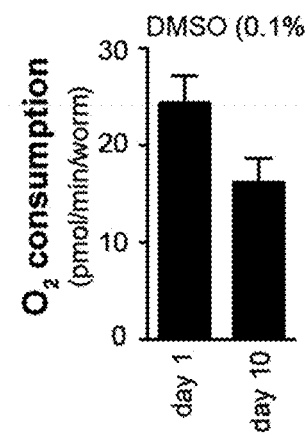
Figure 8D:
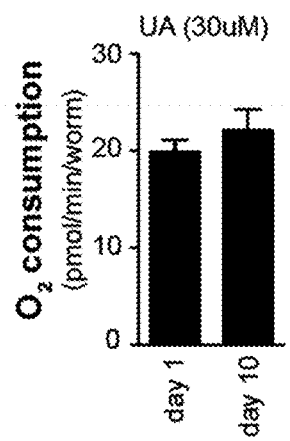

The results depicted in FIGS. 8A and 8B illustrate that urolithin A increases the maximal mitochondrial capacity of 10-day-old aged C. elegans, as depicted by a prolonged effect on increased uncoupled respiration in worms treated with urolithin A versus control (DMSO)-treated worms. Control untreated worms showed a brief increase in uncoupled respiration which quickly returned to basal levels of oxygen consumption. Urolithin A-treated worms showed a more extended elevation in oxygen consumption. The extent of enhanced mitochondrial activity is shown by comparing the area under the curves (AUC) during the decoupling period with the average coupled respiration employed as the baseline. It was observed that urolithin A significantly increased uncoupled respiration in aged worms as compared to control untreated worms over the 30-minute period evaluated. FIG. 8C shows that aged, 10-day-old C. elegans have a decrease in basal respiration in comparison with young, 1-day-old C. elegans. FIG. 8D shows that treatment of worms with urolithin A at 30 µM normalizes the respiration rates, and aged, 10-day-old C. elegans show comparable levels of oxygen consumption to young, 1-day-old C. elegans.

Example 9

Urolithin A Increases Autophagy in C. elegans

C. elegans strains were cultured at 20° C. on nematode growth media (NGM) agar plates seeded with OP50 bacteria and containing 50 µM urolithin A or a corresponding concentration of DMSO as a control. The worms were treated from eggs to the second day of the adulthood. The strains used were the DA2122 (adIs2122[lgg-1::GFP+rol-6 (su1006)]), which is a transgenic line expressing the LGG-1 protein (homolog of LC3 in human) fused with the green fluorescent protein (GFP). For picture acquisition, worms were immobilized with tetramisole (Sigma) and mounted on 6% agarose pads on glass slides. Images were acquired using Zeiss LSM 700 upright confocal microscope (Carl Zeiss AG, Oberkochen, Germany) from the same part of C. elegans. For each condition multiple worms were observed and imaged with the same initial parameters. Image processing and quantification of autophagic events was performed with the Fiji software.

The results depicted in FIGS. 9A and 9B illustrate that urolithin A increases the number of autophagic events, as depicted by the increased number of LGG-1::GFP dots per focal field (plan) in worms treated with urolithin A versus control (DMSO)-treated worms. This observation was confirmed by the fact that food deprivation, a dietary intervention that increases autophagy in C. elegans, shows the same profile as urolithin A-treated worms. This result provides clear evidence that urolithin A treatment is an inducer of autophagy in worms and could explain the longevity phenotype associated with such a treatment, as it has been already described that induction of autophagy, by dietary manipulation or treatment with specific compounds, increases life expectancy in a number of animal species. Hansen M et al. (2008) *PLoS Genetics* 4:e24; Eisenberg T et al. (2009) *Nat Cell Biol* 11:1305-14; Bjedov I et al. (2010) *Cell Metab* 11:35-46.

Example 10

The Autophagic Pathway is Involved in the Longevity Phenotype Induced by Urolithin A in C. elegans Lifespan tests were performed as described. Mouchiroud L et al. (2011) *Aging Cell* 10:39-54. Briefly, worms were observed using a Nikon SMZ1500 stereomicroscope (Nikon, Melville, NY, USA). Briefly, 10 L4 worms were transferred on plates containing NGM medium with vehicle (DMSO 0.1%, final concentration) or urolithin A dissolved in DMSO (final concentration 50 µM) and seeded with *E. coli* RNAi clones as indicated. After 3 days (corresponding to day 0), newly developed 60-100 L4 worms were used per condition, scored and transferred to fresh plates every 3 days starting from day 1 (young adult worms). All lifespan experiments were performed at 20° C. Animals that crawled off the plate or had an "exploded vulva" phenotype were censored.

Survival analyses were performed using the Kaplan Meier method and the significance of differences between survival curves calculated using the log rank test. Differences between two groups were assessed using two-tailed t-tests. Analysis of variance, assessed by Bonferroni's multiple comparison test, was used when comparing more than two groups. The statistical software used was GraphPad Prism 5 (GraphPad Software, Inc.) and all p-values <0.05 were considered significant.

Gene silencing was carried out as previously described by using the RNA interference (RNAi) process. Mouchiroud L et al. (2011) *Aging Cell* 10:39-54. In C. elegans, RNAi is made by feeding. Briefly, the nematodes were fed with bacteria modified with a plasmid encoding a dsRNA targeting a gene of interest. The worms eat these bacteria which will simply allow the inactivation of this gene. As a control, worms were fed with the RNAi clones HT115, which encodes an empty vector.

To determine the requirement of the autophagic pathway for the lifespan phenotype induced by urolithin A treatment (FIGS. 10A-10C), two genes encoding major autophagic proteins were inhibited by RNA interference (RNAi). These two proteins were vps-34 (sequence name: B0025.1, homolog of VPS34 in human), which encodes a phosphatidylinositol 3-kinase (PI3K) that regulates multiple steps in vesicular trafficking and that is required for autophagy mechanism, and bec-1 (sequence name: T19E7.3, homolog of beclin in human), which encodes a class III phosphatidylinositol 3-kinase complex that plays a role in localizing autophagy proteins to preautophagosomal structures. The inhibition of their expression by RNAi has already been described to suppress the lifespan phenotype induced by dietary restriction, which is an experimental condition that promotes autophagy in *C. elegans*. Hansen M et al. (2008) *PLoS Genetics* 4:e24.

TABLE 17

Proteins Involved in the Autophagy Pathway in Different Species

| Yeast Name | C. elegans Name | Mouse Name | Role in Autophagy |
|---|---|---|---|
| ATG8 | LGG-1 | LC3 | Autophago some formation—marker of autophagosome membrane |
| ATG6 | BEC-1 | BECN1 | Beclin1 regulates the kinase activity of Vps34 at the endoplasmic reticulum |
| Vps34p | VPS-34 | VP534 | Vps34 has been shown to interact with Vps15, a protein kinase. Vps15 can activate the lipid kinase activity of Vps34 and interact with Rab5, which has been hypothesized to recruit the Vps34/15 complex to early endosomes. |

The results depicted in FIGS. 10A-10C illustrate that urolithin A increased the lifespan of worms through the activation of the autophagy mechanism. The fact that the lifespan extension observed in worms treated with urolithin A and fed with the empty vector is suppressed when these worms are fed with bacteria expressing RNAi against vps-34 or bec-1 reveals that these two proteins are each required and essential for the longevity phenotype. Such an observation shows that urolithin A treatment promotes the activity of vps-34 and bec-1, and leads to the induction of the autophagy mechanism to extend longevity.

Example 11

Urolithins Maintain Muscle Function in *C. elegans* During the Aging Process

To examine the effect of urolithins on muscle function, pharyngeal pumping was examined in *C. elegans* worms at day 7 and day 14. Worms were observed using a Nikon SMZ1500 stereomicroscope (Nikon, Melville, NY, USA). Ten L4 worms were transferred on plates containing NGM medium with vehicle (DMSO 0.1%, final concentration) or the compound of interest (urolithin A (UA), urolithin B (UB), urolithin C (UC), urolithin D (UD)) dissolved in DMSO (final concentration 50 μM) and seeded with *E. coli* RNAi clones as indicated. After 3 days (corresponding to day 0), newly developed 60 to 100 L4 worms were used per condition, scored and transferred to fresh plates every 3 days starting from day 1 (young adult worms). Experiments were performed at 20° C. Animals that crawled off the plate or had an "exploded vulva" phenotype were censored.

The pharyngeal pumping rates at day 7 and 14 were measured for 10 worms by transferring single worms to an unseeded plate and scoring for pharyngeal pumping under a dissecting microscope for 30 seconds. The pharyngeal pumping rates were then computed by extrapolating the pumping made by worms during this 30 second period.

Figure 11:
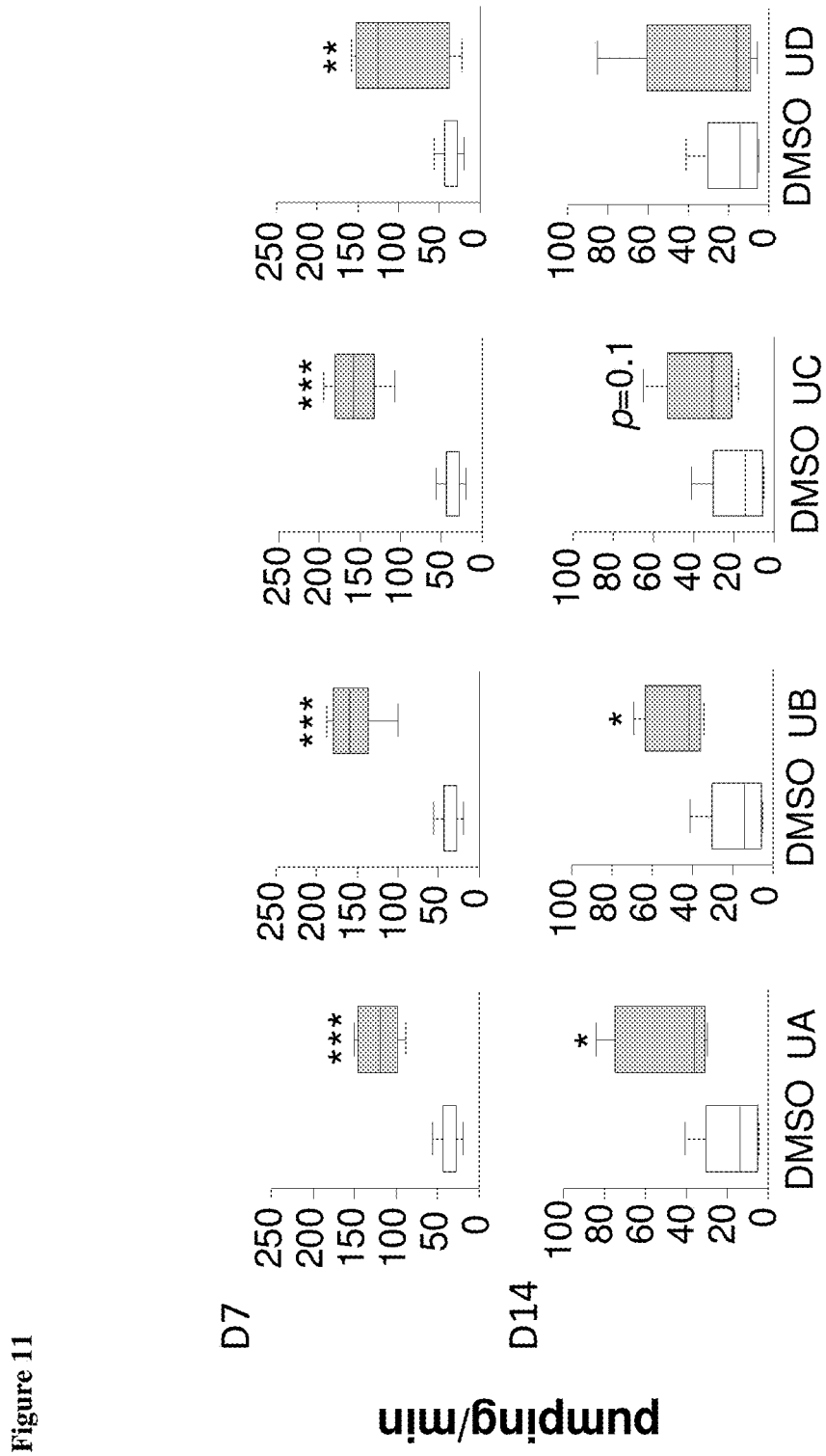
FIG. 11 is a set of graphs demonstrating the effects of urolithin A (UA), urolithin B (UB), urolithin C (UC) and urolithin D (UD) treatment on pharyngeal pumping in *C. elegans* worms after 7 and 14 days of treatment. (* p<0.05;  p<0.01; *p<0.001)

Pharyngeal pumping at day 7 were markedly increased for all urolithins tested (FIG. 11), demonstrated the ability of urolithin treatment to improve muscle function in young worms. This improved muscle function is maintained in aging worms and urolithin treatment also improves muscle function in worms at day 14. In the aged worms (day 14) urolithin treatment, and in particular urolithins A and B, decreases the age related decline in muscle activity (pharyngeal pumping).

To examine the effect of urolithins on muscle activity during aging, *C. elegans* mobility was examined over time. Synchronized populations of wild-type nematodes were prepared by standard methods and cultivated at 20° C. on NGM agar containing *E. Coli* (OP50) with or without test compounds (ellagic acid (EA), urolithins A (UA), and B (UB)). At Day 0, five plates were prepared, each containing 10 young adult worms. Worms were assayed for mobility at different ages, day 1, 3, 5 and 8 of adulthood. The wild type (N2, Bristol) worm strain was employed for these studies.

For *C. elegans* movement tracking, 45 seconds of video were recorded using a Nikon DS-L2/DS-Fi1 camera and controller setup, attached to both a computer and a standard bright field microscope, tracking an entire plate of 10 worms, with 5 plates per condition. The movement of worms during this time was calculated using an adapted version of the freely-available software Parallel Worm Tracker for MATLAB. The total movement over the 45 second tracking was averaged across all worms for each condition. This experiment was repeated twice with between 40 and 70 worms per condition.

Figure 12:
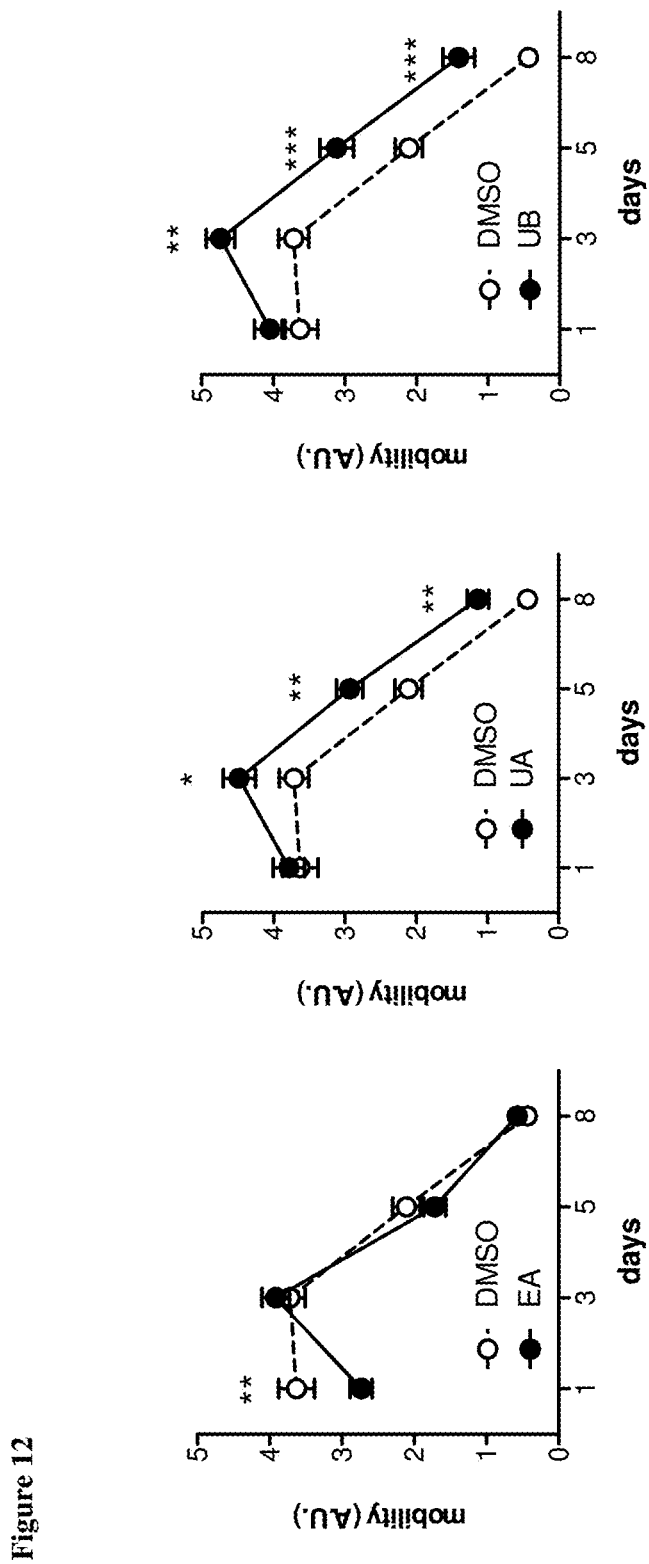
FIG. 12 are three line graphs demonstrating the effects of ellagic acid (EA), urolithin A (UA) and urolithin B (UB) treatment on motility in young *C. elegans* worms at days 1, 3, 5, and 8 of treatment. (* p<0.05;  p<0.01; *p<0.001)

Ellagic acid treatment has no effect on this age related mobility decline (FIG. 12). In contrast, urolithin treatment with 50 μM of either urolithin A or B, demonstrate a marked ability to reduce muscle function decline and maintain muscle function in aging *C. elegans* worms. This demonstrates the ability of urolithin treatment to preserve muscle function during the aging process.

To further characterize the effect of urolithins on muscle function and mobility, *C. elegans* were treated and their mobility observed under time-lapse microscopy. The effects of urolithin A on muscle function in *C. elegans* were examined. Briefly, worms were observed using a Nikon SMZ1500 stereomicroscope (Nikon, Melville, NY, USA). Briefly, 5 worms coming from different plates were transferred on plates containing NGM medium with vehicle (DMSO 0.1%, final concentration) or compound of interest (ellagic acid (EA), urolithin A (UA), urolithin B (UB), urolithin C (UC), urolithin D (UD)) dissolved in DMSO (final concentration 50 μM) and seeded with *E. coli* RNAi clones as indicated. Time lapse was performed by recording 20 pictures of mobile worms with a 10 second interval by using a Zeiss Axioplan-2 microscope (Carl Zeiss MicroImaging, Thornwood, NY, USA). Worm tracking was realized using the ImageJ software. Experiments were repeated three times.

Figure 13:
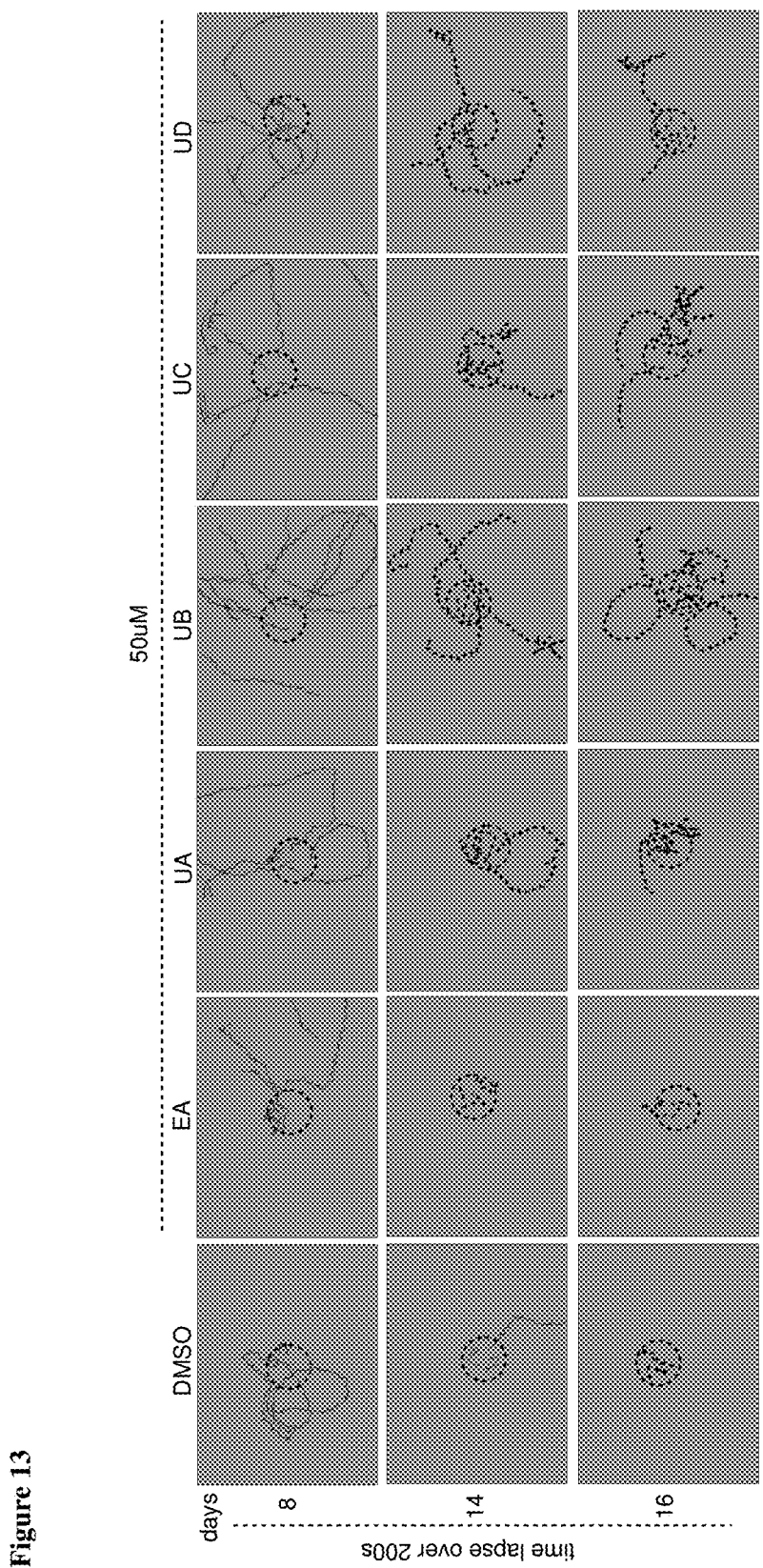
FIG. 13 is a set of images demonstrating time-lapse traces of *C. elegans* motility following treatment with ellagic acid (EA), urolithin A (UA), urolithin B (UB), urolithin C (UC) and urolithin D (UD) treatment on days 8, 14 and 16 of treatment.

Urolithin treatment resulted in a marked increase in motility that was maintained to varying degrees during the aging process (FIG. 13). The strongest effect was observed for urolithin B. The results presented here demonstrate the ability of all urolithin treatments to improve muscle function in *C. elegans* and preserve muscle function against age related muscle activity decline.

Example 12

Urolithins Induce Autophagy in Mammalian Cells

The ability of urolithins to induce autophagy in mammalian cells was also examined. ModeK cells derived from intestine, were cultured in RPMI 1640 medium including 4.5 g/L glucose, 10% fetal calf serum, 1 mM Sodium Pyruvate, 10 mM HEPES, 0.1 mM NEAA, 2-Mercaptoethanol Penicillin 100 UI/mL and Streptomycin 100 μg/mL. Cells were cultured at 37° C. under a 5% $CO_2$ atmosphere. Cells were treated with increasing concentrations of urolithin A (10 μM, 20 μM and 50 μM). Treatment was performed for eight hours, after which cells were lysed and prepared for Western Blot analysis. Protein expression levels were examined for autophagy related proteins LC3-I and II (Cell Signaling antibody #4108), p62 (Cell Signalling antibody #5114), AMPKα (Cell Signaling antibody #2603), and p-AMPKα (Cell Signaling antibody #2531). The housekeeping protein, HSP90 (BD Transduction Laboratories antibody #610418) level was measured as a loading control.

Figure 14:
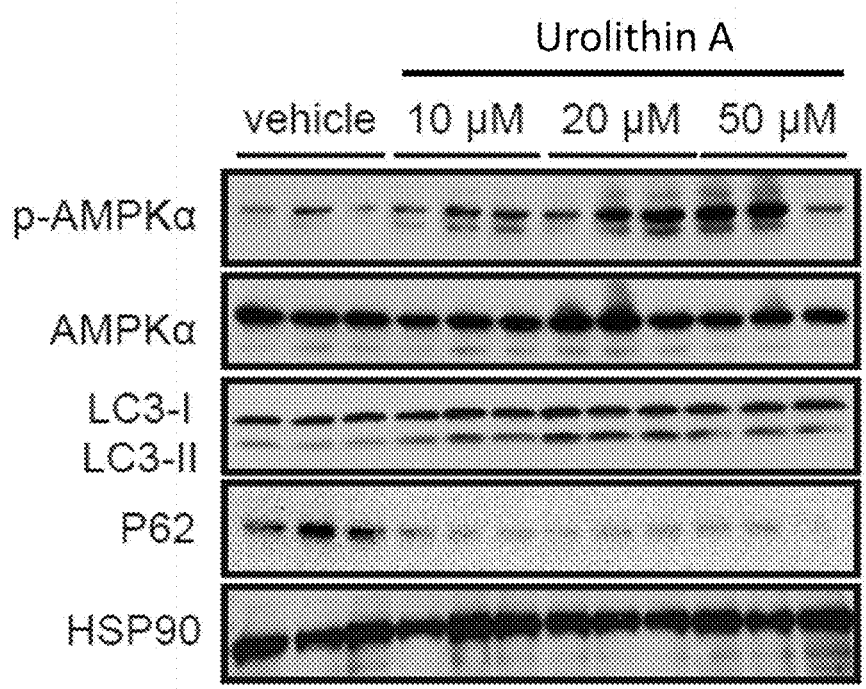
FIG. 14 is a western blot of ModeK cells, a mouse intestinal epithelial cell line, demonstrating the effect of urolithin A treatment on the autophagy marker ratio LC3-II/LC3-I, p62, and on the ratio of p-AMPKα/AMPKα. Bar graph demonstrates the quantified fold increase in the ratio of LC3-II to LC3-I, and the ratio of p-AMPKα to AMPKα levels observed in the western blots. ctl, control.
Figure 14:
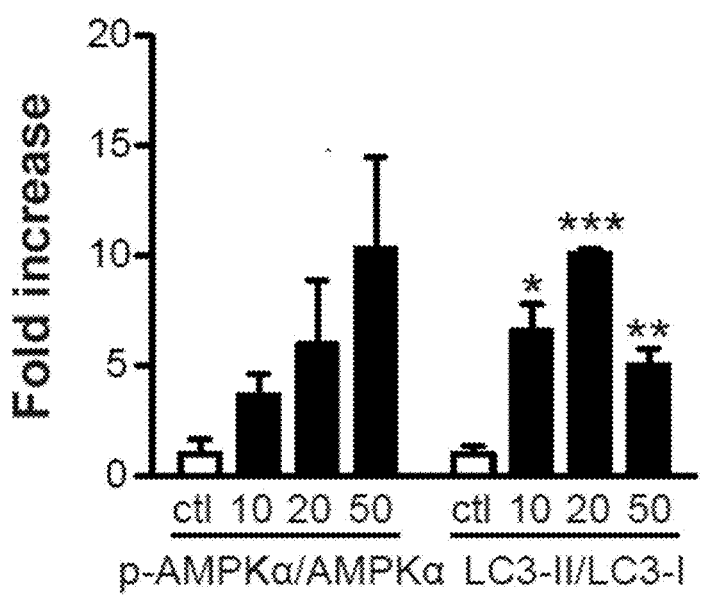

Increasing concentrations of urolithin A resulted in increasing levels of phosphorylated AMPKα (FIG. 14). The ratio of p-AMPKα/AMPKα increased in a dose-dependent manner in response to treatment with urolithin A, ranging from 4-fold to over 10-fold induction. Urolithin A treatment also resulted in significant increases in the LC3-II/LC3-I ratio (a hallmark of autophagy), at all doses tested. The ratio of LC3-II/LC3-I increased as high as 10-fold in treated cells as compared to the vehicle-treated cells at the doses tested. The levels of p62 decreased with the addition of urolithin A, in accordance with autophagy process. These results demonstrate the ability of urolithin A to induce autophagy.

Induction of autophagy by urolithins was also demonstrated in mammalian primary hepatocytes. Primary hepatocytes were isolated by perfusion through the supra-hepatic inferior vena cava from 7- to 9-week-old wildtype C57BL/6J mice, as described previously (Ryu et al., 2011). Isolated primary hepatocytes were cultured in Medium 199 including 4.5 g/L glucose, 10% fetal calf serum, 0.1 mM NEAA, 10 mM HEPES and 50 µg/mL gentamicin. These cells were then treated with either 10 µM, 20 µM or 50 µM of urolithin A for a 16 hour period, after which cells were lysed and prepared for Western Blot analysis. Protein expression levels were examined for autophagy related proteins LC3-I and II (Cell Signaling antibody #4108), p62 (Cell Signalling antibody #5114), AMPKα (Cell Signaling antibody #2603), and p-AMPKα (Cell Signaling antibody #2531). The housekeeping protein, HSP90 (BD Transduction Laboratories antibody #610418) level was measured as a loading control.

Figure 15:
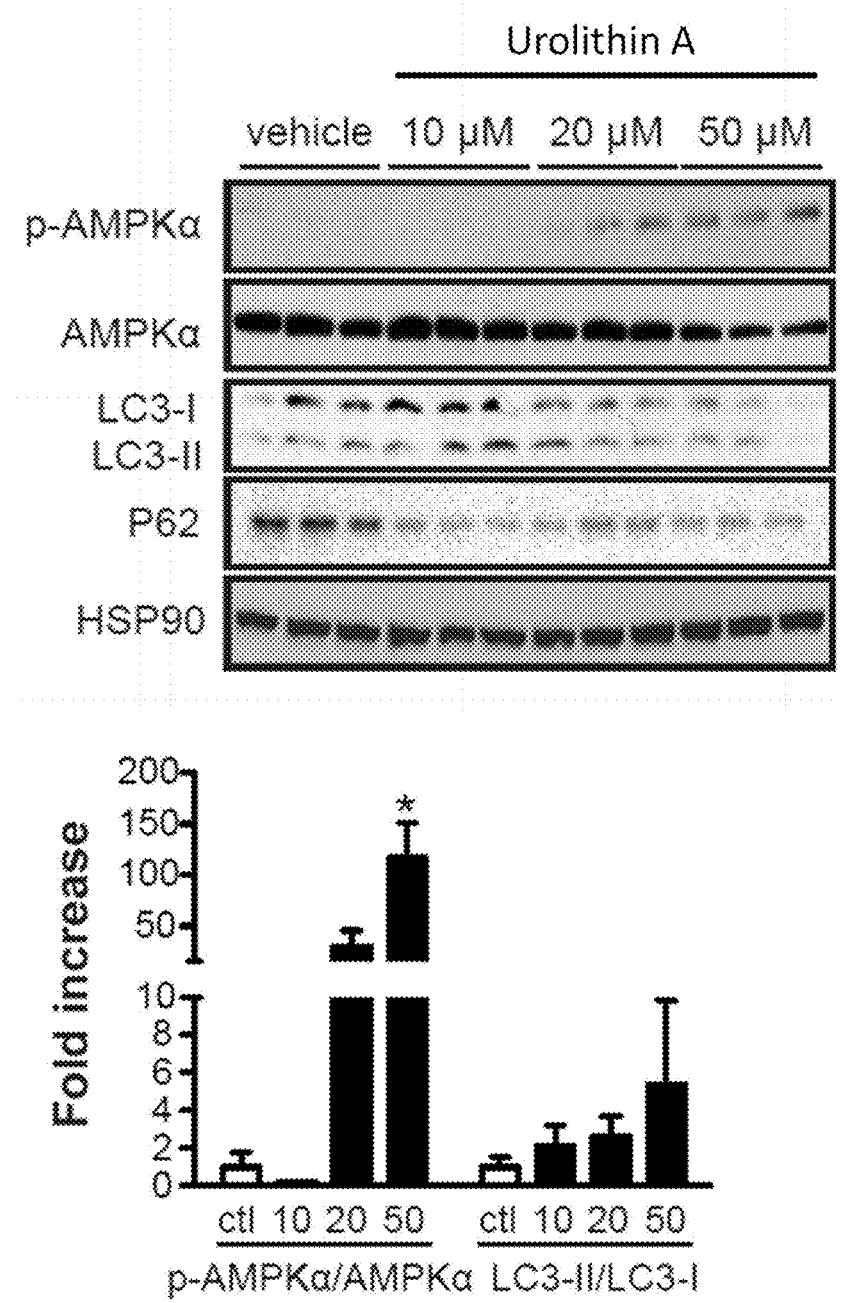
FIG. 15 is a western blot of primary mouse hepatocytes, demonstrating the effect of urolithin A treatment on the autophagy marker ratio LC3-II/LC3-I, p62, and on the ratio of p-AMPKα/AMPKα. Bar graph demonstrates the quantified fold increase in the ratio of LC3-II to LC3-I, and the ratio of p-AMPKα to AMPKα levels observed in the western blots. ctl, control.

Urolithin A treatment at 20 and 50 µM led to increased levels of phosphorylated AMPKα, with in treated cells the ratio of p-AMPKα/AMPK-α significantly rising well above 10-fold the ratio of p-AMPKα/AMPK-α observed in control cells. Importantly, a dose-dependent effect and increase in the ratio of LC3-II to LC3-I was observed following treatment with urolithin A, a hallmark of autophagy (FIG. 15). P62 protein levels were observed to decrease following exposure to urolithin A. This dose effect of urolithin A on the ratio of LC3-II/LC3-I protein ratio, along with the decrease in p62, demonstrates the ability of urolithin A to induce autophagy in mammalian primary hepatocytes and demonstrates a general autophagy activity of urolithins in primary cells.

Example 13

Urolithins Induce Autophagy Across Species in Mammalian Cells

The ability of urolithins to induce autophagy in muscle cells across species was examined using mouse C2C12 myoblasts and human primary skeletal muscle cells.

C2C12 myoblast were cultured in Dulbecco's modified Eagle's medium (DMEM) including 4.5 g/L glucose, 20% fetal calf serum, and 50 µg/mL gentamicin. Urolithin A was dissolved in DMSO in a stock solution of 1 mM. Cells were treated at final concentrations of urolithin A of 10 µM, 20 µM, and 50 µM for a period 16 hours. Control cells were treated with DMSO at an equivalent final concentration for the same period and served as the untreated control.

Human primary skeletal myocytes were cultured in vitro and exposed to increasing concentrations of urolithin A, including 10 µM, 20 µM, and 50 µM for 16 hours. Human skeletal myoblasts were grown in DMEM plus 2% horse serum. Control cells were treated with DMSO at an equivalent final concentration for the same period and served as the untreated control.

Figure 16:
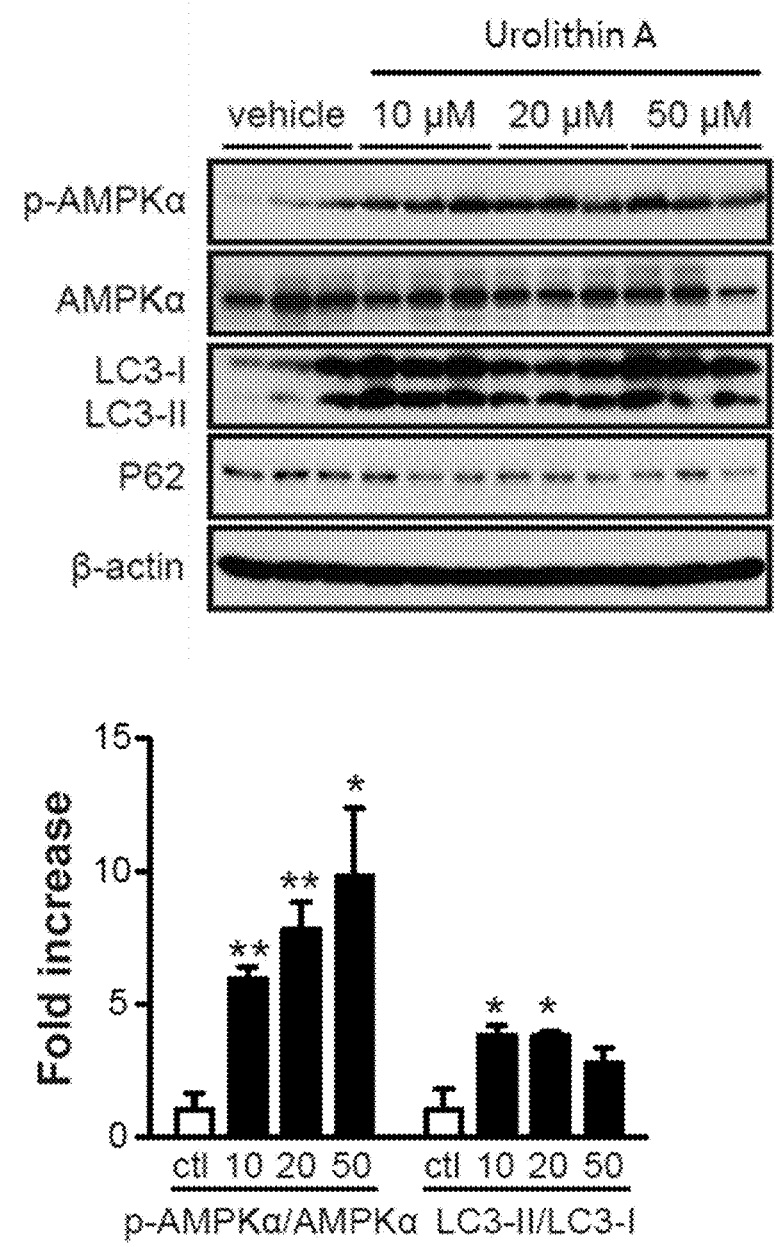
FIG. 16 is a western blot of C2C12 mouse myocytes, demonstrating the effect of urolithin A treatment on the autophagy marker ratio LC3-II/LC3-I, p62, and on the ratio of p-AMPKα/AMPKα. Bar graph demonstrates the quantified fold increase in the ratio of LC3-II to LC3-I, and the ratio of p-AMPKα to AMPKα levels observed in the western blots. ctl, control.
Figure 17:
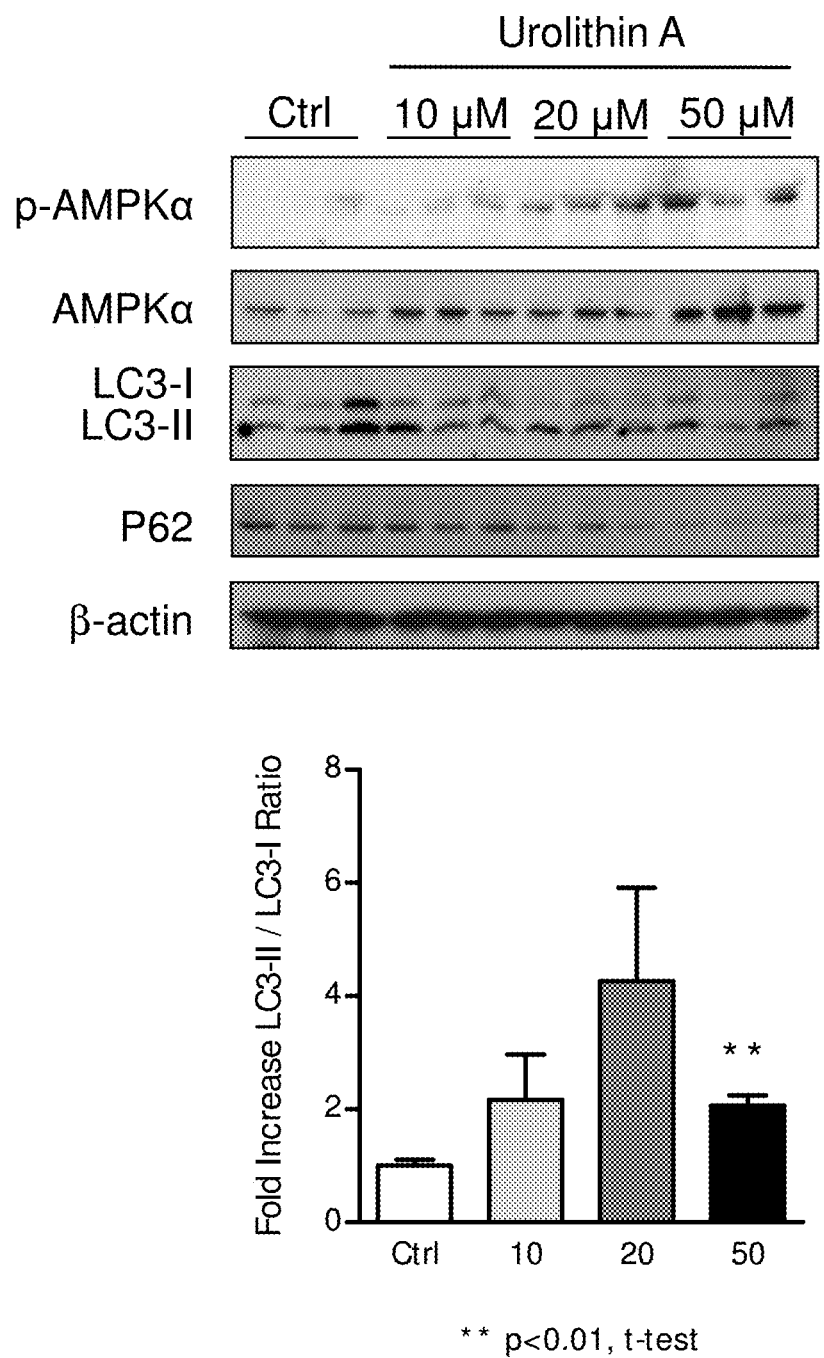
FIG. 17 is a western blot of human primary myoblasts, demonstrating the effect of urolithin A treatment on the autophagy marker ratio LC3-II/LC3-I, p62, and on the ratio of p-AMPKα/AMPKα. Bar graph demonstrates the quantified fold increase in the ratio of LC3-II to LC3-I levels observed in the western blots. Ctrl, control.

At the end of treatment, cells were lysed with RIPA buffer and applied to SDS-PAGE and analyzed by western blot. Protein expression levels were examined for autophagy-related proteins LC3-I and LC3-II (Cell Signaling antibody #4108), p62 (Cell Signaling antibody #5114), AMPKα (Cell Signaling antibody #2603), and p-AMPKα (Cell Signaling antibody #2531). The housekeeping protein, β-actin (Cell Signaling Antibody #4967) level was measured as a loading control. Representative results are shown in FIGS. 16 and 17.

In both mouse C2C12 muscle cells (FIG. 16) and human primary myoblasts (FIG. 17) urolithin A treatment led to a dose-dependent increase in autophagy as verified by an increase in the ratio of LC3-II to LC3-I, accompanied by a decrease in the levels of p62, as observed by the change in density of the bands in the western blots. Also, phosphorylated AMPKα (pAMPKα) levels increased, with the ratio of pAMPKα/AMPKα increasing several fold in response to exposure to urolithin A.

Example 14

Urolithins Induce Autophagy in Primary Cells

Human Aortic Endothelial Cells (HAOEC) are primary endothelial cells isolated from normal human aorta. They were sourced from Cell Applications Inc. (CAI), San Diego, USA and obtained cryopreserved at the second passage from the European Collection of Cell Cultures (ECACC). The cells were thawed and cultured with Endothelial Cell Growth Medium, provided by the ECACC, catalog number 06091509 (CAI No. 211-500), in a 37° C., 5% $CO_2$ humidified incubator; media was changed 24 hours after thawing. Endothelial Cell Growth Medium was changed every other day until the cells reached 80% confluency. Cells were then subcultured into four 6-well dishes and after overnight incubation were treated with different concentrations of urolithin A, 10 µM, 20 µM, and 50 µM, or a DMSO control for a period of 16 hours, 3 wells per treatment. Control cells were treated with DMSO at an equivalent final concentration for the same period and served as the untreated control.

Figure 18:
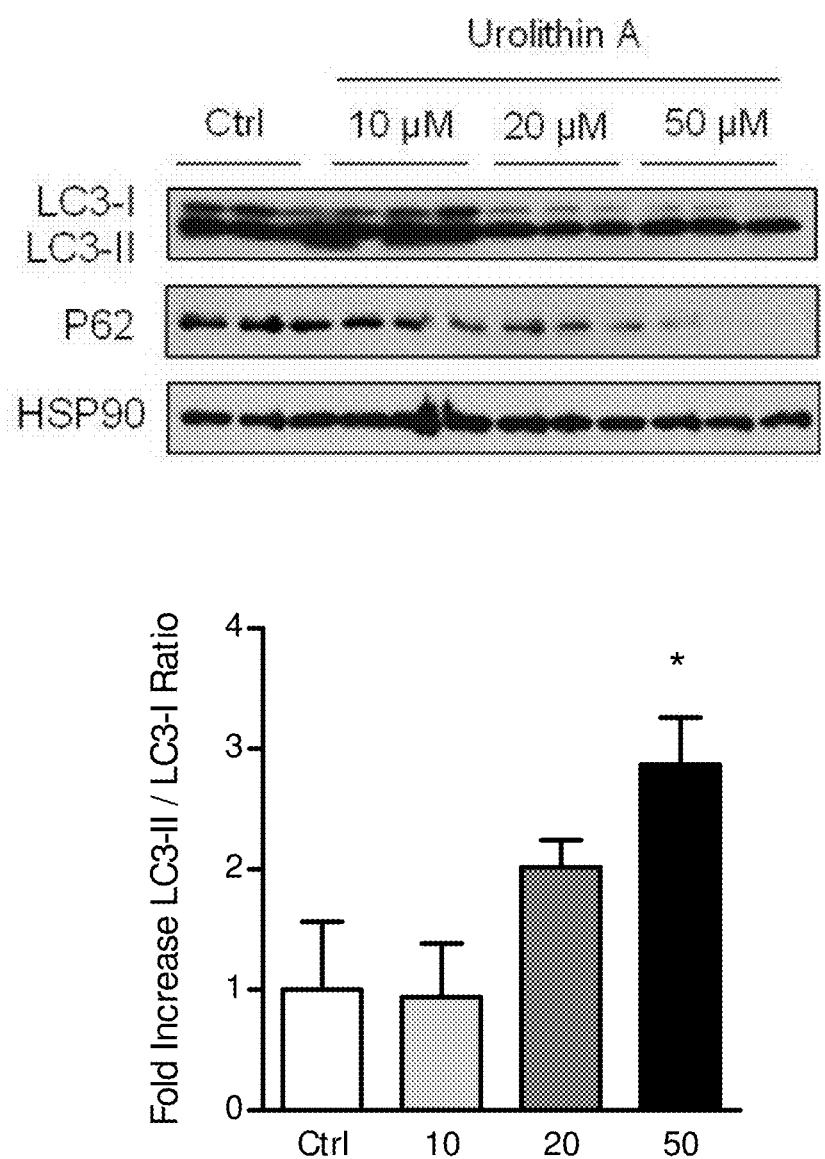
FIG. 18 is a western blot of human primary aortic endothelial cells, demonstrating the effect of urolithin A treatment on the autophagy marker ratio LC3-II/LC3-I and the protein p62. Bar graph demonstrates the quantified fold increase in the ratio of LC3-II to LC3-I levels observed in the western blots. Ctrl, control.

At the end of treatment, cells were lysed with RIPA buffer and applied to SDS-PAGE and analyzed by western blot. Protein expression levels were examined for autophagy-related proteins LC3-I and LC3-II (Cell Signaling antibody #4108), and p62 (Cell Signaling antibody #5114). The housekeeping protein, HSP90 (BD Transduction Laboratories antibody #610418) level was measured as a loading control. Representative results are shown in FIG. 18.

In human primary aortic endothelial cells (FIG. 18) urolithin A treatment led to a dose-dependent increase in autophagy as verified by an increase in the ratio of LC3-II to LC3-I to as high as 3-fold induction at 50 µM of urolithin A, which was also accompanied by a decrease in the levels of p62, as observed by the change in density of the bands in the western blots. These results clearly indicate that urolithins increase autophagy in endothelial cells.

Example 15

Urolithins Induce Autophagy in Mammals

To determine the ability of urolithin A to induce autophagy in vivo, healthy 10-week-old C57BL/6J mice were treated with either a standard rodent diet or a diet containing urolithin A mixed with food to reach a dosing of 55 mg/kg/day delivered to the mice. Following 8 weeks of treatment with urolithin A, mice were sacrificed and the liver of each animal was surgically isolated. The isolated livers were then placed in lysis buffer and prepared for western blot analysis.

Protein expression levels were examined for autophagy related proteins LC3-I and LC3-II (Cell Signaling antibody #4108), p62 (Cell Signalling antibody #5114), AMPKα (Cell Signaling antibody #2603), and p-AMPKα (Cell Signaling antibody #2531). The housekeeping protein, HSP90 (BD Transduction Laboratories antibody #610418) level was measured as a loading control. Each lane in the Western blot represents a protein sample for the liver of a single mouse, to permit observation of the effects aver a number of treated animals.

Figure 19:
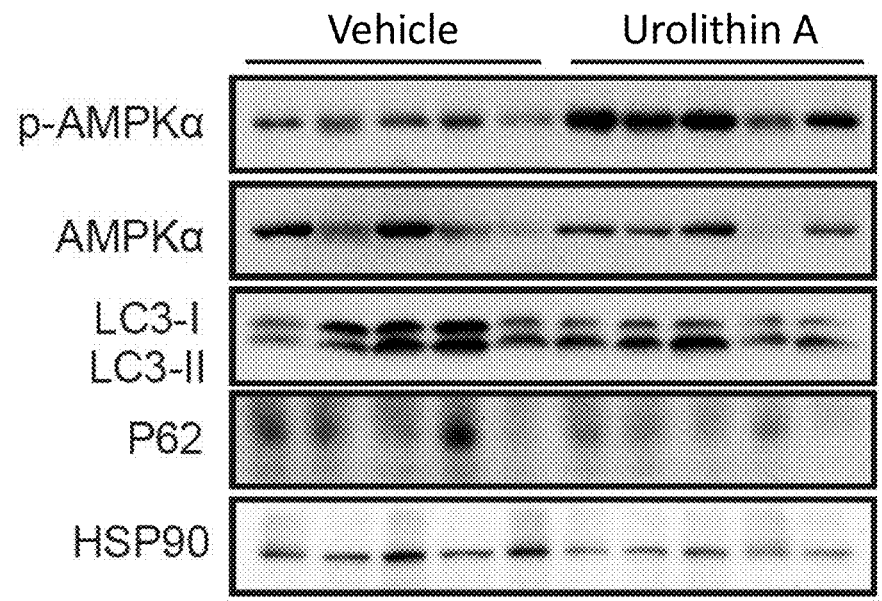
FIG. 19 is a western blot of livers isolated from untreated control mice and mice administered urolithin A at a dose of 55 mg/kg/day admixed in food. Urolithin A treatment increased the autophagy marker ratio LC3-II/LC3-I, decreased p62, and increased the ratio of p-AMPKα/AMPKα. Bar graph demonstrates the quantified fold increase in the ratio of LC3-II to LC3-I, and the ratio of p-AMPKα to AMPKα levels observed in the western blots. ctl, control.
Figure 19:
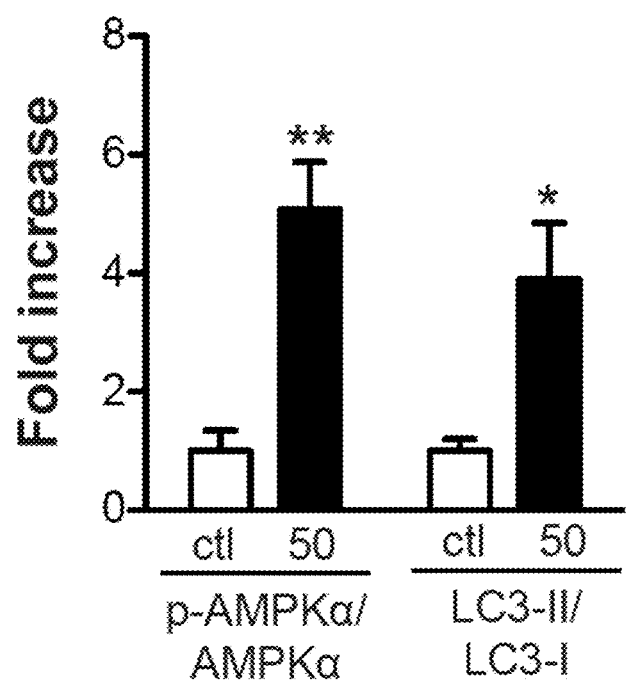

Urolithin A treatment at an oral dose of 55 mg/kg/d that was admixed into the animal chow diet led to increased levels of phosphorylated AMPKα (pAMPKα), as well as an increase in the ratio of LC3-II to LC3-I, a hallmark of autophagy, in a healthy mouse liver following oral consumption (FIG. 19). The increase in autophagy induced by the oral treatment was observed to be on average approximately 400% over the control untreated mice based on the ratio of LC3-II/LC3-I. p62 protein levels also decreased with urolithin A treatment. These results demonstrate the ability of urolithin A to induce autophagy in mammalian cells and tissues following oral consumption.

Example 16

Urolithin a Improves Motor Activity in Mammals

To examine the effect of urolithin A treatment on activity and muscle function in mammals, 10-week-old C57BL/6J mice were treated with either a standard rodent diet or a diet containing urolithin A mixed with food to reach a dosing of 55 mg/kg/day delivered to the mice. Following 11 weeks of treatment with urolithin A, a 23 cm in diameter running wheel was placed in the cage of each mouse. Spontaneous exercise activity was measured over a five day period at 20 min intervals, allowing the capture of the circadian rhythm of the exercise activity.

Figure 20:
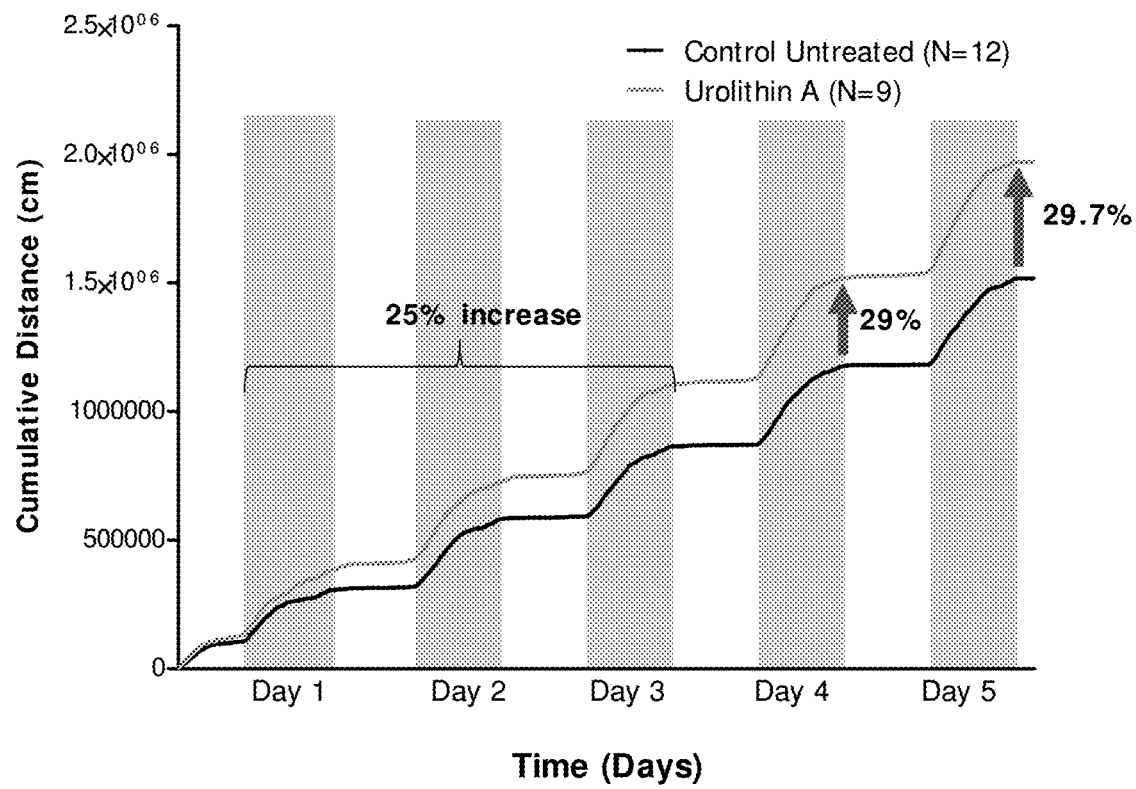
FIG. 20 is a graph depicting the effect of orally consumed urolithin A at 55 mg/kg/day on the motor activity of C57BL/6J mice. Young treated mice increased their spontaneous voluntary running on a running wheel by at least 25% during the five-day period investigated.
Figure 20:
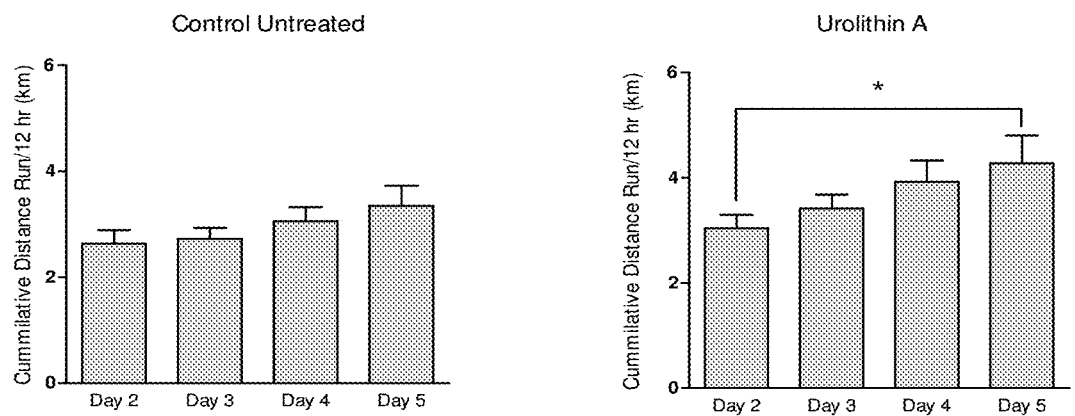

Urolithin A treatment resulted in a significant and sustained increase in the distance covered by the mice each day (FIG. 20). During the initial 3 days the urolithin A treated animals showed an increase of 25% over untreated controls in the cumulative distance covered. This difference increased further to 29% on the final two days tested. These results demonstrate the ability of urolithin A treatment to improve motor activity in mammals. A clear training effect was observed in which mice administered urolithin A not only increased their spontaneous running activity, but there was an increase over time. Additionally, this demonstrated that the benefits persist over time.

Example 17

Urolithin A Improves Motor Activity in Aged Mammals

To examine the effects of urolithin A treatment on motor activity in aged mammals 17-month-old C57BL/6J mice were treated with either a high fat rodent diet or a high fat rodent diet containing urolithin A mixed with food to reach a dosing of 50 mg/kg/day delivered to the mice.

Following 30 weeks of treatment with urolithin A, mice were housed individually and a 23 cm diameter running wheel was placed in the cage of each mouse. Spontaneous exercise activity was measured continuously over a two day period allowing the capture of the circadian rhythm of the exercise activity. Afterwards, mice were returned to their home cages.

Figure 21:
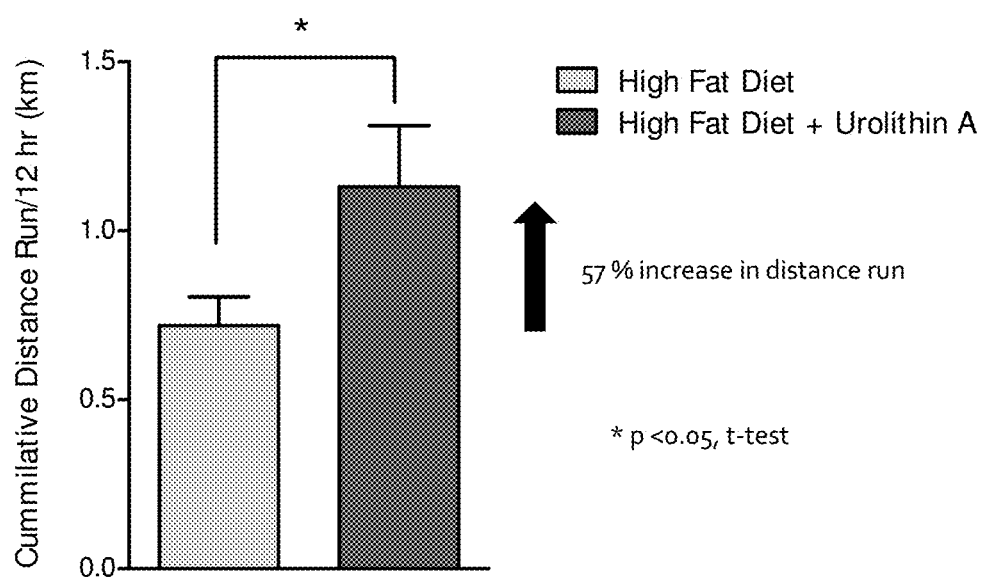
FIG. 21 is a bar graph depicting the effect of orally consumed urolithin A on running in aged C57BL/6J mice.

Mice became habituated to the presence of the activity wheel on day 1. To measure the effect of urolithin A treatment on activity as well as muscle function, the cumulative distance that animals covered during the peak running period (dark phase) of day 2 was measured. As shown in FIG. 21, urolithin A treatment resulted in an increase of 57% ($p<0.05$) in cumulative distance run in treated aged mice fed a high fat diet. This clearly shows the positive benefits of urolithins on spontaneous activity and running during aging. This provides evidence that the delivery of urolithin to an aging population will improve locomotor activity and running ability and help prevent the natural decline observed.

Example 18

Urolithin A Improves Muscle Strength in Aged Mammals

To examine the effects of urolithin A treatment on muscle function in aged mammals, 17-month-old C57BL/6J mice were treated with either a high fat rodent diet or a high fat rodent diet containing urolithin A mixed with food to reach a dosing of 50 mg/kg/day delivered to the mice.

Following 26 weeks of treatment with urolithin A, mice were assessed for their neuromuscular function by means of a grip test. Using the grip test, one can measure the forelimb grip strength of mice. Mice were placed on a grid to enable their fore paws grasp the support. To measure the grip strength, mice are pulled backward in the sensor axis until they are no longer able to hold the grid.

Figure 22:
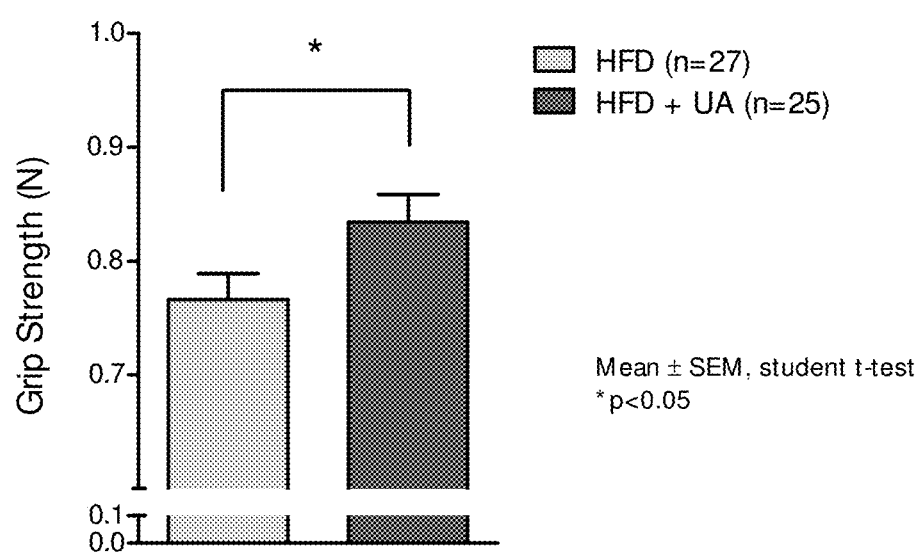
FIG. 22 is a bar graph depicting the effect of orally consumed urolithin A on grip strength in aged C57BL/6J mice.

Representative results are presented in FIG. 22. Mice receiving urolithin A showed a greater grip strength than untreated mice.

Example 19

Urolithin A Improves Locomotor Activity in Aged Mammals

Locomotor activity may be also assessed by measuring animal movements using infrared detection. To determine the effects of urolithin A on spontaneous locomotor activity in aged animals, 16-month-old C57BL/6J mice were treated with either a standard rodent diet or a diet containing urolithin A mixed with food to reach a dosing of 50 mg/kg/day delivered to mice. Following 34 weeks of treatment with urolithin A, mice were placed in a locomotor activity monitoring system, TSE Systems. Infrared transmitters and receivers are placed in the x, y, and z axis. Interruption of the infrared beams in the x, y axis by the passage of the mouse, allows for a measurement of the horizontal movement (ambulation). Interruption of the infrared beams in the z axis by the mouse, allows for the measurement of rearing behavior. Each beam interruption results in one count being recorded. Total counts were measured for each 30 minute period over a two day period. The total counts observed during the 12 hour dark period, which corresponds to the time of highest activity in mice, were summed for each animal.

Figure 23:
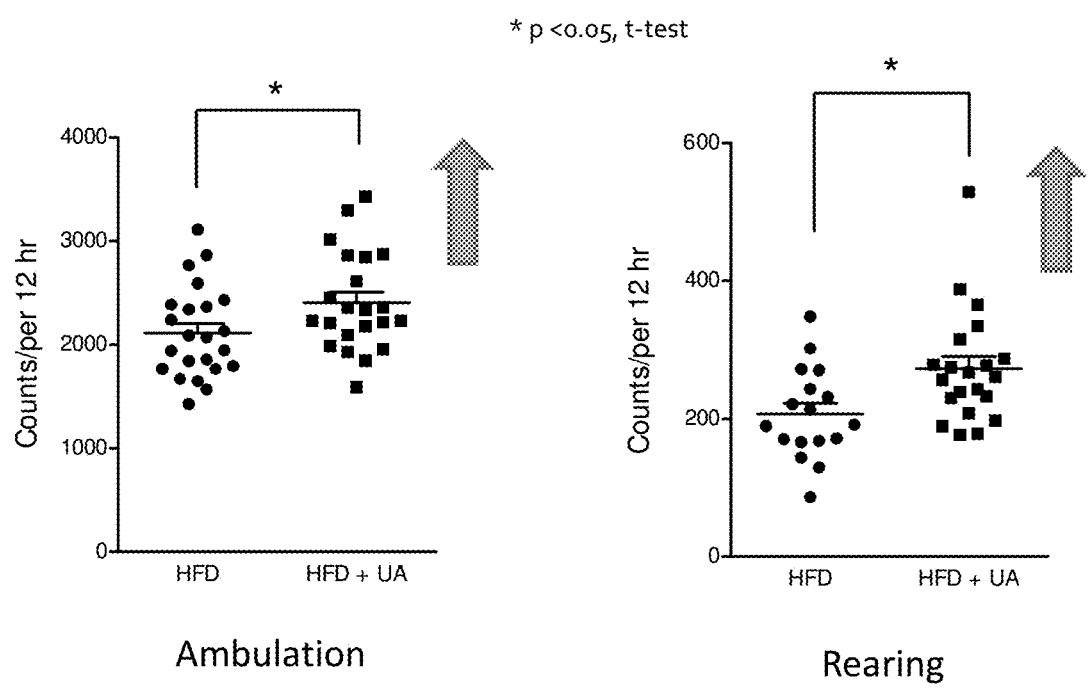
FIG. 23 is pair of graphs depicting the effect of orally consumed urolithin A on an ambulation and rearing in aged C57BL/6J mice. HFD, high fat diet; UA, urolithin A.

FIG. 23 shows that aged mice treated with urolithin A showed a 14% increase in ambulation and a 25% increase in rearing. These results demonstrate the ability of urolithin A to increase mobility in aged animals.

Example 20

Urolithin A Increases Autophagy in Skeletal Muscle of Aged Mammals

Figure 24:
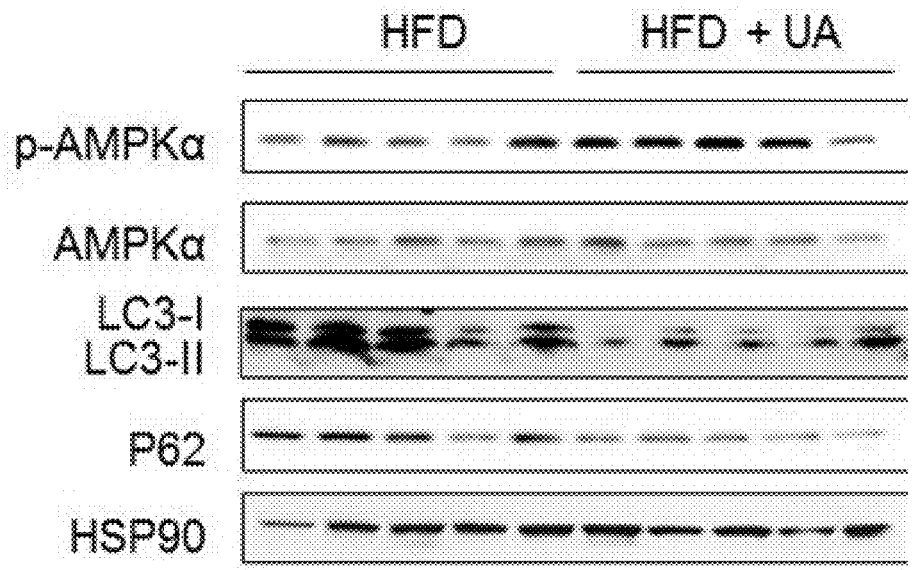
FIG. 24 is a western blot of skeletal muscle isolated from aged high fat diet (HFD) untreated control mice, and from aged high fat diet mice administered urolithin A (UA) at a dose of 50 mg/kg/day admixed in food. Urolithin A treatment increased the autophagy marker ratio LC3-II/LC3-I and decreased the levels of p62. Bar graph demonstrates the quantified fold increase in the ratio of LC3-II to LC3-I levels observed in the western blots. Ctrl, control.
Figure 24:
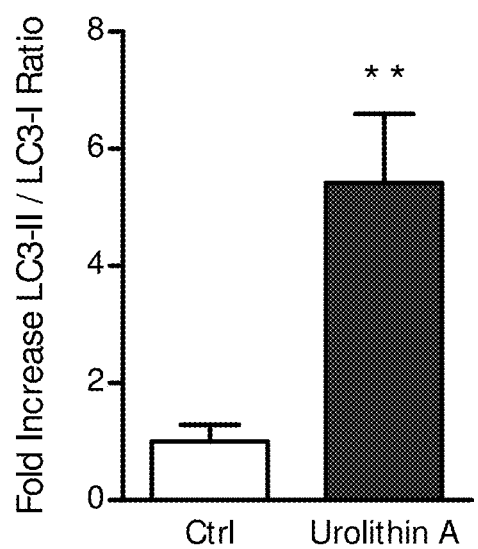

Following 34 weeks of treatment, the mice from Example 19 were sacrificed and the organs were collected. The gastrocnemius muscles were assessed for the presence of autophagy by the assessment of the change in the ratio of the autophagy markers LC3 and p62 using western blot analysis. Each lane corresponds to a muscle sample from an individual mouse. Representative results are shown in FIG. 24. The ratio of LC3-II/LC3-I increased in the muscles of urolithin A (UA)-treated mice versus untreated mice. This was accompanied by a decrease in the levels of p62 in the muscles of UA treated versus untreated mice. These shifts in the levels of LC3 and p62 in the muscle of mice are consistent with an increase in the level of autophagy taking place. This demonstrates that the oral administration of urolithin A leads to autophagy at the organ level, including muscle. Mice receiving UA in their diets also displayed an increase activation of AMPK in their muscle as observed by an increase in the ratio of p-AMPKα/AMPKα.

Example 21

Urolithins Induce Autophagy in Mouse Muscle Cells

To determine the ability of urolithin A to induce autophagy in mouse muscle cells, undifferentiated C2C12 mouse myoblasts were seeded in T25 flasks and incubated overnight. Cells were incubated in 5% $CO_2$ at 37° C. These cells were treated with one of the urolithins—urolithin A (UA), urolithin B (UB), urolithin C (UC) or urolithin D (UD)—dissolved in a 0.1% solution of DMSO for 24 hours. In one experiment UA, UB, UC and UD were dosed at a concentration of 100 μM for C2C12 myoblast treatment. In a separate study, C2C12 myoblasts were incubated at increasing concentrations of UA (10 μM, 50 μM and 100 μM). For each experiment a control culture was treated with 0.1% DMSO for the same period and served as the untreated control. In the final 30 minutes of incubation, lysosome degradation inhibitor was added to the culture. The cells were then washed with phosphate buffer solution and then treated with a 1% solution of trypsin enzyme to remove the adhesive cells from the cell culture dishes. The cells were then treated with EMD Millipore selective permeabilization reagent to permeabilize the cells so as to make the internal cellular proteins accessible to antibody treatment. Cells were then incubated with antibody to LC3B according to kit protocol (EMD Millipore FlowCellect™ Autophagy LC3 Antibody-based Assay Kit (Cat no. FCCH100171)). The cells were then washed and resuspended in the kit assay buffer. The resulting cells were then run through a flow cytometer and LC3B-FITC fluorescence was quantified to measure the level of LC3B in C2C12 cells for the various treatments. When cells undergo autophagy their intracellular levels of LC3-II increase which is detected by this method. This autophagy can be detected by fluorescent antibody labeling of LC3B, which can be measured quantitatively using flow cytometry. An increase in cellular autophagy is reflected by an increasing signal in the histogram of LC3B FITC.

Figure 25:
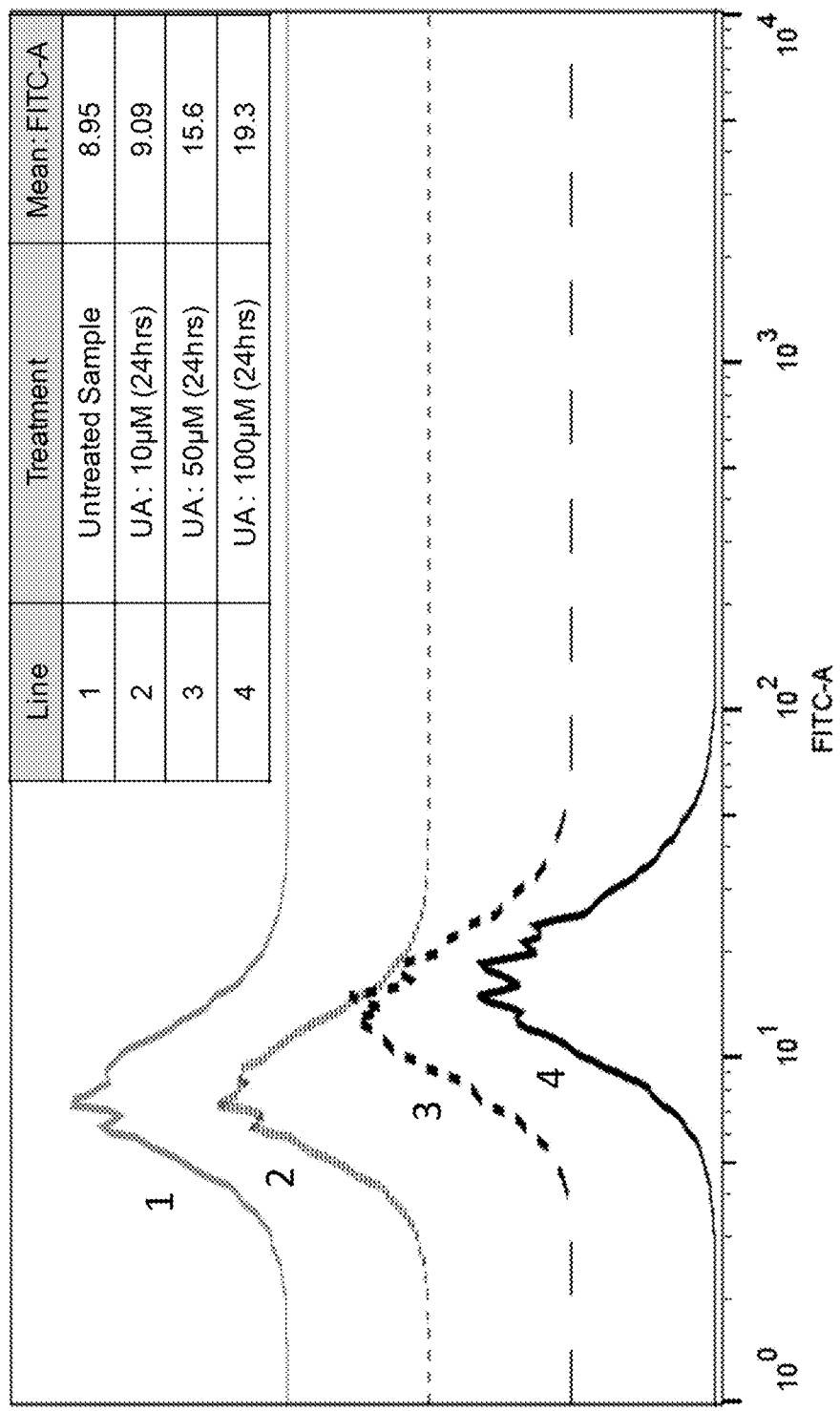
FIG. 25 shows the effect of urolithin A (UA) on autophagy in C2C12 myoblasts. Myoblasts incubated 24 hrs with increasing doses of UA showed a dose response, with increasing autophagy as the UA concentration was raised (10 μM, 50 μM and 100 μM), which was demonstrated by the increasing shift in the histogram representing the LC3-B cell levels, a marker of autophagy, as compared to untreated controls.
Figure 26:
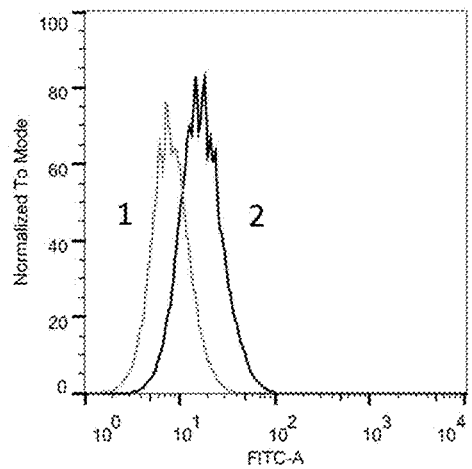
FIG. 26 shows the effect of urolithin A (UA), urolithin B (UB), urolithin C (UC), and urolithin D (UD) on autophagy in C2C12 cells. Myoblasts incubated with UA, UB, UC, or UD at 100 μM experienced an increase in autophagy as demonstrated by the shift in the histogram representing the LC3-B cell levels as compared to untreated controls.
Figure 26:
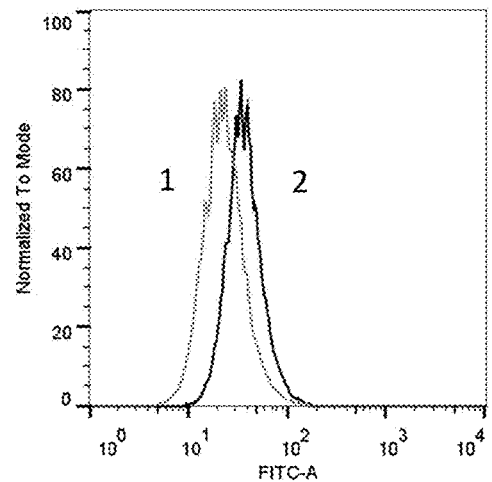
Figure 26:
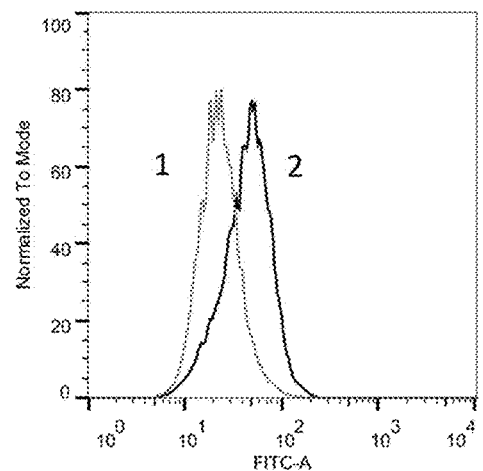
Figure 26:
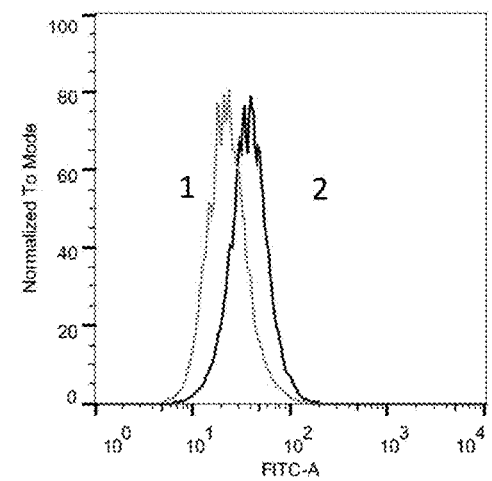

Urolithin A treatment of C2C12 cells results in an increase in LC3B expression that is dose dependent (FIG. 25) demonstrating the ability of urolithin A to induce autophagy in mouse muscle cells in a dose-dependent manner (10 μM, 50 μM and 100 μM). In a separate study, induction of autophagy was also observed in C2C12 mouse myoblasts following treatment with urolithin A (UA), urolithin B (UB), urolithin C (UC) and urolithin D (UD) at 100 μM after 24 hrs of treatment (FIG. 26). Incubation with UA, UB, UC and UD all led to a increasing signal of LC3B as shown by the positive shift of the histogram. This data demonstrates the ability of the urolithins as a class of compounds to induce autophagy in mammalian myoblasts.

Example 22

Synthesis of Urolithins and Urolithin Precursors

Figure 27:
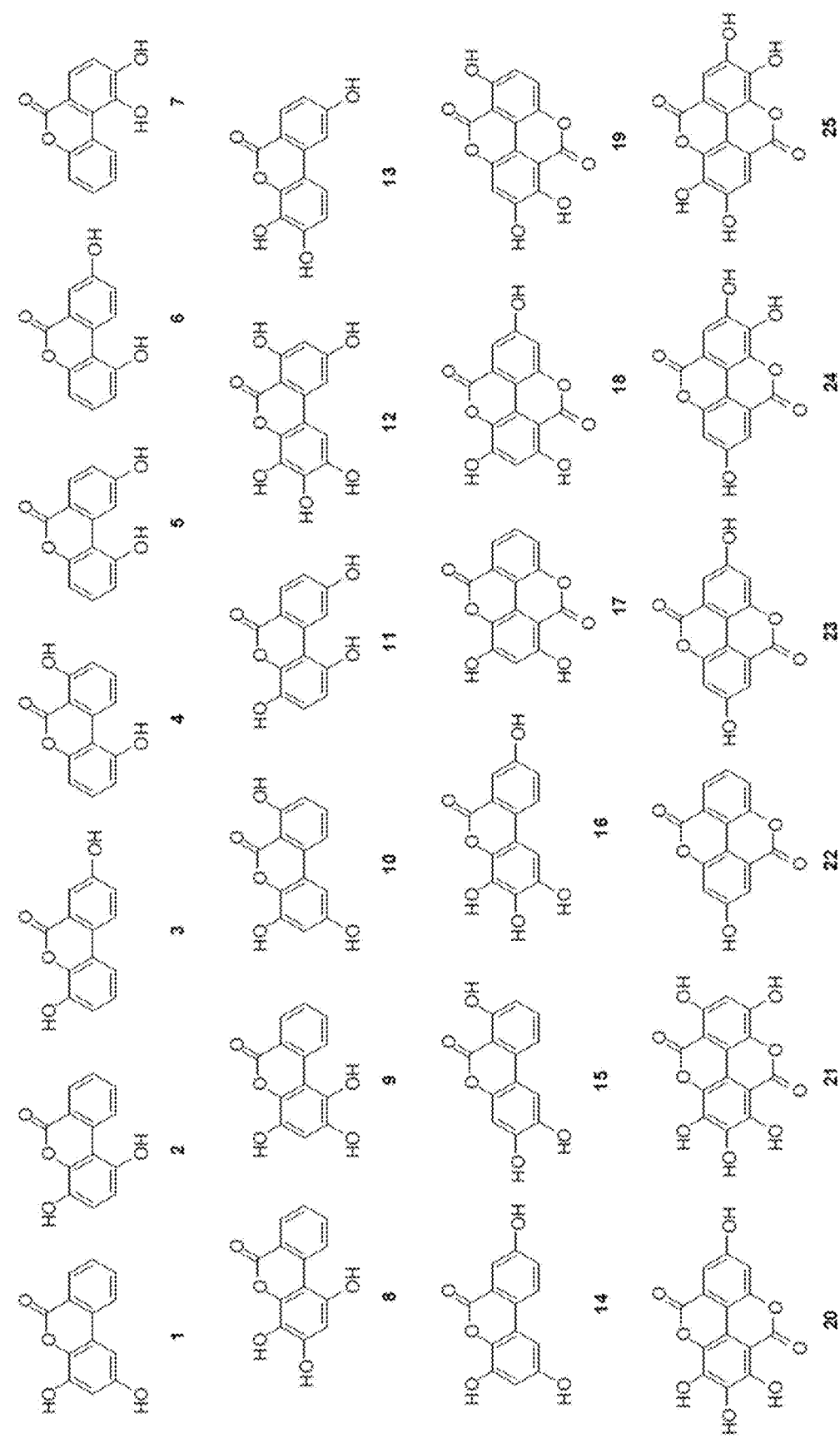
FIG. 27 depicts twenty-five compounds of the invention.

Examples of urolithin compounds of the invention are shown in FIG. 27 as compounds 1 through 16. Examples of urolithin precursors of this invention are shown in FIG. 27 as compounds 17 through 25.

Figure 28:
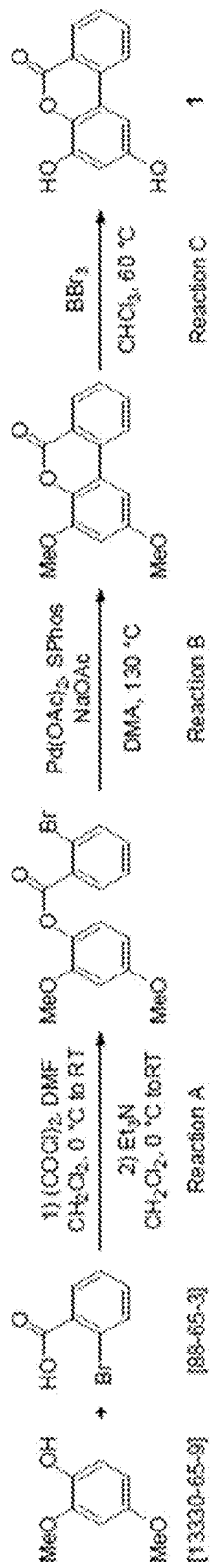
FIG. 28 depicts prophetic synthetic routes to the compounds in FIG. 27.
Figure 28:
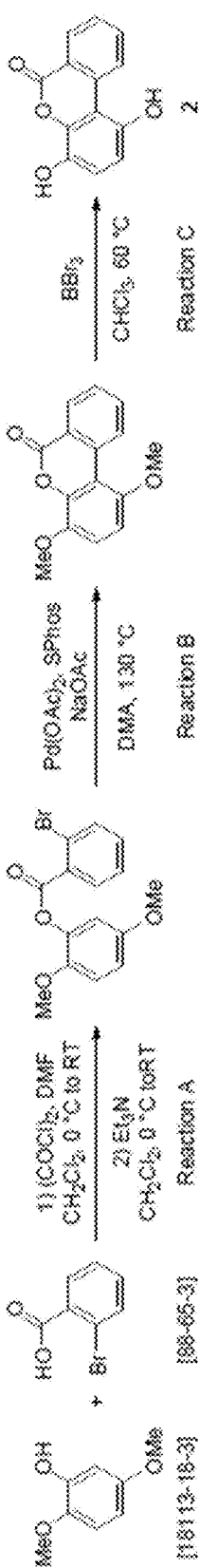
Figure 28:
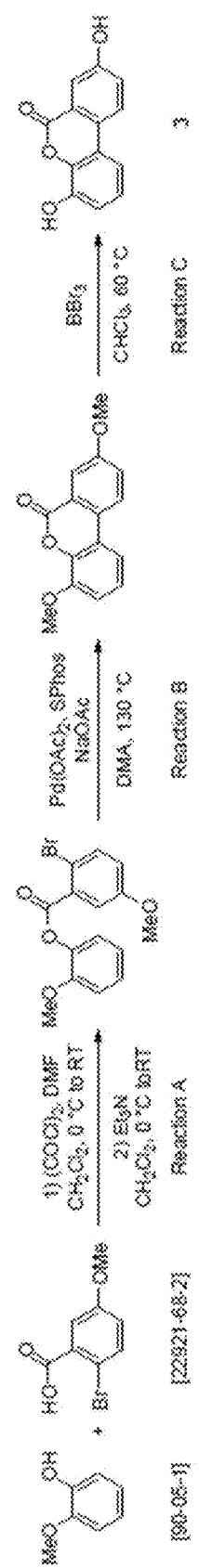
Figure 28:
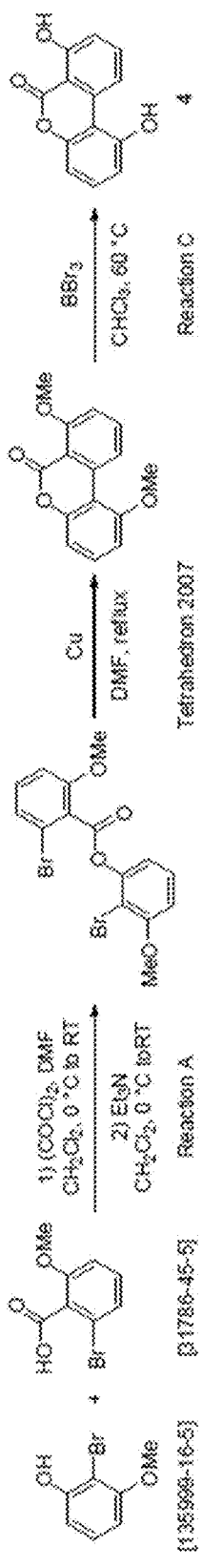
Figure 28:
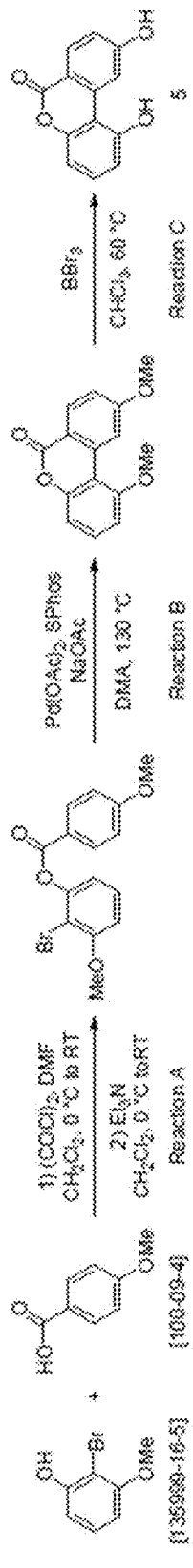
Figure 28:
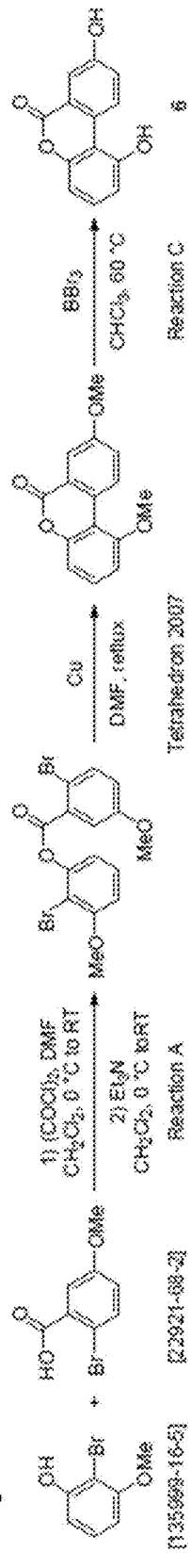
Figure 28:
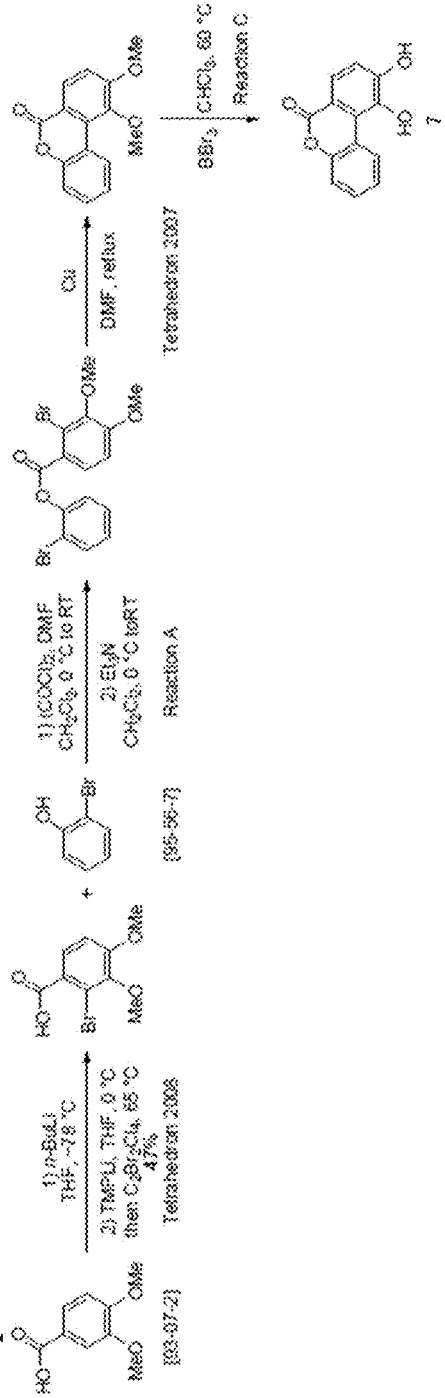
Figure 28:
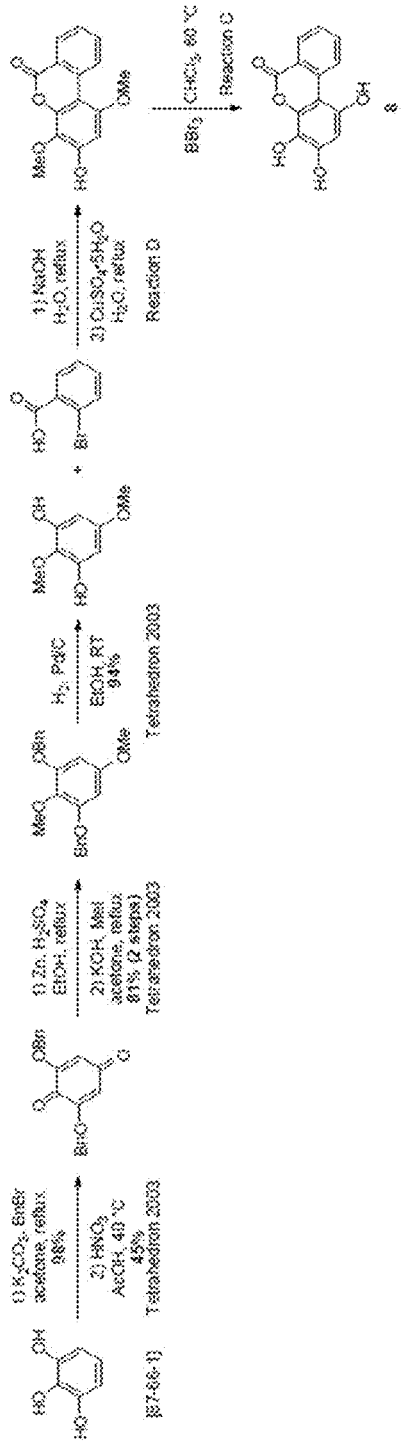
Figure 28:
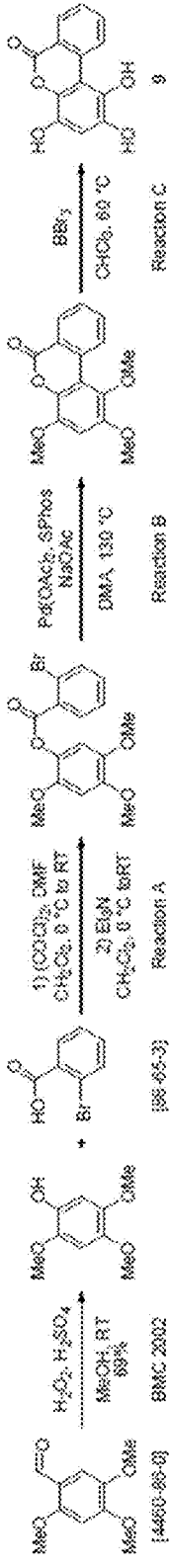
Figure 28:
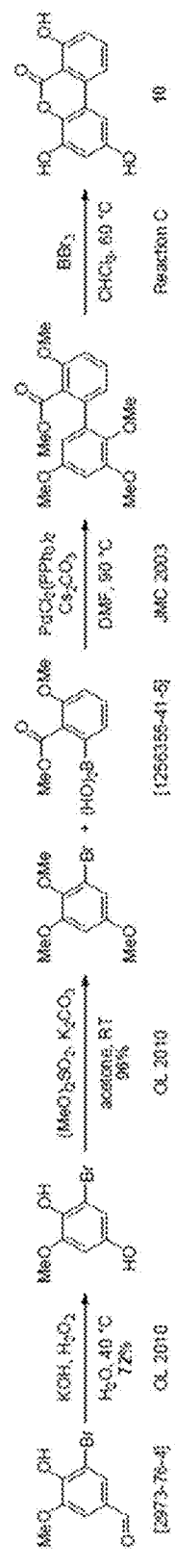
Figure 28:
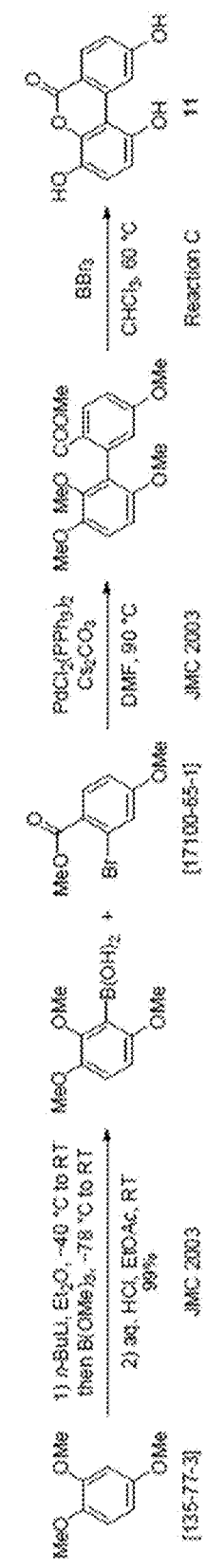
Figure 28:
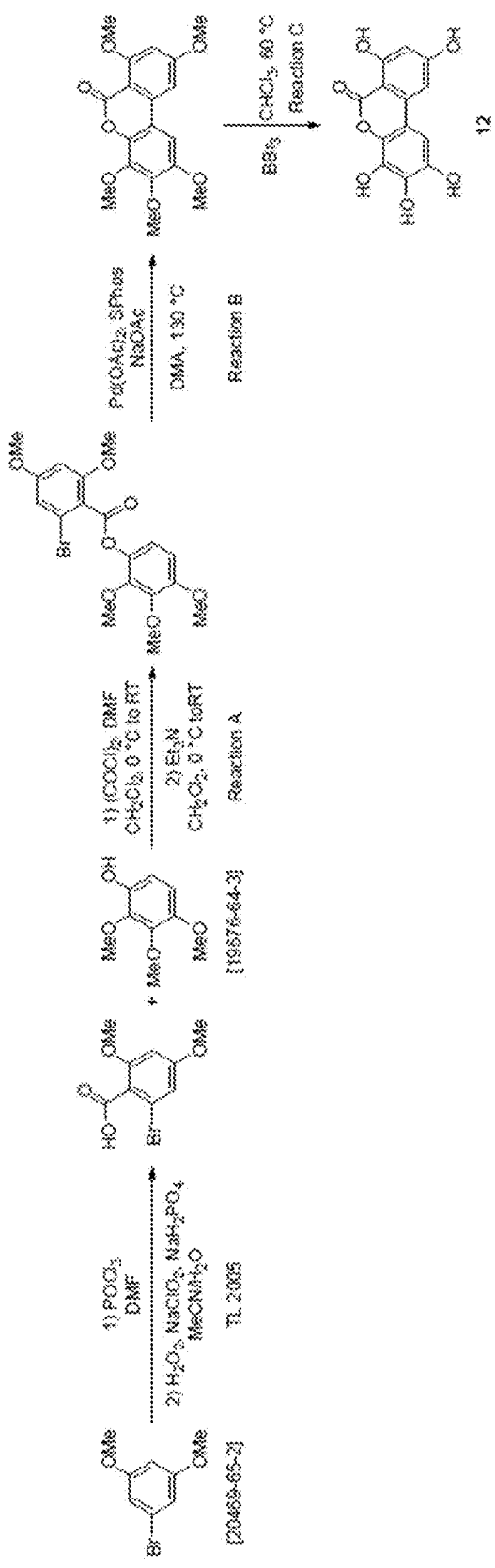
Figure 28:
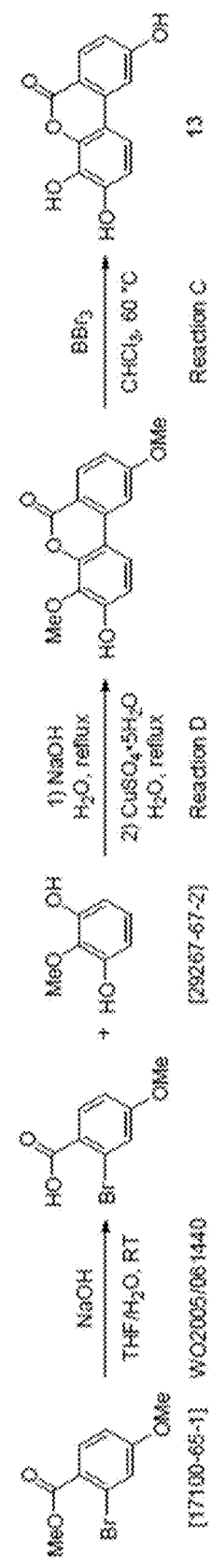
Figure 28:
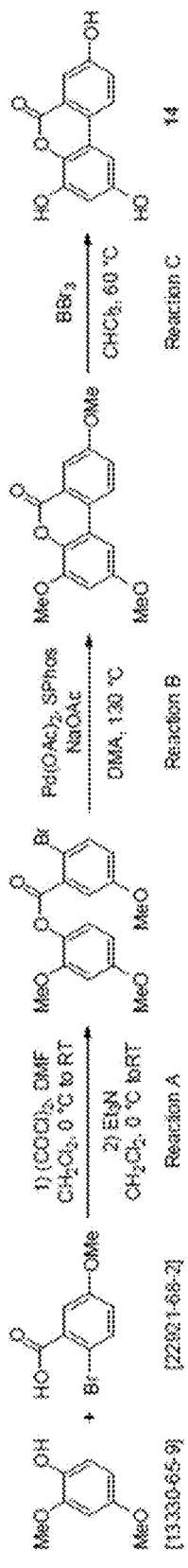
Figure 28:
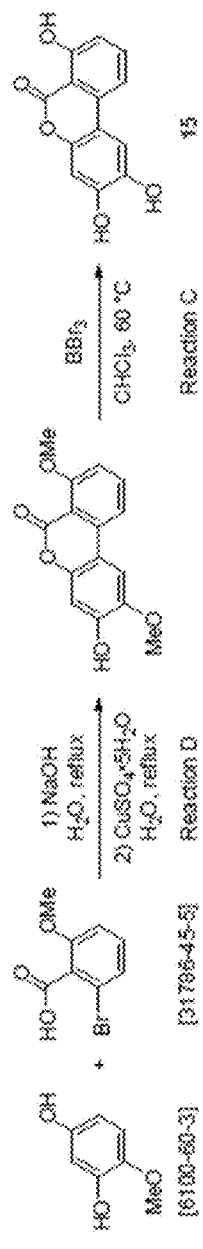
Figure 28:
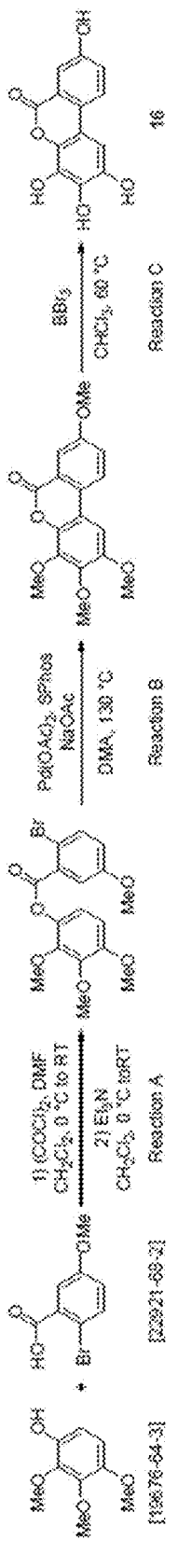
Figure 28:
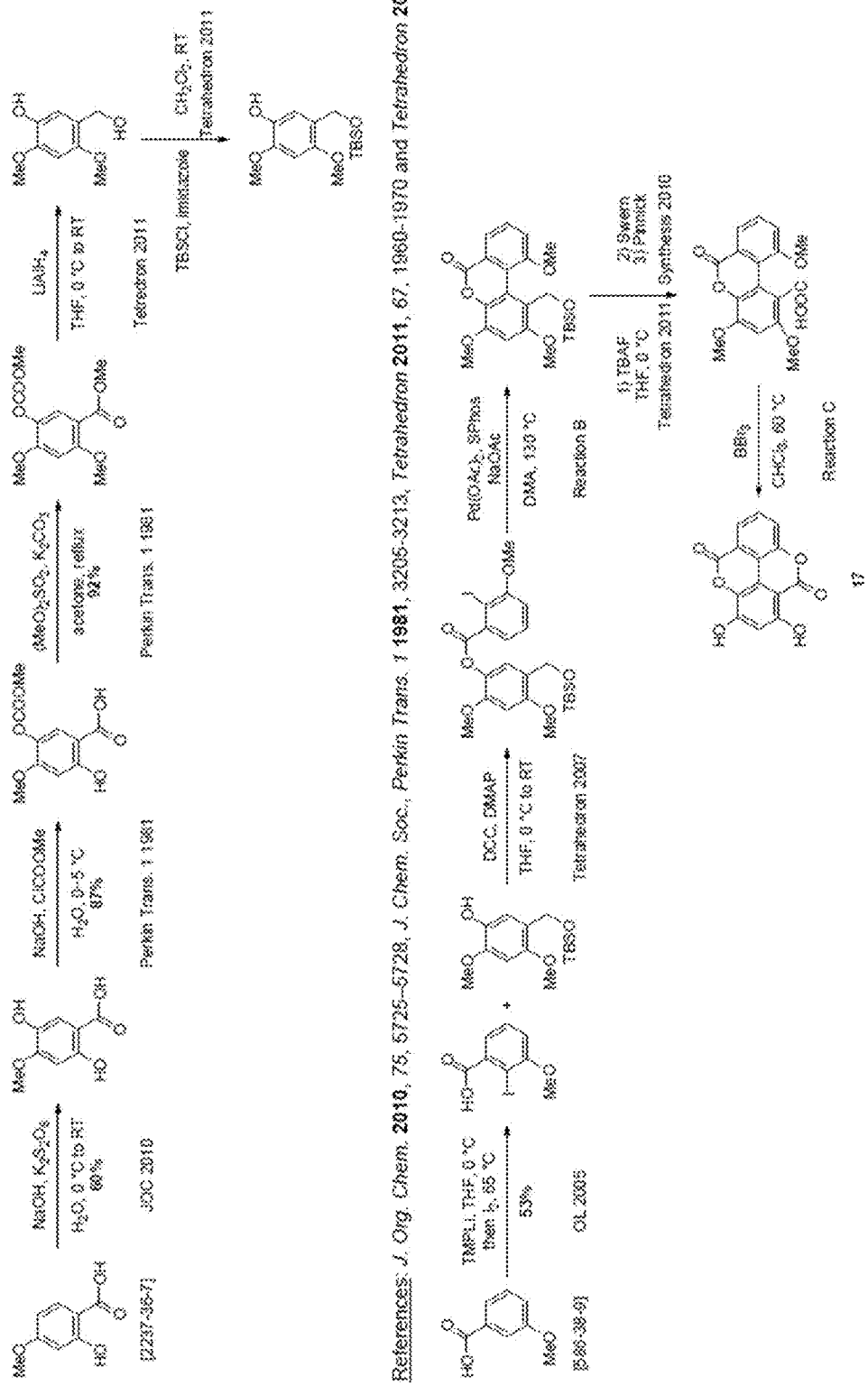
Figure 28:
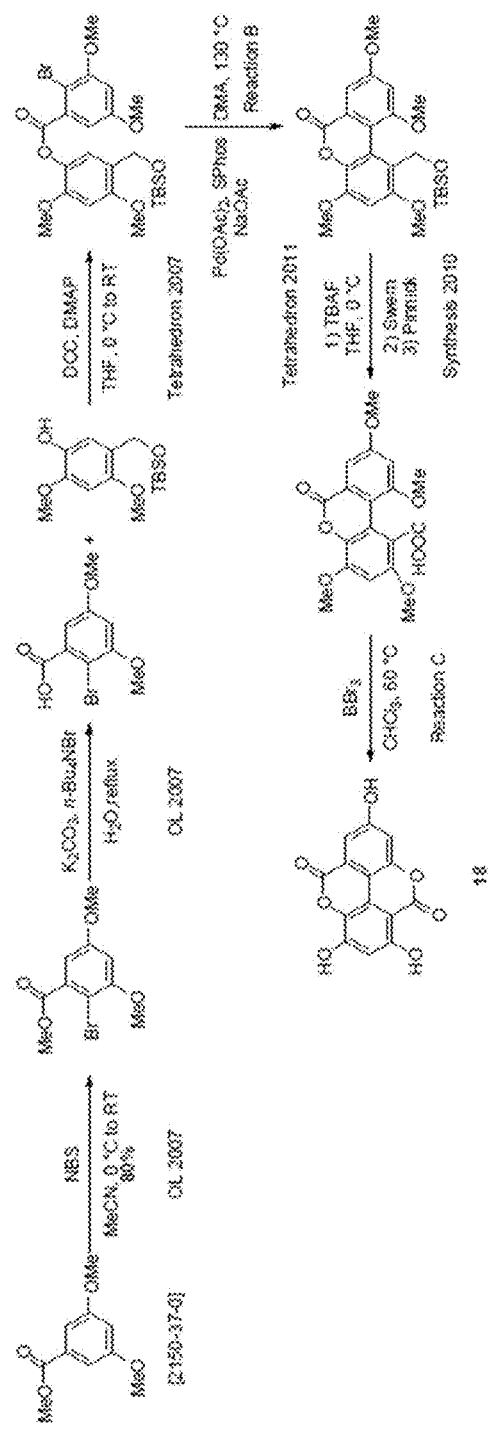
Figure 28:
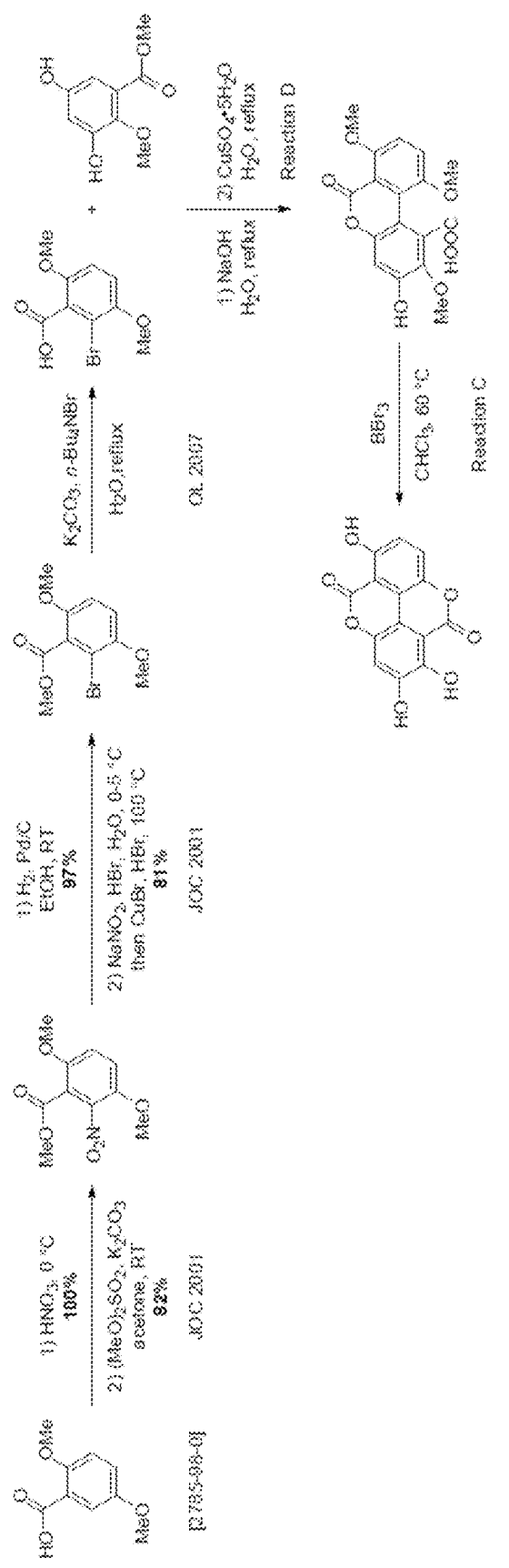
Figure 28:
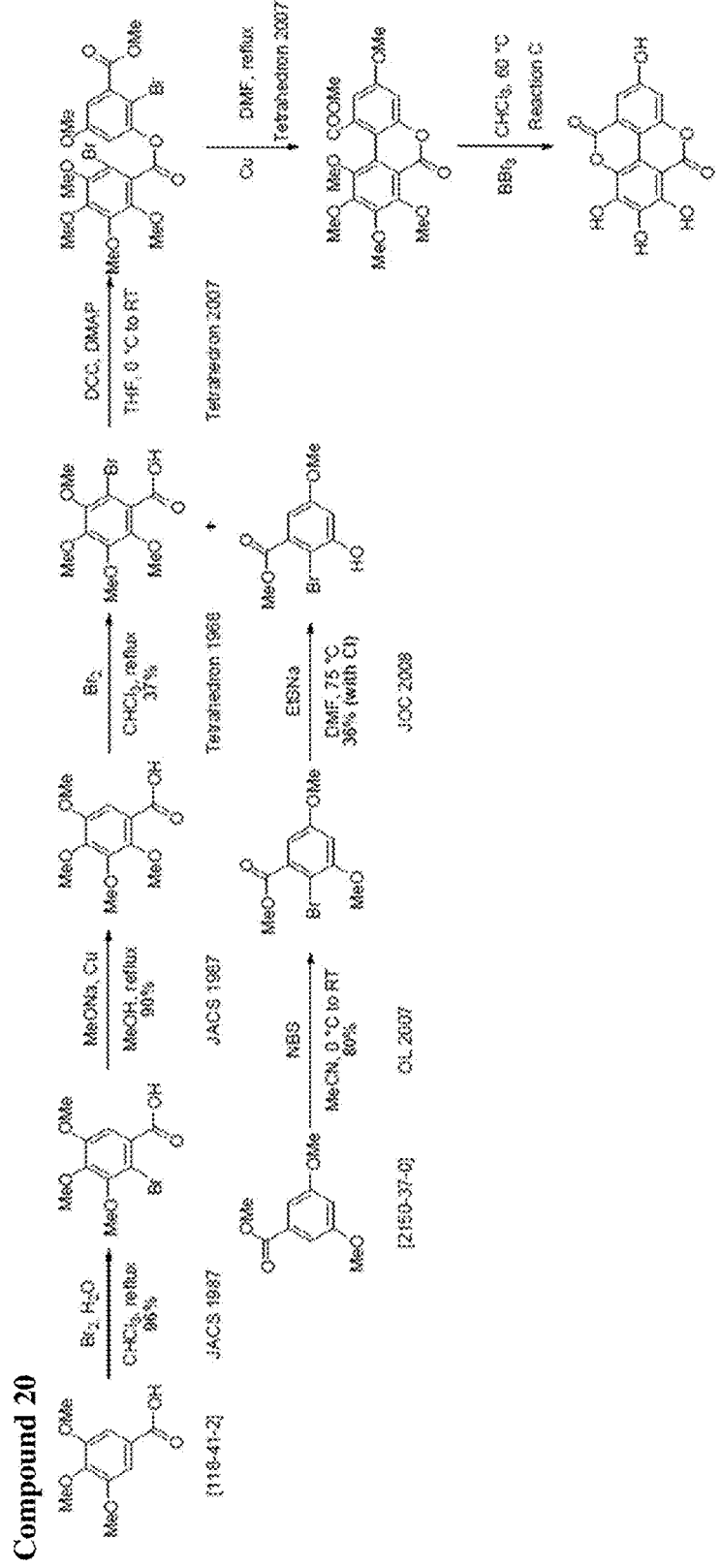
Figure 28:
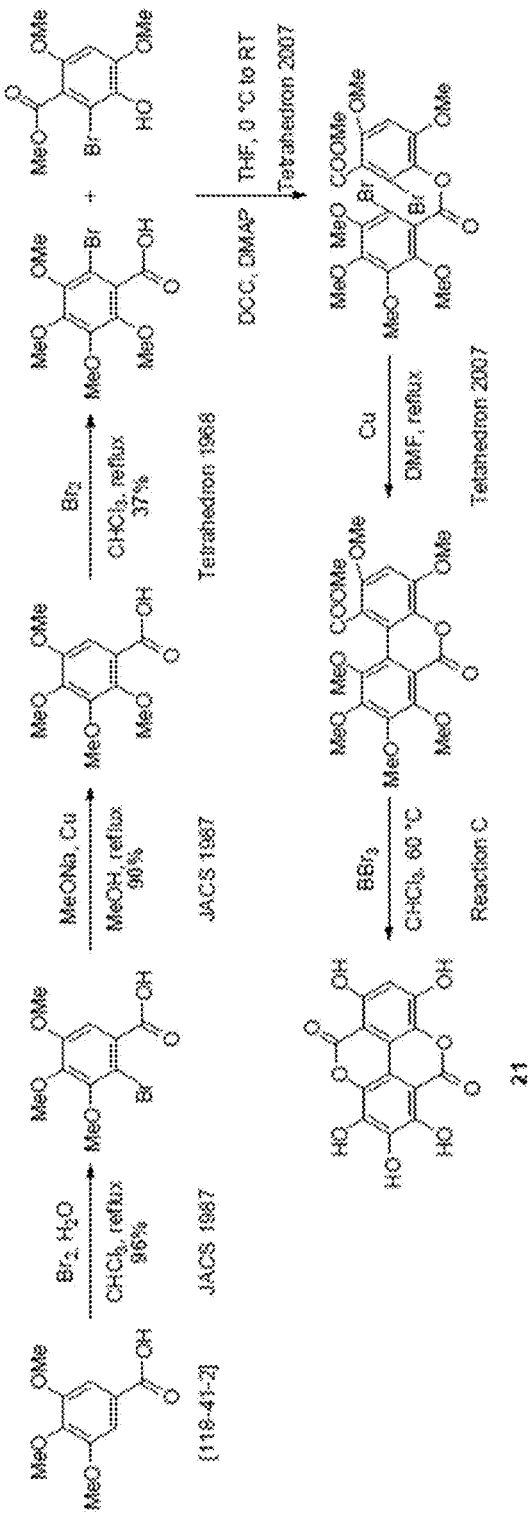
Figure 28:
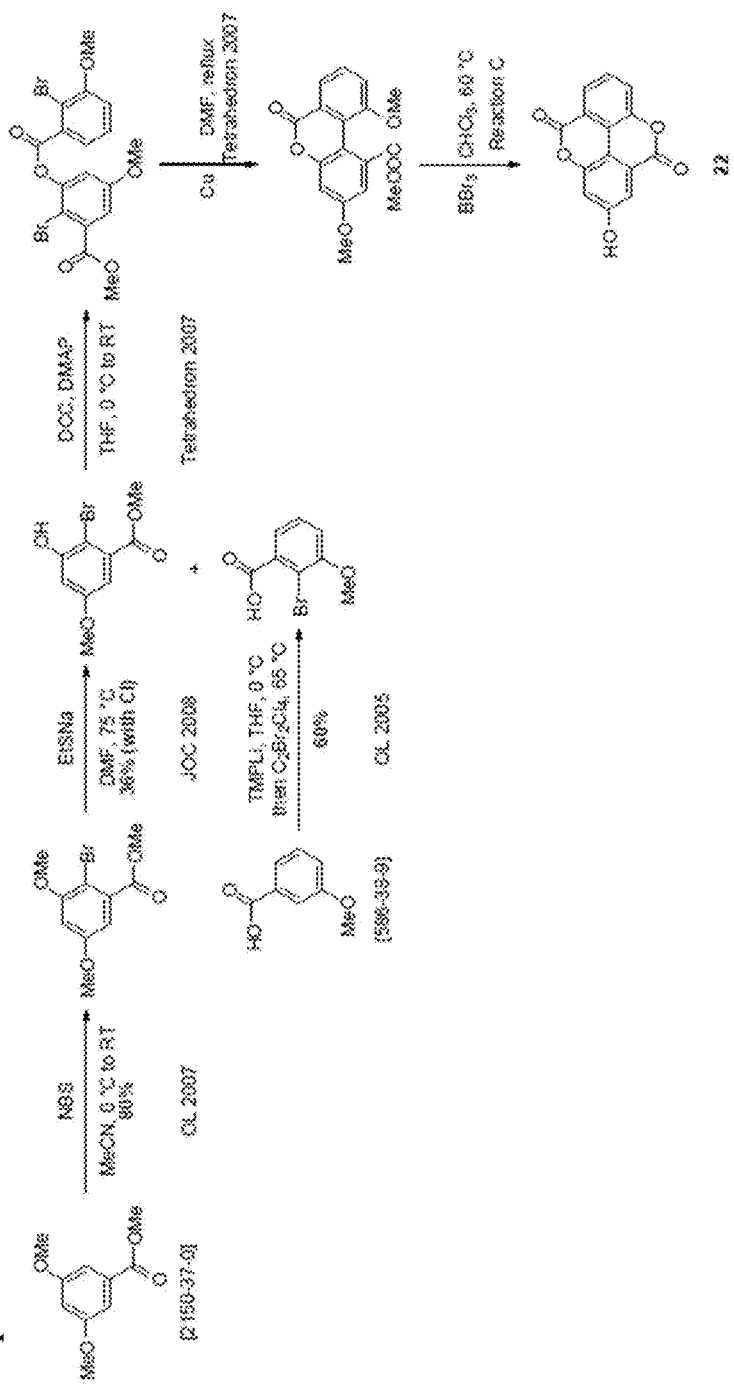
Figure 28:
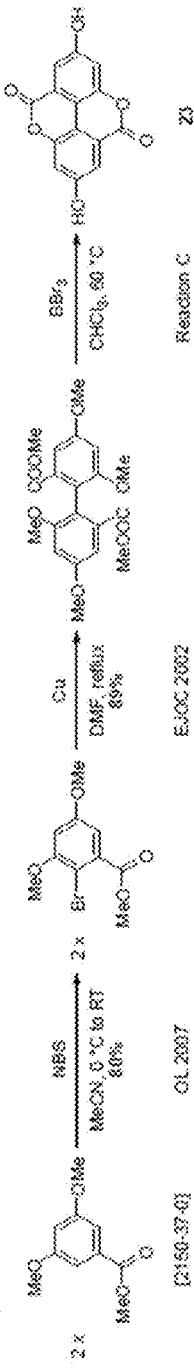
Figure 28:
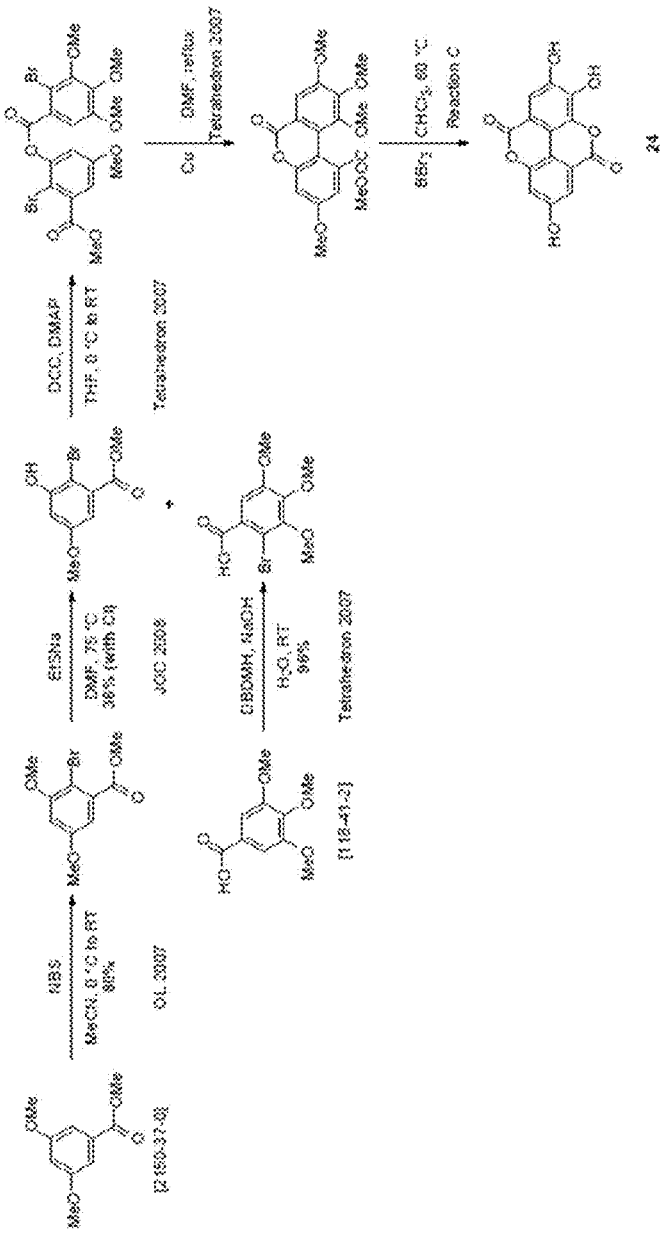
Figure 28:
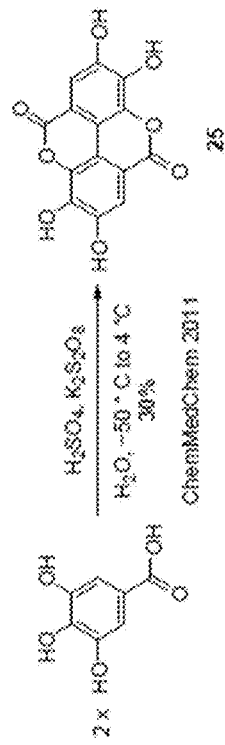

FIG. 28 describes methods to synthesize the compounds 1 to 25 to enable their therapeutic use in the present invention. Several chemical reactions are conserved and the details are provided below as Reactions A, B, C and D.

Reaction A

Oxalyl chloride (1 eq.) and dimethylformamide (cat.) were added to a suspension of the benzoic acid (1 eq.) in dichloromethane. The reaction mixture was stirred for 16 hours at room temperature and concentrated under reduced pressure. The residue was immediately solubilized in dichloromethane and cooled to 0° C. The phenol (1.1 eq.) and triethylamine (1.5 eq.) were successively added and the mixture was stirred for 5 minutes. Acetonitrile was finally added and the resulting solution was stirred for 16 hours at room temperature. The reaction was quenched by addition of a saturated solution of ammonium chloride and the layers were separated. The aqueous phase was extracted with dichloromethane and the combined organic layers were dried over sodium sulphate, filtered and concentrated under reduced pressure. The crude was purified by column chromatography on silica gel.

Reaction B

Sodium acetate (2 eq.), (S)-Phos (0.1 eq.) and palladium diacetate (0.1 eq.) were successively added to a solution of the ester (1 eq.) in dimethylacetamide under an argon atmosphere. The reaction mixture was stirred at 130° C. for 3 days. The reaction was quenched by addition of water and the mixture was extracted with dichloromethane. The combined organic layers were washed with brine, dried over sodium sulfate and concentrated under reduced pressure. The remaining dimethylacetamide was eliminated using a Hickman apparatus. The residue was purified by column chromatography on silica gel.

Reaction C

Boron tribromide (1.25 eq. by methoxy moiety) was added to a solution of the protected urolithin (1 eq.) in chloroform. The mixture was then heated up to 60° C. and stirred for 4 days. The reaction was quenched by addition of methanol and the mixture was evaporated to dryness. The residue was purified by column chromatography on C18.

Reaction D

A mixture of the diphenol (2 eq.), the bromobenzoic acid (1 eq.) and NaOH (2.2 eq.) in water was heated at reflux and stirred for 2 hours. Water and $CuSO_4 \cdot 5H_2O$ (0.1 eq.) were added and the mixture was stirred under reflux for an additional 1 hour. The reaction was then cooled down to room temperature and the precipitate was filtered on a glass frit (porosity 4). The product was then dissolved in absolute ethanol and concentrated in order to remove water. The residue was dissolved in hot methanol and filtered on paper.

We claim:

1. A method of treating a disease or condition selected from the group consisting of sarcopenia, sarcopenia of aging, osteoarthritis, muscular atrophy, muscle disuse atrophy, skeletal muscular atrophy, cardiac deterioration, cardiac deterioration with aging, negative consequences linked to aging, improving activity during aging, reducing age-related cataracts, improving balance or coordination, and frailty, comprising administering to a subject in need thereof a therapeutically effective amount of a urolithin, or a pharmaceutically acceptable salt thereof.

2. The method of claim 1, wherein the disease or condition is sarcopenia.

3. The method of claim 1, wherein the disease or condition is sarcopenia of aging.

4. The method of claim 1, wherein the disease or condition is osteoarthritis.

5. The method of claim 1, wherein the disease or condition is muscular atrophy.

6. The method of claim 1, wherein the disease or condition is muscle disuse atrophy.

7. The method of claim 1, wherein the disease or condition is skeletal muscular atrophy.

8. The method of claim 1, wherein the disease or condition is cardiac deterioration.

9. The method of claim 1, wherein the disease or condition is cardiac deterioration of aging.

10. The method of claim 1, wherein the disease or condition is negative consequences linked to aging.

11. The method of claim 1, wherein the disease or condition is improving activity during aging.

12. The method of claim 1, wherein the disease or condition is reducing age-related cataracts.

13. The method of claim 1, wherein the disease or condition is improving balance or coordination.

14. The method of claim 1, wherein the disease or condition is frailty.

15. The method of claim 1, wherein the urolithin is administered orally.

16. The method of claim 1, wherein the urolithin is selected from the group consisting of urolithin A, urolithin B, and any combination thereof.

17. The method of claim 1, wherein the urolithin is urolithin A.

18. The method of claim 1, wherein the urolithin is urolithin B.

19. The method of claim 1, wherein the subject is a human.

20. The method of claim 1, wherein the urolithin is administered orally; the urolithin is urolithin A; and the subject is a human.

* * * * *